United States Patent
Chatterjee et al.

(10) Patent No.: US 7,611,897 B2
(45) Date of Patent: Nov. 3, 2009

(54) AP1 AMINE OXIDASE VARIANTS

(75) Inventors: Ranjini Chatterjee, Belmont, CA (US); Jonathan P. Duvick, Des Moines, IA (US); James English, San Leandro, CA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 862 days.

(21) Appl. No.: 10/872,750

(22) Filed: Jun. 21, 2004

(65) Prior Publication Data

US 2005/0050586 A1    Mar. 3, 2005

Related U.S. Application Data

(63) Continuation of application No. 10/636,974, filed on Aug. 6, 2003, now abandoned, and a continuation-in-part of application No. 10/072,307, filed on Feb. 6, 2002, now abandoned.

(60) Provisional application No. 60/478,188, filed on Jun. 13, 2003, provisional application No. 60/401,629, filed on Aug. 6, 2002, provisional application No. 60/266,918, filed on Feb. 6, 2001, provisional application No. 60/300,324, filed on Jun. 22, 2001.

(51) Int. Cl.
   *C12N 5/10*     (2006.01)
   *C12N 15/00*    (2006.01)
   *C12N 15/82*    (2006.01)
   *C07H 21/04*    (2006.01)

(52) U.S. Cl. .................. 435/419; 435/320.1; 435/468; 536/23.2

(58) Field of Classification Search ........................ None
   See application file for complete search history.

(56) References Cited

U.S. PATENT DOCUMENTS

| | | | |
|---|---|---|---|
| 5,716,820 A | 2/1998 | Duvick | |
| 5,792,931 A | 8/1998 | Duvick | |
| 6,211,434 B1 | 4/2001 | Duvick | |
| 6,211,435 B1 * | 4/2001 | Duvick et al. | ............... 800/279 |
| 6,388,171 B1 * | 5/2002 | Duvick et al. | ............... 800/279 |

FOREIGN PATENT DOCUMENTS

| WO | WO 00/01460 | 1/2000 |
|---|---|---|
| WO | WO 00/04159 | 1/2000 |
| WO | WO 00/20573 | 4/2000 |

OTHER PUBLICATIONS

Guo et al., PNAS, 2004, vol. 101 (25): 9205-9210.*
Arnold et al.( Chem. Eng. Sci. 1996, 51, 5091-5102).*
Brown, D. at al., "Aspergillus has Distinct Faty Acid Syntheses for Primary and Secondary Matabolism", Proc. Natl. Acad. Sci. USA 93::14873-14877 (1996).
Busby & Wogan, Chemical Carcinogens (Searle ed), American Chemical Society, Washington D.C., pp. 945-1136 (1985.
Katz, L et al, "Polyketide Syntheses: Prospects for Hybrid Antibiotics" Annu. Rev. Microbiol. 47:875-912 (1993).
Kelkar, I. et al, "Aspergillus nidulans stcL. Encodes a Putative Cytochrome P-450 Monooxygenase Required for Bisfuran Desaturation During Altatoxin/Sterigmatocystin Biosyntheses" J. Biol. Chem. 272(1589-94 (1997).
Kimura, M. et al., "Trichothecene 3-O-Acetyltransferase Protects Both the Producing Organism and Transformed Yeast from Related Mycotoxins", J. Biol. Chem. 273:1654-1661 (1998).
Scott, P., "Fumonisins" International Journal of Food Microbiology 18:257-270 (1993).
Silvia, J. et al., "Isolation and Characterization of the Versicolorin B Synthase Gene from *Aspergilluys parasiticus*" J. Biol. Chem. 271:13600-608 (1996).

* cited by examiner

*Primary Examiner*—Nashaat T Nashed
*Assistant Examiner*—Younus Meah
(74) *Attorney, Agent, or Firm*—McKee, Voorhees & Sease, P.L.C.

(57) ABSTRACT

New fumonisin detoxifying or fumonisin-derivative detoxifying homologues (both nucleic acids and proteins) are provided. Compositions which include these new proteins, recombinant cells, antibodies to the new homologues, and methods of using the homologues are also provided.

25 Claims, 13 Drawing Sheets

| FBI pH 5.5 | Clone | Km | Vmax | Vmax/Km | X Improved | | AP1 pH 5.5 | Clone | Km | Vmax | Vmax/Km | X Improved |
|---|---|---|---|---|---|---|---|---|---|---|---|---|
| 50-225 uM [S] | 4F13 G12 | 62 | 15 | 0.242 | 7.1 | | 50-225 uM [S] | 4F13 G12 | 365 | 44.2 | 0.121 | 6.1 |
| | 4F15 A11 | 58 | 13.6 | 0.234 | 6.9 | | | 4F15 A11 | 438 | 46 | 0.105 | 5.3 |
| | 4F15 C3 | 39 | 9 | 0.231 | 6.8 | | | 4F15 C3 | 563 | 27.6 | 0.049 | 2.5 |
| | 4F6 A11 | 191 | 28.3 | 0.148 | 4.4 | | | 4F6 A11 | 288 | 28.3 | 0.098 | 4.9 |
| | 4F3 B5 | 101.8 | 16.4 | 0.161 | 4.7 | | | 4F3 B5 | 378 | 25.3 | 0.067 | 3.4 |
| | 4F2 G10 | 41.2 | 9.4 | 0.228 | 6.7 | | | 4F2 G10 | 2209 | 61.3 | 0.028 | 1.4 |
| | 4F19 F2 | 235 | 59.5 | 0.253 | 7.4 | | | 4F19 F2 | 652 | 18 | 0.028 | 1.4 |
| | 4F21 C8 | 113 | 22 | 0.195 | 5.7 | | | 4F21 C8 | 305.5 | 55.9 | 0.183 | 9.2 |
| | 4F22 B2 | 161 | 21.5 | 0.134 | 3.9 | | | 4F22 B2 | 444 | 64.5 | 0.145 | 7.3 |
| | 4F28 G1 | 172 | 23.9 | 0.139 | 4.1 | | | 4F28 G1 | ND | ND | ND | ND |
| | WT | 349 | 11.8 | 0.034 | 1 | | | WT | 450 | 9.2 | 0.02 | 1 |

22 hits (>3X Improved)

11 hits ;>3X improved)

Figure 1

Results: Kinetic parameters of pH-optimized candidates R3H1 and B12 compared to wild type APAO

| Variant | FB1, pH 5.5 | | | | AP1, pH 5.5 | | | |
|---|---|---|---|---|---|---|---|---|
| | kcat | km | kcat/km | Fold Impr | kcat | km | kcat/km | Fold Impr |
| WT | 150.0 | 98.0 | 1.5 | 1.0 | 240.0 | 430.0 | 0.6 | 1.0 |
| R3H1 | 2800.0 | 70.0 | 40.0 | 26.1 | 662.0 | 544.0 | 1.2 | 2.2 |
| B12 | 701.0 | 62.0 | 11.3 | 7.4 | 200.0 | 280.0 | 0.7 | 1.3 |

Figure 2

Several R3H1 & B12 mutations map to a putative substrate binding region of APAO

MPAO

Maize Polyamine Oxidase (MPAO) 3.0 Å crystal structure (Binda et al. 1999, Structure 7:265) Substrate "tunnel" shown in wire form.

APAO

APAO (truncated, amino acids 142-600) 3-D Model after Binda et al. Putative substrate "tunnel" shown in center right.

Mutations: B12 △◇   R3H1 ▲◈   Both ▲◆

Figure 6

R3H1 retains its high substrate specificity for fumonisins
Substrate Specificity at pH 7.4

Fig. 8A
| | rfu/min/ug (prior to preincubation) | %activity (after preincubation) |
|---|---|---|
| R3H1 | 1325 | 0.21 |
| g6 | 1804 | 0.59 |
| 1b6 | 1612 | 0.55 |
| 1h8 | 1804 | 0.35 |
| 3e7 | 1558 | 0.71 |
Fig. 8B
| | km | kcat |
|---|---|---|
| R3H1 | 259.12 | 2164.50 |
| g6 | 154.19 | 1612.90 |
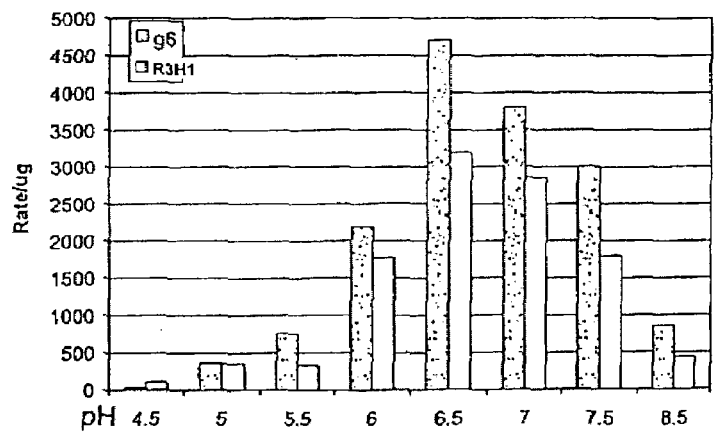
Fig. 8C
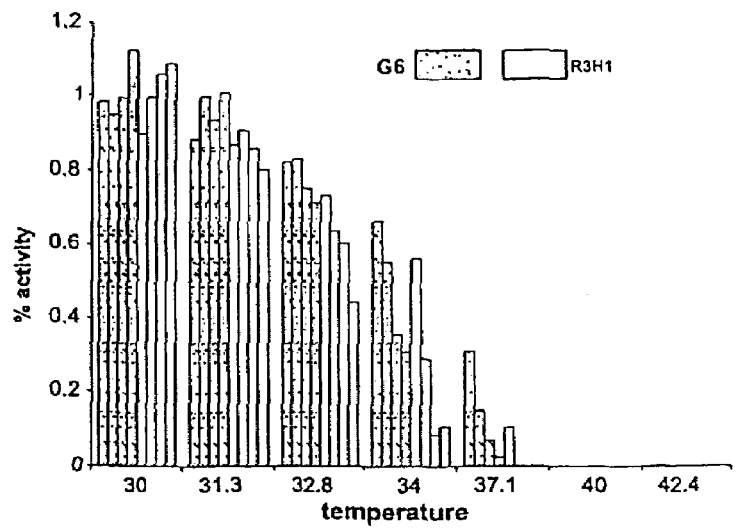
Fig. 8D

AP1 AMINE OXIDASE VARIANTS

CROSS-REFERENCES TO RELATED APPLICATIONS

This application is a continuation of U.S. patent application Ser. No. 10/636,974, filed Aug. 6, 2003, which claims priority to and benefit of U.S. Provisional Patent Application Ser. No. 60/401,629, filed on Aug. 6, 2002, the disclosures of which are incorporated herein by reference in their entirety for all purposes and U.S. Provisional Patent Application Ser. No. 60/478,188, filed on Jun. 13, 2003, the disclosure of which is incorporated herein in its entirety for all purposes; and this application is a continuation-in-part of and claims priority to and benefit of co-pending U.S. application Ser. No. 10/072,307 filed on Feb. 6, 2002 the disclosure of which is incorporated herein by reference in its entirety for all purposes, which claims priority to and benefit of U.S. Provisional Patent Application Ser. No. 60/266,918 filed on Feb. 6, 2001, the disclosure of which is incorporated herein by reference in its entirety for all purposes and U.S. Provisional Patent Application Ser. No. 60/300,324, filed on Jun. 22, 2001, the disclosure of which is incorporated herein in its entirety for all purposes.

SUBMISSION ON COMPACT DISC

The contents of the following submission on compact discs are incorporated herein by reference in its entirety: A compact disc copy of the Sequence Listing (COPY 1) (file name: 549162000201, date recorded: Aug. 6, 2003, size: 465 KB); a duplicate compact disc copy of the Sequence Listing (COPY 2) (file name: 549162000201, date recorded: Aug. 6, 2003, size: 465 KB); a computer readable form copy of the Sequence Listing (CRF COPY) (file name: 549162000201, date recorded: Aug. 6, 2003, size: 465 KB).

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to the generation of new and novel fumonisin detoxification and fumonisin-derivative detoxification homologues and nucleic acids encoding the same.

BACKGROUND OF THE INVENTION

Trading of mycotoxin-contaminated agricultural commodities is tightly regulated at both national and international levels. Each year, compliance with these regulations causes the loss of millions of dollars in agricultural produce in the United States alone. Trade sanctions and health effects from mycotoxin-contaminated grains add significantly to the losses (see, e.g., Brown et al. (1996) *PNAS USA* 93:14873-14877).

Accordingly, it is highly desirable to transform various mycotoxins produced by fungal pathogens in crops into inactive compounds which present no human or animal toxicity. This would alleviate important food pollution problems, as well as lessen the costs associated with complying with detecting and destroying mycotoxin-contamination in various crop commodities. Pioneering work in the of construction of nucleic acids for mycotoxin detoxification was done by co-workers of the inventor, see, WO 00/20573. The present invention extends this work to the detoxification of fumonisins.

The term "mycotoxin" generically refers to a number of toxic molecules produced by fungal species, including polyketides and polyketide derived secondary metabolites (such as fumonisins, aflatoxins, sterigmatocystins, alperisins, trichothecenes, fumifungins, and the like). Polyketides are a large, structurally diverse class of secondary metabolites synthesized by bacteria, fungi, and plants and are formed by a polyketide synthase (PKS) through the sequential condensation of small carboxylic acids. See, e.g., Katz and Donadio (1993) *Annu Rev Microbiol* 47:875-912; Brown et al. (1996) *PNAS USA* 93:14873-14877; Silva et al. (1996) *J Biol Chem* 271:13600-608; Kelkar, I. (1997) *J Biol Chem* 272:1589-94; Busby & Wogan (1985) in *Chemical Carcinogens* (Searle ed., 1985) pp. 945-1136, American Chemical Society, Washington D.C.; Kimura et al. (1998) *J Biol Chem* 273:1654-1661.

Fumonisins are a structurally distinct family of mycotoxins with at least 15 known members, produced by several *Fusarium* species (see, e.g., Scott (1993) *Int J Food Microbiol* 18:257-270 and the references therein). Fumonisins have potential toxic and carcinogenic effects in mammals, and have been associated with a number of animal toxicoses, including equine leukoencephalomalacia and porcine pulmonary edema. Fumonisins mimic sphingolipid precursors inhibiting sphingolipid biosynthesis, a property which is thought to be related to their toxic (e.g., hepatotoxic, renotoxic) and carcinogenic effects. For example, Fumonisin B 1 (FB1), the most prevalent of the fumonisins is the diester of propane-1,2,3-tricarboxylic acid and 2-amino-12,16-dimethyl-3,5,10,14,15-pentahydroxyeicosane (empirical formula $C_{34}H_{59}NO_{15}$).

*Fusarium* infections are widespread among field grown corn (it should be noted that the terms 'corn' and 'maize' are used interchangeably herein), and detectable levels of fumonisins, while more prevalent in corn exhibiting signs of physical damage and infestation, can be found worldwide in food and feed products in the absence of overt symptoms, making it difficult to monitor and eradicate this potentially dangerous toxin. Fumonisins are stable upon exposure to light, and can withstand temperatures commonly used during food processing. For example, following dry milling of corn, fumonisins are found in the resulting bran, germ and flour, and are similarly stable in maize and polenta. However, fumonisins can be hydrolyzed upon treatment with hot alkali solution (i.e., as is performed in some grain treatments/preparations).

Biological approaches to detoxifying fumonisins have thus far focused on isolating proteins and nucleic acids from naturally occurring organisms capable of metabolizing fumonisins. For example, esterases capable of degrading fumonisins to their de-esterified form, e.g., amino polyol 1 (AP1) and related compounds have been described (see, e.g., U.S. Pat. No. 5,716,820, U.S. Pat. No. 5,792,931). Similarly, naturally occurring amino polyol amine oxidase (APAO) enzymes capable of oxidatively deaminating AP 1 to the 2-oxo derivative of AP1 or its cyclic ketal form have also been described in WO 00/04159 and WO 00/01460. These naturally occurring APAO enzymes have little activity, however, on intact fumonisins.

The present invention offers new and useful sequences encoding polypeptides with an ability to detoxify fumonisins and fumonisin-derivatives and analogs as well as methods related to detoxification of these mycotoxins. This detoxification is particularly useful in crops, thereby solving each of the problems outlined above, as well as providing a variety of other features which will be apparent upon review.

SUMMARY OF THE INVENTION

The invention provides novel enzymes useful for detoxification of mycotoxins having primary amine groups, such as fumonisins, fumonisin derivatives and related molecules, including fumonisin hydrolysis products such as amino polyols, e.g., AP1 and similarly configured molecules. For example, fumonisins detoxified by the polypeptides of the invention include fumonisin B1, fumonisin B2, fumonisin B3, fumonisin B4, fumonisin C1, and the like (e.g., structurally similar molecules, etc., such as those having C-2 or C-1 amine groups, etc.). As such, the polypeptides described herein are one set of fumonisin detoxification and fumonisin-derivative detoxification ("FD/FDD") homologue polypeptides. The invention also includes nucleic acids encoding the polypeptides, antibodies to the polypeptides, and uses thereof; data sets containing character strings representing the polynucleotide and polypeptide sequences described herein, and automated systems for using the character strings.

In one aspect, the invention includes an isolated or recombinant polypeptide with improved fumonisin detoxification characteristics relative to naturally occurring enzymes involved in fumonisin degradation, e.g., a wild type amino polyol amine oxidase enzyme. Generally, such polypeptides are fumonisin amine oxidases. For example, isolated or recombinant polypeptides of the invention have a fumonisin or fumonisin derivative detoxification activity that is at least about 1.5-fold greater than a naturally occurring (or wild-type) enzyme, such as those exemplified by SEQ ID NOs:52, 54, 56, 58, 60, 62, and 64. In some cases, the fumonisin detoxification activity is at least about 2×, in many cases at least about 5×, often at least about 10×, frequently at least about 20×, or more (e.g., 50×, 100×, 250×, 500×, or more) greater than the fumonisin or fumonisin derivative detoxification activity of any of the naturally occurring polypeptides.

The polypeptides of the invention typically exhibit improved fumonisin or fumonisin derivative detoxification activity, at a pH that is lower than the pH exhibited by any of the naturally occurring enzymes, e.g., represented by SEQ ID NOs: 52, 54, 56, 58, 60, 62 or 64. For example, the polypeptides of the invention exhibit an improved fumonisin detoxification activity at a pH range of between about 5.0 and 7.9. Frequently, the polypeptides of the invention exhibit the improved fumonisin detoxification activity between about pH 5.5 and pH 7.4. Often, the improved fumonisin detoxification activity is exhibited at a pH between 5.5 and 6.8. In some embodiments, the improved fumonisin detoxification activity exhibits an optimum of about pH 5.5. Polypeptides exhibiting an improved fumonisin detoxification activity at about pH 5.5 are particularly useful for in vivo applications where detoxification occurs within the apoplast of a plant cell.

For example, an improved fumonisin detoxification activity of an FD/FDD polypeptide can be conferred by alterations in the binding of, or alterations in the conversion activity of, a fumonisin, a fumonisin derivative, or a fumonisin-like analog substrate. For example, the polypeptide of the invention having an improved fumonisin detoxification activity can have a higher $k_{cat}$ than any of the naturally occurring enzymes, e.g., exemplified by SEQ ID NOs:52, 54, 56, 58, 60, 62 and 64. Alternatively, or in addition, the polypeptide of the invention has a lower $K_M$ than any of the naturally occurring enzymes described above.

Additionally, improvements in fumonisin detoxification activity can correlate with increased thermostability relative to a wild type enzyme involved in fumonisin detoxification.

The polypeptides of the invention having an improved fumonisin detoxification activity are typically at least about 70% identical to SEQ ID NO:50, over a comparison window of at least 125 contiguous amino acids. In one embodiment, the polypeptide comprises a sequence selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 or a subsequence or fragment thereof with fumonisin detoxification activity. In some embodiments, the polypeptides are at least about 75% identical to SEQ ID NO:50 over a comparison window of 125 contiguous amino acids. Commonly, the polypeptides are at least about 80%, frequently at least about 85%, often at least about 90%, sometimes at least about 95% or more, e.g., 97%, 98%, or 99% identical to SEQ ID NO:50 over a comparison window of at least 125 contiguous amino acids.

The invention also includes polypeptides which are substantially identical over at least 125, at least 150, at least 175, at least 200, at least 225, at least 250, at least 275, or at 300 contiguous amino acids of such a polypeptide with improved fumonisin detoxification activity. For example, in some embodiments, the polypeptides of the invention are substantially identical (e.g., at least about 70%, 75%, 80%, 85%, 90%, 95%, 97%, 98%, or 99% identical) over at least about 125, or more contiguous amino acids of any one of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. In one embodiment, the polypeptides of the invention are identical for at least about 125 contiguous amino acids of any one of SEQ ID NOs:26-50, SEQ ID NOs: 70-72, and SEQ ID NOs:85, 87, 89, 91, 93, 95, 97, 99, 101, 103, 105, 107, 109, 111, 113, 115, 117, 119, 121, 123, 125, and 127. For example, a polypeptide of the invention is a protein with an amino acid sequence of any one of SEQ ID NOs:26-50, SEQ ID NOs:70-72, and SEQ ID NOs: 85, 87, 89, 91, 93, 95, 97, 99, 101, 103, 105, 107, 109, 111, 113, 115, 117, 119, 121, 123, 125, and 127. In other embodiments, the polypeptides of the invention include one or more mutated amino acids, e.g., conservative amino acid substitutions. For example, certain embodiments include, e.g., an alanine residue at position 118, a serine residue at position 136, an asparagine residue at position 193, a phenylalanine residue at position 209, a lysine residue at position 210, an isoleucine residue at position 237, a glutamic acid residue at position 272, a proline residue at position 274, and/or a glutamic acid residue at position 473, wherein the recited positions refer to amino acid positions of the wild type APAO polypeptide sequence (SEQ ID NO: 52). In some embodiments, the polypeptides have an altered glycosylation pattern relative to any one of SEQ ID NOs:52, 54, 56, 58, 60, 62 or 64. An altered glycosylation pattern results from the addition and/or deletion of at least one glycosylation site. Optionally the altered glycosylation site is at an amino acid at positions 201-206 (NDSNQS) (SEQ ID NO: 73).

In some embodiments the polypeptides of the invention are encoded by polynucleotides selected from among: (a) a polynucleotide sequence of SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126; (b) a polynucleotide sequence that encodes a polypeptide selected from SEQ ID NOs:26-50, SEQ 11D NOs:70-72, and SEQ ID NOs:85, 87, 89, 91, 93, 95, 97, 99, 101, 103, 105, 107, 109, 111, 113, 115, 117, 119, 121, 123, 125, and 127; and (c) a complementary sequence of a polynucleotide sequence which hybridizes under highly stringent conditions over substantially the entire length of polynucleotide sequence (a) or (b). In various embodiments, the polypeptide comprises partial or full length sequences (e.g., at least 125, at least 150, at least 175, at least 200, at least 225, at least 250, at least 275, or at least or more amino acids).

These sequences can be present separately or as components of larger proteins. In various embodiments, the polypeptide comprises about 580, about 585, about 590, about 595, or more (e.g., 596, 597, 598, 599 or 600) contiguous amino acids of the encoded protein. For example, the polypeptides of the invention can be incorporated in fusion proteins. In other embodiments, any polypeptide described above may further include a secretion/localization sequence, e.g., a signal sequence, a membrane localization sequence, an organelle targeting sequence (e.g., an apoplast targeting sequence or a peroxisome targeting sequence), and the like. For example, a polypeptide of the invention can include a leader sequence, e.g., a leader sequence directing secretion from a cell (such as a plant cell). In the latter instance, the polypeptides typically have an increased fumonisin detoxification activity upon secretion from a cell, relative to any of the polypeptides corresponding to SEQ ID NOs:52, 54, 56, 58, 60, 62 and 64. Similarly, any polypeptide described above may further include a sequence that facilitates purification, e.g., an epitope tag (such as, a FLAG epitope), a polyhistidine tag, a GST fusion, and the like. The polypeptide optionally includes a methionine at the N-terminus. Any polypeptide described above optionally includes one or more modified amino acids, such as a glycosylated amino acid, a PEG-ylated amino acid, a farnesylated amino acid, an acetylated amino acid, a biotinylated amino acid, a carboxylated amino acid, a phosphorylated amino acid, an acylated amino acid, or the like.

The invention also includes truncated polypeptide versions or fragments of the polypeptides of the invention (e.g., as listed in SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127) as well as the polynucleotides encoding such truncated polypeptides. The polypeptide fragments can be truncated from either the N-terminus or the C-terminus or from both the N-terminus and the C-terminus. The truncated polypeptides of the invention have the ability to detoxify at least one fumonisin or fumonisin derivative or analog. Additionally, the truncated polypeptides of the invention optionally have the other desirable characteristics of the full length polypeptides of the invention (e.g., as listed in SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127) as listed and detailed throughout (e.g., improved kinetics over wild-type APAO, enzymatic activity at physiological pH (e.g., pH 5.5), etc.).

The invention also includes polypeptides which specifically bind polyclonal antisera raised against one or more antigen comprising a polypeptide selected from those comprising the amino acid sequences set forth at SEQ ID NOs: 26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 or fragments thereof. In particular, polypeptides which bind an antisera raised against any amino acid sequence set forth at SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, where the antisera is subtracted with one or more proteins selected from one or more (and optionally all) proteins selected from, e.g., those with clone numbers ESP002C2, ESP002C3, ESP003C12, RAT011C1, RAT011C2, RAT011C4 found in publications WO 00/04159 and WO 00/04160, or wild-type APAO from *Exophiala spinifera* ("APAO") (see, SEQ ID NOs: 52, 54, 56, 58, 60, 62), or other homologues found in, e.g., GenBank by one of skill in the art.

The invention also includes antibodies produced by administering one or more polypeptide described above to a mammal, where the antibody does not bind to known FD/FDD, e.g., wild type APAO, homologue encoding sequences selected from, e.g., those corresponding to clone numbers ESP001, ESP002C2, ESP002C3, ESP003C12, RAT011C1, RAT011C2, RAT011C4 found in publications WO 00/04159 and WO 00/04160 (see, SEQ ID Nos: 52, 54, 56, 58, 60, 62), or other homologues found in, e.g., a public database such as, e.g., GenBank.

The invention also includes antibodies which specifically bind a polypeptide comprising a sequence selected from SEQ ID NOs:26-50, SEQ ID NOs:70-72, SEQ ID NOs:85, 87, 89, 91, 93, 95, 97, 99, 101, 103, 105, 107, 109, 111, 113, 115, 117, 119, 121, 123, 125, and 127 and. The antibodies are, e.g., polyclonal, monoclonal, chimeric, humanized, single chain, Fab fragments, fragments produced by an Fab expression library, or the like.

Another aspect of the invention relates to isolated or recombinant nucleic acids encoding fumonisin and fumonisin-derivative detoxification homologues. In particular, the nucleic acids of the invention encode enzymes with fumonisin or fumonisin derivative or analog detoxification activity, and related coding and non-coding nucleic acids. For example, isolated or recombinant nucleic acids of the invention include a polynucleotide sequence that encodes a polypeptide that is at least 70% or more identical to SEQ ID NO:50 over a comparison window of at least 125 amino acids which has a fumonisin detoxification activity or a fumonisin derivative detoxification activity that is at least 1.5-fold greater than any of SEQ ID NOs: 52, 54, 56, 58, 60, 62 or 64 at pH 5.5. Similarly, nucleic acids that encode polypeptides that are at least about 75%, 80%, 85%, 90%, 95%, 97%, 98%, 99% or more identical to SEQ ID NO:50, and or to any of SEQ ID NOs:26-49, SEQ ID NOs:70-72, and SEQ ID NOs: 85, 87, 89, 91, 93, 95, 97, 99, 101, 103, 105, 107, 109, 111, 113, 115, 117, 119, 121, 123, 125, and 127 are included in the invention. In one embodiment, the nucleic acids encode at least about 125 contiguous amino acids, e.g., at least 150, at least 175, at least 200, at least 225, at least 250, at least 275, at least 300 or more amino acids, such as the full length of any of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. In an embodiment, the nucleic acid is selected from among SEQ ID NOs:1-25, SEQ ID NOs:67-69, and SEQ ID NOs:84, 86, 86, 99, 92, 94, 96, 98, 100, 102, 104, 106, 108, 110, 112, 114, 116, 118, 120, 122, 124, and 126.

In other embodiments, the nucleic acids of the invention with the desired fumonisin or fumonisin derivative detoxification activity as described above are nucleic acids that hybridize under low stringency or medium stringency conditions to a polynucleotide sequence selected from among: (a) a polynucleotide sequence selected from the group consisting of SEQ ID NOs:1-,25, SEQ ID NOs:67-69 and SEQ ID NOs:84, 86, 88, 90, 92, 94, 96, 98, 100, 102, 104, 106, 108, 110, 112, 114, 116, 118, 120, 122, 124, and 126, or a complementary polynucleotide sequence thereof; (b) a polynucleotide sequence encoding a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127,or a complementary polynucleotide sequence thereof; and (c) a polynucleotide sequence comprising a fragment of (a) or (b), wherein the fragment encodes a polypeptide having at least one fumonisin detoxification activity or at least one fumonisin derivative detoxification activity.

Isolated and/or recombinant nucleic acids selected from among polynucleotide sequences including SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, and complementary polynucleotide sequences thereof; as well as, polynucleotide sequences encoding a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, and complementary polynucleotide sequences thereof, are also a feature of the invention. Similarly, a polynucleotide sequence which hybridizes under highly stringent conditions over substantially the entire length of any of the preceding polynucleotide sequences is a feature of the invention. Similarly, fragments of the above which encode a polypeptide having fumonisin or fumonisin derivative detoxification activity are features of the invention.

The invention also includes an isolated or recombinant nucleic acid comprising a polynucleotide sequence encoding a polypeptide, where the polypeptide comprises an amino acid sequence which is substantially identical over at least 125 contiguous amino acids of any one of SEQ ID NOs:26-50, SEQ ID NOs:70-72 and SEQ ID NOs:85, 87, 89, 91, 93, 95, 97, 99, 101, 103, 105, 107, 109, 111, 113, 115, 117, 119, 121, 123, 125, and 127. In various embodiments, the encoded polypeptide is substantially identical over about 150, about 175, about 200, about 225, about 250, about 275, or about 300 or more contiguous amino acid residues or substantially identical variants of any one of the polypeptide sequences listed or encoded by any nucleic acid listed. In other embodiments, the encoded polypeptide is at least about 580 or at least about 595 amino acids in length. In another embodiment, the encoded polypeptide is about 600 amino acids in length. The polypeptides can exist separately or as components of one or more fusion proteins, e.g., including a signaling or leader sequence, a targeting sequence or the like.

In other embodiments, the nucleic acids of the invention encode polypeptides that detoxify or degrade a fumonisin or a fumonisin-derivative. Other embodiments of the invention include nucleic acids that encode polypeptides which deaminate a fumonisin or a fumonisin-derivative. Preferably, the encoded polypeptide detoxifies, degrades, or deaminates a mycotoxin that is a fumonisin or a fumonisin derivative or analog, e.g., a fumonisin B1, a fumonisin B2, a fumonisin B3, a fumonisin B4, a fumonisin C1, or the like, or structurally related mycotoxins and/or analogs (see, FIG. 9 for structures of AP1 and FB1). In one embodiment, the encoded polypeptide is a fumonisin amine oxidase. Optionally, the nucleic acids of the invention encode polypeptides with altered kinetic parameters (e.g., $K_{cat}$, $K_M$), such as improved fumonisin or fumonisin derivative detoxification activity at a selected pH, e.g., pH 5.5, relative to a wild-type APAO (amino polyol (AP1) amine oxidase) from, e.g., *Exophiala spinifera*.

In general, nucleic acids and polypeptides, e.g., proteins, derived by mutation, recursive recombination, or other alterations of the sequences herein are a feature of the invention. Similarly, those produced by recombination, including recursive recombination, are a feature of the invention. Mutation and recombination methods using the nucleic acids described herein are a feature of the invention. For example, one method of the invention includes recombining one or more nucleic acid described above with one or more additional nucleic acids (including, but not limited to those noted herein), the additional nucleic acid encoding a polypeptide with a fumonisin or a fumonisin derivative (or other structurally analogous mycotoxin or mycotoxin derivative) detoxification activity or subsequence thereof. The recombining steps are optionally performed in vivo or in vitro. Also included in the invention are a recombinant nucleic acid produced by this method, a cell containing the recombinant nucleic acid, a nucleic acid library produced by this method and a population of cells containing the library.

The invention also includes a vector comprising any nucleic acid described above, suitable for transforming a prokaryotic or eukaryotic cell, such as a plant. The vector can comprise a plasmid, a cosmid, a phage, or a virus (or virus fragment). In an embodiment, the vector includes a T-DNA sequence. The vector can be, e.g., an expression vector, a cloning vector, a packaging vector, an integration vector, or the like. For example, an expression vector typically includes a promoter operably linked to the polynucleotide sequence of the invention. Such a promoter can be either constitutive or inducible, and, if desired, is a tissue specific promoter. Frequently, the promoter is heterologous with respect to the polynucleotide of the invention, and is selected to cause sufficient expression of the encoded polypeptide to result in detoxification of fumonisin or a fumonisin derivative in a cell or tissue in which it is expressed. Optionally, any vector of the invention comprises a second polynucleotide sequence encoding a second polypeptide that confers a detectable phenotypic trait upon a cell or organism expressing the polypeptide (e.g., a plant, plant explant, fingus, bacteria, etc.), such as a selectable marker, e.g., herbicide resistance, pest resistance, biocide resistance, fumonisin esterase activity, or a visible marker.

The invention also includes a cell comprising any nucleic acid (or vector) of the invention, or which expresses any polypeptide noted herein. In one embodiment, the cell expresses a polypeptide encoded by the nucleic acid. Typically, the polynucleotide and/or polypeptide are heterologous to the cell. In some embodiments, the cells incorporating the nucleic acids and/or expressing the polypeptides of the invention are plant cells. Transgenic plants, transgenic plant cells and transgenic plant explants incorporating the nucleic acids of the invention are also a feature of the invention. In some embodiments, the transgenic plants, transgenic plant cells or transgenic plant explants express an exogenous polypeptide with fumonisin detoxification or fumonisin derivative detoxification activity encoded by the nucleic acid of the invention. A seed produced by such a transgenic plant is also a feature of the invention. In such instances, one or more parental codons of the nucleic acid can be substituted with a synonymous codon that is preferentially used by the translation machinery of a plant cell. Alternatively, the cell can be a microorganism cell, such as a bacteria, a fungus or a yeast cell.

The invention also includes compositions comprising two or more nucleic acids described herein. The composition may comprise a library of nucleic acids, where the library contains at least 5, at least 10, at least 20 or at least 50 or more nucleic acids.

The invention also includes compositions produced by digesting one or more nucleic acid described herein with a restriction endonuclease, an RNAse, or a DNAse; and, compositions produced by incubating one or more nucleic acid described herein in the presence of deoxyribonucleotide triphosphates and a nucleic acid polymerase, e.g., a thermostable polymerase.

Methods for producing transgenic organisms (e.g., plants, fungi, bacteria, etc.) comprising a nucleic acid of the invention expressing a polypeptide at an effective level to deaminate fumonisin are also feature of the invention. Additionally, the invention includes methods of reducing pathogenicity of a fungus producing a fumonisin, comprising producing a transgenic cell (also optionally including a plant cell in a plant and optionally wherein the cell comprises a fumonisin esterase encoding polynucleotide linked to a promoter) with a heterologous nucleic acid of the invention operably linked to a promoter and expressing the nucleic acid at a level effective to produce sufficient hydrogen peroxide to reduce fungal infection. Further, the invention includes methods of creating or enhancing disease resistance in a plant by introducing into a plant cell a recombinant expression cassette comprising any of the nucleic acids noted herein operably linked to a promoter that drives expression in a plant, culturing the plant cell under plant cell growing conditions, and regenerating from the plant cell a whole plant, wherein the plant has enhanced or newly created disease resistance.

Methods for producing the polypeptides of the invention are also included. One such method comprises introducing into a population of cells any nucleic acid described herein, operatively linked to a regulatory sequence effective to produce the encoded polypeptide, culturing the cells in a culture medium to produce the polypeptide, and isolating the polypeptide from the cells or from the culture medium. The nucleic acid may be part of a vector, such as a recombinant expression vector.

In general, nucleic acids and proteins derived by mutation, recursive recombination, or other alterations of the sequences herein are a feature of the invention. Similarly, those produced by recombination, including recursive recombination, are a feature of the invention. Mutation and recombination methods using the nucleic acids described herein are a feature of the invention. For example, one method of the invention includes recombining one or more nucleic acid described above with one or more additional nucleic acid (including, but not limited to those noted herein), the additional nucleic acid encoding an FD/FDD homologue or subsequence thereof. The recombining steps are optionally performed in vivo or in vitro. Also included in the invention are a recombinant nucleic acid produced by this method, a cell containing the recombinant nucleic acid, a nucleic acid library produced by this method and a population of cells containing the library.

These and other features of the invention will become more fully apparent when the following detailed description is read in conjunction with the accompanying figures.

BRIEF DESCRIPTION OF THE FIGURES

FIG. 1: Kinetic parameters of selected homologues 4F13G12, 4F15A11, 4F15C3, 4F6A11, 4F3B5, 4F2G10, 4F19F2, 4F21C8, 4F22B2, 4F28G1, and a wild-type APAO.

FIG. 2: Kinetic parameters of selected homologues R3H1 and B12.

FIG. 6: Graph showing substrate specificity of exemplary homologue.

FIG. 8: Panels A through D show selected kinetic parameters of exemplary homologues of the invention.

DETAILED DESCRIPTION OF THE INVENTION

Definitions

Figure 3:
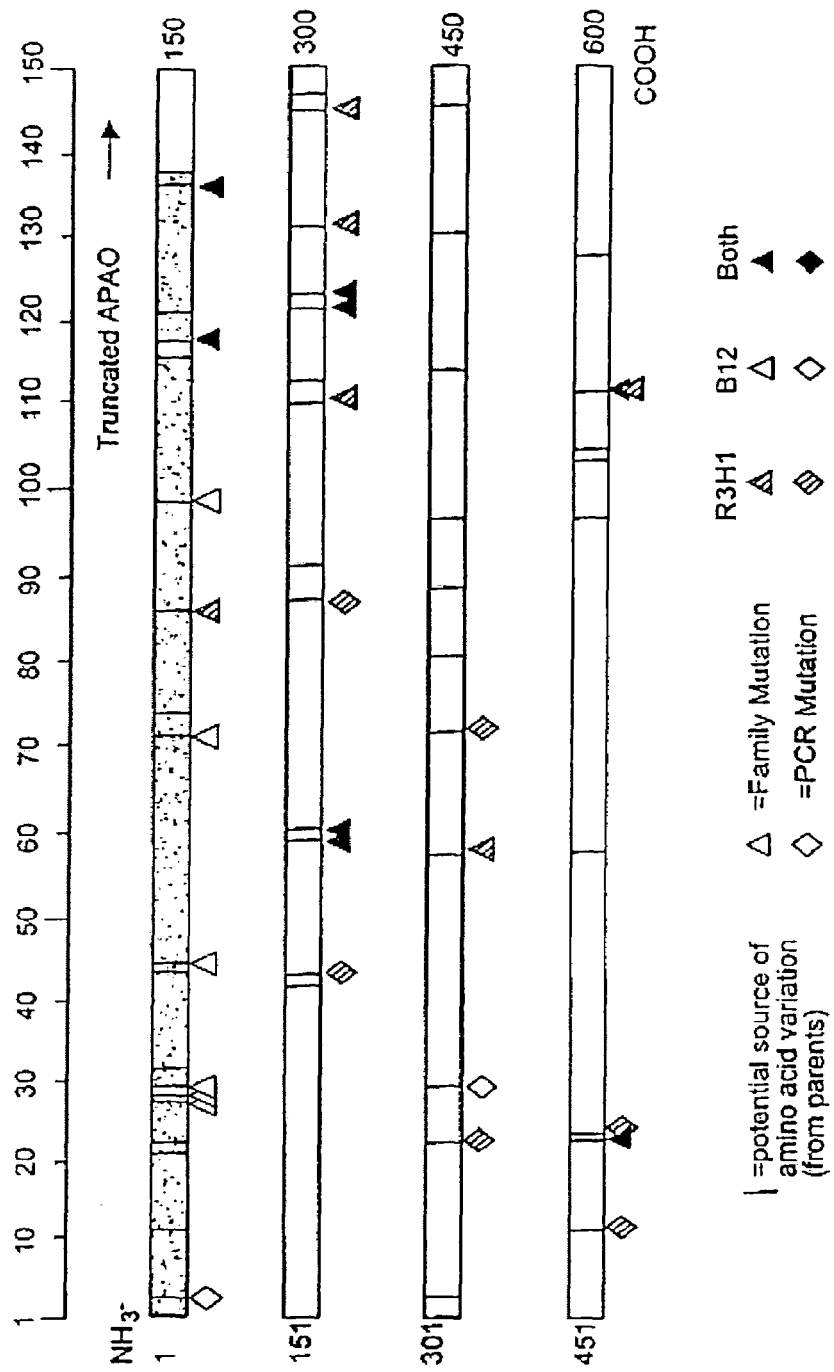
FIG. 3: Comparison of specific amino acid residue positions between two exemplary homologues.

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a device" includes a combination of two or more such devices, reference to "a gene fusion construct" includes mixtures of constructs, and the like.

Unless defined otherwise, all technical and scientific terms used herein have the same meaning as commonly understood by one of ordinary skill in the art to which the invention pertains. Although specific examples of appropriate materials and methods are described herein, any methods and materials similar or equivalent to those described herein can be used in the practice for testing of the present invention.

In describing and claiming the present invention, the following terminology will be used in accordance with the definitions set out below. The terms "polynucleotide," "nucleotide sequence," and "nucleic acid" are used to refer to a polymer of nucleotides (A,C,T,U,G, etc. or naturally occurring or artificial nucleotide analogues), e.g., DNA or RNA, or a representation thereof, e.g., a character string, etc, depending on the relevant context. A given polynucleotide or complementary polynucleotide can be determined from any specified nucleotide sequence. Similarly, an "amino acid sequence" is a polymer of amino acids (a protein, polypeptide, etc.) or a character string representing an amino acid polymer, depending on context. The terms "protein," "polypeptide," and "peptide" are used interchangeably herein.

A nucleic acid, protein, peptide, polypeptide, or other component is "isolated" when it is partially or completely separated from components with which it is normally associated (other peptides, polypeptides, proteins (including complexes, e.g., polymerases and ribosomes which may accompany a native sequence), nucleic acids, cells, synthetic reagents, cellular contaminants, cellular components, etc.) in the cell from which it was originally derived. A nucleic acid, polypeptide, or other component is isolated when it is partially or completely recovered or separated from other components of its natural environment such that it is the predominant species present in a composition, mixture, or collection of components (i.e., on a molar basis it is more abundant than any other individual species in the composition). In preferred embodiments, the preparation contains more than 70%, typically more than 80%, or preferably more than 90% of the isolated species.

In one aspect, a "substantially pure" or "isolated" nucleic acid (e.g., RNA or DNA), polypeptide, protein, or composition also means where the object species (e.g., nucleic acid or polypeptide) comprises at least about 50, 60, or 70 percent by weight (on a molar basis) of all macromolecular species present. A substantially pure or isolated composition can also comprise at least about 80, 90, or 95 percent (or more) by weight of all macromolecular species present in the composition. An isolated species can also be purified to essential homogeneity (contaminant species cannot be detected in the composition by conventional detection methods) wherein the composition consists essentially of derivatives of a single macromolecular species.

The term "isolated nucleic acid" may refer to a nucleic acid (e.g., DNA or RNA) that is not immediately contiguous with both of the coding sequences with which it is immediately contiguous (i.e., one at the 5' and one at the 3' 3 end) in the naturally occurring genome of the organism from which the nucleic acid is derived. Thus, this term includes, e.g., a cDNA or a genomic DNA fragment produced by polymerase chain reaction (PCR) or restriction endonuclease treatment, whether such cDNA or genomic DNA fragment is incorporated into a vector, integrated into the genome of the same or a different species than the organism, including, e.g., a virus, from which it was originally derived, linked to an additional coding sequence to form a hybrid gene encoding a chimeric polypeptide, or independent of any other DNA sequences. The DNA may be double-stranded or single-stranded, sense or antisense.

A nucleic acid or polypeptide is "recombinant" when it is artificial or engineered, or derived from an artificial or engineered protein or nucleic acid. The term "recombinant" when used with reference e.g., to a cell, nucleotide, vector, or polypeptide typically indicates that the cell, nucleotide, or vector has been modified by the introduction of a heterologous (or foreign) nucleic acid or the alteration of a native nucleic acid, or that the polypeptide has been modified by the introduction of a heterologous amino acid, or that the cell is derived from a cell so modified. Recombinant cells express nucleic acid sequences (e.g., genes) that are not found in the native (non-recombinant) form of the cell or express native nucleic acid sequences (e.g., genes) that would be abnormally expressed, under-expressed, or not expressed at all. The term "recombinant nucleic acid" molecule (e.g., DNA or RNA) means, for example, a nucleotide sequence that is not naturally occurring or is made by the combination (for example, artificial combination) of at least two segments of sequence that are not typically included together, not typically associated with one another, or are otherwise typically separated from one another. A recombinant nucleic acid can comprise a nucleic acid molecule formed by the joining together or combination of nucleic acid segments from different sources and/or a nucleic acid that is artificially synthesized. The term "recombinantly produced" refers to an artificial combination usually accomplished by either chemical synthesis means, recursive sequence recombination of nucleic acid segments or other diversity generation methods (such as, e.g., recursive recombination) of nucleotides, or manipulation of isolated segments of nucleic acids, e.g., by genetic engineering techniques known to those of ordinary skill in the art. "Recombinantly expressed" typically refers to techniques for the production of a recombinant nucleic acid in vitro and transfer of the recombinant nucleic acid into cells in vivo, in vitro, or ex vivo where it may be expressed or propagated. A "recombinant polypeptide" or "recombinant protein" usually refers to a polypeptide or protein, respectively, that results from a cloned or recombinant gene or nucleic acid.

An "antigen" refers to a substance that is capable of eliciting the formation of antibodies in a host or generating a specific population of lymphocytes reactive with that substance. Antigens are typically macromolecules (e.g., proteins and polysaccharides) that are foreign to the host.

A "subsequence" or "fragment" (which terms may be used interchangeably herein) is any portion of an entire sequence, up to and including the complete sequence.

Numbering of an amino acid or nucleotide polymer corresponds to numbering of a selected amino acid polymer or nucleic acid when the position of a given monomer component (amino acid residue, incorporated nucleotide, etc.) of the polymer corresponds to the same residue position in a selected reference polypeptide or polynucleotide.

A vector is a composition for facilitating cell transformation by a selected nucleic acid, or expression of the nucleic acid in the cell. Vectors include, e.g., plasmids, cosmids, viruses, YACs, bacteria, poly-lysine, etc. An "expression vector" is a nucleic acid construct, generated recombinantly or synthetically, with a series of specific nucleic acid elements that permit transcription of a particular nucleic acid in a host cell. The expression vector can be part of a plasmid, virus, or nucleic acid fragment. The expression vector typically includes a nucleic acid to be transcribed operably linked to a promoter.

The term "heterologous" as used herein describes a relationship between two or more elements which indicates that the elements are not normally found in proximity to one another in nature. Thus, for example, a polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). An example of a heterologous polypeptide is a polypeptide expressed from a recombinant polynucleotide in a transgenic organism. Heterologous polynucleotides and polypeptides are forms of recombinant molecules.

The term "encoding" refers to the ability of a nucleotide sequence to code for one or more amino acids. The term does not require a start or stop codon. An amino acid sequence can be encoded in any one of six different reading frames provided by a polynucleotide sequence and its complement.

"Substantially an entire length of a polynucleotide or amino acid sequence" refers to at least about 50%, at least about 60%, generally at least about 70%, generally at least about 80%, or typically at least about 90%, 95%, 96%, 97%, 98%, or 99% or more of a length of an amino acid sequence or nucleic acid sequence.

"Naturally occurring" as applied to an object indicates that the object can be found in nature. For example, a polypeptide or polynucleotide sequence that is present in an organism, including viruses, that can be isolated from a source in nature and which has not been intentionally modified by man in a laboratory is naturally occurring. In one aspect, a "naturally occurring" nucleic acid molecule (e.g., DNA or RNA) is a nucleic acid molecule that exists in the same state as it exists in nature; that is, the nucleic acid molecule is not isolated, recombinant, or cloned.

The term "immunoassay" includes an assay that uses an antibody or immunogen to bind or specifically bind an antigen. The immunoassay is typically characterized by the use of specific binding properties of a particular antibody to isolate, target, and/or quantify the antigen.

The term "homology" generally refers to the degree of similarity between two or more structures. The term "homologous sequences" refers to regions in macromolecules that have a similar order of monomers. When used in relation to nucleic acid sequences, the term "homology" refers to the degree of similarity between two or more nucleic acid sequences (e.g., genes) or fragments thereof. Typically, the degree of similarity between two or more nucleic acid sequences refers to the degree of similarity of the composition, order, or arrangement of two or more nucleotide bases (or other genotypic feature) of the two or more nucleic acid sequences. The term "homologous nucleic acids" generally refers to nucleic acids comprising nucleotide sequences having a degree of similarity in nucleotide base composition, arrangement, or order. The two or more nucleic acids may be of the same or different species or group. The term "percent homology" when used in relation to nucleic acid sequences, refers generally to a percent degree of similarity between the nucleotide sequences of two or more nucleic acids.

When used in relation to polypeptide (or protein) sequences, the term "homology" refers to the degree of similarity between two or more polypeptide (or protein) sequences or fragments thereof. Typically, the degree of similarity between two or more polypeptide (or protein) sequences refers to the degree of similarity of the composition, order, or arrangement of two or more amino acids of the two or more polypeptides (or proteins). The two or more polypeptides (or proteins) may be of the same or different species or group. The term "percent homology" when used in relation to polypeptide (or protein) sequences, refers generally to a percent degree of similarity between the amino acid sequences of two or more polypeptide (or protein) sequences. The term "homologous polypeptides" or "homologous proteins" generally refers to polypeptides or proteins, respectively, that have amino acid sequences and functions that are similar. Such homologous polypeptides or proteins may be related by having amino acid sequences and functions that are similar, but are derived or evolved from different or the same species using the techniques described herein.

The term "gene" broadly refers to any segment of DNA associated with a biological function. Genes include coding sequences and/or regulatory sequences required for their expression. Genes also include non-expressed DNA nucleic acid segments that, e.g., form recognition sequences for other proteins (e.g., promoter, enhancer, or other regulatory regions).

Generally, the nomenclature used hereafter and the laboratory procedures in cell culture, molecular genetics, molecular biology, nucleic acid chemistry, and protein chemistry described below are those well known and commonly employed by those of ordinary skill in the art. Standard techniques, such as described in Sambrook et al., *Molecular Cloning—A Laboratory Manual* (2nd Ed.), Vols. 1-3, Cold Spring Harbor Laboratory, Cold Spring Harbor, N.Y., 1989 (hereinafter "Sambrook") and *Current Protocols in Molecular Biology*, F. M. Ausubel et al., eds., Current Protocols, a joint venture between Greene Publishing Associates, Inc. and John Wiley & Sons, Inc. (supplemented through 2003) (hereinafter "Ausubel"), are used for recombinant nucleic acid methods, nucleic acid synthesis, cell culture methods, and transgene incorporation, e.g., electroporation, injection, and lipofection. Generally, oligonucleotide synthesis and purification steps are performed according to specifications. The techniques and procedures are generally performed according to conventional methods in the art and various general references which are provided throughout this document. The procedures therein are believed to be well known to those of ordinary skill in the art and are provided for the convenience of the reader.

As used herein, an "antibody" refers to a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (e.g., antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains, respectively. Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the F(ab)'2 dimer into an Fab' monomer. The Fab' monomer is essentially an Fab with part of the hinge region (see, Paul, W. E., ed. (1993) *Fundamental Immunology*, Raven Press, N.Y., for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Antibodies include single chain antibodies, including single chain Fv (sFv) antibodies in which a variable heavy and a variable light chain are joined together (directly or through a peptide linker) to form a continuous polypeptide.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the methods of the invention is generally as broad as the class of higher and lower plants, including angiosperms (monocotyledonous and dicotyledonous plants), gymnosperms, ferns, and multicellular algae. It includes plants of a variety of ploidy levels, including aneuploid, polyploid, diploid, haploid and hemizygous. In some optional embodiments, the class of plants capable of use in some methods of the invention is generally as broad as the class of higher and lower plants amenable to transformation techniques (e.g., chosen from such groups listed above).

As used herein, the term "fumonisin" encompasses all structural variants and analogs (also referred to herein as "structurally related mycotoxins" or "structurally related fumonisins") of fumonisin. The term includes fumonisin variants and analogs capable of being, or expected of being, degraded (either wholly or in part) by the activity of an enzyme/polypeptide/polypeptide fragment/etc. of the present invention. Typically, such degradation is to be taken to mean deamination of the fumonisin or fumonisin variant/analog. Such structurally related fumonisins have a chemical structure related to fumonisin and include, e.g., AP1, AAL toxin, fumonisin B1, fumonisin B2, fumonisin B3, fumonisin B4, and fumonisin C1 (as well as their derivatives (see, supra)). Furthermore, other mycotoxins which have similar chemical structures to fumonisin, including ones that are synthetically constructed and/or ones which contain a C-2 or C-1 amine groups and one or more adjacent hydroxyl groups are included within the term. The term "fumonisin derivative" relates to any chemically and/or structurally modified fumonisin, such as the hydrolyzed form of fumonisin (i.e., AP1) whether such modification is done naturally (e.g., through enzymatic action of a naturally occurring organism) or through human action.

"Detoxification" of a fumonisin or of a fumonisin-derivative or analog means any modification of the fumonisin or of the fumonisin-derivative or analog molecule that causes a decrease in that molecule's toxicity from about a 1% or less decrease in toxicity to about a 5%, about 10%, about 25%, about 50%, about 75%, about 90%, about 95%, about 99%, or more decrease in toxicity. Detoxification can be the result of any number of changes to the fumonisin or fumonisin-derivative or analog including, but not limited to the addition or deletion of a chemical moiety, the cleavage of a chemical bond, oxidation, reduction, etc. Here, in typical embodiments, the detoxification results from (and is taken to typically mean) a deamination of the fumonisin (or derivative or analog). Detoxification is also described herein by "degradation," "neutralization," and/or "modification."

A variety of additional terms are defined or otherwise characterized herein.

Polynucleotides

The invention provides polynucleotides that encode transcription and/or translation products that are subsequently spliced to ultimately produce functional fumonisin degrading polypeptides. Splicing can be accomplished in vitro or in vivo, and can involve cis or trans splicing. The substrate for splicing can be polynucleotides (e.g., RNA transcripts) or polypeptides. An example of cis splicing of a polynucleotide is when an intron inserted into a coding sequence is removed and the two flanking exon regions are spliced to generate a functional polypeptide encoding sequence. An example of trans splicing is when a polynucleotide is encrypted by separating the coding sequence into two or more fragments that can be separately transcribed and then spliced to form the full-length fumonisin detoxification encoding sequence. The use of a splicing enhancer sequence (which can be introduced into a construct of the invention) can facilitate splicing either in cis or trans. Cis and trans splicing of polypeptides are described in more detail elsewhere herein. More detailed description of cis and trans splicing can be found in U.S. Pat. Nos. 6,365,377 and 6,531,316.

Thus, some polynucleotides of the invention do not directly encode a full-length fumonisin detoxification polypeptide, but rather encode a fragment or fragments of a fumonisin detoxification polypeptide. These fumonisin detoxification polynucleotides can be used to express a functional fumonisin detoxification polypeptide through a mechanism involving splicing, where splicing can occur at the level of polynucleotide (e.g., intron/exon) and/or polypeptide (e.g., intein/extein). This can be useful, for example, in controlling expression of fumonisin detoxification activity, since functional fumonisin detoxification polypeptide will only be expressed if all required fragments are expressed in an environment that permits splicing processes to generate functional product. In another example, introduction of one or more insertion sequences into a fumonisin detoxification polynucleotide can facilitate recombination with a low homology polynucleotide; use of an intron or intein for the insertion sequence facilitates the removal of the intervening sequence, thereby restoring function of the encoded variant.

The polypeptides of the invention and their encoding nucleic acids fill an unmet need by providing fumonisin detoxification enzymes that can detoxify fumonisins (e.g., FB1) and/or fumonisin-derivatives (e.g., AP1) or fumonisin analogs. In some embodiments, the polynucleotides of the invention encode enzymes (or fragments of such) capable of degrading fumonisin (and its derivatives/analogs at plant apoplast pH (e.g., pH 5.5). These aspects of the present invention are useful in, e.g., construction of transgenic crop plants that are resistant to or more tolerant of fumonisin and/or fumonisin derivatives and are able to degrade or neutralize fumonisin and/or fumonisin derivatives thus making the plants safer for human and animal consumption. Additionally, aspects of the present invention are useful in applications to foodstuffs, notably grains, etc., to degrade/neutralize fumonisin.

Fumonisin Detoxification Homologue Sequences

The invention provides isolated or recombinant novel fumonisin detoxification polypeptides and homologues thereof, and isolated or recombinant polynucleotides encoding the polypeptides. The invention also provides truncated versions of the isolated or recombinant fumonisin detoxification polypeptides (e.g., see, SEQ ID NO:21 and SEQ ID NO:46 (truncated version of R3H1)) as well as polynucleotides encoding such truncated polypeptides (e.g., fragments of polynucleotides which encode functional fumonisin detoxification polypeptides). The truncated fumonisin detoxification polypeptides can be truncated from either the C-terminus or the N-terminus or from both the N-terminus and the C-terminus. The truncated polypeptides of the invention optionally display the ability to detoxify at least one fumonisin and/or at least one fumonisin-derivative. Additionally, the truncated polypeptides of the invention optionally have the other capabilities of the non-truncated polypeptides of the invention as are listed and detailed throughout the present specification (e.g., improved kinetics over wild-type APAO, enzymatic activity at physiological pH (e.g., pH 5.5), etc.). Some of the fumonisin detoxification homologues of the invention include embodiments comprising fumonisin detoxifying and/or fumonisin-derivative detoxifying ability at a pH range of between 5.0 and 7.4, of between 5.0 and 7.0, of between 5.0 and 6.5, of between 5.0 and 6.0, or of between 5.0 and 5.5.

In some aspects, the current invention comprises an isolated or recombinant nucleic acid with a polynucleotide sequence encoding a polypeptide that is at least about 70%, at least about 75%, at least about 80%, at least about 85%, at least about 90%, at least about 95%, at least about 96%, at least about 97%, at least about 98%, at least about 99%, or at least about 99.5%, or more identical to (or which is substantially identical to, or comprises) to one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 (e.g., to SEQ ID NO:50) over a comparison window of at least 100, at least 125, at least 150, at least 175, at least 200, at least 225, at least 250, at least 275, or at least 300 contiguous amino acids (or complementary polynucleotide sequences thereof) wherein the polypeptide has a fumonisin detoxification activity or a fumonisin-derivative detoxification activity that is at least 1.5×, at least 2×, at least 5×, at least 10×, at least 15×, at least 20×, or at least 25× or more greater than any of the polypeptides corresponding to SEQ ID NOs:51-64.

Optionally, the above polynucleotide encodes a polypeptide that displays increased FD/FDD activity at pH 5.5 or has an optimum pH lower than that for the polypeptides encoded by SEQ ID NOs:51-64. Optionally, the above polynucleotide encodes a polypeptide that displays greater thermostability than that of any polypeptide encoded by SEQ ID NOs:51-64 and/or optionally has increased FD/FDD activity upon secretion from a eukaryotic cell (e.g., a plant cell) relative to that activity of any polypeptide encoded by SEQ ID NOs:51-64. In some embodiments, the polynucleotide encodes a polypeptide which comprises a leader sequence that directs secretion of the polypeptide from a plant cell (e.g., an apoplast targeting sequence, a peroxisomal targeting sequence, etc.), alternately and/or additionally, the polynucleotide encodes a polypeptide which comprises a polypeptide purification sequence. In yet other aspects, the invention comprises a nucleic acid comprising a unique subsequence in a nucleic acid selected from SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, which is unique as compared to a nucleic acid comprising any one of SEQ ID NOs:51, 53, 55, 57, 59, 61, 63, or to the nucleic acid encoding any of SEQ ID NOs: 52, 54, 56, 58, 60, 62, 64.

Furthermore, in some embodiments, such above polynucleotide encodes a polypeptide that is at least about 70%, at least about 75%, at least about 80%, at least about 85%, at least about 90%, at least about 95%, at least about 96%, at least about 97%, at least about 98%, at least about 99%, or at least about 99.5%, or more identical to, or is substantially identical to, or is chosen from any one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, or that is chosen from the group comprising SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126. The FD/FDD activity of a polypeptide encoded by such an above polynucleotide is, in typical embodiments, the ability to deaminate fumonisin and/or fumonisin derivatives (e.g., fumonisin B1, fumonisin B2, fumonisin B3, fumonisin B4, fumonisin C1, or a structural analog, etc.), i.e., the polypeptide encoded by the polynucleotide is a fumonisin amine oxidase. In yet other embodiments, the above polynucleotide encodes a polypeptide which displays one or more of: a $k_{cat}$ (optionally at pH5.5) greater than or higher than the $k_{cat}$ of any of the polypeptides encoded by SEQ ID NOs:51-64; a $K_M$ value (optionally at pH 5.5) lower than the $K_M$ value of any of the polypeptides encoded by SEQ ID NOs:51-64; or a $k_{cat}/K_M$ value higher than, or greater than the $k_{cat}/K_M$ value of any of the polypeptides encoded by SEQ ID NOs:51-64 when catalyzing a fumonisin or fumonisin-derivative reaction (e.g., a fumonisin deamination reaction)

In some embodiments of the invention, the above polynucleotides encode polypeptides comprising variants wherein one or more amino acid has been mutated. In yet other embodiments, the above polynucleotides encode polypeptides wherein the polypeptide comprises an alanine residue at position 118, a serine residue at position 136, a phenylalanine reside at position 209, a lysine residue at position 210, an isoleucine residue at position 237, a glutamic acid residue at position 272, a proline residue at position 274, and a glutamic acid residue at position 473, wherein the recited positions refer to amino acid positions of the polypeptide of the wild type APAO enzyme (SEQ ID NO: 52). In yet other embodiments, the above polynucleotide encodes a polypeptide comprises an aspartic acid residue at position 193. Some embodiments of the current invention also comprise polynucleotides encoding polypeptides with an altered glycosylation site.

In some embodiments, the polynucleotide of the invention comprises a promoter operably linked to the polynucleotide, wherein the promoter is optionally tissue-specific and/or wherein such construct comprises a vector (e.g., wherein the vector comprises a first polynucleotide sequence comprising the promoter operably linked to the polynucleotide of the invention and a second polynucleotide encoding a second polypeptide that confers a detectable phenotypic trait on a cell or organism expressing the second polypeptide at an effective level, such as herbicide resistance, pest resistance, a visible marker, etc.; or wherein the vector comprises a T-DNA; or wherein the vector is a plant transformation vector). Furthermore, the optional promoter is optionally heterologous with respect to the polynucleotide and is optionally effective to cause sufficient expression of the encoded polypeptide to cause detoxification (e.g., typically through deamination) of a fumonisin and/or a fumonisin-derivative. In other embodiments, the polynucleotides of the invention comprise a selectable marker and/or function as a selectable marker. Some embodiments of the invention comprise polynucleotides wherein a parental codon of the polynucleotide sequence has been replaced by a synonymous codon that is preferentially used in a plant relative to the parental codon.

In yet other embodiments the invention comprises an isolated or recombinant nucleic acid which encodes a polypeptide that (optionally at pH 5.5) has a fumonisin detoxification and/or a fumonisin-derivative detoxification (e.g., fumonisin deamination) activity that is at least 1.5×, at least 2×, at least 5×, at least 10×, at least 15×, at least 20×, or at least 25× or more greater than any of the polypeptides corresponding to SEQ ID NOs:51-64 (or a complementary polynucleotide sequence thereof), and wherein the polynucleotide sequence hybridizes under low or medium stringency conditions to a polynucleotide sequence selected from: a polynucleotide sequence selected from SEQ ID NOs: 1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126 (or a complementary polynucleotide sequence thereof); a polynucleotide sequence encoding a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 (or a complementary polynucleotide sequence thereof); and a polynucleotide sequence comprising a fragment of any of the above wherein such fragment encodes a polypeptide having at least one fumonisin detoxification or fumonisin-derivative detoxification activity. In other embodiments the invention comprises an isolated or recombinant nucleic acid selected from: a) a polynucleotide sequence from the groups consisting of SEQ ID NOs: 1-25, SEQ ID NOs: 67-69, and SEQ ID NOs: 84, 86, 88, 90, 92, 94, 96, 98, 100, 102, 104, 106, 108, 110, 112, 114, 116, 118, 120, 122, 124, and 126 (or a complementary polynucleotide sequence thereof); b) a polynucleotide sequence encoding a polypeptide selected from SEQ ID NOs: 26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 (or a complementary polynucleotide sequence thereof); c) a polynucleotide sequence which hybridizes under highly stringent conditions over substantially the entire length of a polynucleotide sequence encoding a polypeptide selected from a or b (or a complementary polynucleotide sequence thereof); and a polynucleotide sequence comprising a fragment of a, b, or c, wherein the fragment encodes a polypeptide having at least one fumonisin detoxification or fumonisin-derivative detoxification activity (e.g., a fumonisin deamination activity).

Some fumonisin detoxification polypeptides of the present invention exhibit an ability to detoxify fumonisin and fumonisin-derivatives (e.g., FB1 and AP1). In contrast to known naturally occurring APAO enzymes (e.g., ESP002C2, ESP002C3, ESP003C12, RAT011C1, RAT011C2, RAT011C4), which exhibit little activity at plant apoplast pH (5.5) or towards FB1 (the native substrate of naturally occurring APAO being hydrolyzed FB1), some fumonisin detoxification polypeptides of the present invention exhibit activity at pH 5.5, as well as activity towards FB1. As shown in FIGS. 1 and 2, exemplary polypeptides of the invention exhibit at least a three-fold or more increase in enzymatic activity with respect to either FB1 and/or AP1 as compared to wild-type APAO. Some fumonisin detoxification polypeptides of the present invention exhibit an ability to degrade, detoxify, or neutralize, etc., fumonisin and/or fumonisin-derivatives at a range of pH levels, i.e., in addition to their ability to do so at pH 5.5.

Figure 4:
FIG. 4: Comparison of protein structure between maize polyamine oxidase and exemplary homologues.
Figure 4:
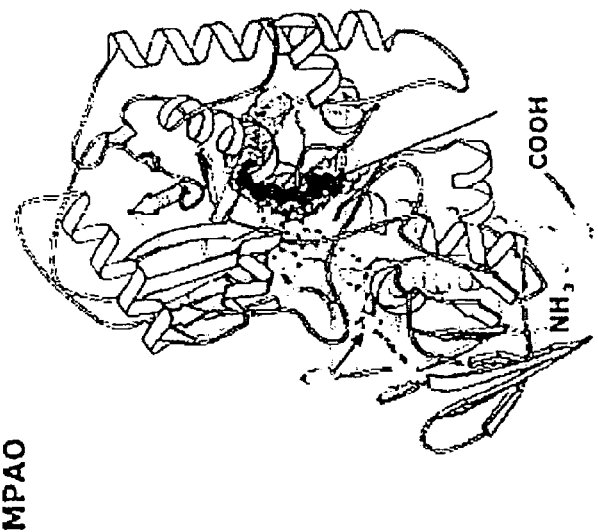

Of the fumonisin detoxification molecules of the present invention, the amino acid sequences of 2 exemplary homologues are compared in FIG. 3. As is shown in FIG. 3, homologues R3H1 and B12 share 8 amino acid changes from wild-type APAO, namely: Ala 118, Ser 136, Phe 209, Lys 210, Ile 237, Glu 272, Pro 274, and Glu 473, i.e., the amino acid in position 118 of the wild-type APAO enzyme (SEQ ID NO: 52) is changed to alanine, etc. Additionally, homologue R3H1 contains a unique asparagine to aspartic acid change at position 193. The numbering of the above sequence residues is based upon the full-length sequence (i.e., the numbers correspond to the residues' positions in the sequence prior to truncation). As seen in, e.g., FIG. 2, homologue R3H1 displays high $k_{cat}$ values that are believed to correlate with the unique amino acid change at position 193 (and which is greater than that of wild-type). FIG. 4 illustrates the location of several amino acid changes of R3H 1 and B 12 homologues as compared to maize polyamine oxidase. As can be seen from the figure, several of the R3H1 and B12 changes occur in a putative substrate binding region.

Figure 5:
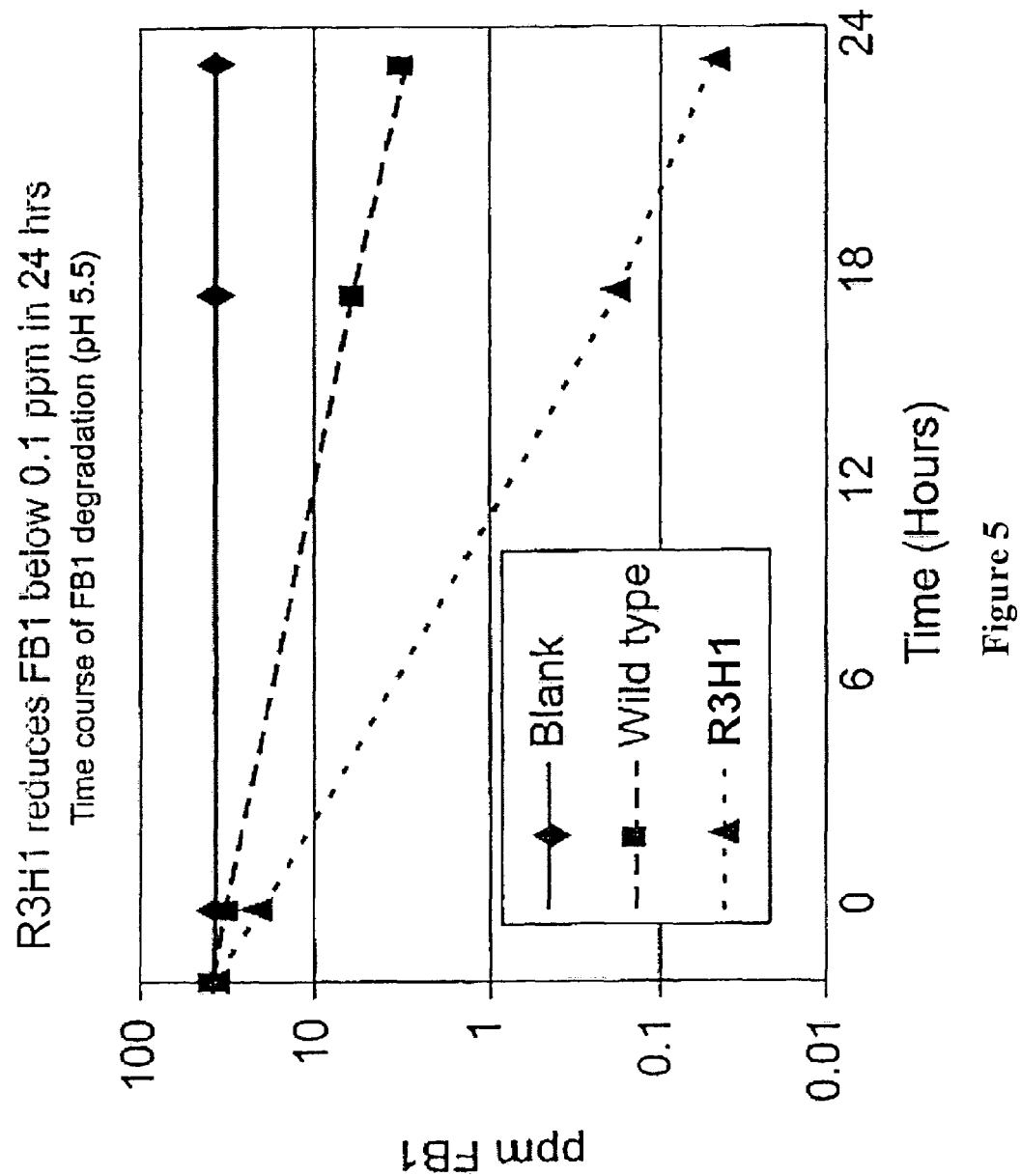
FIG. 5: Graph showing degradation activity of exemplary homologue.
Figure 7:
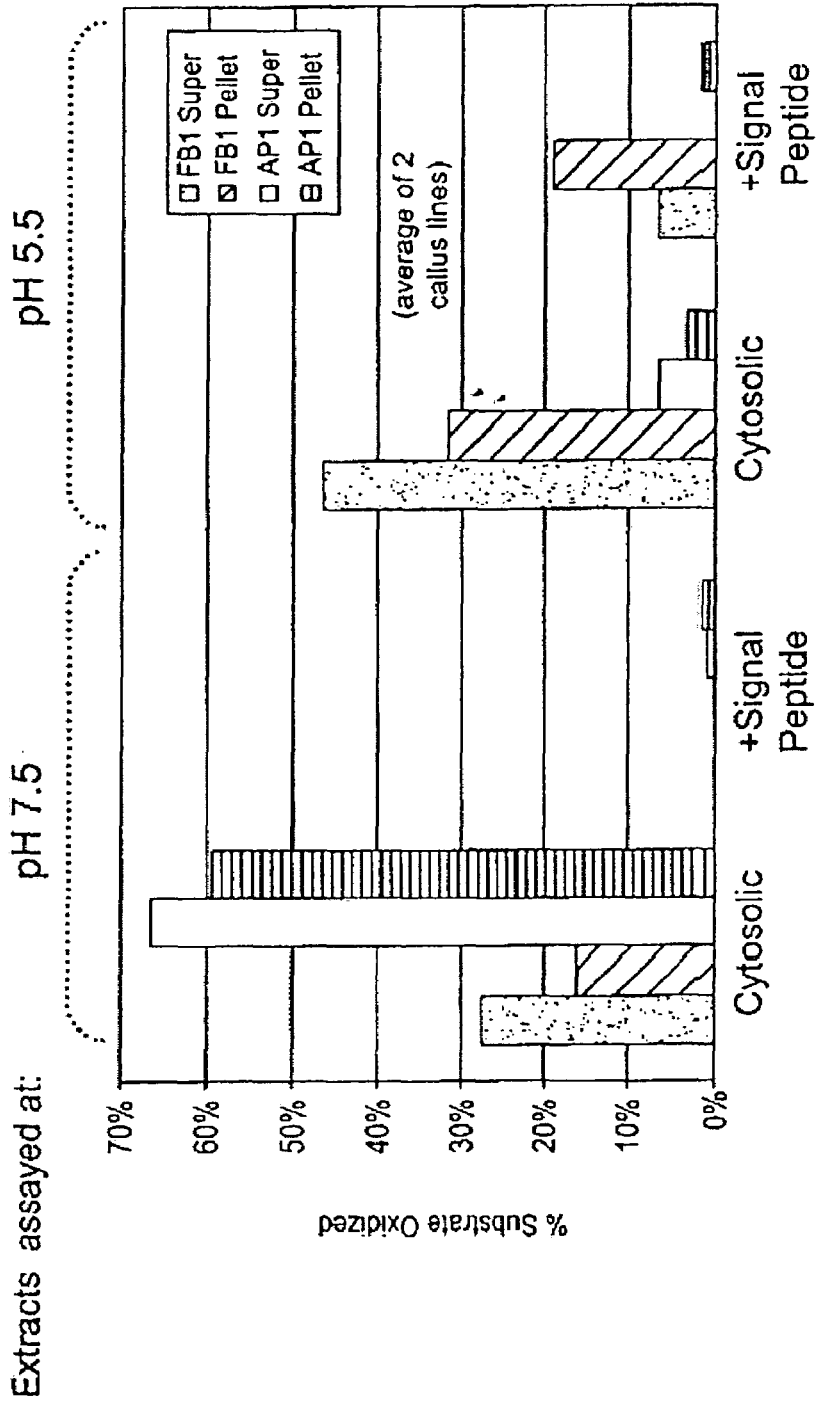
FIG. 7: Graph showing enzymatic activity of exemplary homologue in transgenic maize callus.
Figure 9:
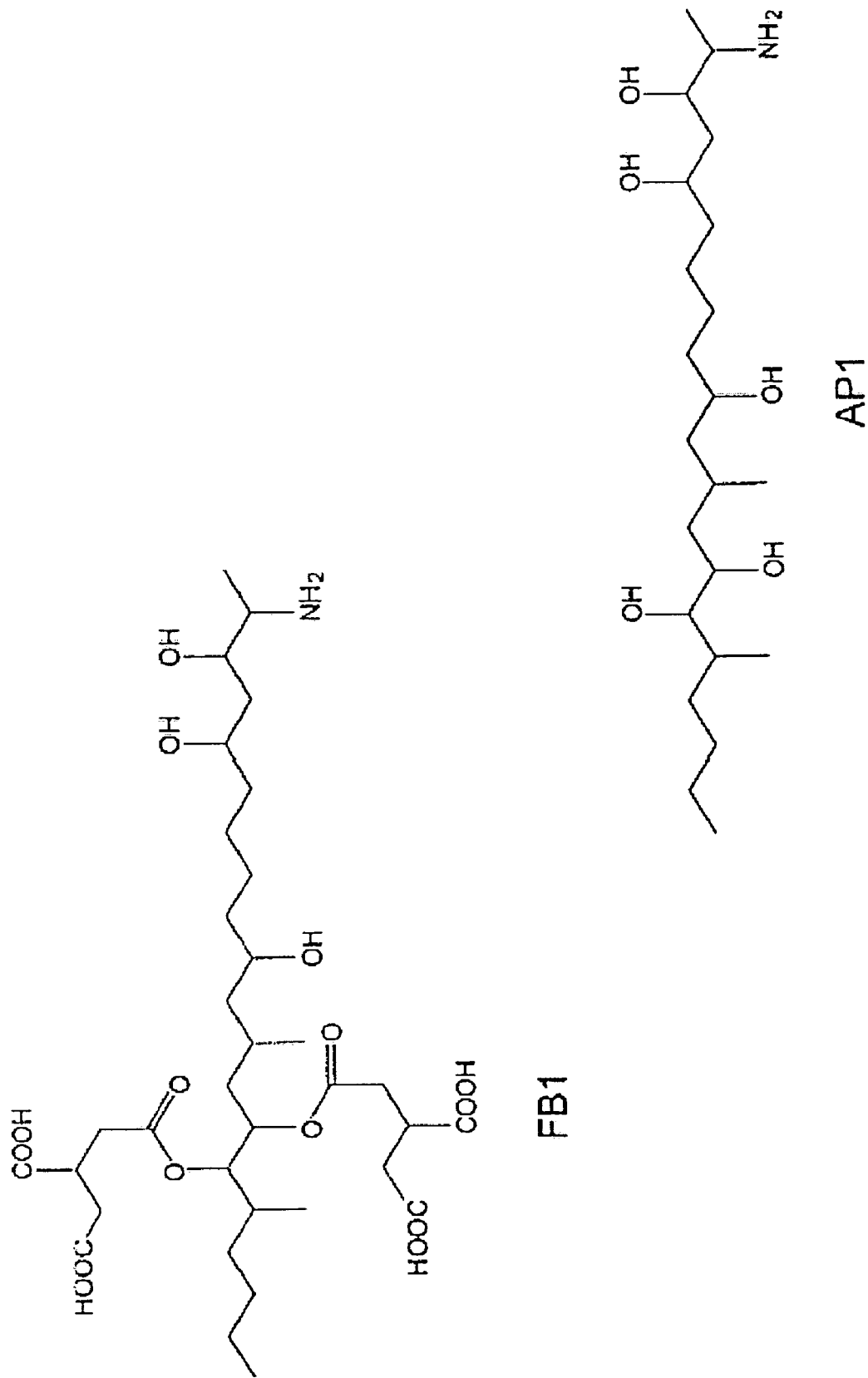
FIG. 9: Illustration of the chemical structures of FB1 and AP1.

FIGS. 5, 6, and 7 further illustrate the characteristics of homologue R3H1. FIG. 5 illustrates the time course of FB1 degradation at pH 5.5 by R3H1 as compared to FB1 degradation at pH 5.5 by wild-type amine oxidase (SEQ ID NO:52). The R3H1 homologue degrades a greater amount of FB1 (as measured in parts per million) than either a blank control or the wild-type amine oxidase. FIG. 6 illustrates the substrate specificity of homologue R3H1 (i.e., as against putrescine, lysine, serotonin, spermine, or FB2) at pH 7.4. As shown, R3H1 has high specificity for fumonisins (e.g., FB2) as opposed to non-fumonisins. FIG. 7 illustrates homologue R3H1's degradation activity in transgenic maize calluses when expressed in cytosol or fused to a signal sequence at pH 7.5 and 5.5 as compared against the wild-type APAO (SEQ ID NO:52).

Other embodiments of the invention include the fumonisin detoxification homologues comprising mutations in and/or about amino acid residues 201 through 206 (i.e., NDSNQS (SEQ ID NO:73)), thus including mutations of any glycosylation sites within such area. Additionally, other embodiments of the invention include fumonisin detoxification homologues that have had mutations introduced (e.g., mutated through use of oligos, etc.) at amino acid positions 201 and 204.

Making Polynucleotides

Polynucleotides and oligonucleotides of the invention can be prepared by standard solid-phase methods, according to known synthetic methods. Typically, fragments of up to about 100 bases are individually synthesized, then joined (e.g., by enzymatic or chemical ligation methods, or polymerase mediated recombination methods) to form essentially any desired continuous sequence. For example, the polynucleotides and oligonucleotides of the invention encoding fumonisin detoxification polypeptides can be prepared by chemical synthesis using, e.g., the classical phosphoramidite method described by, e.g., Beaucage et al. (1981) *Tetrahedron Lett* 22:1859-69, or the method described by Matthes et al. (1984) *EMBO J* 3:801-05, e.g., as is typically practiced in automated synthetic methods. According to the phosphoramidite method, oligonucleotides are synthesized, e.g., in an automatic DNA synthesizer, purified, annealed, ligated and cloned in appropriate vectors.

In addition, essentially any nucleic acid can be custom ordered from any of a variety of commercial sources, such as The Midland Certified Reagent Company (mcrc@oligos.com), The Great American Gene Company (www.genco.com), ExpressGen Inc. (www.expressgen. com), Operon Technologies Inc. (Alameda, Calif.) and many others. Similarly, peptides and antibodies can be custom ordered from any of a variety of sources, such as PeptidoGenic (pkim@ccnet.com), HTI Bio-products, inc. (www.htibio.com), BMA Biomedicals Ltd. (U.K.), BioSynthesis, Inc., and many others.

Certain polynucleotides of the invention can also be obtained by screening cDNA libraries (e.g., libraries generated by recombining homologous nucleic acids as in typical recursive recombination methods) using oligonucleotide probes which can hybridize to, or PCR-amplify, polynucleotides which encode the fumonisin detoxification homologue polypeptides and fragments of those polypeptides. Procedures for screening and isolating cDNA clones are well known to those of skill in the art. Such techniques are described in, for example, Sambrook and Ausubel. Some polynucleotides of the invention can be obtained by altering a naturally occurring backbone, e.g., by mutagenesis or oligonucleotide recombination. In other cases, such polynucleotides can be made in silico or through oligonucleotide recombination methods as described in the references cited herein.

As described in more detail herein, the polynucleotides of the invention include some sequences which encode mature fumonisin detoxification polypeptide homologues of the sequences and sequences complementary to these sequences, and novel fragments of coding sequence and complements thereof. The polynucleotides can be in the form of RNA or in the form of DNA, and include MRNA, cRNA, synthetic RNA and DNA, and cDNA. The polynucleotides can be double-stranded or single-stranded, and if single-stranded, can be the coding strand or the non-coding (anti-sense, complementary) strand. The polynucleotides optionally include the coding sequence of a fumonisin detoxification homologue (i) in isolation, (ii) in combination with additional coding sequence, so as to encode, e.g., a fusion protein, a pre-protein, a preproprotein, or the like, (iii) in combination with non-coding sequences, such as introns, control elements such as a promoter, a terminator element, or 5' and/or 3' untranslated regions effective for expression of the coding sequence in a suitable host, and/or (iv) in a vector or host environment in which fumonisin detoxification homologue coding sequence is a heterologous gene. Sequences can also be found in combination with typical compositional formulations of nucleic acids, including in the presence of carriers, buffers, adjuvants, excipients and the like.

Using Polynucleotides

The polynucleotides and fragments thereof of the invention have a variety of uses in, for example: recombinant production (i.e., expression) of the fumonisin detoxification homologue polypeptides of the invention; as transgenes (e.g., to confer fumonisin detoxification ability in transgenic plants); as immunogens; as diagnostic probes for the presence of complementary or partially complementary nucleic acids (including for detection of natural fumonisin detoxification coding nucleic acids); as substrates for further reactions, e.g., recursive recombination reactions or mutation reactions to produce new and/or improved fumonisin detoxification homologues, and the like.

Expression of Polypeptides

In accordance with the present invention, polynucleotide sequences which encode mature fumonisin detoxification homologues, fragments of fumonisin detoxification proteins, related fusion proteins, or functional equivalents thereof, collectively referred to herein as "fumonisin detoxification or fumonisin-derivative detoxification homologue polypeptides," or "FD/FDD homologue polypeptides" or, more simply, "fumonisin detoxification or fumonisin-derivative detoxification homologues," or "FD/FDD homologues," are used in recombinant DNA molecules that direct the expression of the FD/FDD homologues in appropriate host cells. Due to the inherent degeneracy of the genetic code, other nucleic acid sequences which encode substantially the same or functionally equivalent amino acid sequences are also used to synthesize, clone and express the FD/FDD homologues.

Modified Coding Sequences

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang, S. P. et al. (1991) *Gene* 105:61-72). Codons can be substituted to reflect the preferred codon usage of the host, a process called "codon optimization" or "controlling for species codon bias."

Optimized coding sequences containing codons preferred by a particular prokaryotic or eukaryotic host (see, e.g., Murray, E. et al. (1989) *Nuc Acids Res* 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (Dalphin, M. E. et al. (1996) *Nuc Acids Res* 24:216-218).

The polynucleotide sequences of the present invention can be engineered in order to alter the FD/FDD homologue coding sequence of the invention for a variety of reasons, including but not limited to, alterations which modify the cloning, processing and/or expression of the gene product. For example, alterations may be introduced using techniques which are well known in the art, e.g., site-directed mutagenesis, to insert new restriction sites, to alter glycosylation patterns, to change codon preference, to introduce splice sites, etc. Further details regarding silent and conservative substitutions are provided below.

Vectors, Promoters and Expression Systems

The present invention also includes recombinant constructs comprising one or more of the nucleic acid sequences, as broadly described above. The constructs comprise a vector, such as a plasmid, a cosmid, a phage, a virus, a bacterial artificial chromosome (BAC), a yeast artificial chromosome (YAC), and the like, into which a nucleic acid sequence of the invention (e.g., one which encodes for a polypeptide having FD/FDD ability or a fragment thereof) has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

The invention further provides vectors with stacked traits, i.e., vectors that encode an FD/FDD ability and that also include a second polynucleotide sequence encoding, e.g., a second polypeptide that confers a detectable phenotypic trait upon a cell or organism (e.g., a plant, plant explant, fungus, bacteria, etc.) expressing the second polypeptide at an effective level. The detectable phenotypic trait can function as a selectable marker, e.g., by conferring herbicide resistance, pest resistance, or providing some sort of visible marker. Other examples of such "stacked traits" include, e.g., fumonisin modification activity, chitinase activity, antifungal activity, mycotoxin detoxification activity, herbicidal activity, pesticidal activity, nematicidal activity, fumonisin esterase activity, etc.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, or with other genes implicated in fumonisin detoxification metabolic pathways. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001; and thioredoxins (U.S. application Ser. No. 10/005,429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combine with any combination of other suppression cassettes or overexpression cassettes to generate the desired combination of traits in the plant.

General texts which describe molecular biological techniques useful herein, including the use of vectors, promoters and many other relevant topics, include Berger and Kimmel, eds. (1987), *Guide to Molecular Cloning Techniques*, in *Methods Enzymol* 152: 673-684, Academic Press (hereinafter "Berger"); Sambrook and Ausubel. Examples of techniques sufficient to direct persons of skill through in vitro amplification methods, including the polymerase chain reaction (PCR), the ligase chain reaction (LCR), Qβ-replicase amplification and other RNA polymerase mediated techniques (e.g., NASBA), for the production of the homologous nucleic acids of the invention are found in Berger, Sambrook, and Ausubel, as well as U.S. Pat. No. 4,683,202; Innis et al. eds. (1990) *PCR Protocols: A Guide to Methods and Applications*, Academic Press Inc. San Diego, Calif.; Arnheim & Levinson (1990) *Chemical & Engineering News* 36-47; *The Journal Of NIH Research* (1991) 3:81-94; Kwoh et al. (1989) *PNAS USA* 86:1173-1177; Guatelli et al. (1990) *PNAS USA* 87:1874-1878; Lomeli et al. (1989) *J Clin Chem* 35:1826-1831; Landegren et al., (1988) *Science* 241:1077-1080; Van Brunt (1990) *Biotechnology* 8:291-294; Wu and Wallace, (1989) *Gene* 4:560-569; Barringer et al. (1990) *Gene* 89:117-122, and Sooknanan and Malek (1995) *Biotechnology* 13:563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) *Nature* 369:684-685 and the references therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, Ausubel, Sambrook and Berger, all supra.

The present invention also relates to host cells which are transformed with vectors of the invention, and the production of polypeptides of the invention by recombinant techniques. Host cells are genetically engineered (i.e., transduced, transformed or transfected) with the vectors of this invention, which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the FD/FDD homologue gene. The culture conditions, such as temperature, pH, and the like, are those previously used with the host cell selected for expression, and will be apparent to those skilled in the art and in the references cited herein, including, e.g., Payne et al. (1992) *Plant Cell and Tissue Culture in Liquid Systems* John Wiley & Sons, Inc. New York, N.Y. (hereinafter "Payne") and the references cited therein.

Transgenic Plants

As noted herein, it is particularly desirable to transform plants with nucleic acids to reduce the level of fumonisins or fumonisin-derivatives in the plants. Reduction of such mycotoxins and/or their derivatives benefits the plants by making them resistant to mycotoxicosis, as well as making the plants safer for human and animal consumption. See, references cited supra.

In some embodiments, the present invention includes a cell comprising any nucleic acid (or vector) of the invention, which optionally expresses a polypeptide noted herein. In some embodiments, such cell expresses a polypeptide encoded by a nucleic acid. Typically, the polynucleotide and/or polypeptide are heterologous to the cell and are optionally operably linked to a regulatory sequence. Some such heterologous polynucleotides/polypeptides express/are exogenous polypeptides with fumonisin (and/or fumonisin-derivative) detoxification activity (e.g., typically deamination). The fumonisin so detoxified is optionally a class B fumonisin, or is FB1. In some embodiments, the cells incorporating the nucleic acids and/or expressing the polypeptides of the invention are plant cells or fungal cells, or are bacterial cells. Transgenic plants, transgenic plant cells, and transgenic plant explants incorporating the nucleic acids of the invention are also features of the invention. In some embodiments, the transgenic plants, transgenic plant cells or transgenic plant explants express an exogenous polypeptide with fumonisin detoxification and/or fumonisin-derivative detoxification activity encoded by a nucleic acid of the invention. A seed produced by such transgenic plant is also a feature of the invention. In such instances, one or more parental codon of the nucleic acid can be substituted with a synonymous codon that is preferentially used by the translation machinery of a plant cell. Alternatively, the cell can be a microorganism cell, such as a bacteria, a fungus, or a yeast cell. In some embodiments, the transgenic plant into which any nucleic acid and/or polypeptide of the invention exists may be selected from the following: *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Bromus, Asparagus, Antirrhinum, Heterocallis, Nemesia, Pelargonium, Panicum, Pennisetum, Ranunculus, Senecio, Salpiglossis, Cucumis, Browaalia, Lolium, Malus, Apium, Gossypium, Vicia, Lathyrus, Lupinus, Pachyrhizus, Wisteria, Stizolobium, Agrostis, Phleum, Dactylis, Sorgum, Setaria, Zea, Oryza, Triticum, Secale, Avena, Hordeum, Saccharum, Poa, Festuca, Stenotaphrum, Cynodon, Coix, Olyreae, Phareae, Glycine, Pisum, Cicer, Phaseolus, Lens, Arachis*, corn, rice, cotton, soybean, sorghum, wheat, oat, barley, millet, sunflower, rapeseed, canola, pea, bean, lentil, peanut, yam, bean, cowpea, velvet bean, clover, alfalfa, lupine, vetch, lotus, sweet clover, wisteria, sweetpea, and a nut plant. It should be noted again, that as used herein, the term ‘corn’ is to be understood to refer to ‘maize.’

Methods for producing transgenic organisms (e.g., plants, fingi, bacteria, etc.) comprising a nucleic acid of the invention expressing a polypeptide at an effective level to deaminate fumonisin are also feature of the invention (e.g., wherein the polypeptide expressed is a fumonisin amine oxidase). Additionally, other features of the invention comprise methods of producing a transgenic plant or plant cell through: a) transforming a plant or plant cell with any polynucleotide of the invention (e.g., any of SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126 and fragments/modifications/complements/etc. of such) and b) optionally regenerating a transgenic plant from the transformed plant cell. A method for selecting a plant or cell containing a nucleic acid construct is also a feature of the invention wherein such method comprises: a) providing a transgenic plant or cell containing a nucleic acid construct comprising any nucleic acid of the invention, and b) growing the plant or cell in the presence of, e.g., fumonisin under conditions where a polypeptide is expressed at an effective level whereby the transgenic plant or cell grows at a rate that is discernibly greater than the plant or cell would grow if it did not contain the nucleic acid construct. Also, a transgenic plant or explant that expresses any polypeptide of the invention (or fragment thereof which optionally encodes an active enzyme with FD/FDD activity) is a feature of the invention, as is such plant or explant that further expresses a polypeptide selected from: a polypeptide having fumonisin modification activity, a polypeptide having chitinase activity, a polypeptide having antifungal activity, a polypeptide having mycotoxin detoxification activity, a polypeptide having herbicidal activity, a polypeptide having pesticidal activity, and a polypeptide having nematicidal activity.

Therefore, transgenic plants, or plant cells, incorporating the FD/FDD nucleic acids, and/or expressing the corresponding polypeptides of the invention are a feature of the invention. The transformation of plant cells and protoplasts can be carried out in essentially any of the various ways known to those skilled in the art of plant molecular biology, including, but not limited to, the methods described herein. See, in general, Wu and Grossman, eds. (1987) *Methods Enzymol*, Vol. 153 (*Recombinant DNA Part D*), Academic Press, incorporated herein by reference. As used herein, the term “transformation” means alteration of the genotype of a host plant by the introduction of a nucleic acid sequence, e.g., a “heterologous” or “foreign” nucleic acid sequence. The heterologous nucleic acid sequence need not necessarily originate from a different source but it will, at some point, have been external to the cell into which it is introduced.

In addition to Berger, Ausubel, Payne and Sambrook, useful general references for plant cell cloning, culture and regeneration include Jones (ed.) (1995) *Plant Gene Transfer and Expression Protocols—Methods in Molecular Biology*, Vol. 49 Humana Press Towata, N.J. (hereinafter “Jones”); and Gamborg and Phillips (eds.) (1995) *Plant Cell, Tissue and Organ Culture; Fundamental Methods* Springer Lab Manual, Springer-Verlag (Berlin Heidelberg New York) (hereinafter “Gamborg”). A variety of cell culture media are described in Atlas and Parks (eds.) *The Handbook of Microbiological Media* (1993) CRC Press, Boca Raton, Fla. (hereinafter “Atlas”). Additional information for plant cell culture is found in available commercial literature such as the *Life Science Research Cell Culture Catalogue* (1998) from Sigma-Aldrich, Inc (St Louis, Mo.) (hereinafter “Sigma-LSRCCC”) and, e.g., the *Plant Culture Catalogue* and supplement (1997) also from Sigma-Aldrich, Inc (St Louis, Mo.) (hereinafter “Sigma-PCCS”). Additional details regarding plant cell culture are found in Croy, (ed.) (1993) *Plant Molecular Biology Bios* Scientific Publishers, Oxford, U.K. (hereinafter “Croy”).

In an embodiment of this invention, recombinant vectors including one or more of the FD/FDD nucleic acids, e.g., selected from SEQ ID NOs:1-25, SEQ ID NOs:67-69, and SEQ ID NOs:84, 86, 88, 90, 92, 94, 96, 98, 100,102, 104, 106, 108, 110, 112, 114, 116, 118, 120, 122, 124, and 126, suitable for the transformation of plant cells are prepared. A DNA sequence encoding the desired FD/FDD protein, e.g., selected from among SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, is conveniently used to construct a recombinant expression cassette which can be introduced into a desired plant. In the context of the present invention, an expression cassette will typically comprise a selected FD/FDD nucleic acid sequence operably linked to a promoter sequence and other transcriptional and translational initiation regulatory sequences which are sufficient to direct the transcription of the FD/FDD sequence in the intended tissues (e.g., entire plant, leaves, roots, etc.) of the transformed plant.

For example, a strongly or weakly constitutive plant promoter that directs expression of an FD/FDD nucleic acid in all tissues of a plant can be favorably employed. Such promoters are active under most environmental conditions and states of development or cell differentiation. Examples of constitutive promoters include the 1'- or 2'-promoter of *Agrobacterium tumefaciens*, and other transcription initiation regions from various plant genes known to those of skill. When overexpression of an FD/FDD nucleic acid of the invention is detrimental to the plant, one of skill will recognize that weak constitutive promoters can be used for low-levels of expression. In those cases where high levels of expression are not harmful to the plant, a strong promoter, e.g., a t-RNA, or other pol III promoter, or a strong pol II promoter, (e.g., the cauliflower mosaic virus promoter, CaMV, 35S promoter) can be used.

Alternatively, a plant promoter can be under environmental control. Such promoters are referred to as “inducible” promoters. Examples of environmental conditions that may alter transcription by inducible promoters include pathogen attack, anaerobic conditions, or the presence of light. In some cases, it is desirable to use promoters that are "tissue-specific" and/ or are under developmental control such that the FD/FDD gene is expressed only in certain tissues or stages of development, e.g., leaves, roots, shoots, etc. Endogenous promoters of genes related to herbicide tolerance and related phenotypes are particularly useful for driving expression of FD/FDD nucleic acids, e.g., P450 monooxygenases, glutathione-S-transferases, homoglutathione-S-transferases, glyphosate oxidases and 5-enolpyruvyl-shikimate-2-phosphate synthases.

Tissue specific promoters can also be used to direct expression of heterologous structural genes, including the FD/FDD nucleic acids described herein. Thus the promoters can be used in recombinant expression cassettes to drive expression of any gene whose expression is desirable in the transgenic plants of the invention, e.g., FD/FDD and/or other genes conferring fumonisin neutralizing capability, or genes which influence other useful characteristics, e.g., heterosis.

In general, the particular promoter used in the expression cassette in plants depends on the intended application. Any of a number of promoters which direct transcription in plant cells can be suitable. The promoter can be either constitutive or inducible. In addition to the promoters noted above, promoters of bacterial origin which operate in plants include the octopine synthase promoter, the nopaline synthase promoter and other promoters derived from Ti plasmids. See, e.g., Herrera-Estrella et al. (1983) *Nature* 303:209. Viral promoters include the 35S and 19S RNA promoters of CaMV. See, e.g., Odell et al., (1985) *Nature* 313:810. Other plant promoters include the ribulose-1,3-bisphosphate carboxylase small subunit promoter and the phaseolin promoter. The promoter sequence from the E8 gene (see, Deikman and Fischer (1988) *EMBO J* 7:3315) and other genes are also favorably used. Alternatively, novel promoters with useful characteristics can be identified from any viral, bacterial, or plant source by methods, including sequence analysis, enhancer or promoter trapping, and the like, known in the art.

In preparing expression vectors containing any of the FD/FDD encoding nucleic acids of the invention, sequences other than the promoter and the recursively recombined gene are also favorably used. If proper polypeptide expression is desired, a polyadenylation region can be derived from the natural gene, from a variety of other plant genes, or from T-DNA. Signal/localization peptides, which, e.g., facilitate translocation of the expressed polypeptide to internal organelles (e.g., chloroplasts) or extracellular secretion, can also be employed.

The vector comprising the FD/FDD nucleic acid also typically includes a marker gene which confers a selectable phenotype on plant cells. For example, the marker may encode biocide tolerance, particularly antibiotic tolerance, such as tolerance to kanamycin, G418, bleomycin, hygromycin, or herbicide tolerance, such as tolerance to chlorosulfuron, or phosphinothricin. Reporter genes, which are used to monitor gene expression and protein localization via visualizable reaction products (e.g., beta-glucuronidase, beta-galactosidase, and chloramphenicol acetyltransferase) or by direct visualization of the gene product itself (e.g., green fluorescent protein, GFP, see, e.g., Sheen et al. (1995) *Plant J* 8:777) can be used for, e.g., monitoring transient gene expression in plant cells. Transient expression systems can be employed in plant cells, for example, in screening plant cell cultures for herbicide tolerance activities or, as in the present case, for FD/FDD activity.

Plant Transformation

Protoplasts

Numerous protocols for establishment of transformable protoplasts from a variety of plant types and subsequent transformation of the cultured protoplasts are available in the art and are incorporated herein by reference. For examples, see, Hashimoto et al. (1990) *Plant Physiol* 93:857; Fowke and Constabel (eds.) (1994) *Plant Protoplasts*; Saunders et al. (1993) *Applications of Plant In vitro Technology Symposium*, UPM 16-18; and Lyznik et al. (1991) *BioTechniques* 10:295, each of which is incorporated herein by reference.

Chloroplasts

Chloroplasts are a site of action for many activities, and, in some instances, the FD/FDD sequences may be fused to chloroplast transit sequence peptides to facilitate translocation of the gene products into the chloroplasts. In these cases, it can be advantageous to transform the FD/FDD nucleic acids into chloroplasts of the plant host cells. Numerous methods are available in the art to accomplish chloroplast transformation and expression (see, e.g., Daniell et al. (1998) *Nat Biotechnol* 16:346; O'Neill et al. (1993) *Plant J* 3:729; Maliga (1993) *TIBTECH* 11:1). The expression construct comprises a transcriptional regulatory sequence, functional in plants, operably linked to a polynucleotide encoding the FD/FDD polypeptide. Expression cassettes that are designed to function in chloroplasts (such as an expression cassette including an FD/FDD nucleic acid) include the sequences necessary to ensure expression in chloroplasts. Typically, the coding sequence is flanked by two regions of homology to the chloroplastid genome to effect a homologous recombination with the chloroplast genome; often a selectable marker gene is also present within the flanking plastid DNA sequences to facilitate selection of genetically stable transformed chloroplasts in the resultant transplastonic plant cells (see, e.g., Maliga (1993) and Daniell (1998), supra, and references cited therein).

General Plant Transformation Methods

DNA constructs containing any of the FD/FDD nucleic acids of the invention can be introduced into the genome of the desired plant host by a variety of conventional techniques. Techniques for transforming a wide variety of higher plant species are well known and described in the technical and scientific literature. See, e.g., Payne, Gamborg, Croy, Jones, etc. all supra, as well as, e.g., Weising et al. (1988) *Ann Rev Genet* 22:421.

For example, DNAs can be introduced directly into the genomic DNA of a plant cell using techniques such as electroporation or micro-injection of plant cell protoplasts, or the DNA constructs can be introduced directly to plant tissue using ballistic methods, such as DNA particle bombardment. Alternatively, the DNA constructs can be combined with suitable T-DNA flanking regions and introduced into a conventional *Agrobacterium tumefaciens* host vector. The virulence functions of the *Agrobacterium* host will direct the insertion of the construct and adjacent marker into the plant cell DNA when the plant cell is infected by the bacteria.

Micro-injection techniques are known in the art and well described in the scientific and patent literature. The introduction of DNA constructs using polyethylene glycol precipitation is described in Paszkowski et al (1984) *EMBO J* 3:2717. Electroporation techniques are described in Fromm et al. (1985) *PNAS USA* 82:5824. Ballistic transformation techniques are described in Klein et al. (1987) *Nature* 327:70; and Weeks et al. *Plant Physiol* 102:1077.

In some embodiments, *Agrobacterium* mediated transformation techniques are used to transfer the FD/FDD sequences of the invention into plants. *Agrobacterium*-mediated transformation is widely used for the transformation of dicots, however, certain monocots can also be transformed by *Agrobacterium*. For example, *Agrobacterium* transformation of rice is described by Hiei et al. (1994) *Plant J* 6:271; U.S. Pat. No. 5,187,073; U.S. Pat. No. 5,591,616; Li et al. (1991) *Sci China* 34:54; and Raineri et al. (1990) *Bio/Technology* 8:33. Transformed maize, barley, triticale and asparagus by *Agrobacterium* mediated transformation have also been described (Xu et al. (1990) *Chin J Bot* 2:81).

*Agrobacterium* mediated transformation techniques take advantage of the ability of the tumor-inducing (Ti) plasmid of *A. tumefaciens* to integrate into a plant cell genome and to co-transfer a nucleic acid of interest (e.g., any nucleic acid of the present invention encoding FD/FDD capability, or a fragment of such nucleic acid) into a plant cell. Typically, an expression vector is produced wherein the nucleic acid of interest, again, such as an FD/FDD nucleic acid of the invention, is ligated into an autonomously replicating plasmid which also contains T-DNA sequences. T-DNA sequences typically flank the expression cassette nucleic acid of interest and comprise the integration sequences of the plasmid. In addition to the expression cassette, T-DNA also typically includes a marker sequence, e.g., antibiotic resistance genes. The plasmid with the T-DNA and the expression cassette are then transfected into *Agrobacterium* cells. Typically, for effective transformation of plant cells, the *A. tumefaciens* bacterium also possesses the necessary vir regions on a plasmid, or integrated into its chromosome. For a discussion of *Agrobacterium* mediated transformation, see, Firoozabady and Kuehnle, (1995) in Gamborg (supra).

Regeneration of Transgenic Plants

Transformed plant cells which are derived by plant transformation techniques, including those discussed above, can be cultured to regenerate a whole plant which possesses the transformed genotype (e.g., an FD/FDD nucleic acid or fragment thereof), and thus the desired phenotype, such as, e.g., the capability to detoxify, degrade or neutralize fumonisins or fumonisin-derivatives. Such regeneration techniques rely on manipulation of certain phytohormones in a tissue culture growth medium, typically relying on a biocide and/or herbicide marker which has been introduced together with the desired nucleotide sequences. Alternatively, selection for the capability to detoxify, degrade, or neutralize fumonisins or fumonisin-derivatives conferred by the FD/FDD nucleic acids of the invention can be performed. Plant regeneration from cultured protoplasts is described in Evans et al. (1983) *Protoplasts Isolation and Culture, Handbook of Plant Cell Culture*, pp. 124-176, Macmillan Publishing Company, New York; and Binding (1985) *Regeneration of Plants, Plant Protoplasts* pp. 21-73, CRC Press, Boca Raton, Fla. Regeneration can also be obtained from plant callus, explants, organs, or parts thereof. Such regeneration techniques are described generally in Klee et al. (1987) *Ann Rev Plant Phys* 38:467. See also, e.g., Payne and Gamborg.

After transformation with *Agrobacterium*, the explants are transferred to selection medium. One of skill will realize that the selection medium depends on the selectable marker that was co-transfected into the explants. After a suitable length of time, transformants will begin to form shoots. After the shoots are, e.g., about 1-2 cm in length, the shoots should be transferred to a suitable root and shoot medium. Selection pressure should be maintained in the root and shoot medium.

Typically, the transformants will develop roots in, e.g., about 1-2 weeks and form plantlets. After the plantlets are, e.g., about 3-5 cm in height, they are placed in, e.g., sterile soil in fiber pots. Those of skill in the art will realize that different acclimation procedures are used to obtain transformed plants of different species. For example, after developing a root and shoot, cuttings, as well as somatic embryos of transformed plants, are transferred to medium for establishment of plantlets. For a description of selection and regeneration of transformed plants, see, e.g., Dodds and Roberts (1995) *Experiments in Plant Tissue Culture*, 3rd Ed., Cambridge University Press.

The transgenic plants of this invention can be characterized either genotypically or phenotypically to determine the presence of the FD/FDD nucleic acids of the invention. Genotypic analysis can be performed by any of a number of well-known techniques, including PCR amplification of genomic DNA and hybridization of genomic DNA with specific labeled probes. Phenotypic analysis includes, e.g., survival of plants in the presence of a selected fumonisin or fumonisin-derivative. Other types of selections for fumonisin resistance or fumonisin-derivative resistance are discussed infra.

Essentially any plant can be transformed with the FD/FDD nucleic acids of the invention. Suitable plants for the transformation and expression of the novel FD/FDD nucleic acids of this invention include agronomically and horticulturally important species. Such species include, but are not restricted to members of the families: Graminae (including corn, rye, triticale, barley, millet, rice, wheat, oat, etc.); Leguminosae (including pea, bean, lentil, peanut, yam bean, cowpea, velvet bean, soybean, clover, alfalfa, lupine, vetch, lotus, sweet clover, wisteria, and sweetpea); Compositae (the largest family of vascular plants, including at least 1,000 genera, including important commercial crops such as sunflower) and Rosaciae (including raspberry, apricot, almond, peach, rose, etc.), as well as nut plants (including, walnut, pecan, hazelnut, etc.), and forest trees (including *Pinus, Quercus, Pseudotsuga, Sequoia, Populus*, etc.)

Additionally, preferred targets for modification by the FD/FDD nucleic acids of the invention, as well as those specified above, include plants from the genera: *Agrostis, Allium, Antirrhinum, Apium, Arachis, Asparagus, Atropa, Avena* (e.g., oat), *Bambusa, Brassica, Bromus, Browaalia, Camellia, Cannabis, Capsicum, Cicer, Chenopodium, Chichorium, Citrus, Coffea, Coix, Cucumis, Curcubita, Cynodon, Dactylis, Datura, Daucus, Digitalis, Dioscorea, Elaeis, Eleusine, Festuca, Fragaria, Geranium, Glycine, Helianthus, Heterocallis, Hevea, Hordeum* (e.g., barley), *Hyoscyamus, Ipomoea, Lactuca, Lens, Lilium, Linum, Lolium, Lotus, Lycopersicon, Majorana, Malus, Mangifera, Manihot, Medicago, Nemesia, Nicotiana, Onobrychis, Oryza* (e.g., rice), *Panicum, Pelargonium, Pennisetum* (e.g., millet), *Petunia, Pisum, Phaseolus, Phleum, Poa, Prunus, Ranunculus, Raphanus, Ribes, Ricinus, Rubus, Saccharum, Salpiglossis, Secale* (e.g., rye), *Senecio, Setaria, Sinapis, Solanum, Sorghum, Stenotaphrum, Theobroma, Trifolium, Trigonella, Triticum* (e.g., wheat), *Vicia, Vigna, Vitis, Zea* (e.g., corn), and the *Olyreae*, the *Pharoideae* and many others. As noted, plants in the family Graminae are a particularly preferred target plants for the methods of the invention.

Common crop plants which are targets of the present invention include corn, rice, triticale, rye, cotton, soybean, sorghum, wheat, oat, barley, millet, sunflower, canola, pea, bean, lentil, peanut, yam bean, cowpea, velvet bean, clover, alfalfa, lupine, vetch, lotus, sweet clover, wisteria, sweetpea and nut plants (e.g., walnut, pecan, etc).

Non-Plant Expression Vectors/Systems

The FD/FDD homologue proteins of the invention can also be produced in non-plant cells such as animals, yeast, fungi, bacteria and the like. In addition to Sambrook, Berger, Gamborg, Atlas and Ausubel, details regarding cell culture can be found in; e.g., Freshney (1994) *Culture of Animal Cells, a Manual of Basic Technique*, third edition, Wiley-Liss, New York (hereinafter "Freshney").

The polynucleotides of the present invention and fragments thereof, which encode the FD/FDD molecules, may be included in any one of a variety of expression vectors for expressing a polypeptide. Such vectors include chromosomal, non-chromosomal and synthetic DNA sequences, e.g., derivatives of SV40, bacterial plasmids, phage DNA, baculovirus, yeast plasmids, vectors derived from combinations of plasmids and phage DNA, viral DNA such as vaccinia, adenovirus, fowl pox virus, pseudorabies, adeno-associated virus, retroviruses and many others. Any vector that transduces genetic material into a cell, and, if replication is desired, which is replicable and viable in the relevant host can be used.

The nucleic acid sequence in the expression vector is operatively linked to an appropriate transcription control sequence (promoter) to direct MRNA synthesis. Examples of such promoters include: CaMV, LTR or SV40 promoter, *E. coli* lac or trp promoter, phage lambda $P_L$ promoter, and other promoters known to control expression of genes in prokaryotic or eukaryotic cells or their viruses. The expression vector also contains a ribosome binding site for translation initiation, and a transcription terminator. The vector optionally includes appropriate sequences for amplifying expression, e.g., an enhancer. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli*.

The vector containing the appropriate DNA sequence encoding the FD/FDD polypeptide, as well as an appropriate promoter or control sequence, may be employed to transform an appropriate host to permit the host to express the protein. Examples of appropriate expression hosts include: bacterial cells, such as *E. coli, Streptomyces*, and *Salmonella typhimurium*; flugal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; plant cells or explants, etc. It is understood that not all cells or cell lines need to be capable of producing fully functional FD/FDD homologues; for example, antigenic fragments of an FD/FDD homologue may be produced in a bacterial or other expression system. The invention is not limited by the host cells employed.

In bacterial systems, a number of expression vectors may be selected depending upon the use intended for the FD/FDD homologue. For example, when large quantities of FD/FDD homologue or fragments thereof are needed for the induction of antibodies, vectors which direct high level expression of fusion proteins that are readily purified may be desirable. Such vectors include, but are not limited to, multifunctional *E. coli* cloning and expression vectors such as BLUESCRIPT (Stratagene), in which the FD/FDD homologue coding sequence may be ligated into the vector in-frame with sequences for the amino-terminal Met and the subsequent 7 residues of beta-galactosidase so that a hybrid protein is produced; pIN vectors (Van Heeke & Schuster (1989) *J Biol Chem* 264:5503-5509); pET vectors (Novagen, Madison Wis.); and the like.

Similarly, in the yeast *Saccharomyces cerevisiae*, a number of vectors containing constitutive or inducible promoters such as alpha factor, alcohol oxidase and PGH may be used for production of the FD/FDD homologue proteins of the invention. For reviews, see Ausubel, Berger, and Grant et al. (1987; *Methods Enzymol* 153:516-544).

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome will result in a viable virus capable of expressing FD/FDD homologues in infected host cells (Logan and Shenk (1984) *PNAS USA* 81:3655-3659). In addition, transcription enhancers, such as the rous sarcoma virus (RSV) enhancer, may be used to increase expression in mammalian host cells.

Similarly, in plant cells, expression can be driven from a transgene integrated into a plant chromosome, or cytoplasmically from an episomal or viral nucleic acid. In the case of stably integrated transgenes, it is often desirable to provide sequences capable of driving constitutive or inducible expression of the genes, e.g., the FD/FDD homologue sequences of the invention. Numerous plant derived regulatory sequences have been described, including sequences which direct expression in a tissue specific manner, e.g., TobRB7, patatin B33, GRP gene promoters, the rbcS-3A promoter, and the like. Alternatively, high level expression can be achieved by transiently expressing exogenous sequences of a plant viral vector, e.g., CaMV, TMV, BMV, etc.

Additional Expression Elements

Specific initiation signals can aid in efficient translation of an FD/FDD homologue coding sequence and fragments thereof. These signals can include, e.g., the ATG initiation codon and adjacent sequences. In cases where an FD/FDD homologue coding sequence and its initiation codon and upstream sequences are inserted into the appropriate expression vector, no additional translational control signals may be needed. However, in cases where only coding sequence (e.g., a mature protein coding sequence), or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (see, e.g., Scharf D. et al. (1994) *Results Probl Cell Differ* 20:125-62; Bittner et al. (1987) *Methods Enzymol* 153:516-544).

Secretion/Localization Sequences

Polynucleotides of the invention encoding the FD/FDD homologues and fragments thereof can also be fused, for example, in-frame to a nucleic acid encoding a secretion/localization sequence, to target polypeptide expression to a desired cellular compartment, membrane, or organelle, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like. Signal peptides for localization in the apoplastic space (i.e., extracellular space) are also optionally used in combination with the FD/FDD homologues of the current invention. See, e.g., the PR1b signal sequence as described in Lind et al. (1992), *Plant Mol Biol* 18:47-53, PR-1a, b and c signals described in Pfitzner et al. (1987), *Nucl Acids Res* 15:4449-

4465 or the barley alpha amylase (BAA) secretion sequence (Rahmatullah et al. (1989) *Plant Mol Biol* 12:119). Similarly, localization to peroxisomal space, e.g., peroxisomal targeting, is optionally accomplished through use of, e.g., the signal described by Keller et al. (1991) *J Cell Biol,* 114, p. 893.-904.

Expression Hosts

In a further embodiment, the present invention relates to host cells containing the above-described constructs. The host cell can be a eukaryotic cell, such as a mammalian cell, a yeast cell, or a plant cell, or the host cell can be a prokaryotic cell, such as a bacterial cell. Introduction of the construct into the host cell can be effected by calcium phosphate transfection, DEAE-Dextran mediated transfection, electroporation, or other common techniques (see, e.g., Davis et al. (1986) *Basic Methods in Molecular Biology*, Elsevier, N.Y.).

A host cell strain is optionally chosen for its ability to modulate the expression of the inserted sequences or to process the expressed protein (e.g., a fumonisin detoxification enzyme) in the desired fashion. Such modifications of the protein include, but are not limited to, acetylation, carboxylation, glycosylation, phosphorylation, lipidation and acylation. Post-translational processing which cleaves a "pre" or a "prepro" form of the protein may also be important for correct insertion, folding and/or function. Different host cells such as *E. coli, Bacillus* sp., yeast or mammalian cells such as CHO, HeLa, BHK, MDCK, 293, WI38, etc. have specific cellular machinery and characteristic mechanisms for such post-translational activities and may be chosen to ensure the correct modification and processing of the introduced, foreign protein.

For long-term, high-yield production of recombinant proteins, stable expression can be used. For example, plant cells, explants or tissues (e.g., shoots or leafdiscs) which stably express an FD/FDD polypeptide of the invention are transduced using expression vectors which contain viral origins of replication or endogenous expression elements and a selectable marker gene. Following the introduction of the vector, cells may be allowed to grow for a period of time appropriate for the cell type (e.g., 1 or more hours for bacterial cells, 1-4 days for plant cells, or 2-4 weeks for some plant explants) before they are switched to a selective medium. The purpose of the selectable marker is to confer resistance to selection, and its presence allows growth and recovery of cells that successfully express the introduced sequences. For example, resistant clumps of stably transformed cells can be proliferated using tissue culture techniques appropriate to the cell type.

Host cells transformed with a nucleotide sequence encoding an FD/FDD polypeptide capable of detoxifying, degrading, or neutralizing a fumonisin or a fumonisin-derivative are optionally cultured under conditions suitable for the expression and recovery of the encoded protein from cell culture. The protein or fragment thereof produced by a recombinant cell may be secreted, membrane-bound, or contained intracellularly, depending on the sequence and/or the vector used. As will be understood by those of skill in the art, expression vectors containing polynucleotides encoding mature FD/FDD homologues of the invention can be designed with signal sequences which direct secretion of the mature polypeptides through a prokaryotic or eukaryotic cell membrane.

Additional Polypeptide and Polynucleotide Sequences

The FD/FDD polypeptide encoding polynucleotides of the present invention may also comprise a coding sequence or fragment thereof fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the FD/FDD homologue sequence is useful to facilitate purification.

For example, one expression vector possible to use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) *Protein Expression Purif* 3:263-281, while the enterokinase cleavage site provides a method for separating the FD/FDD homologue polypeptide from the fusion protein. pGEX vectors (Amersham Pharmacia Biotech) are optionally used to express foreign polypeptides as fusion proteins with glutathione S-transferase (GST). Other expression systems, such as, e.g., pPICz vectors (Invitrogen) that allow for expression in *Pichia* are also optionally used. In general, such fusion proteins are soluble and can easily be purified from lysed cells by adsorption to ligand-agarose beads (e.g., glutathione-agarose in the case of GST-fusions) followed by elution in the presence of free ligand.

Polypeptide Production and Recovery

Following transformation of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Eukaryotic or microbial cells employed in expression of the FD/FDD proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See e.g., Sambrook, Ausubel, Freshney and Berger, as well as Doyle and Griffiths (1997) *Mammalian Cell Culture: Essential Techniques* John Wiley and Sons, NY; Humason (1979) *Animal Tissue Techniques*, fourth edition W.H. Freeman and Company; and Ricciardelli, et al., (1989) *In vitro Cell Dev Biol* 25:1016-1024. For plant cell culture and regeneration see, Payne, Gamborg, and Croy. Cell culture media in general are set forth in Atlas. Additional information for cell culture is found in available commercial literature such as Sigma-LSRCCC and Sigma-PCCS.

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature FD/FDD proteins or fragments thereof. Finally, high performance liquid chromatography (HPLC) can be employed in the final purification steps. In addition to the references noted supra, a variety of purification methods are well known in the art, including, e.g., those set forth in Sandana (1997) *Bioseparation of Proteins*, Academic Press, Inc.; Bollag et al. (1996) *Protein Methods*, 2$^{nd}$ Edition, Wiley-Liss, NY; Walker (1996) *The Protein Protocols Handbook* Humana Press, NJ; Harris and Angal (1990) *Protein Purification Applications: A Practical Approach*, IRL Press at Oxford, Oxford, England; Scopes (1993) *Protein Purification: Principles and Practice*, 3$^{rd}$ Edition, Springer Verlag, NY; Janson and Ryden (1998) *Protein Purification: Principles, High Resolution Methods and Applications*, Second Edition Wiley-VCH, NY; and Walker (1998) *Protein Protocols on CD-ROM* Humana Press, NJ (hereinafter "Walker").

In Vitro Expression Systems

Cell-free transcription/translation systems can also be employed to produce FD/FDD polypeptides or fragments thereof using DNAs or RNAs of the present invention. Several such systems are commercially available. A general guide to in vitro transcription and translation protocols is found in Tymms (1995) *In vitro Transcription and Translation Protocols: Methods in Molecular Biology* Volume 37, Garland Publishing, NY.

Modified Amino Acids

Polypeptides of the invention may contain one or more modified amino acid. The presence of modified amino acids may be advantageous in, for example, (a) increasing polypeptide half-life, (b) reducing polypeptide antigenicity, or (c) increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a PEG-ylated amino acid, a biotinylated amino acid, a carboxylated amino acid, a phosphorylated amino acid, and the like. References adequate to guide one of skill in the modification of amino acids are replete throughout the literature. Example protocols are found in Walker.

In Vivo Uses

Polynucleotides or fragments thereof which encode an FD/FDD homologue polypeptide of the invention, or complements of the polynucleotides (e.g., antisense or ribozyme molecules), are optionally administered to a cell to accomplish a useful process or to express a useful product. These in vivo applications, including gene therapy, include a multitude of techniques by which gene expression may be altered in cells. Such methods include, for instance, the introduction of genes for expression of, e.g., useful polypeptides, such as the FD/FDD homologues of the present invention or fragments thereof.

There are many applications involving in vivo use of FD/FDD polynucleotides of the invention. Non-limiting examples include the following scenarios. One example of in vivo use for the FD/FDD polynucleotides of the invention involves large scale production of FD/FDD enzyme for use as a fumonisin (or fumonisin-derivative) detoxification treatment for fo Use as Probes Also contemplated are uses of polynucleotides, also referred to herein as oligonucleotides, typically having at least 12 bases, sometimes at least 15, occasionally at least 20, 25, 30, 35, 40, 45, or 50 or more bases, which hybridize under highly stringent conditions to an FD/FDD homologue polynucleotide sequence described herein or a fragment thereof. The polynucleotides may be used as probes, primers, sense and antisense agents, and the like, according to methods as noted supra. One non-limiting example of the use of FD/FDD sequences of the invention as probes involves their use, e.g., in the discovery or synthesis of new fumonisin or other mycotoxin degrading enzymes. The polynucleotide sequences of the invention, or fragments thereof, can be used to screen both naturally occurring and synthetically constructed groups of polypeptides for ones which are similar to the products of the invention and which therefore may show useful fumonisin degrading abilities.

Sequence Variations

Silent Variations

It will be appreciated by those skilled in the art that due to the degeneracy of the genetic code, a multitude of nucleic acids sequences encoding FD/FDD homologue polypeptides of the invention may be produced, some which may bear minimal sequence homology to the nucleic acid sequences explicitly disclosed herein.

TABLE 1

Codon Table

| Amino acids | | | Codon | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUC | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

For instance, inspection of the codon table (Table 1) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Using, as an example, the nucleic acid sequence corresponding to nucleotides 1-15 of SEQ ID NO:1, ATG GCA CTT GCA CCG (SEQ ID NO: 74), a silent variation of this sequence includes ATG GCC TTA GCG CCA (SEQ ID NO: 75), both sequences which encode the amino acid sequence MALAP (SEQ ID NO: 76), corresponding to amino acids 1-5 of SEQ ID NO:26.

Such "silent variations" are one species of "conservatively modified variations", discussed below. One of skill will recognize that each codon in a nucleic acid (except AUG and UGC, which are ordinarily the only codons for methionine and tryptophan, respectively) can be modified by standard techniques to encode a functionally identical polypeptide. Accordingly, each silent variation of a nucleic acid that encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code (e.g., as set forth in Table 1) as applied to the nucleic acid sequence encoding an FD/FDD homologue polypeptide of the invention or fragments thereof. All such variations of every nucleic acid herein are specifically provided and described by consideration of the sequence in combination with the genetic code. Any variant can be produced as noted herein and one of skill is fully able to generate any silent substitution of the sequences listed herein.

Conservative Variations

"Conservatively modified variations" or, simply, "conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 3%, 2% or 1% or less) in an encoded sequence are "conservatively modified variations" where the alterations result in the deletion of an amino acid, addition of an amino acid, or substitution of an amino acid with a chemically similar amino acid.

FD/FDD homologue polypeptides of the present invention include conservatively modified variations of the sequences disclosed herein as SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 and fragments thereof. Such conservatively modified variations comprise substitutions, additions or deletions which alter, add or delete a single amino acid or a small percentage of amino acids (typically less than about 5%, more typically less than about 4%, 3%, 2%, or 1%) in any of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127.

Conservative substitution tables providing functionally similar amino acids are well known in the art. Table 2 sets forth six groups which contain amino acids that are "conservative substitutions" for one another.

TABLE 2

Conservative Substitution Groups

| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 4%, 3%, 2% and often less than 1%, of the amino acids of the polypeptide sequence, with a conservatively selected amino acid of the same conservative substitution group.

For example, a conservatively modified variation (e.g., deletion) of the 600 amino acid polypeptide identified herein as SEQ ID NO:26 will have a length of at least 570 amino acids, preferably at least 576 amino acids, more preferably at least 588 amino acids, and still more preferably at least 594 amino acids, corresponding to a deletion of less than about 5%, 4%, 2% or 1% of the polypeptide sequence. This conservatively modified variation will contain.

Another example of a conservatively modified variation (e.g., a "conservatively substituted variation") of the polypeptide identified herein as SEQ ID NO:26 will contain "conservative substitutions", according to the six substitution groups set forth in Table 2, supra, in up to about 30 residues (i.e., less than about 5%) of the 600 amino acid polypeptide.

In a further example, if four conservative substitutions were localized in the region corresponding to amino acids 1-26 of SEQ ID NO:26, examples of conservatively substituted variations of this region, MALAP SYINP PNVAS PAGYS HVGVGP (SEQ ID NO: 77) would include:

MAVAP SYINP PQVAS PAGYA HLGVGP (SEQ ID NO: 78) and

MSLAP SWINP PNVAA PAGWS HVGVGP (SEQ ID NO: 79) and the like, in accordance with the conservative substitutions listed in Table 2 (in the above example, conservative substitutions are underlined). Listing of a protein sequence herein, in conjunction with the above substitution table, provides an express listing of all conservatively substituted proteins.

The FD/FDD polypeptide sequence homologues of the invention, including conservatively substituted sequences, can be present as part of larger polypeptide sequences such as occur upon the addition of one or more domains for purification of the protein (e.g., poly his segments, FLAG tag segments, etc.). These additional functional domains either have little or no effect on the activity of the FD/FDD portion of the protein, or the additional domains can be removed by post synthesis processing steps such as by treatment with a protease, inclusion of an intein or the like.

A feature of the invention is an FD/FDD homologue polypeptide comprising at least 125 contiguous amino acids of any one of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. In various embodiments, the polypeptide comprises at least about 100, at least about 150, at least about 175, at least about 200, at least about 225, at least about 250, at least about 275, or at least about 300 or more contiguous amino acid residues of any one of SEQ ID NOs:26-50, SEQ ID NOs:70-72 and SEQ ID NOs:85, 87, 89, 91, 93, 95, 97, 99, 101, 103, 105, 107, 109, 111, 113, 115, 117, 119, 121, 123, 125, and 127. In some optional embodiments, such fragments optionally comprise a polypeptide with FD/FDD activity (optionally, in yet other embodiments an FD/FDD activity at select pH such at 5.5).

In other embodiments, the polypeptide is at least 585, 590, or 595 amino acids in length amino acids, preferably at least 598 amino acids, more preferably at least 599 amino acids, and still more preferably at least 600 amino acids in length.

Finally, the addition of sequences which do not alter the encoded activity of a nucleic acid molecule, such as the addition of a non-functional sequence, is a conservative variation of the basic nucleic acid.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in which one or a few amino acids in an amino acid sequence are substituted with different amino acids with highly similar properties, are also readily identified as being highly similar to a disclosed construct. Such conservative variations of each disclosed sequence are a feature of the present invention.

Nucleic Acid Hybridization

Nucleic acids "hybridize" when they associate, typically in solution. Nucleic acids hybridize due to a variety of well-characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes*, part I, chapter 2, "Overview of principles of hybridization and the strategy of nucleic acid probe assays," (Elsevier, N.Y.) (hereinafter "Tijssen"), as well as in Ausubel, Hames and Higgins (1995) *Gene Probes* 1, IRL Press at Oxford University Press, Oxford, England (hereinafter "Hames and Higgins 1") and Hames and Higgins (1995) *Gene Probes* 2, IRL Press at Oxford University Press, Oxford, England (hereinafter "Hames and Higgins 2") provide details on the synthesis, labeling, detection and quantification of DNA and RNA, including oligonucleotides.

"Stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijssen, Hames and Higgins 1 and Hames and Higgins 2.

For purposes of the present invention, generally, "highly stringent" hybridization and wash conditions are selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. Very stringent conditions are selected to be equal to the $T_m$ for a particular probe.

The $T_m$ of the nucleic acid duplexes indicates the temperature at which the duplex is 50% denatured under the given conditions and represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can produce non-specific hybridization signals and high background signals. Higher stringency conditions (e.g., using lower salt and higher temperature that is closer to the hybridization temperature) lowers the background signal, typically with only the specific signal remaining. See, Rapley, R. and Walker, J. M. eds. (1998), *Molecular Biomethods Handbook*, Humana Press, Inc. (hereinafter "Rapley and Walker"), which is incorporated herein by reference in its entirety for all purposes.

The $T_m$ of a DNA-DNA duplex can be estimated using the following equation:

$T_m(° C.)=81.5° C.+16.6(\log_{10} M)+0.41(\% G+C)-0.72(\% f)-500/n$, where M is the molarity of the monovalent cations (usually Na+), (% G+C) is the percentage of guanosine (G) and cytosine (C) nucleotides, (% f) is the percentage of formamide and n is the number of nucleotide bases (i.e., length) of the hybrid. See, Rapley and Walker.

The $T_m$ of an RNA-DNA duplex can be estimated as follows:

$T_m(° C.)=79.8° C.+18.5(\log_{10} M)+0.58(\% G+C)-11.8(\% G+C)^2-0.56(\% f)-820/n$, where M is the molarity of the monovalent cations (usually Na+), (% G+C) is the percentage of guanosine (G) and cytosine (C) nucleotides, (% f) is the percentage of formamide and n is the number of nucleotide bases (i.e., length) of the hybrid. Id.

Equations 1 and 2 are typically accurate only for hybrid duplexes longer than about 100-200 nucleotides. Id.

The $T_m$ of nucleic acid sequences shorter than 50 nucleotides can be calculated as follows:

$T_m(° C.)=4(G+C)+2(A+T)$, where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook for a description of SSC buffer). Often the high stringency wash is preceded by a low stringency wash to remove background probe signal. An example low stringency wash is 2×SSC at 40° C. for 15 minutes.

In general, a signal to noise ratio of 2.5×-5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under high stringency conditions. Lower stringency conditions are appropriate for sequences that are less complementary. See, e.g., Rapley and Walker, supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the FD/FDD nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listings herein. For example, it is desirable to identify test nucleic acids which hybridize to the exemplar nucleic acids herein under stringent conditions.

Thus, one measure of stringent hybridization is the ability to hybridize to one of the listed nucleic acids (e.g., nucleic acid sequences SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, and complementary polynucleotide sequences thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions are gradually increased until a probe comprising one or more nucleic acid sequences selected from SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, and complementary polynucleotide sequences thereof, binds to a perfectly matched complementary target (again, a nucleic acid comprising one or more nucleic acid sequences selected from SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, and complementary polynucleotide sequences thereof), with a signal to noise ratio that is at least 2.5.times., and optionally 5.times. or more as high as that observed for hybridization of the probe to an unmatched target. In this case, the unmatched target is a nucleic acid corresponding to, e.g., a known FD/FDD homologue, such as an FD/FDD homologue nucleic acid that is present in a public database such as GenBank™ at the time of filing of the subject application. Examples of such unmatched target nucleic acids include, e.g., nucleic acids encoding ESP002C2, ESP002C3, ESP003C12, RAT011C1, RAT011C2, RAT011C4 (see, SEQ ID Nos: 51, 53, 55, 57, 59, 61 and 63) where the clone identification numbers correspond to those in PCT publications WO 00/04159 and WO 00/04160, as well as the nucleic acid sequence encoding wild type APAG (SEQ ID NO:52). Additional such sequences can be identified in, e.g., GenBank by one of ordinary skill in the art.

A test nucleic acid is said to specifically hybridize to a probe nucleic acid when it hybridizes at least one-half as well to the probe as to the perfectly matched complementary target, i.e., with a signal to noise ratio at least one-half as high as hybridization of the probe to the target under conditions in which the perfectly matched probe binds to the perfectly matched complementary target with a signal to noise ratio that is at least about 2.5×-10×, typically 5×-10× as high as that observed for hybridization to any of the unmatched target nucleic acids such as, nucleic acids encoding ESP002C2, ESP002C3, ESP003C 12, RAT011C1, RAT011C2, RAT011C4, where the clone identification numbers correspond to those in PCT publications WO 00/04159 and WO 00/04160, or encoding wild type APAO (SEQ ID NO:51) or, e.g., other similar FD/FDD sequences presented in, e.g., GenBank.

Ultra high-stringency hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids, such as, nucleic acids encoding ESP002C2, ESP002C3, ESP003C12, RAT011C1, RAT011C2, RAT011C4 (where the numbers correspond to clone numbers in PCT publications WO 00/04159 and WO 00/04160), or the nucleic acid encoding wild type APAO (SEQ ID NO:51) or, e.g., to other similar FD/FDD molecule sequences presented in, e.g., GenBank. A target nucleic acid which hybridizes to a probe under such conditions, with a signal to noise ratio of at least one-half that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 30×, 40×, 50×, 75×, 100×, 200×, 300×, 400×, or 500× or more as high as that observed for hybridization to any of the unmatched target nucleic acids, such as those represented by: ESP002C2, ESP002C3, ESP003C12, RAT011C1, RAT011C2, RAT011C4 (where the numbers correspond to clone numbers in patents W/O 00/04159 and W/O 00/04160), or wild-type APAO or, e.g., other similar FD/FDD sequences presented in, e.g., GenBank can be identified. A target nucleic acid which hybridizes to a probe under such conditions, with a signal to noise ratio of at least one-half that of the perfectly matched complementary target nucleic acid is said to bind to the probe under ultra-ultra-high stringency conditions.

Target nucleic acids which hybridize to the nucleic acids represented by SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126 under high, ultra-high and ultra-ultra high stringency conditions are a feature of the invention. Examples of such nucleic acids include those with one or a few silent or conservative nucleic acid substitutions as compared to a given nucleic acid sequence.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code, or when antisera generated against one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 which has been subtracted using the polypeptides encoded by known or existing FD/FDD sequences, including, e.g., those encoded by the following: ESP002C2, ESP002C3, ESP003C12, RAT011C1, RAT011C2, RAT011C4 (where the numbers correspond to clone numbers in PCT publications WO 00/04159 and WO 00/04160), or wild type APAO (SEQ ID NO:52) or, e.g., other similar FD/FDD sequences presented in, e.g., GenBank. Further details on immunological identification of polypeptides of the invention are found below. Additionally, for distinguishing between duplexes with sequences of less than about 100 nucleotides, a TMAC1 hybridization procedure known to those of ordinary skill in the art can be used. See, e.g., Sorg, U. et al. *Nucleic Acids Res.* (1991) 19:4782, incorporated herein by reference in its entirety for all purposes.

In one aspect, the invention provides a nucleic acid which comprises a unique subsequence in a nucleic acid selected from SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126. The unique subsequence is unique as compared to a nucleic acid corresponding to any of, e.g., ESP002C2, ESP002C3, ESP003C12, RAT011C1, RAT011C2, RAT011C4 (where the numbers correspond to clone numbers in POT publications WO 00/04159 and WO 00/04160), or wild type APAO (SEQ ID NO:51) or, e.g., other similar FD/FDD sequences presented in, e.g., GenBank. Such unique subsequences can be determined by aligning any of SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126 against the complete set of nucleic acids, e.g., those corresponding to, e.g., nucleic acids encoding ESP002C2, ESP002C3, ESP003C12, RAT011C1, RAT011C2, RAT011C4, or the nucleic acid encoding wild type APAO (SEQ ID NO:51) or other sequences available, e.g., in a public database, at the filing date of the subject application. Alignment can be performed using the BLAST algorithm set to default parameters. Any unique subsequence is useful, e.g., as a probe to identify the nucleic acids of the invention.

Similarly, the invention includes a polypeptide which comprises a unique amino acid subsequence of a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. Here, the unique subsequence is unique as compared to a polypeptide or amino acid sequence corresponding to, e.g., any of ESP002C2, ESP002C3, ESP003C12, RAT011C1, RAT011C2, RAT011C4 (where the numbers correspond to clone numbers in PCT publications WO 00/04159 and WO 00/04160) or the wild type APAO (SEQ ID NO:52). Here again, the polypeptide is aligned against the existing polypeptides (the control polypeptides). Note that where the sequence corresponds to a non-translated sequence such as a pseudogene, the corresponding polypeptide is generated simply by in silico translation of the nucleic acid sequence into an amino acid sequence, where the reading frame is selected to correspond to the reading frame of homologous FD/FDD nucleic acids. Such polypeptides are optionally made by synthetic or recombinant approaches, or can even be ordered from companies specializing in polypeptide production.

In addition, the present invention provides a target nucleic acid which hybridizes under at least stringent or highly stringent conditions (or conditions of greater stringency) to a unique coding oligonucleotide which encodes a unique subsequence in a polypeptide selected from: SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, wherein the unique subsequence is unique as compared to an amino acid subsequence of a known FD/FDD polypeptide sequence shown in, e.g., GenBank or to a polypeptide corresponding to any of the control polypeptides (see, above). Unique sequences are determined as noted above.

In one example, the stringent conditions are selected such that a perfectly complementary oligonucleotide to the coding oligonucleotide hybridizes to the coding oligonucleotide with at least about a 5-10× higher signal to noise ratio than for hybridization of the perfectly complementary oligonucleotide to a control nucleic acid corresponding to any of the control polypeptides. Conditions can be selected such that higher ratios of signal to noise are observed in the particular assay which is used, e.g., about 15×, 20×, 30×, 50× or more. In this example, the target nucleic acid hybridizes to the unique coding oligonucleotide with at least a 2× higher signal to noise ratio as compared to hybridization of the control nucleic acid to the coding oligonucleotide. Again, higher signal to noise ratios can be selected, e.g., about 2.5×, about 5×, about 10×, about 20×, about 30×, about 50× or more. The particular signal will depend on the label used in the relevant assay, e.g., a fluorescent label, a colorimetric label, a radioactive label, or the like.

In another aspect, the invention provides a polypeptide that comprises a unique subsequence in a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, wherein the unique subsequence is unique as compared to a polypeptide sequence corresponding to a known FD/FDD polypeptide, such as, e.g., an FD/FDD polypeptide sequence present in GenBank.

Percent Sequence Identity—Sequence Similarity

As noted above, the peptides employed in the subject invention need not be identical, but can be substantially identical, to the corresponding sequence of an FD/FDD molecule or related molecule. The peptides can be subject to various changes, such as insertions, deletions, and substitutions, either conservative or non-conservative, where such changes might provide for certain advantages in their use. The polypeptides of the invention can be modified in a number of ways so long as they comprise a sequence substantially identical (as defined below) to a sequence in an FD/FDD molecule.

Alignment and comparison of relatively short amino acid sequences (less than about 30 residues) is typically straightforward. Comparison of longer sequences can require more sophisticated methods to achieve optimal alignment of two sequences. Optimal alignment of sequences for aligning a comparison window can be conducted by the local homology algorithm of Smith and Waterman (1981) *Adv Appl Math* 2:482, by the homology alignment algorithm of Needleman and Wunsch (1970) *J Mol Biol* 48:443, by the search for similarity method of Pearson and Lipman (1988) *PNAS USA* 85:2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, with the best alignment (i.e., resulting in the highest percentage of sequence similarity over the comparison window) generated by the various methods being selected.

The term sequence identity means that two polynucleotide sequences are identical (i.e., on a nucleotide-by-nucleotide basis) over a window of comparison. The term "percentage of sequence identity" or "percent sequence identity" is calculated by comparing two optimally aligned sequences over the window of comparison, determining the number of positions at which the identical residues occur in both sequences to yield the number of matched positions, dividing the number of matched positions by the total number of positions in the window of comparison (i.e., the window size), and multiplying the result by 100 to yield the percentage of sequence identity. In one aspect, the present invention provides FD/FDD homologue nucleic acids having at least about 80%, 85%, 90%, 95%, 96%, 97%, 98%, 99%, 99.5% or more sequence identity with the nucleic acids of any of SEQ ID NOs:1-25, SEQ ED NOs:67-69, and SEQ ID NOs:84, 86, 88, 90, 92, 94, 96, 98, 100, 102, 104, 106, 108, 110, 112, 114, 116, 118, 120, 122, 124, and 126 or fragments thereof. In other embodiments the invention provides FD/FDD homologue polypeptides with an ability to detoxify fumonisins or fumonisin-derivatives wherein the polypeptide has at least a 70%, at least a 75%, at least an 80%, at least an 85%, at least 90%, at least a 91%, at least a 92%, at least a 93%, at least a 94%, at least a 95%, at least a 96%, at least a 97%, at least a 98%, at least a 99%, or at least 99.5% or more identity to at least one of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 over a comparison window of at least 100, at least 110, at least 115, at least 120, at least 125, at least 130, at least 135, at least 140, at least 150, at least 175, at least 200, at least 225, at least 250, or at least 275 or morn contiguous amino acids. In some optional embodiments, the above percent identities over the listed contiguous amino acid lengths apply to FD/FDD homologues of the invention which possess at least partial fumonisin detoxification ability and/or which possess a pH optimum in a pH range of from about 5.0 to about 7.4.

As applied to polypeptides, the term substantial identity means that two peptide sequences, when optimally aligned, such as by the programs GAP or BESTFIT using default gap weights (described in detail below), share at least about 80 percent sequence identity, preferably at least about 90 percent sequence identity, more preferably at least about 95 percent sequence identity or more (e.g., 96, 97, 98, 99, or 99.5 or more percent sequence identity). Alternatively, parameters are set such that one or more sequences of the invention, e.g., SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 are identified by alignment to a query sequence selected from among SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, while sequences corresponding to unrelated polypeptides, e.g., those corresponding to clone numbers ESP002C2, ESP002C3, ESP003C12, RAT011C1, RAT011C2, RAT011C4 from PCT publications WO 00/04159 and WO00/04160 or wild-type APAO (SEQ ID NO:52) or other similar fumonisin detoxification molecules found in, e.g., GenBank, are not identified.

Preferably, residue positions which are not identical differ by conservative amino acid substitutions. Conservative amino acid substitution refers to the interchangeability of residues having similar side chains. For example, a group of amino acids having aliphatic side chains is alanine, valine, leucine, and isoleucine, and also includes glycine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. In one aspect, the present invention provides FD/FDD homologue polypeptides having at least about 80%, 85%, 90%, 95%, 96%, 97%, 98%, 99%, 99.5%, or more percent sequence identity with the polypeptides of any of SEQ ID NOs:26-50, SEQ ID NOs:70-72, and SEQ ID NOs: 85, 87, 89, 91, 93, 95, 97, 99, 101, 103, 105, 107, 109, 111, 113, 115, 117, 119, 121, 123, 125, and 127.

A preferred example of an algorithm that is suitable for determining percent sequence identity and sequence similarity is the FASTA algorithm, which is described in Pearson, W. R. & Lipman, D. J., (1988) *PNAS USA* 85:2444. See also, W. R. Pearson, (1996) *Methods Enzymol* 266:227-258. Preferred parameters used in a FASTA alignment of DNA sequences to calculate percent identity are optimized, BL50 Matrix 15: −5, k-tuple=2; joining penalty=40, optimization=28; gap penalty −12, gap length penalty=−2; and width=16.

Other preferred examples of algorithm that are suitable for determining percent sequence identity and sequence similarity are the BLAST and BLAST 2.0 algorithms, which are described in Altschul et al., (1977) Nuc Acids Res 25:3389-3402 and Altschul et al., (1990) J Mol Biol 215:403-410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.rilm.nih.gov/). This algorithm involves first identifying high scoring sequence pairs (HSPs) by identifying short words of length 'W' in the query sequence, which either match or satisfy some positive-valued threshold score 'T' when aligned with a word of the same length in a database sequence. T is referred to as the neighborhood word score threshold (Altschul). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters 'M' (reward score for a pair of matching residues; always >0) and 'N' (penalty score for mismatching residues; always <0). For amino acid sequences, a scoring matrix is used to calculate the cumulative score. Extension of the word hits in each direction are halted when: the cumulative alignment score falls off by the quantity 'X' from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (B) of 10, M=5, N=−4 and a comparison of both strands. For amino acid sequences, the BLASTP program uses as defaults a wordlength of 3, and expectation (B) of 10, and the BLOSUM62 scoring matrix (see, Henikoff & Henikoff, (1989) PNAS USA 89:10915) uses alignments (B) of 50, expectation (B) of 10, M5, N=−4, and a comparison of both strands. Again, as with other suitable algorithms, the stringency of comparison can be increased until the program identifies only sequences that are more closely related to those in the sequence listings herein (i.e., SEQ JD NOs:1-25, SEQ ED NOs:67-69, and SEQ ID NOs:84, 86, 88, 90, 92, 94, 96, 98, 100, 102, 104, 106, 108, 110, 112, 114, 116, 118, 120, 122, 124, and 126 or, alternatively, SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127), than to sequences that are more closely related to other sequences such as, e.g., clone numbers ESP002C2, ESP002C3, ESP003C12, RAT001C 1, RAT011C2, RAT011C4 from PCT publications WO 00/04159 and WO00/04160 or wild-type APAO (SEQ ID NOs:51-52) or similar molecules found in, e.g., GenBank. In other words, the stringency of comparison of the algorithms can be increased so that all known prior art (e.g., clone numbers ESP002C2, ESP002C3, ESP003C12, RAT011C1, RAT011C2, RAT011C4 from PCT publications WO 00/04159 and WO 00/04160) or wild-type APAO (SEQ ID NOs:51 and 52) or other similar molecules found in, e.g., GenBank) is excluded.

The BLAST algorithm also performs a statistical analysis of the similarity between two sequences (see, e.g., Karlin & Altschul, (1993) *PNAS USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method of Feng & Doolittle, (1987) *J Mol Evol* 35:351-360. The method used is similar to the method described by Higgins & Sharp, (1989) *CABIOS* 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., (1984) *Nuc Acids Res* 12:387-395).

Another preferred example of an algorithm that is suitable for multiple DNA and amino acid sequence alignments is the CLUSTALW program (Thompson, J. D. et al., (1994) *Nuc Acids Res* 22:4673-4680). CLUSTALW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, (1992) *PNAS USA* 89:10915-10919).

It will be understood by one of ordinary skill in the art, that the above discussion of search and alignment algorithms also applies to identification and evaluation of polynucleotide sequences, with the substitution of query sequences comprising nucleotide sequences, and where appropriate, selection of nucleic acid databases.

Substrates and Formats for Sequence Recombination

The polynucleotides of the invention and fragments thereof are optionally used as substrates for a variety of recombination and recursive recombination reactions, in addition to standard cloning methods as set forth in, e.g., Ausubel, Berger and Sambrook, i.e., to produce additional FD/FDD homologues and fragments thereof with desired properties. A variety of such reactions are known, including those developed by the inventors and their co-workers. Methods for producing a variant of any nucleic acid of the invention listed herein comprising recursively recombining such polynucleotide with a second (or more) polynucleotide, thus forming a library of variant polynucleotides are also features of the invention, as are the libraries produced, the cells comprising the libraries, and any recombinant polynucleotide produces by such methods. Additionally, such methods optionally comprise selecting a variant polynucleotide from such libraries based on FD/FDD activity, as is wherein such recursive recombination is done in vitro or in vivo.

A variety of diversity generating protocols, including nucleic acid recursive recombination protocols, is available and fully described in the art. The procedures can be used separately, and/or in combination to produce one or more variants of a nucleic acid or set of nucleic acids, as well variants of encoded proteins. Individually and collectively, these procedures provide robust, widely applicable ways of generating diversified nucleic acids and sets of nucleic acids (including, e.g., nucleic acid libraries) useful, e.g., for the engineering or rapid evolution of nucleic acids, proteins, pathways, cells and/or organisms with new and/or improved characteristics.

While distinctions and classifications are made in the course of the ensuing discussion for clarity, it will be appreciated that the techniques are often not mutually exclusive. Indeed, the various methods can be used singly or in combination, in parallel or in series, to access diverse sequence variants.

The result of any of the diversity generating procedures described herein can be the generation of one or more nucleic acids, which can be selected or screened for nucleic acids with or which confer desirable properties, or that encode proteins with or which confer desirable properties. Following diversification by one or more of the methods herein, or otherwise available to one of skill, any nucleic acids that are produced can be selected for a desired activity or property, e.g. FD/FDD activity, or, such activity at a desired pH, etc. This can include identifying any activity that can be detected, for example, in an automated or automatable format, by any of the assays in the art, see, e.g., discussion of screening of FD/FDD activity, infra. A variety of related (or even unrelated) properties can be evaluated, in serial or in parallel, at the discretion of the practitioner.

Descriptions of a variety of diversity generating procedures for generating modified nucleic acid sequences, e.g., those coding for polypeptides having FD/FDD activity, or fragments thereof, are found in the following publications and the references cited therein: Soong, N. et al. (2000) *Nat Genet* 25(4):436-439; Stemmer, et al. (1999) *Tumor Targeting* 4:1-4; Ness et al. (1999) *Nat Biotechnol* 17:893-896; Chang et al. (1999) *Nat Biotechnol* 17:793-797; Minshull and Stemmer (1999) *Curr Opin Chem Biol* 3:284-290; Christians et al. (1999) *Nat Biotechnol* 17:259-264; Crameri et al. (1998) *Nature* 391:288-291; Crameri et al. (1997) *Nat Biotechnol* 15:436-438; Zhang et al. (1997) *PNAS USA* 94:4504-4509; Patten et al. (1997) *Curr Opin Biotechnol* 8:724-733; Crameri et al. (1996) *Nat Med* 2:100-103; Crameri et al. (1996) *Nat Biotechnol* 14:315-319; Gates et al. (1996) *J Mol Biol* 255: 373-386; Stemmer (1996) "Sexual PCR and Assembly PCR" In: *The Encyclopedia of Molecular Biology*. VCH Publishers, New York. pp. 447-457; Crameri and Stemmer (1995) *BioTechniques* 18:194-195; Stemmer et al., (1995) *Gene*, 164: 49-53; Stemmer (1995) *Science* 270: 1510; Stemmer (1995) *Bio/Technology* 13:549-553; Stemmer (1994) *Nature* 370: 389-391; and Stemmer (1994) *PNAS USA* 91:10747-10751.

Mutational methods of generating diversity include, for example, site-directed mutagenesis (Ling et al. (1997) *Anal Biochem* 254(2): 157-178; Dale et al. (1996) *Methods Mol Biol* 57:369-374; Smith (1985) *Ann Rev Genet* 19:423-462; Botstein & Shortle (1985) *Science* 229:1193-1201; Carter (1986) *Biochem J* 237:1-7; and Kunkel (1987) "The efficiency of oligonucleotide directed mutagenesis" in *Nucleic Acids & Molecular Biology* (Eckstein, F. and Lilley, D. M. J. eds., Springer Verlag, Berlin)); mutagenesis using uracil containing templates (Kunkel (1985) *PNAS USA* 82:488-492; Kunkel et al. (1987) *Methods Enzymol* 154, 367-382; and Bass et al. (1988) *Science* 242:240-245); oligonucleotide-directed mutagenesis (Zoller & Smith (1983) *Methods Enzymol* 100: 468-500; Zoller & Smith (1987) *Methods Enzymol* 154: 329-350 (1987); Zoller & Smith (1982) *Nucleic Acids Res* 10:6487-6500), phosphorothioate-modified DNA mutagenesis (Taylor et al. (1985) *Nucl Acids Res* 13: 8749-8764; Taylor et al. (1985) *Nucl Acids Res* 13: 8765-8787 (1985); Nakamaye & Eckstein (1986) *Nucl Acids Res* 14: 9679-9698; Sayers et al. (1988) *Nucl Acids Res* 16:791-802; and Sayers et al. (1988) *Nucl Acids Res* 16: 803-814); mutagenesis using gapped duplex DNA (Kramer et al. (1984) *Nucl Acids Res* 12: 9441-9456; Kramer & Fritz (1987) *Methods Enzymol* 154:350-367; Kramer et al. (1988) *Nucl Acids Res* 16: 7207; and Fritz et al. (1988) *Nucl Acids Res* 16: 6987-6999).

Additional suitable methods include point mismatch repair (Kramer et al. (1984) *Cell* 38:879-887), mutagenesis using repair-deficient host strains (Carter et al. (1985) *Nucl Acids Res* 13: 4431-4443; and Carter (1987) *Methods in Enzymol* 154: 382-403), deletion mutagenesis (Eghtedarzadeh & Henikoff (1986) *Nucl Acids Res* 14: 5115), restriction-selection and restriction-purification (Wells et al. (1986) *Phil Trans R Soc Lond* A 317: 415-423), mutagenesis by total gene synthesis (Nambiar et al. (1984) *Science* 223: 1299-1301; Sakamar and Khorana (1988) *Nucl Acids Res* 14: 6361-6372; Wells et al. (1985) *Gene* 34:315-323; and Grundström et al. (1985) *Nucl Acids Res* 13: 3305-3316), double-strand break repair (Mandecki (1986) *PNAS USA*, 83:7177-7181; and Arnold (1993) *Curr Opin Biotech* 4:450-455). Additional details on many of the above methods can be found in *Methods Enzymol* Volume 154, which also describes useful controls for trouble-shooting problems with various mutagenesis methods.

Additional details regarding various diversity generating methods can be found in the following U.S. patents, PCT publications and applications, and EPO publications: U.S. Pat. No. 5,723,323, U.S. Pat. No. 5,763,192, U.S. Pat. No.

5,814,476, U.S. Pat. No. 5,817,483, U.S. Pat. No. 5,824,514, U.S. Pat. No. 5,976,862, U.S. Pat. No. 5,605,793, U.S. Pat. No. 5,811,238, U.S. Pat. No. 5,830,721, U.S. Pat. No. 5,834,252, U.S. Pat. No. 5,837,458, WO 95/22625, WO 96/33207, WO 97/20078, WO 97/35966, WO 99/41402, WO 99/41383, WO 99/41369, WO 99/41368, EP 752008, EP 0932670, WO 99/23107, WO 99/21979, WO 98/31837, WO 98/27230, WO 98/27230, WO 00/00632, WO 00/09679, WO 98/42832, WO 99/29902, WO 98/41653, WO 98/41622, WO 98/42727, WO 00/18906, WO 00/04190, WO 00/42561, WO 00/42559, WO 00/42560, WO 01/23401, and PCT/US01/06775.

In brief, several different general classes of sequence modification methods, such as mutation, recombination, etc., are applicable to the present invention (i.e., to generate FD/FDD homologues) and are set forth, e.g., in the references above.

The following exemplify some of the different types of preferred formats for diversity generation in the context of the present invention, including, e.g., certain recombination based diversity generation formats.

Nucleic acids can be recombined in vitro by any of a variety of techniques discussed in the references above, including e.g., DNAse digestion of nucleic acids to be recombined followed by ligation and/or PCR reassembly of the nucleic acids. For example, sexual PCR mutagenesis can be used in which random (or pseudo random, or even non-random) fragmentation of the DNA molecule is followed by recombination, based on sequence similarity, between DNA molecules with different but related DNA sequences, in vitro, followed by fixation of the crossover by extension in a polymerase chain reaction. This process and many process variants are described in several of the references above, e.g., in Stemmer (1994) *PNAS USA* 91:10747-10751. Thus FD/FDD homologues of the invention are optionally generated through such methods, or optionally are used in such methods as starting points for generation of further diversity.

Similarly, nucleic acids can be recursively recombined in vivo, e.g., by allowing recombination to occur between nucleic acids in cells. Many such in vivo recombination formats are set forth in the references noted above. Such formats optionally provide direct recombination between nucleic acids of interest, or provide recombination between vectors, viruses, plasmids, etc., comprising the nucleic acids of interest, as well as other formats. Details regarding such procedures are found in the references noted above. Thus, again, the FD/FDD homologues of the invention are optionally generated through such recursive recombination techniques, or optionally are used in such methods as starting points for generation of further diversity (i.e., to generate, e.g., additional FD/FDD homologues).

Whole genome recombination methods can also be used in which whole genomes of cells or other organisms are recombined, optionally including spiking of the genomic recombination mixtures with desired library components (e.g., genes corresponding to the pathways of the present invention, i.e., fumonisin detoxification, etc.). These methods have many applications, including those in which the identity of a target gene is not known. Details on such methods are found, e.g., in WO 98/31837 and WO 00/04190.

Synthetic recombination methods can also be used, in which oligonucleotides corresponding to targets of interest are synthesized and reassembled in PCR or ligation reactions which include oligonucleotides which correspond to more than one parental nucleic acid, thereby generating new recombined nucleic acids. Oligonucleotides can be made by standard nucleotide addition methods, or can be made, e.g., by tri-nucleotide synthetic approaches. Details regarding such approaches are found in the references noted above, including, e.g., WO 00/42561, WO 01/23401, WO 00/42560, and WO 00/42559.

In silico methods of recombination can be effected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis/gene reassembly techniques. This approach can generate random, partially random or designed variants. Many details regarding in silico recombination, including the use of genetic algorithms, genetic operators and the like in computer systems, combined with generation of corresponding nucleic acids (and/or proteins), as well as combinations of designed nucleic acids and/or proteins (e.g., based on cross-over site selection) as well as designed, pseudo-random or random recombination methods are described in WO 00/42560 and WO 00/42559. Extensive details regarding in silico recombination methods are found in these applications. This methodology is generally applicable to the present invention in providing for recombination of the FD/FDD homologues in silico and/or the generation of corresponding nucleic acids or proteins.

Many methods of accessing natural diversity, e.g., by hybridization of diverse nucleic acids or nucleic acid fragments to single-stranded templates, followed by polymerization and/or ligation to regenerate full-length sequences, optionally followed by degradation of the templates and recovery of the resulting modified nucleic acids can be similarly used. In one method employing a single-stranded template, the fragment population derived from the genomic library(ies) is annealed with partial, or, often approximately full length ssDNA or RNA corresponding to the opposite strand. Assembly of complex chimeric genes from this population is then mediated by nuclease-base removal of non-hybridizing fragment ends, polymerization to fill gaps between such fragments and subsequent single stranded ligation. The parental polynucleotide strand can be removed by digestion (e.g., if RNA or uracil-containing), magnetic separation under denaturing conditions (if labeled in a manner conducive to such separation) and other available separation/ purification methods. Alternatively, the parental strand is optionally co-purified with the chimeric strands and removed during subsequent screening and processing steps. Additional details regarding this approach are found, e.g., in PCT/US01/ 06775.

In another approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library of enriched sequences which hybridize to the probe. A library produced in this manner provides a desirable substrate for further diversification using any of the procedures described herein.

Any of the preceding general recombination formats can be practiced in a reiterative fashion (e.g., one or more cycles of mutation/recombination or other diversity generation methods, optionally followed by one or more selection methods) to generate a more diverse set of recombinant nucleic acids.

The above references provide these and other basic recombination formats as well as many modifications of these formats. Regardless of the format which is used, the nucleic acids of the invention can be recombined (with each other, or with related (or even unrelated) sequences) to produce a diverse set of recombinant nucleic acids, including, e.g., sets of homologous nucleic acids. In general, the sequence recombination techniques described herein provide particular advantages in that they provide for recombination between the nucleic acids of SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126, or derivatives thereof, in any available format, thereby providing a very fast way of exploring the manner in which different combinations of sequences can affect a desired result.

Following recombination, any nucleic acids which are produced can be selected for a desired activity. In the context of the present invention, this can include testing for and identifying any activity that can be detected, e.g., any of the usual FD/FDD activities, by any of the assays in the art, e.g., in an automatable format. A variety of related (or even unrelated) properties can be assayed for, using any available assay.

A recombinant nucleic acid produced by recursively recombining one or more polynucleotide of the invention with one or more additional nucleic acid also forms a part of the invention. The one or more additional nucleic acid may include another polynucleotide of the invention; optionally, alternatively, or in addition, the one or more additional nucleic acid can include, e.g., a nucleic acid encoding a naturally-occurring FD/FDD homologue or a subsequence thereof, or any homologous FD/FDD sequence or subsequence thereof (e.g., as found in GenBank or other available literature), or, e.g., any other homologous or non-homologous nucleic acid (certain recombination formats noted above, notably those performed synthetically or in silico, do not require homology for recombination).

The recombining steps may be performed in vivo, in vitro, in planta, or in silico as described in more detail in the references above. Also included in the invention is a cell containing any resulting recombinant nucleic acid, nucleic acid libraries produced by recursive recombination of the nucleic acids set forth herein, and populations of cells, vectors, viruses, plasmids or the like comprising the library or comprising any recombinant nucleic acid resulting from recombination (or recursive recombination) of a nucleic acid as set forth herein with another such nucleic acid, or an additional nucleic acid. Corresponding sequence strings in a database present in a computer system or computer readable medium are a feature of the invention.

DNA mutagenesis and recursive recombination provide a robust, widely applicable, means of generating diversity useful for the engineering of proteins, pathways, cells and organisms with improved characteristics. In addition to the basic formats described above, it is sometimes desirable to combine recursive recombination methodologies with other techniques for generating diversity. In conjunction with (or separately from) recursive recombination methods, a variety of diversity generation methods can be practiced and the results (i.e., diverse populations of nucleic acids) screened for in the systems of the invention. Additional diversity can be introduced by methods which result in the alteration of individual nucleotides or groups of contiguous or non-contiguous nucleotides, i.e., mutagenesis methods. Many mutagenesis methods are found in the above-cited references; additional details regarding mutagenesis methods can be found in the references listed below.

Mutagenesis methods include, for example, recombination (see: PCT/US98/05223, WO98/42727); site-directed mutagenesis, mutagenesis using uracil containing templates, oligonucleotide-directed mutagenesis, phosphorothioate-modified DNA mutagenesis, and mutagenesis using gapped duplex DNA. A variety of references for these methods of mutagenesis have been provided supra.

Additional suitable methods include point mismatch repair, mutagenesis using repair-deficient host strains, deletion mutagenesis, restriction-selection and restriction-selection and restriction-purification, mutagenesis by total gene synthesis, and double-strand break repair. A variety of references for these various mutagenesis techniques have been provided supra. Furthermore, additional details on many of the above methods can be found in *Methods in Enzymology* Volume 154, which also describes useful controls for troubleshooting problems with various mutagenesis methods.

Mutagenesis employing polynucleotide chain termination methods have also been proposed (see e.g., U.S. Pat. No. 5,965,408 and other references supra), and can be applied to the present invention. In this approach, double stranded DNAs corresponding to one or more genes sharing regions of sequence similarity are combined and denatured, in the presence or absence of primers specific for the gene. The single stranded polynucleotides are then annealed and incubated in the presence of a polymerase and a chain terminating reagent (e.g., ultraviolet, gamma or X-ray irradiation; ethidium bromide or other intercalators; DNA binding proteins, such as single strand binding proteins, transcription activating factors, or histones; polycyclic aromatic hydrocarbons; trivalent chromium or a trivalent chromium salt; or abbreviated polymerization mediated by rapid thermocycling; and the like), resulting in the production of partial duplex molecules. The partial duplex molecules, e.g., containing partially extended chains, are then denatured and re-annealed in subsequent rounds of replication or partial replication resulting in polynucleotides which share varying degrees of sequence similarity and which are diversified with respect to the starting population of DNA molecules. Optionally, the products, or partial pools of the products, can be amplified at one or more stages in the process. Polynucleotides produced by a chain termination method, such as described above, are suitable substrates for any other described recombination format.

Diversity also can be generated in nucleic acids or populations of nucleic acids using a recombinational procedure termed "incremental truncation for the creation of hybrid enzymes" ("ITCHY") described in Ostermeier et al. (1999) *Nat Biotech* 17:1205. This approach can be used to generate an initial library of variants which can optionally serve as a substrate for one or more in vitro or in vivo recombination methods. See, also, Ostermeier et al. (1999) *PNAS USA*, 96: 3562-67; Ostermeier et al. (1999) *Biological and Medicinal Chemistry*, 7: 2139-44.

Mutational methods which result in the alteration of individual nucleotides or groups of contiguous or non-contiguous nucleotides can be favorably employed to introduce nucleotide diversity, i.e., to introduce nucleotide diversity into FD/FDD homologues, etc. Many mutagenesis methods are found in the above-cited references; additional details regarding mutagenesis methods can be found in following, which can also be applied to the present invention.

For example, error-prone PCR can be used to generate nucleic acid variants. Using this technique, PCR is performed under conditions where the copying fidelity of the DNA polymerase is low, such that a high rate of point mutations is obtained along the entire length of the PCR product. Examples of such techniques are found in the references above and, e.g., in Leung et al. (1989) *Technique* 1:11-15 and Caldwell et al. (1992) *PCR Methods Applic* 2:28-33. Similarly, assembly PCR can be used, in a process which involves the assembly of a PCR product from a mixture of small DNA fragments. A large number of different PCR reactions can occur in parallel in the same reaction mixture, with the products of one reaction priming the products of another reaction.

Sexual PCR mutagenesis can be used in which homologous recombination occurs between DNA molecules of different but related DNA sequence in vitro, by random fragmentation of the DNA molecule based on sequence homology, followed by fixation of the crossover by primer extension in a PCR reaction. This process is described in the references above, e.g., in Stemmer (1994) *PNAS USA* 91:10747-10751. Recursive ensemble mutagenesis can be used in which an algorithm for protein mutagenesis is used to produce diverse populations of phenotypically related mutants whose members differ in amino acid sequence. This method uses a feedback mechanism to control successive rounds of combinatorial cassette mutagenesis. Examples of this approach are found in Arkin & Youvan (1992) *PNAS USA* 89:7811-7815.

Oligonucleotide directed mutagenesis can be used to introduce site-specific mutations in a nucleic acid sequence of interest. Examples of such techniques are found in the references above and, e.g., in Reidhaar-Olson et al. (1988) *Science,* 241:53-57. Similarly, cassette mutagenesis can be used in a process that replaces a small region of a double stranded DNA molecule with a synthetic oligonucleotide cassette that differs from the native sequence. The oligonucleotide can contain, e.g., completely and/or partially randomized native sequence(s).

Exponential ensemble mutagenesis can be used for generating combinatorial libraries with a high percentage of unique and functional mutants. Small groups of residues in a sequence of interest are randomized in parallel to identify, at each altered position, amino acids which lead to functional proteins. Examples of such procedures are found in Delegrave & Youvan (1993) *Biotechnology Research* 11:1548-1552.

In vivo mutagenesis can be used to generate random mutations in any cloned DNA of interest by propagating the DNA, e.g., in a strain of *E. coli* that carries mutations in one or more of the DNA repair pathways. These "mutator" strains have a higher random mutation rate than that of a wild-type parent. Propagating the DNA in one of these strains will eventually generate random mutations within the DNA. Such procedures are described in the references noted above.

Other procedures for introducing diversity into a genome, e.g. a bacterial, fungal, animal or plant genome can be used in conjunction with the above described and/or referenced methods. For example, in addition to the methods above, techniques have been proposed which produce nucleic acid multimers suitable for transformation into a variety of species (see, e.g. U.S. Pat. No. 5,756,316 and the references supra). Transformation of a suitable host with such multimers, consisting of genes that are divergent with respect to one another, (e.g., derived from natural diversity or through application of site directed mutagenesis, error prone PCR, passage through mutagenic bacterial strains, and the like), provides a source of nucleic acid diversity for DNA diversification, e.g., by an in vivo recombination process as indicated above.

Alternatively, a multiplicity of monomeric polynucleotides sharing regions of partial sequence similarity can be transformed into a host species and recombined in vivo by the host cell. Subsequent rounds of cell division can be used to generate libraries, members of which include a single, homogenous population, or pool of monomeric polynucleotides. Alternatively, the monomeric nucleic acid can be recovered by standard techniques, e.g., PCR and/or cloning, and recombined in any of the recombination formats, including recursive recombination formats, described above.

Methods for generating multispecies expression libraries have been described (in addition to the reference noted above, see, e.g., U.S. Pat. No. 5,783,431 and U.S. Pat. No. 5,824,485) and their use to identify protein activities of interest has been proposed (In addition to the references noted above, see, U.S. Pat. No. 5,958,672). Multispecies expression libraries include, in general, libraries comprising cDNA or genomic sequences from a plurality of species or strains, operably linked to appropriate regulatory sequences, in an expression cassette. The cDNA and/or genomic sequences are optionally randomly ligated to further enhance diversity. The vector can be a shuttle vector suitable for transformation and expression in more than one species of host organism, e.g., bacterial species, eukaryotic cells. In some cases, the library is biased by preselecting sequences which encode a protein of interest, or which hybridize to a nucleic acid of interest. Any such libraries can be provided as substrates for any of the methods herein described.

The above described procedures have been largely directed to increasing nucleic acid and/or encoded protein diversity. However, in many cases, not all of the diversity is useful, e.g., functional, and contributes merely to increasing the background of variants that must be screened or selected to identify the few favorable variants. In some applications, it is desirable to preselect or prescreen libraries (e.g., an amplified library, a genomic library, a cDNA library, a normalized library, etc.) or other substrate nucleic acids prior to diversification, e.g., by recombination-based mutagenesis procedures, or to otherwise bias the substrates towards nucleic acids that encode functional products. For example, in the case of antibody engineering, it is possible to bias the diversity generating process toward antibodies with functional antigen binding sites by taking advantage of in vivo recombination events prior to manipulation by any of the described methods. For example, recombed CDRs derived from B cell cDNA libraries can be amplified and assembled into framework regions (e.g., Jirholt et al. (1998) *Gene* 215: 471) prior to diversifying according to any of the methods described herein.

Libraries can be biased towards nucleic acids which encode proteins with desirable enzyme activities. For example, after identifying a clone from a library which exhibits a specified activity (e.g., an FD/FDD homologue that detoxifies a fumonisin, etc.), the clone can be mutagenized using any known method for introducing DNA alterations. A library comprising the mutagenized homologues is then screened for a desired activity, which can be the same as or different from the initially specified activity. An example of such a procedure is proposed in U.S. Pat. No. 5,939,250. Desired activities can be identified by any method known in the art. For example, WO 99/10539 proposes that gene libraries can be screened by combining extracts from the gene library with components obtained from metabolically rich cells and identifying combinations which exhibit the desired activity. It has also been proposed (e.g., WO 98/58085) that clones with desired activities can be identified by inserting bioactive substrates into samples of the library, and detecting bioactive fluorescence corresponding to the product of a desired activity using a fluorescent analyzer, e.g., a flow cytometry device, a CCD, a fluorometer, or a spectrophotometer.

Libraries can also be biased towards nucleic acids which have specified characteristics, e.g., hybridization to a selected nucleic acid probe. For example, application WO 99/10539 proposes that polynucleotides encoding a desired activity (e.g., an enzymatic activity, for example: a lipase, an esterase, a protease, a glycosidase, a glycosyl transferase, a phosphatase, a kinase, an oxygenase, a peroxidase, a hydrolase, a hydratase, a nitrilase, a transaminase, an amidase or an acylase) can be identified from among genomic DNA sequences in the following manner. Single stranded DNA molecules from a population of genomic DNA are hybridized to a ligand-conjugated probe. The genomic DNA can be derived from either a cultivated or uncultivated microorganism, or from an environmental sample. Alternatively, the genomic DNA can be derived from a multicellular organism, or a tissue derived therefrom. Second strand synthesis can be conducted directly from the hybridization probe used in the capture, with or without prior release from the capture medium or by a wide variety of other strategies known in the art. Alternatively, the isolated single-stranded genomic DNA population can be fragmented without further cloning and used directly in, e.g., a recombination-based approach, that employs a single-stranded template, as described above.

In one such method the fragment population derived the genomic library(ies) is annealed with partial, or, often approximately full length ssDNA or RNA corresponding to the opposite strand. Assembly of complex chimeric genes from this population is then mediated by nuclease-based removal of non-hybridizing fragment ends, polymerization to fill gaps between such fragments and subsequent single stranded ligation. The parental strand can be removed by digestion (if RNA or uracil-containing), magnetic separation under denaturing conditions (if labeled in a manner conducive to such separation) and other available separation/purification methods. Alternatively, the parental strand is optionally co-purified with the chimeric strands and removed during subsequent screening and processing steps. As set forth in "Single-stranded nucleic acid template-mediated recombination and nucleic acid fragment isolation" by Affholter (U.S. Ser. No. 60/186,482, filed Mar. 2, 2000), recursive recombination using single-stranded templates and nucleic acids of interest which bind to a portion of the template can also be performed.

In one approach, single-stranded molecules are converted to double-stranded DNA (dsDNA) and the dsDNA molecules are bound to a solid support by ligand-mediated binding. After separation of unbound DNA, the selected DNA molecules are released from the support and introduced into a suitable host cell to generate a library enriched in sequences which hybridize to the probe. A library produced in this manner provides a desirable substrate for any of the recursive recombination reactions described herein.

"Non-Stochastic" methods of generating nucleic acids and polypeptides are alleged in Short "Non-Stochastic Generation of Genetic Vaccines and Enzymes" WO 00/46344. These methods, including proposed non-stochastic polynucleotide reassembly and site-saturation mutagenesis methods be applied to the present invention as well. Random or semi-random mutagenesis using doped or degenerate oligonucleotides is also described in, e.g., Arkin and Youvan (1992) *Biotechnology* 10:297-300; Reidhaar-Olson et al. (1991) *Methods Enzymol.* 208:564-86; Lim and Sauer (1991) *J Mo. Biol* 219:359-76; Breyer and Sauer (1989) *J Biol Chem* 264: 13355-60; and U.S. Pat. Nos. 5,830,650 and 5,798,208, and EP Patent 0527809 B1.

It will readily be appreciated that any of the above described techniques suitable for enriching a library prior to diversification can also be used to screen the products, or libraries of products, produced by the diversity generating methods.

Kits for mutagenesis, library construction and other diversity generation methods are also commercially available. For example, kits are available from, e.g., Stratagene (e.g., Quick-Change™ site-directed mutagenesis kit; and Chameleon™ double-stranded, site-directed mutagenesis kit), Bio/Can Scientific, Bio-Rad (e.g., using the Kunkel method described above), Boehringer Mannheim Corp., Clonetech Laboratories, DNA Technologies, Epicentre Technologies (e.g., 5 prime 3 prime kit); Genpak Inc, Lemargo Inc, Life Technologies (Gibco BRL), New England Biolabs, Pharmacia Biotech, Promega Corp., Quantum Biotechnologies, Amersham International plc (e.g., using the Eckstein method above), and Anglian Biotechnology Ltd (e.g., using the Carter/Winter method above).

The above references provide many mutational formats, including recombination, recursive recombination, recursive mutation and combinations or recombination with other forms of mutagenesis, as well as many modifications of these formats. Regardless of the diversity generation format that is used, the nucleic acids of the invention can be recombined (with each other, or with related (or even unrelated) sequences) to produce a diverse set of recombinant nucleic acids, including, e.g., sets of homologous nucleic acids, as well as corresponding polypeptides.

Other Polynucleotide Compositions

The invention also includes compositions comprising any two or more polynucleotides (e.g., 2 or more, 5 or more, or 20, 50, 100 or more, etc.) of the invention (e.g., as substrates for recombination). The composition can comprise a library of recombinant nucleic acids, where the library contains at least 2, at least 3, at least 5, at least 10, at least 20, or at least 50 or more nucleic acids. The nucleic acids are optionally cloned into expression vectors, providing expression libraries. Additionally, in various aspects the invention also includes fragments of polypeptides that have fumonisin and/or fumonisin-derivative detoxification activity.

The invention also includes compositions produced by digesting one or more polynucleotide of the invention with a restriction endonuclease, an RNAse, or a DNAse (e.g., as is performed in certain of the recombination formats noted above); and compositions produced by fragmenting or shearing one or more polynucleotide of the invention by mechanical means (e.g., sonication, vortexing, and the like), which can also be used to provide substrates for recombination in the methods above. Similarly, compositions comprising sets of oligonucleotides corresponding to more than one nucleic acid of the invention are useful as recombination substrates and are a feature of the invention. For convenience, these fragmented, sheared, or oligonucleotide synthesized mixtures are referred to as fragmented nucleic acid sets.

Also included in the invention are compositions produced by incubating one or more of the fragmented nucleic acid sets in the presence of ribonucleotide or deoxyribonucleotide triphosphates and a nucleic acid polymerase. This resulting composition forms a recombination mixture for many of the recombination formats noted above. The nucleic acid polymerase may be an RNA polymerase, a DNA polymerase, or an RNA-directed DNA polymerase (e.g., a "reverse transcriptase"); the polymerase can be, e.g., a thermostable DNA polymerase (such as, VENT, TAQ, or the like).

FD/FDD Homologue Polypeptides

The invention provides isolated or recombinant fumonisin detoxification or fumonisin-derivative detoxification homologue polypeptides, referred to herein as "FD/FDD homologue polypeptides" or "FD/FDD homologues." An isolated or recombinant FD/FDD homologue polypeptide of the invention includes a polypeptide comprising a sequence selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, and conservatively modified variations thereof.

In some aspects, the invention comprises an isolated or recombinant polypeptide that is at least about 70%, at least about 75%, at least about 80%, at least about 85%, at least about 90%, at least about 95%, at least about 96%, at least about 97%, at least about 98%, at least about 99%, or at least about 99.5%, or more identical to (or is substantially identical to, or comprises) one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 (e.g., to SEQ ID NO:50) over a comparison window of at least 100, at least 125, at least 150, at least 175, at least 200, at least 225, at least 250, at least 275, or at least 300 contiguous amino acids wherein the polypeptide has a fumonisin detoxification activity or a fumonisin derivative detoxification activity that is at least 1.5×, at least 2×, at least 5×, at least 10×, at least 15×, at least 20×, or at least 25× or more greater than any of the polypeptides corresponding to ESP002C2, ESP002C3, ESP003C12, RAT011C1, RAT011D2, RAT011C4, or wild-type APAO (i.e., as listed in SEQ ID NOs:51-64). Optionally, the above polypeptide displays its increased FD/FDD activity at pH 5.5 or has an optimum pH lower than that for the polypeptides encoded by SEQ ID NOs:51-64. Additionally, the above polypeptide displays a greater thermostability (i.e., a higher thermostability) than that of any of the polypeptides encoded by SEQ ID NOs:51-64 and/or optionally has increased FD/FDD activity upon secretion from a eukaryotic cell (e.g., a plant cell) relative to that activity of any polypeptide encoded by SEQ ID NOs:51-64. In some embodiments, the polypeptide comprises a leader sequence that directs secretion of the polypeptide from a plant cell (e.g., an apoplast targeting sequence, a peroxisomal targeting sequence, etc.), alternately and/or additionally, the polypeptide optionally comprises a polypeptide purification sequence.

Furthermore, in some embodiments, such above polypeptide is at least about 70%, at least about 75%, at least about 80%, at least about 85%, at least about 90%, at least about 95%, at least about 96%, at least about 97%, at least about 98%, at least about 99%, or at least about 99.5%, or more identical to or is substantially identical to, or is chosen from any one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. Such polypeptide is also, in some embodiments encoded by a polynucleotide selected from SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126. The FD/FDD activity of such polypeptide is, in typical embodiments, the ability to deaminate fumonisin and/or fumonisin derivatives (e.g., fumonisin B1, fumonisin B2, fumonisin B3, fumonisin H4, fumonisin C1, or a structural analog, etc.), i.e., the polypeptide is a fumonisin amine oxidase. In yet other embodiments, the above polypeptide of the invention displays one or more of: a $k_{cat}$ (optionally at pH 5.5) greater than, or higher than the $k_{cat}$ of any of the polypeptides encoded by SEQ ID NOs:51-64; a $K_M$ value (optionally at pH 5.5) lower than the $K_M$ value of any of the polypeptides encoded by SEQ ID NOs:51-64; or a $k_{cat}/K_M$ value higher than, or greater than the $k_{cat}/K_M$ value of any of the polypeptides encoded by SEQ ID NOs:51-64 when catalyzing a fumonisin or fumonisin-detoxification reaction (e.g., a fumonisin deamination reaction).

In some optional embodiments of the invention, the above polypeptide comprises variants wherein one or more amino acid has been mutated. In yet other embodiments, the above polypeptide comprises an alanine residue at position 118, a serine residue at position 136, a phenylalanine reside at position 209, a lysine residue at position 210, an isoleucine residue at position 237, a glutamic acid residue at position 272, a proline residue at position 274, and a glutamic acid residue at position 473, wherein the recited positions refer to amino acid positions in the polypeptide of the wild type APAO enzyme (SEQ ID NO: 52). In yet other embodiments, the above polypeptide comprises an aspartic acid residue at position 193.

In some embodiments, the alteration of residue 193 can optionally change enzymatic performance of the polypeptide (e.g., $k_{cat}$ of a fumonisin detoxification reaction, such as fumonisin deamination, catalyzed by the polypeptide can be changed). For example, an aspartic acid at residue 193 (as opposed to an asparagine at residue 193, as is found in wild-type APAO, see SEQ ID NO: 52) optionally leads to an increased $k_{cat}$ of the fumonisin detoxification (deamination) reaction. Some embodiments of the current invention also comprise polypeptides with an altered glycosylation site.

Methods of Use of FD/FDD Polypeptides

The polypeptides of the current invention are useful in numerous ways. For example, a method of detoxifying, degrading, neutralizing, deaminating, or modifying at least one mycotoxin or mycotoxin derivative through incubation of such mycotoxin with at least one polypeptide of the invention (as described herein) where such polypeptide detoxifies, degrades, neutralizes, deaminates, or modifies the mycotoxin/mycotoxin-derivative is an optional feature of the invention. This optionally includes wherein the mycotoxin is a fumonisin, a fumonisin-derivative and/or a fumonisin analogue and wherein such mycotoxin is present in harvested foodstuffs (e.g., grain), unharvested foodstuffs (e.g., crops/plants in field, etc.), silage, etc. and also wherein the degradation/detoxification occurs during harvesting, processing, or storage, of the material.

Other features of the invention illustrating (non-limiting) uses of the polynucleotides/polypeptides of the invention can be found sic passim (see, e.g., In vivo Uses, supra).

Further aspects of the invention include a method of reducing pathogenicity of a fungus producing fumonisin comprising: a) providing a transgenic cell with any nucleic acid of the invention operably linked to a promoter wherein the nucleic acid is heterologous to the cell, and b) expressing the nucleic acid at a level effective to detoxify the fumonisin, thereby reducing the pathogenicity of the fungus. Such method also optionally comprises wherein the cell is a plant cell in a plant and wherein the cell is a microorganism and wherein the cell comprises a fumonisin esterase encoding polynucleotide operably linked to a promoter.

Another feature of the invention includes a method of detecting fumonisins comprising: a) introducing any polypeptide of the invention into a sample containing fumonisin, b) allowing the polypeptide to catalyze the deamination of fumonisin, and c) detecting a product of the deamination reaction. Such methods are especially useful in detecting contamination of foodstuffs by fumonisin producing fungi (e.g., *Fusarium moniliforme* or *F. proliferatum*), since, as detailed above, such contamination can have severe health consequences to animals and humans who consume contaminated products. Additionally since mycotoxin contaminated products are monitored/controlled, discovery of contamination can present monetary savings as well (e.g., detection of contaminated corn prevents purchase of such).

The FD/FDD polypeptides of the current invention are also optionally used in conjunction with other enzymes to help in detoxification/degradation/etc. of mycotoxins (e.g., fumonisin, etc.). For example, fumonisin esterase, which reduces, but does not eliminate the toxicity of fumonisin can optionally be used in combination with the FD/FDD polypeptides of the invention. The fumonisin esterase converts, e.g., FB1 into AP1, which is also a target for the deamination action of the FD/FDD polypeptides of the invention. Such optional combinations of enzymes (e.g., FD/FDD enzymes and fumonisin esterase) can be co-expressed in an expression system or they can be expressed separately and applied sequentially or in combination to such things as grains, crops, etc.

Another feature of the invention comprises a method of use, as described supra, wherein the FD/FDD polypeptides of the invention are used to decontaminate foodstuffs (e.g., grain) prior to use/consumption of such. The decontamination optionally occurs during the processing of the foodstuff, during processing of a plant material for silage, or during the growth of a crop (e.g., while the crop/plant is still in field, etc.). Such methods optionally comprise presenting the FD/FDD enzymes to the foodstuff/plant/etc. at an appropriate stage in the process/growth cycle/harvest period and in an amount effective to achieve the desired goal (i.e., in an amount effective to reduce and/or eliminate the contamination).

Yet other methods featured in the current invention comprise treatment of foodstuffs/silage/crop plants with microorganisms which comprise the FD/FDD homologues of the invention and which optionally express the same. For example, various bacteria, yeasts, etc. are capable of being engineered with the FD/FDD homologues of the invention and then inducibly and/or constitutively expressing such polypeptides. These microorganisms are optionally sprayed or inoculated (here meaning deposition of a microorganism which will multiply on, or within, the plant/seed/etc.) onto crops/plants/seeds/etc. where they optionally express (and optionally secrete extracellularly), the FD/FDD homologues of the invention, thereby detoxifying fumonisin on/in the plant or seed, etc. The microorganisms used can optionally be deposited in a suspended liquid form, a lyophilized dust form, or any other convenient manner to effectively coat/inoculate the plant/seed with the FD/FDD expressing microorganism at the appropriate time. A number of suitable microorganisms are known to those skilled in the art, and selection of the appropriate microorganism will vary depending upon, e.g., the type of plant/seed to be protected, the environmental conditions present, etc.

Additionally, the current invention comprises methods for production of ruminant microorganisms which contain and optionally express the FD/FDD polypeptides of the invention. Such microorganisms are optionally inoculated into, e.g., silage, etc. to act as a ruminant inoculate so as to protect animals from fumonisin poisoning.

Another feature of the invention comprises methods of use of the FD/FDD polypeptides of the invention in detection of fumonisins and fumonisin-derivatives/analogs. For example, putatively contaminated grain can optionally be tested and any amount of contamination optionally quantified through use of the FD/FDD polypeptides herein. Through determination and measurement of the end products, etc. from fumonisin degradation (see, description of assays, infra) the amount of fumonisin contamination in a sample can be determined.

Making Polypeptides

Recombinant methods for producing and isolating FD/FDD homologue polypeptides of the invention are described above. In addition to recombinant production, the polypeptides may be produced by direct peptide synthesis using solid-phase techniques (see, e.g., Stewart et al. (1969) Solid-Phase Peptide Synthesis, WE Freeman Go, San Francisco; Merrifield J (1963) J Am Chem Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide full-length FD/FDD homologues or fragments thereof. Alternately, such sequences may be ordered from any number of companies which specialize in production of polypeptides. Most commonly FD/FDD polypeptides are produced by expressing coding nucleic acids and recovering polypeptides, e.g., as described above. For example, one feature of the current invention is a method of producing a polypeptide through: a) introducing into a population of cells (e.g., plant cells, yeasts, etc.) any nucleic acid of the invention as described herein (e.g., any of SEQ ID NOs:1-25, SEQ ID NOs:67-69, and SEQ ID NOs:84, 86, 88, 90, 92, 94, 96, 98, 100, 102, 104, 106, 108, 110, 112, 114, 116, 118, 120, 122, 124, and 126 or fragments/modifications/complements thereof) which is operably linked to a regulatory sequence effective to produce the encoded polypeptide, b) culturing the cells in a culture medium to produce the polypeptide, and c) isolating the polypeptide from the cells or culture medium.

Using Polypeptides

Antibodies

In another aspect of the invention, an FD/FDD homologue polypeptide of the invention is used to produce antibodies which have, e.g., diagnostic uses, e.g., related to the activity, distribution, and expression of FD/FDD homologues, e.g. in various tissues of a transgenic plant.

Other optional embodiments of the invention comprise polypeptides that are specifically bound by polyclonal antisera raised against one or more antigen from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 (or a fragment thereof), wherein the antisera is subtracted with one of more polypeptide from SEQ ID NOs:51-64. Additionally, the invention also optionally includes polypeptides which comprise a unique subsequence in a polypeptide selected from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, wherein the subsequence is unique as compared to a polypeptide corresponding to any of SEQ ID NOs:51-64.

Antibodies to FD/FDD homologues of the invention may be generated by methods well known in the art. Such antibodies may include, but are not limited to, polyclonal, monoclonal, chimeric, humanized, single chain, Fab fragments and fragments produced by a Fab expression library.

FD/FDD homologue polypeptides for antibody induction do not require biological activity; however, the polypeptide or oligopeptide are antigenic. Peptides used to induce specific antibodies may have an amino acid sequence consisting of at least 10 amino acids, preferably at least 15 or 20 amino acids. Short stretches of an FD/FDD homologue polypeptide may be fused with another protein, such as keyhole limpet hemocyanin, and antibody produced against the chimeric molecule.

Methods of producing polyclonal and monoclonal antibodies are known to those of skill in the art, and many antibodies are available. See, e.g., Coligan (1991) *Current Protocols in Immunology* Wiley/Greene, N.Y.; and Harlow and Lane (1989) *Antibodies: A Laboratory Manual*, Cold Spring Harbor Press, NY (hereinafter "Harlow and Lane"); Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256:495-497. Other suitable techniques for antibody preparation include selection of libraries of recombinant antibodies in phage or similar vectors. See, Huse et al. (1989) *Science* 246:1275-1281; and Ward et al. (1989) *Nature* 341:544-546. Specific monoclonal and polyclonal antibodies and antisera will usually bind with a $K_D$ of at least about 0.1 µM, preferably at least about 0.01 µM or better, and most typically and preferably, 0.001 µM or better.

Additional details about antibody production and engineering techniques can be found in Borrebaeck (ed.) (1995) *Antibody Engineering, 2$^{nd}$ Edition*, Freeman and Company, NY; McCafferty et al. (1996) *Antibody Engineering, A Practical Approach* IRL at Oxford Press, Oxford, England; and Paul (1995) *Antibody Engineering Protocols* Humana Press, Towata, N.J.

Defining Polypeptides by Immunoreactivity

Because the polypeptides of the invention provide a variety of new polypeptide sequences as compared to other FD/FDD homologues, the polypeptides also provide new structural features which can be recognized, e.g., in immunological assays. The generation of antisera which specifically binds the polypeptides of the invention, as well as the polypeptides which are bound by such antisera, are a feature of the invention.

The invention includes FD/FDD homologue proteins that specifically bind to or that are specifically immunoreactive with an antibody or antisera generated against an immunogen comprising an amino acid sequence selected from one or more of SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127. To eliminate cross-reactivity with other polypeptides, the cross-reactive antibody or antisera is removed from the antisera by, for example, immunosorption with polypeptides encoded by sequences such as those represented by clone numbers ESP002C2, ESP002C3, ESP003C12, RAT011C1, RAT011C2, RAT011C4 from PCT publications WO 00/04159 and WO 00/04160 or wild-type APAO (SEQ ID NO:52) or by similar homologous mycotoxin detoxifying molecules found in, e.g., GenBank (the polypeptides). Where the accession number corresponds to a nucleic acid, a polypeptide encoded by the nucleic acid is generated and used for antibody/antisera subtraction purposes. Where the nucleic acid corresponds to a non-coding sequence, e.g., a pseudo gene, an amino acid which corresponds to the reading frame of the nucleic acid is generated (e.g., synthetically), or is minimally modified to include a start codon, promoter or the like for recombinant production.

In one typical format, the immunoassay uses a polyclonal antiserum which was raised against one or more polypeptide comprising one or more of the sequences corresponding to one or more of: SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127, or a substantial subsequence thereof (i.e., at least about 30% of the full length sequence provided). The full set of potential polypeptide immunogens derived from SEQ ID NOs:26-50, SEQ ID NOs:70-72, and SEQ ID NOs:85, 87, 89, 91, 93, 95, 97, 99, 101, 103, 105, 107, 109, 111, 113, 115, 117, 119, 121, 123, 125, and 127 are collectively referred to below as "the immunogenic polypeptides." The resulting antisera is optionally selected to have low cross-reactivity against the control polypeptides (e.g., ESP002C2, ESP002C3, ESP003C12, RAT011C1, RAT011C2, RAT011C4 and wild type APOA) and any other known related polypeptides and any such cross-reactivity is removed by immunoabsorbtion with one or more of the control polypeptides, prior to use of the polyclonal antiserum in the immunoassay. Sequences which are substantially identical to such sequences can also be used, e.g., which are about 80%, about 90%, about 95%, about 98%, about 99%, about 99.5% or more identical, e.g., as determined using BLAST or the other algorithms described above, e.g., using default parameters.

In order to produce antisera for use in an immunoassay, one or more of the immunogenic polypeptides is produced and purified as described herein. For example, recombinant protein may be produced in a bacterial cell line. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, Harlow and Lane for a standard description of antibody generation, immunoassay formats and conditions that can be used to determine specific immunoreactivity). Alternatively, one or more synthetic or recombinant polypeptide derived from the sequences disclosed herein is conjugated to a carrier protein and used as an immunogen.

Polyclonal sera are collected and titered against the immunogenic polypeptide in an immunoassay, for example, a solid phase immunoassay with one or more of the immunogenic proteins immobilized on a solid support. Polyclonal antisera with a titer of $10^6$ or greater are selected, pooled and subtracted with the control polypeptides, e.g. those identified from, e.g., GenBank or elsewhere as per above, to produce subtracted pooled titered polyclonal antisera.

The subtracted, pooled, titered polyclonal antisera are tested for cross reactivity against the control polypeptides. Preferably at least two of the immunogenic FD/FDD homologues are used in this determination, preferably in conjunction with at least two of the control polypeptides, to identify antibodies which are specifically bound by the immunogenic protein(s).

In this comparative assay, discriminatory binding conditions are determined for the subtracted, titered polyclonal antisera which result in at least about a 5-10 fold higher signal to noise ratio for binding of the titered polyclonal antisera to the immunogenic FD/FDD homologues as compared to binding to any of the control polypeptides. That is, the stringency of the binding reaction is adjusted by the addition of non-specific competitors such as albumin or non-fat dry milk, or by adjusting salt conditions, temperature, or the like. These binding conditions are used in subsequent assays for determining whether a test polypeptide is specifically bound by the pooled, subtracted polyclonal antisera. In particular, test polypeptides which show at least a 2-5× higher signal to noise ratio than the control polypeptides under discriminatory binding conditions, and at least about a one-half signal to noise ratio as compared to the immunogenic polypeptide(s), share substantial structural similarity with the immunogenic polypeptide as compared to known FD/FDD polypeptides, and are, therefore polypeptides of the invention.

In another example, immunoassays in the competitive binding format are used for detection of a test polypeptide. For example, as noted, cross-reacting antibodies are removed from the pooled antisera mixture by immunoabsorbtion with control polypeptides. The immunogenic polypeptide(s) are then immobilized to a solid support which is exposed to the subtracted, pooled antisera. Test proteins are added to the assay to compete for binding to the pooled, subtracted antisera. The ability of the test protein(s) to compete for binding to the pooled, subtracted antisera as compared to the immobilized protein(s) is compared to the ability of the immunogenic polypeptide(s) added to the assay to compete for binding (the immunogenic polypeptides compete effectively with the immobilized immunogenic polypeptides for binding to the pooled antisera). The percent cross-reactivity for the test proteins is calculated, using standard calculations.

In a parallel assay, the ability of the control proteins to compete for binding to the pooled, subtracted antisera is determined as compared to the ability of the immunogenic polypeptide(s) to compete for binding to the antisera. Again, the percent cross-reactivity for the control polypeptides is calculated, using standard calculations. Where the percent cross-reactivity is at least 5-10× as high for the test polypeptides, the test polypeptides are said to specifically bind the pooled, subtracted antisera.

In general, the immunoabsorbed and pooled antisera can be used in a competitive binding immunoassay as described herein to compare any test polypeptide to the immunogenic polypeptide(s). In order to make this comparison, the two polypeptides are each assayed at a wide range of concentrations and the amount of each polypeptide required to inhibit 50% of the binding of the subtracted antisera to the immobilized protein is determined using standard techniques. If the amount of the test polypeptide required is less than twice the amount of the immunogenic polypeptide that is required, then the test polypeptide is said to specifically bind to an antibody generated to the immunogenic protein, provided the amount is at least about 5-10× as high as for a control polypeptide.

As a final determination of specificity, the pooled antisera is optionally fully immunosorbed with the immunogenic polypeptide(s) (rather than the control polypeptides) until little or no binding of the resulting immunogenic polypeptide subtracted, pooled antisera to the immunogenic polypeptide(s) used in the immunosorbtion is detectable. This fully immunosorbed antisera is then tested for reactivity with the test polypeptide. If little or no reactivity is observed (i.e., no more than 2× the signal to noise ratio observed for binding of the fully immunosorbed antisera to the immunogenic polypeptide), then the test polypeptide is specifically bound by the antisera elicited by the immunogenic protein.

Detoxification Properties of FD/FDD Homologues

Assays for Fumonisin Inactivation

Screening for the presence of fumonisin detoxification or fumonisin-derivative detoxification capability can be done in a number of ways.

It is possible to directly select the clones expressing an FD/FDD protein by using, e.g., a yeast strain, if the yeast is susceptible to the compound. For example, Kimura et al (1997) *J Biol Chem* 273(3):1654-1661, describe expression of a mycotoxin detoxifying gene in yeast and selection of the yeast containing such gene in medium containing a potent mycotoxin. This same assay format can be used for any mycotoxin or mycotoxin-derivative which is toxic to yeast, or inhibitory to yeast growth on a medium (i.e., fumonisin or fumonisin-derivative). Similarly, such assays can be performed using any of a variety of other cultured cells, by growing the cells (e.g., prokaryotic or eukaryotic cells) in the presence of a mycotoxin (i.e., fumonisin). Additionally, cells or organisms can be cultured or grown on media wherein, e.g., FB1 is the sole nitrogen source. Thus, only cells or organisms capable of utilizing, e.g., FB1 are able to grow.

In general, the culture of cells, including yeast, animal cells, plant cells and the like are well known and are discussed in detail supra and in references supra. It will be appreciated that it is desirable to transform plant cells with fumonisin or fumonisin-derivative resistant nucleic acids in order to reduce food contamination by such mycotoxins and their derivatives and to improve plant resistance to such mycotoxins and their derivatives, e.g., to enhance yield. Accordingly, it can be convenient to screen for fumonisin detoxification or fumonisin-derivative detoxification using plant cells in culture which correspond to the plant which is desired to be transformed.

If the oxidized products of the detoxification reaction are fluorescent, clones having fumonisin detoxification or fumonisin-detoxification activity are detected by fluorescence of specific molecules resulting from the detoxification. The intensity of fluorescence may help select clones having higher activity (or higher expression). Example 1 illustrates the use of fluorescence to monitor FD/FDD activity using horse radish peroxidase and Amplex Red. See, infra.

Clones expressing the FD/FDD nucleic acids of the invention can be examined for detoxification activity against one or more than one mycotoxin (i.e., fumonisin) in pools of 10, in order to prescreen the initial transformants rapidly. Any pools showing significant activity can be deconvoluted to identify single desirable clones with high activity and/or broad specificity.

Some types of FD/FDD activity can be monitored by HPLC, gas chromatography and mass spectroscopy (MS), as well as a variety of other analytical methods available to one of skill. Incorporation of radio-labeled molecules can be monitored directly by mass shift by MS methods and by an appropriate radioisotope detector with HPLC and GC devices. In a high throughput modality, a method of choice is high throughput MS, or MS with an electron spray-based detection method.

In addition, formation of by-products or end-products of fumonisin detoxification or fumonisin-derivative detoxification can be indirectly measured by various reactive colorimetric reactions through the use of a number of commercially available reactive dyes.

As is apparent from the foregoing, the relevant assay will depend on the application. Many assay formats are suitable for many applications. Advantageously, any of the assays can be practiced in a high-throughput format.

In high throughput assays, it is possible to screen up to several thousand different FD/FDD variants in a single day. For example, each well of a microtiter plate can be used to run a separate assay, or, if concentration or incubation time effects are to be observed, every 5-10 wells can test a single variant. Thus, a single standard microtiter plate can assay about 100 (e.g., 96) FD/FDD reactions. If 1536 well plates are used, then a single plate can easily accommodate from about 100 to about 1500 different reactions; it is possible to assay several different plates per day. Assay screens for up to about 6,000-20,000 different assays, (i.e., involving different nucleic acids, encoded proteins, concentrations, etc.) can also be used. Microfluidic approaches to reagent manipulation also have been developed, e.g., by Caliper Technologies (Mountain View, Calif.).

In addition to fluidic approaches, it is possible, as mentioned above, simply to grow cells on plates of agar which contain fumonisins or fumonisin-derivatives. Cells which have FD/FDD activity (i.e., due to transformation with FD/FDD nucleic acids of the invention) are able to grow on the plates. This approach offers a simple and high-throughput screening method.

The ability to detect a subtle increase in the performance of an FD/FDD sequence over that of a parent strain relies on the sensitivity of the assay. The chance of finding the organisms having an improvement in FD/FDD activity is increased by the number of individual mutants that can be screened by the assay. To increase the chances of identifying a pool of sufficient size, a prescreen that increases the number of mutants processed by 10-fold can be used. The goal of the primary screen will be to quickly identify mutants having equal or better product titers than the parent strain(s) and to move only these mutants forward to liquid cell culture for subsequent analysis.

A number of well known robotic systems have also been developed for solution phase chemistries useful in assay systems. These systems include automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a scientist. Any of the above devices are suitable for use with the FD/FDD homologues of the present invention. The nature and implementation of modifications to these devices (if any) so that they can operate as discussed herein with reference to the integrated system will be apparent to persons skilled in the relevant art.

High throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for the various high throughput devices. Thus, for example, Zymark Corp. provides technical bulletins describing screening systems for detecting the modulation of gene transcription, ligand binding, and the like. Microfluidic approaches to reagent manipulation have also been developed, e.g., by Caliper Technologies (Mountain View, Calif.).

Optical images viewed (and, optionally, recorded) by a camera or other recording device (e.g., a photodiode and data storage device) are optionally further processed in any of the embodiments herein, e.g., by digitizing the image and/or storing and analyzing the image on a computer. As noted above, in some applications, if FD/FDD products are fluorescent, then optical detection approaches can be appropriate. A variety of commercially available peripheral equipment and software is available for digitizing, storing and analyzing a digitized video or digitized optical image, e.g., using PC (Intel x86 or pentium chip compatible DOS™, OS™ WINDOWS™, WINDOWS NT™ or WINDOWS 95™ based machines), MACINTOSH™, or UNIX based (e.g., SUN™ work station) computers.

One conventional system carries light from the assay device to a cooled charge-coupled device (CCD) camera, a common use in the art. A CCD camera includes an array of picture elements (pixels). The light from the specimen is imaged on the CCD. Particular pixels corresponding to regions of the specimen (e.g., individual hybridization sites on an array of biological polymers) are sampled to obtain light intensity readings for each position. Multiple pixels are processed in parallel to increase speed. The apparatus and methods of the invention are easily used for viewing any sample, e.g. by fluorescent or dark field microscopic techniques.

Integrated systems for analysis in the present invention typically include a digital computer with high-throughput liquid control software, image analysis software, data interpretation software, a robotic liquid control armature for transferring solutions from a source to a destination operably linked to the digital computer, an input device (e.g., a computer keyboard) for entering data to the digital computer to control high throughput liquid transfer by the robotic liquid control armature and, optionally, an image scanner for digitizing label signals from labeled assay components. The image scanner interfaces with the image analysis software to provide a measurement of optical intensity. Typically, the intensity measurement is interpreted by the data interpretation software to show whether the FD/FDD products are produced.

In one set of assays, the relative toxicity of fumonisin products produced by modification of FD/FDD enzymes is determined. In particular, toxicity can be evaluated in any of the usual assays for fumonisin toxicity and, optionally, compared to the toxicity of the unmodified fumonisin. In the event that toxicity is reduced, secondary toxic effects of detoxification products can be evaluated using the usual assays for fumonisin activity, or using additional assays such as cell survival assays, e.g., in the presence of increasing levels of the secondary product. This secondary assay helps to determine which FD/FDD activities are most desirable, i.e., using secondary toxicities of fumonisin or fumonisin-derivative metabolites as a measure of unwanted toxicity.

Integrated Systems

The present invention provides computers, computer readable media and integrated systems comprising character strings corresponding to the sequence information herein for the polypeptides and nucleic acids herein, including, e.g., those sequences listed herein and the various silent substitutions and conservative substitutions thereof.

Various methods and genetic algorithms (GOs) known in the art can be used to detect homology or similarity between different character strings, or can be used to perform other desirable functions such as to control output files, provide the basis for making presentations of information including the sequences and the like. Examples include BLAST, discussed supra.

Thus, different types of homology and similarity of various stringency and length can be detected and recognized in the integrated systems herein. For example, many homology determination methods have been designed for comparative analysis of sequences of biopolymers, for spell-checking in word processing, and for data retrieval from various databases. With an understanding of double-helix pair-wise complement interactions among 4 principal nucleobases in natural polynucleotides, models that simulate annealing of complementary homologous polynucleotide strings can also be used as a foundation of sequence alignment or other operations typically performed on the character strings corresponding to the sequences herein (e.g., word-processing manipulations, construction of figures comprising sequence or subsequence character strings, output tables, etc.). An example of a software package with GOs for calculating sequence similarity is BLAST, which can be adapted to the present invention by inputting character strings corresponding to the sequences herein.

Similarly, standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention by inputting a character string corresponding to the FD/FDD homologues of the invention (either nucleic acids or proteins, or both). For example, the integrated systems can include the foregoing software having the appropriate character string information, e.g., used in conjunction with a user interface (e.g., a GUI in a standard operating system such as a Windows, Macintosh or LINUX system) to manipulate strings of characters. As noted, specialized alignment programs such as BLAST can also be incorporated into the systems of the invention for alignment of nucleic acids or proteins (or corresponding character strings).

Integrated systems for analysis in the present invention typically include a digital computer with GO software for aligning sequences, as well as data sets entered into the software system comprising any of the sequences herein. The computer can be, e.g., a PC (Intel x86 or Pentium chip-compatible DOS™, OS2™ WINDOWS™ WINDOWS NT™, WINDOWS95™, WINDOWS98™ LINUX based machine, a MACINTOSH™, Power PC, or a UNIX based (e.g., SUN™ work station) machine) or other commercially common computer which is known to one of skill. Software for aligning or otherwise manipulating sequences is available, or can easily be constructed by one of skill using a standard programming language such as Visualbasic, Fortran, Basic, Java, or the like.

Any controller or computer optionally includes a monitor which is often a cathode ray tube ("CRT") display, a flat panel display (e.g., active matrix liquid crystal display, liquid crystal display), or others. Computer circuitry is often placed in a box which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user and for user selection of sequences to be compared or otherwise manipulated in the relevant computer system.

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation.

The software can also include output elements for controlling nucleic acid synthesis (e.g., based upon a sequence or an alignment of a sequence herein) or other operations which occur downstream from an alignment or other operation performed using a character string corresponding to a sequence herein.

In an additional aspect, the present invention provides kits embodying the methods, compositions, systems and apparatus herein. Kits of the invention optionally comprise one or more of the following: (1) an apparatus, system, system component or apparatus component as described herein; (2) instructions for practicing the methods described herein, and/or for operating the apparatus or apparatus components herein and/or for using the compositions herein; (3) one or more FD/FDD composition or component; (4) a container for holding components or compositions, and, (5) packaging materials.

In a further aspect, the present invention provides for the use of any apparatus, apparatus component, composition or kit herein, for the practice of any method or assay herein, and/or for the use of any apparatus or kit to practice any assay or method herein.

Below is a table of the clones and sequence identifiers for the polynucleotide and polypeptide sequences of the instant invention.

TABLE 3

Clones and Sequence Identifiers for the Sequences of the Invention

| SEQ ID NO: | Clone ID | SEQ ID NO: | Clone ID |
|---|---|---|---|
| SEQ ID NO:1 | A5 | SEQ ID NO:26 | A5 |
| SEQ ID NO:2 | D5 | SEQ ID NO:27 | D5 |
| SEQ ID NO:3 | F7 | SEQ ID NO:28 | F7 |
| SEQ ID NO:4 | F12 | SEQ ID NO:29 | F12 |
| SEQ ID NO:5 | G11 | SEQ ID NO:30 | G11 |
| SEQ ID NO:6 | R3H1 | SEQ ID NO:31 | R3H1 |
| SEQ ID NO:7 | 3B12 | SEQ ID NO:32 | 3B12 |

TABLE 3-continued

Clones and Sequence Identifiers
for the Sequences of the Invention

| SEQ ID NO: | Clone ID | SEQ ID NO: | Clone ID |
|---|---|---|---|
| SEQ ID NO:8 | 4F13G12 | SEQ ID NO:33 | 4F13G12 |
| SEQ ID NO:9 | 4F15A11 | SEQ ID NO:34 | 4F15A11 |
| SEQ ID NO:10 | 4F15C3 | SEQ ID NO:35 | 4F15C3 |
| SEQ ID NO:11 | 4F16C6 | SEQ ID NO:36 | 4F16C6 |
| SEQ ID NO:12 | 4F19F2 | SEQ ID NO:37 | 4F16F2 |
| SEQ ID NO:13 | 4F21C8 | SEQ ID NO:38 | 4F21C8 |
| SEQ ID NO:14 | 4F22B2 | SEQ ID NO:39 | 4F22B2 |
| SEQ ID NO:15 | 4F24F2 | SEQ ID NO:40 | 4F24F2 |
| SEQ ID NO:16 | 4F28G1 | SEQ ID NO:41 | 4F28G1 |
| SEQ ID NO:17 | 4F2G10 | SEQ ID NO:42 | 4F2G10 |
| SEQ ID NO:18 | 4F3B5 | SEQ ID NO:43 | 4F3B5 |
| SEQ ID NO:19 | 4F6A11 | SEQ ID NO:44 | 4F6A11 |
| SEQ ID NO:20 | 6F2J12 | SEQ ID NO:45 | 6F2J12 |
| SEQ ID NO:21 | TrR3H1 | SEQ ID NO:46 | TrR3H1 |
| SEQ ID NO:22 | G6 | SEQ ID NO:47 | G6 |
| SEQ ID NO:23 | H8 | SEQ ID NO:48 | H8 |
| SEQ ID NO:24 | E7 | SEQ ID NO:49 | E7 |
| SEQ ID NO:25 | B6 | SEQ ID NO:50 | B6 |

TABLE 3-continued

Clones and Sequence Identifiers
for the Sequences of the Invention

| SEQ ID NO: | Clone ID | SEQ ID NO: | Clone ID |
|---|---|---|---|
| SEQ ID NO:51 | WT-APAO Esp001 | SEQ ID NO:52 | WT-APAO Esp001 |
| SEQ ID NO:53 | esp002C2 | SEQ ID NO:54 | esp002C2.pro |
| SEQ ID NO:55 | esp002c3 | SEQ ID NO:56 | esp002C3.pro |
| SEQ ID NO:57 | esp003C12 | SEQ ID NO:58 | esp003C12.pro |
| SEQ ID NO:59 | RAT011C1 | SEQ ID NO:60 | rat011C1.pro |
| SEQ ID NO:61 | RAT011C2 | SEQ ID NO:62 | rat011C2.pro |
| SEQ ID NO:63 | RAT011C4 | SEQ ID NO:64 | RAT011C4 |
| SEQ ID NO:65 | APAO(B6)Glyc- | SEQ ID NO:66 | APAO(B6)Glyc- (polypeptide) |
| SEQ ID NO:67 | 2E8 | SEQ ID NO:68 | 6E9 |
| SEQ ID NO:69 | R3H1F | SEQ ID NO:70 | 2E8 (amino acid) |
| SEQ ID NO:71 | 6E9 (AMINO ACID) | SEQ ID NO:72 | R3H1 (amino acid) |
| SEQ ID NO:73 | Altered glycosylation site | SEQ ID NO:74 | Nucleotides 1-15 of SEQ ID NO:1 |
| SEQ ID NO:75 | Silent variation of SEQ ID NO:74 | SEQ ID NO:76 | Amino Acids 1-5 of SEQ ID NO:26 |
| SEQ ID NO:77 | Amino Acids 1-26 of SEQ ID NO:26 | SEQ ID NO:78 | Conservative substitution variant of SEQ ID NO:77 |
| SEQ ID NO:79 | Conservative substitution variant of SEQ ID NO:77 | SEQ ID NO:80 | barley alpha amylase signal sequence DNA |
| SEQ ID NO:81 | barley alpha-amylase type B isozyme mRNA | SEQ ID NO:82 | translation of barley alpha amylase signal sequence |
| SEQ ID NO:83 | translation of barley alpha amylase type B isozyme mRNA | | |
| SEQ ID NO:84 | 1B5 | SEQ ID NO:85 | 1B5 |

TABLE 3-continued

Clones and Sequence Identifiers
for the Sequences of the Invention

| SEQ ID NO: | Clone ID | SEQ ID NO: | Clone ID |
|---|---|---|---|
| SEQ ID NO:86 | 4A9 | SEQ ID NO:87 | 4A9 |
| SEQ ID NO:88 | 4B11 | SEQ ID NO:89 | 4B11 |
| SEQ ID NO:90 | 4D11 | SEQ ID NO:91 | 4D11 |
| SEQ ID NO:92 | 5A3 | SEQ ID NO:93 | 5A3 |
| SEQ ID NO:94 | 5G10 | SEQ ID NO:95 | 5G10 |
| SEQ ID NO:96 | 6B11 | SEQ ID NO:97 | 6B11 |
| SEQ ID NO:98 | 6B3 | SEQ ID NO:99 | 6B3 |
| SEQ ID NO:100 | 7A5 | SEQ ID NO:101 | 7A5 |
| SEQ ID NO:102 | 7B8 | SEQ ID NO:103 | 7B8 |
| SEQ ID NO:104 | 7C10 | SEQ ID NO:105 | 7C10 |
| SEQ ID NO:106 | 7E9 | SEQ ID NO:107 | 7E9 |
| SEQ ID NO:108 | 9A2 | SEQ ID NO109: | 9A2 |
| SEQ ID NO:110 | 9B10 | SEQ ID NO:111 | 9B10 |
| SEQ ID NO:112 | 9B8 | SEQ ID NO:113 | 9B8 |
| SEQ ID NO:114 | 9C5 | SEQ ID NO:115 | 9C5 |
| SEQ ID NO:116 | 9C7 | SEQ ID NO:117 | 9C7 |
| SEQ ID NO:118 | 9D3 | SEQ ID NO:119 | 9D3 |
| SEQ ID NO:120 | 9D9 | SEQ ID NO:121 | 9D9 |

TABLE 3-continued

Clones and Sequence Identifiers
for the Sequences of the Invention

| SEQ ID NO: | Clone ID | SEQ ID NO: | Clone ID |
|---|---|---|---|
| SEQ ID NO:122 | 9F2 | SEQ ID NO:123 | 9F2 |
| SEQ ID NO:124 | 9F3 | SEQ ID NO:125 | 9F3 |
| SEQ ID NO:126 | 9G10 | SEQ ID NO:127 | 9G10 |

EXAMPLES

The following examples are illustrative and not limiting. One of skill will recognize a variety of non-critical parameters that can be altered to achieve essentially similar results.

Example I

Construction and Characterization of Novel FD/FDD Molecules

Novel FD/FDD molecules were constructed which have altered enzymatic activity against FB1 and/or AP1 as compared to the activity of wild-type E. spinifera APAO against FB1 and/or AP1.

Molecules of FD/FDD were generated using methods described in patent applications and patents indicated sic passim, each of which is incorporated herein by reference in its entirety for all purposes. The new FD/FDD constructs displayed diverse amino acid and nucleotide differences from, e.g., wild-type E. spinifera APAO (SEQ ID NOs:51-52) as well as displaying altered enzymatic parameters against FB1 and/or AP1. See, FIGS. 1, 2, 5, 7, and 8.

In order to mimic the conditions of maize apoplasts the enzymatic turnover experiments were performed in the following buffer at pH 5.5: 50 mM MES (K salt) (MES being 2-N-morpholino-ethane sulfonic acid), 2 mM $Na_2PO_4$, 1 mM $NH_4NO_3$, 1 mM $CaCl_2$, and 1 mM $MgCl_2$. The enzyme was dialyzed after purification and quantification (by densitometry) into the above listed buffer and in the presence of 10 µM FAD (flavin-adenine-dinucleotide). After dialysis, the enzyme was diluted at ambient temperature to 5 ppm in the reaction buffer with 50 mM FB1 (Sigma Chemical Co., St. Louis, Mo.) and catalase (to degrade $H_2O_2$). The reactions were subsequently quenched with methanol and the quantity of remaining FB1 was measured using HPLC-Mass Spectrometry.

Kinetic parameters of the FD/FDD molecule constructs were determined by measuring the formation of hydrogen peroxide, a byproduct of FB1 and AP1 deamination (i.e., deamination caused by the FD/FDD molecules of the invention). In the presence of horseradish peroxidase, Amplex Red (Molecular Probes, Eugene, Oreg.) reacts with hydrogen peroxide in a 1:1 stoichiometric ratio to produce a highly fluorescent molecule, resorufin, (oxidized Amplex red). Enzymatic rates for the FD/FDD constructs of the invention were measured as fluorescent units per minute (i.e., the fluorescence of oxidized Amplex Red formed). The kinetic parameters were determined graphically by evaluating the double reciprocal of a rate vs. [substrate] plot, the Lineweaver-Burke reciprocal plot. For examples of exemplary kinetic parameters of FD/FDD molecules, see FIGS. 1, 2, and 8.

Additionally, the nucleic acid and amino acid make-up of the homologues were determined and compared. For example, see, FIG. 3, which compares amino acid sequences from 2 exemplary homologues, R3H1 and B12, which share 8 amino acid changes from wild-type APAO (namely an alanine residue at position 118, a serine residue at position 136, a phenylalanine residue at position 209, a lysine residue at position 210, an isoleucine residue at position 237, a glutamic acid residue at position 272, a proline residue at position 274, and a glutamic acid residue at position 473). Furthermore, homologue R3H1 possesses a unique amino acid mutation at position number 193 (a change from asparagine to aspartic acid).

The enzymatic activity of homologue R3H 1 was further characterized by determining its ability to reduce FB1 (see, FIG. 5); its substrate specificity (see, FIG. 6); its activity in transgenic maize calluses (either when cytosolicly expressed or when fused to a signal sequence) (see, FIG. 7); its enzymatic parameters (see, FIG. **8*b*); its FD/FDD activity over a range or pH (see, FIG. 8*c*); and its thermostability (see, FIG. 8*d***).

Additionally, homologues 2E8 and 6E9 were constructed (see, above) and were screened using in planta transient expression of secreted APAO enzyme followed by turnover of fumonisin B 1 directly in the plant cell media and detection of the keto-FB1 reaction product by high throughput mass spectrometry.

These variants (i.e., 2E8 and 6E9) exhibited 6- and 10-fold increased production of keto FB1, respectively, relative to the homologue B6. Variant 6E9 contains 5 mutant amino acids present in homologues B6, E7, G6, and H8, a PCR-induced mutation resulting in a change from cysteine to arginine at amino acid position 425 and two silent mutations. Variant 2E8 has 2 mutant amino acids present in homologues B6, E7, G6, and H8, a PCR-induced change resulting in arginine at amino acid position 324 (the same position as one of the mutations in B6, E7, G6, and H8 but a different amino acid) and a PCR-induced mutation at amino acid position 384 resulting in substitution of glycine for glutamic acid.

Example II

Expression in Yeast and Selection of Polynucleotides Exhibiting FD/FDD Activity An exemplary homologue, R3H1 (SEQ ID NO:72), was truncated (SEQ ID NO:46) and verified for activity in *Pichia pastoris*. Truncated R3H1 (SEQ ID NO:46) was truncated by 137 amino acid residues from the N-terminal of full length R3H1 (SEQ ID NO:72). The first amino acid residue of truncated R3H1 is a lysine rather than a proline (i.e., position 138 in full length R3H1 (SEQ ID NO:72)).

Polynucleotides of the present invention were inserted into yeast expression vector pPICZαA (Invitrogen) then transformed into *Pichia pastoris*. Variants picked by a Q-bot were placed into YPD (yeast extract, peptone and dextrose) containing zeocin in a 96-well format. The cultures were grown at 30° C., 275 rpm for 2 days. The cultures were then gridded on a 3×2 or 2×2 array, via Q-bot, onto a nylon membrane over a solid induction medium (1.5% Bacto-Agar, 0.5%, peptone, 4% biotin, 1.34% YNB, 400 mM MES pH 5.5 and 0.75% methanol). The cultures were induced for 2 days at 30° C., thus allowing for expression and secretion of molecules expressing fumonisin detoxification activity.

After induction for 2 days, the nylon membranes were transferred to an agarose reaction mix (1.5% agarose, 0.5 mg/ml Amplex Red, 80 U/ml horseradish peroxidase and 280 μM fumonisin B1). Variants with equal or greater activity than the R3H1 homologue were transferred to YPD agar containing zeocin. Single colonies were selected and grown as described above. Membranes containing fumonisin detoxification expressing colonies were lifted off the induction agar and incubated at 52° C. for 45 minutes. These heat-treated colonies were then assayed on the above described agarose reaction mix.

After the incubation at 52° C., clones which displayed activity levels greater than homologue R3H1 were analyzed in liquid culture. The cultures were grown overnight at 29° C., 275 rpm in 10 ml YPD with zeocin followed by subculture into 20 ml of BMGY (phosphate buffered complex medium containing glycerol). After 1 day of growth at 29° C. and 275 rpm, the cultures were spun down and washed once in a modified BMMH medium (MES pH 5.5, buffered minimal medium+histidine+10 M FAD+1% casamino acids) and resuspended in 2 ml of modified BMMH. The cultures were induced for 2 days and subsequently spun down, filtered and assayed using the Amplex Red coupled fluorescent assay for $H_2O_2$ (see, infra).

The resulting cultures were assayed for thermostability by pre-incubating the samples at 37° C. for 10 minutes followed by assaying at room temperature. Fumonisin detoxification activity concentration was determined by coomassie staining and activities were adjusted to rfu/min/μg units (relative fluorescent units per minute per microgram). Four homologues were found to have similar activity to homologue R3H1, but greater thermostability. See, FIG. 8a.

The $k_{cat}$ and $K_M$ for G6 were determined graphically with the Lineweaver-Burk plot and compared with R3H1. See, FIG. 8b. Additionally the enzymatic activity of homologue G6 was determined over a range of pH. See, FIG. 8c. The pH profiles (i.e., the profile of the enzymatic activity over a range of pH) of homologue R3H1 and homologue G6 are similar. Furthermore, the enzymatic activity of homologue G6 was determined after incubation at various temperatures for 10, 20, 30, and 45 minutes. For example, see, FIG. 8d, which displays G6's activity at various temperatures following 10, 20, 30, and 45 minutes pre-incubation. The same manipulations are displayed for homologue R3H1 as well.

Example III

In Planta Turnover of Fumonisin B1 by Exemplary Homologues of the Invention

DNA constructs were made with selected homologues of the invention fused to a plant secretion signal. These constructs were used for transient expression of the selected FD/FDD polypeptides of the invention via *Agrobacterium tumefaciens* in *Nicotiana benthamiana* leaves.

Figure 10:
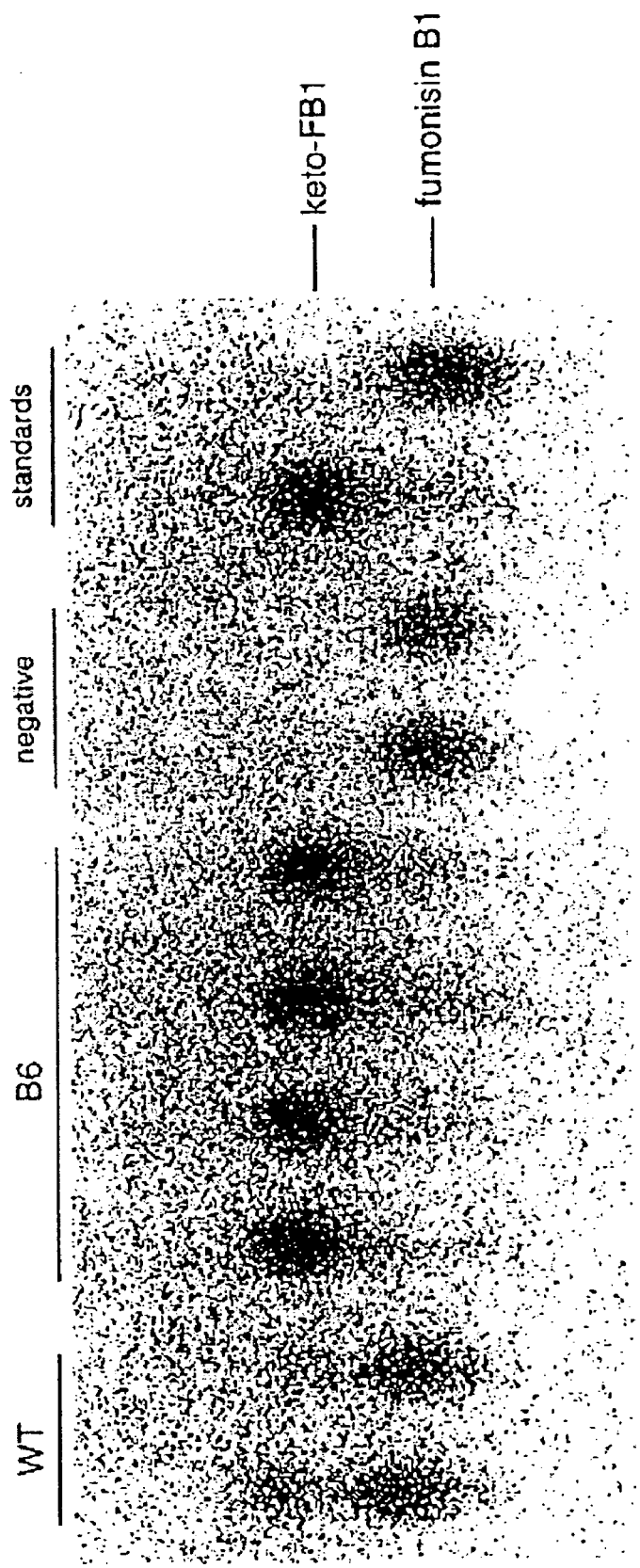
FIG. 10: In planta turnover of fumonisin B1 by exemplary homologues of the invention.

Fumonisin B1 was injected with a syringe into the intercellular spaces of the expressing leaves. The fumonisin B1 was either labeled with $^{14}C$ or not labeled, depending on the method of detection. The leaf tissue was incubated at room temperature for three hours. Samples were then homogenized with 50% methanol, centrifuged and filtered. Conversion of fumonisin B1 to the oxidized keto-FB1 product was assessed by thin layer chromatography followed by autoradiography or by liquid chromatography followed by mass spectrometry. As seen in FIG. 10, wild-type APAO converts very little (~5%) fumonisin B1 to keto-FB1. The B6 homologue of the invention (see, SEQ ID NO:25 and SEQ ID NO:50) converts at least ~98% of fumonisin B1 to keto-FB1. Similar results were also obtained with FD/FDD homologue E7 (see, SEQ ID NO:24 and SEQ ID NO:49). These results were confirmed using the liquid chromatography-mass spectrometry method (not shown). FD/FDD homologue R3H1 of the invention (see, SEQ ID NO:69 and SEQ ID NO:72) converted 80-90% of fumonisin B1 to keto-FB1 (not shown).

Example IV

In Planta Turnover of FB1 in Maize

T-DNA expression constructs were made in which the full-length homologue R3H1(see, SEQ ID NO:69 and SEQ ID NO:72) sequence was modified in order to introduce the homologue B6 (see, SEQ ID NO: 25 and SEQ ID NO:50) mutations at cysteines 359 (C359→S) and 461 (C461→G). In addition, two amino acid substitutions to eliminate potential glycosylation sites were engineered at amino acid 86 (N86→A; by means of A256→G and A257→G) and at amino acid 206 (S206→A, by means of A616→G, G616→C, and A628→G). The resulting open reading frame, designated APAO(B6) Glyc-(SEQ ID NO:65 and SEQ ID NO:66), was fused to a barley alpha amylase signal peptide and engineered into a T-DNA expression vector (designated PHP18303) for maize transformation via *Agrobacterium tumefaciens*. A second vector was prepared which lacked the signal peptide of PHP18303 (designated PHP18473). The promoter in both cases was the maize ubiquitin promoter and first intron, and the polyadenylation signal was from potato proteinase inhibitor II (PINII).

Immature maize embryos of genotype GS3 were excised at 9 days post pollination, co-cultivated with *Agrobacterium* LBA4404 cells harboring PHP18303 or PHP18473 for 2 days to allow for DNA transfer and transient expression of the FD/FDD homologue gene in outer cell layers of the embryos. At that point one set of embryos that had been incubated with each construct was removed for evaluation of total FD/FDD enzyme activity (i.e., here, the ability to degrade fumonisin B1) and ELISA protein following homogenization in 200 mM Na phosphate buffer pH 7 containing protease inhibitor cocktail, TWEEN-20 (0.01%) and 10 micromolar flavin adenine dinucleotide (FAD; Sigma-Aldrich).

The remaining embryos that had been co-cultivated with *Agrobacterium* containing the two constructs were transferred to 0.5 ml microfuge tubes containing 3 microliters of $^{14}$C-labelled fumonisin B 1 (0.3 mg/ml; approximately 1100 dpm per microgram) in 180 mM MES buffer, pH 5.5 containing 10 mM KCl and 0.2 mM CaCl$_2$, pH 5.5. The embryos were deposited scutellar side down in the liquid, the tube was sealed by capping, and allowed to incubate for 24 hours at 25° C.

After 24 hours, the bathing fluid was withdrawn from each tube and the entire amount (approximately 2.5 microliters) was spotted onto a reverse phase C18 thin-layer chromatography (TLC) plate, and plates were developed with MeOH: KCl (8:2). The embryos from the same incubation were then homogenized in 5 microliters of 50% methanol/water (to extract oxo-FB1 and at the same time inactivate any endogenous APAO activity (action against Fumonisin B1). This was accomplished using a sterile, plastic bacterial transfer loop whose loop end had been removed with a razor blade such that the blunt end matched the bottom radius of an 0.5 ml tube to allow effective maceration of the small tissue piece. The homogenate was centrifuged to pellet debris, and the entire supernatant fraction spotted onto reverse phase TLC plates and developed as described above. The relative position and amount of radioactivity per spot was measured by exposing the TLC plate to a phosphorimager screen for 48 hours and then detecting and quantitating the phosporimage using a Molecular Dynamics STORM™ system.

Both PHP18303 and PHP18473 co-cultivation resulted in roughly similar amounts of extractable protein and enzyme activity. For example, construct PHP18473 UBI-APAO(B6) Glyc-PINII had an ELISA reading of 26 ppm and an enzymatic activity level of 19%, while construct PHP18303 UBI-BAA-APAO(B6)(Glyc-PINII had an ELISA reading of 45 ppm and an enzymatic activity level of 23%.

Figure 11:
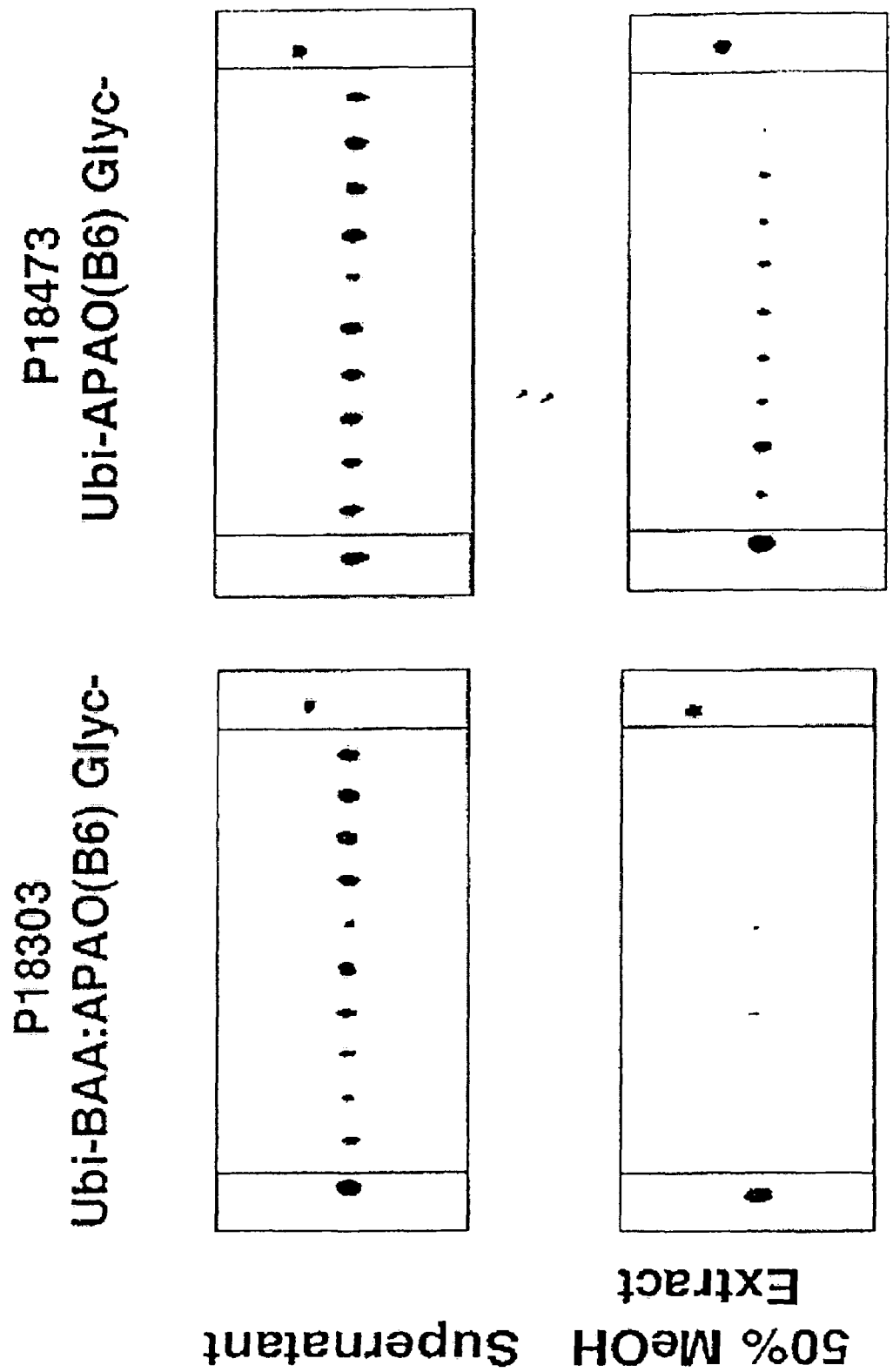
FIG. 11: Thin-layer chromatogram (TLC) showing in planta turnover of FB1 in maize embryos by exemplary homologues of the invention.
Figure 12:
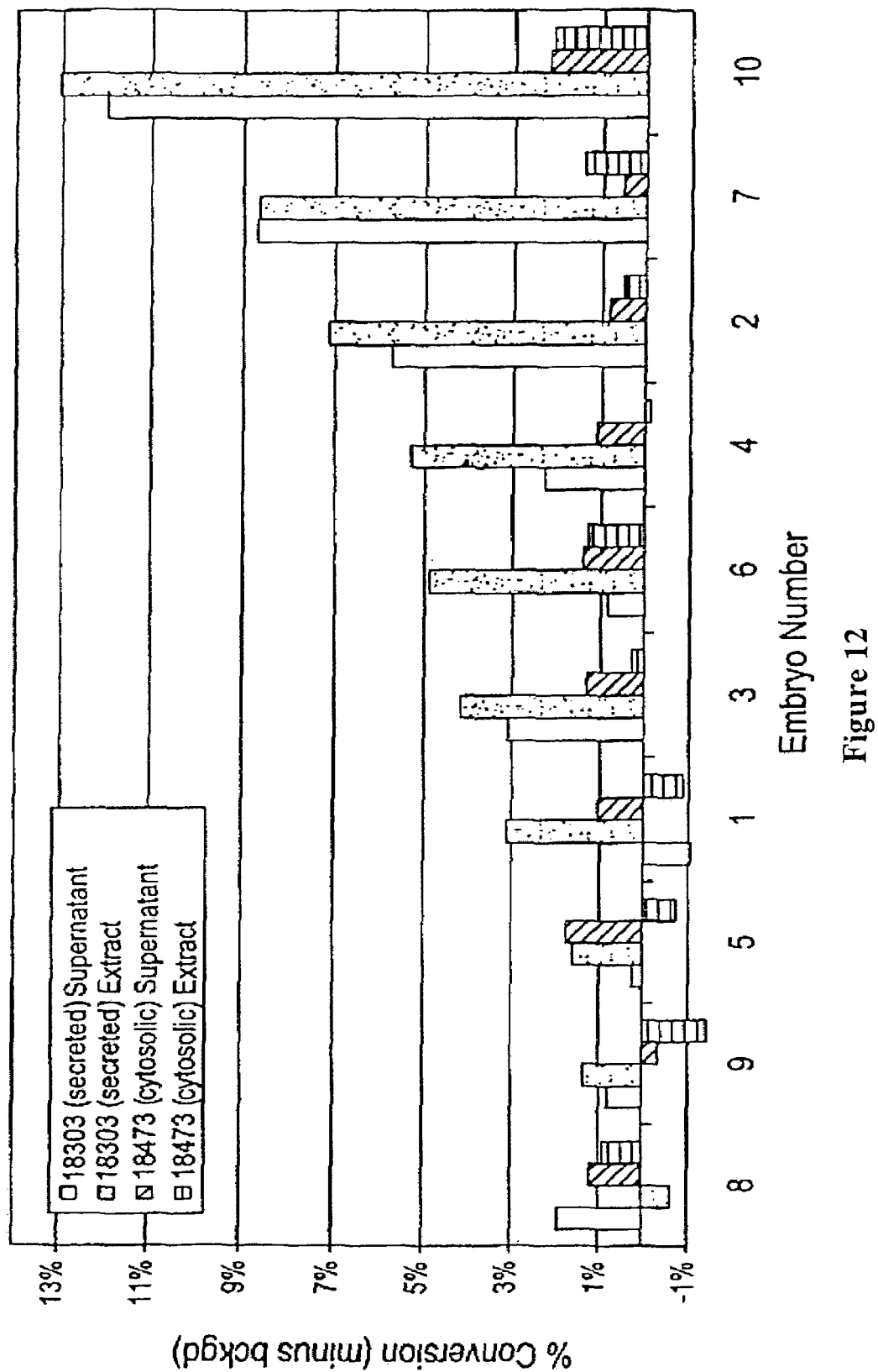
FIG. 12: Quantitation of TLC showing in planta turnover of FB1 in maize embryos by exemplary homologues of the invention.

In the in vivo conversion portion of the experiment, oxo-FB1 product was detected in both supernatant and grindates of several of the embryos co-cultivated with PHP18303, but not in supernatants or grindates of embryos co-cultivated with PHP18473 (see, FIG. 11). FIG. 11 shows phosphorimage of thin-layer chromatogram from imbibed embryo supernatants (upper images) and extracts (lower images). On each panel, the leftmost spot is FB1 standard, and the rightmost spot is oxo-FB1 standard. The middle spots represent label in embryos 1 through 10 for each treatment. This indicates that although overall similar amounts of enzyme activity were generated by transient expression in both cases, only with a signal peptide present was enzyme capable of oxidizing exogenously-applied fumonisin substrate. Typically, only a few percent of cells in an embryo express a given transgene under these conditions, so the low percent conversion (relative to data obtained in tobacco leaves for a similar construct) is to be expected due to the large excess of substrate relative to enzyme.

FIG. 12 illustrates the quantitation of radiolabel data from the TLC place in FIG. 11. Percent conversion was initially calculated as percent of total label per embryo that was detected as oxo-FB1 (i.e., =counts in upper spots/[counts upper+counts lower]×100). A similar calculation was made for a duplicate set of embryos co-cultivated with *Agrobacterium* LBA4404 cells containing a non-APAO T-DNA expression cassette (i.e., beta-glucuronidase); and the average of this "background" value was subtracted from each of the experimental percent conversion values for 18303 and 18473 co-cultivated embryos and supernatants.

The process for treating samples for the TLC assay and for the TLC assay itself comprised use addition of 200 μL extraction buffer (PBST, pH 7, 10 μM FAD, protease inhibitors (complete)) to each sample in Megatiter tubes. The samples had two 5/32" steel bearings added to each tube, which were capped tightly. Each sample was raptored for four cycles, 15 seconds each, with 5-10 minutes on ice between cycles. The samples were spun down and supernatants transferred to new tubes. The supernatants from the same constructs were pooled. The pellets were rinsed in 200 μL of 200 mM MES (pH 5.5) and spun down. These supernatants were combined with the first supernatants (pooled). The pellets were again resuspended in 200 mM MES (pH 5.5) to make pellet suspension. About 200 μL from each sample were pooled (i.e., the ones from the same constructs were pooled) and spun down to rinse, followed by a resuspension in 200 μL of 200 mM MES (pH 5.5). The supernatants were filtered through a 0.2 μM SpinX units. The supernatants were concentrated in Microcon YM-10 units and the concentrates were resuspended to about 200 μL with 200 mM MES (pH 5.5) to assay via TLC. Storage was at −20° C.

The TLC assay for FD/FDD activity (also alternatively termed APAO activity in some instances herein) comprised incubation of 9 μL of each sample with 1 μL $^{14}C$-FB1 (at about 10 mg/mL, in water) at room temperature for 2 days. 1 μL of such was spotted onto C 18 TLC plates. Additionally, about 1 μg $^{14}C$-FB1 and oxo-FB1 were used as controls. The plates were developed in MeOh:4% KCl (at an 8:2 ratio). The plates were exposed to phosphoscreen overnight and a Storm phosphoimager was used to read the results.

Example V

Expression of FD/FDD Homologue R3H1 in Transgenic Maize Callus

T-DNA expression constructs were made in which the full-length R3H 1 homologue sequence was fused to a barley alpha amylase signal peptide at its N-terminus, and the resulting fusion engineered into a T-DNA expression vector (designated PHP17481) for maize transformation via *Agrobacterium tumefaciens*. A second vector was prepared which lacked the signal peptide of PHP17481 (designated PHP18473). Additional constructs were made using wild type APAO, either with a barley alpha amylase signal peptide N-terminal fusion (designated PHP17672) or without signal peptide (PHP17110). The promoter in all cases was the maize ubiquitin promoter and first intron (UBI), and the polyadenylation signal was from potato proteinase inhibitor II (PINII). All constructs contained the BAR gene for herbicide-based selection of transformed tissues on solid media. The signal peptide nucleotide and amino acid sequences used include:

a) barley alpha amylase signal sequence DNA which was fused in-frame upstream of the R3H1 open reading frame in PHPHP17490 and 17292 and which was obtained by synthesis based on published sequence of accession K02638, the sequence of which is:

```
ATG GCC AAC AAG CAC CTG TCC CTC TCC  (SEQ ID NO:80)

CTC TTC CTC GTG CTC CTC

GGC CTC TCC GCC TCC CTC GCC TCC GGC;
``` b) barley alpha-amylase type B isozyme mRNA, complete cds, clone pHV19, accession K02638, the sequence of which is:

ATG GCG AAC AAA CAC TTG TCC CTC TCC    (SEQ ID NO:81)

CTC TTC CTC GTC CTC CTT

GGC CTG TCG GCC AGC TTG GCC TCC GGG;

c) translation of barley alpha amylase signal sequence (which was fused in-frame upstream of R3H1 in PHPHP17490 and 17292), the sequence of which is:

MANKHLSLSLFLVLLGLSASLASG;    (SEQ ID NO:82)

d) translation of barley alpha-amylase type B isozyme mRNA, complete cds, clone pHV19, the sequence of which is:

MANKHLSLSLFLVLLGLSASLASG.    (SEQ ID NO:83)

Immature embryos of genotype GS3 were transformed with the above constructs via *Agrobacterium* co-cultivation, and stably-transformed callus was obtained by continuing herbicide selection on solid medium. FD/FDD expression level was evaluated in a minimum of five independent transformants per construct, and the line with the highest level off expression was chosen for further evaluation.

The amount of homologue protein present in each line was evaluated by an indirect ELISA assay employing polyclonal antisera raised in rabbits using wild-type APAO expressed in pGEX4t system (Amersham). The standard was APAO expressed in soluble pGEX4T1, which was subsequently GST-cleaved and purified according to manufacturers instructions. The results for such ELISA assay are as follows: PHP17110 (UBI-APAO-PINII)=249 ppm; PHP17672 (UBI-BAA-APAO-PINII)=94 ppm; PHP17481 (UBI-APAO (R3H1)-PINII)=451 ppm; PHP17490 (UBI-BAA-APAO (R3H1)-PINII)=170 ppm.

Equal weighed amounts of each callus lines were homogenized in phosphate buffered saline+Tween (pH 7.5) containing 10 uM flavin adenine dinucleotide cofactor (FAD; Sigma-Aldrich), and supernatants were filtered and concentrated using Microcon YM-10 ultrafiltration membranes (Amicon Corp.). Concentrates were reconstituted in MES buffer, pH 5.5 for R3H1-expressing callus, or phosphate buffer, pH 7.5, for wild type APAO-expressing callus. Following a second ultrafiltration step and reconstitution in the same buffer, extracts were assayed for fumonisin degrading activity using $^{14}$C-fumonisin B1 (1.0 microgram per microliter final concentration, in the appropriate buffer; obtained from J. David Miller, Carleton Univ.) as a substrate in an overnight incubation at 25° C. Resolution of oxidized product from FB1 was accomplished by thin-layer chromatography on silica gel $C_{18}$ plates using MeOH:4%KCl (8:2). The relative position and amount of radioactivity per spot was measured by exposing the TLC plate to a phosphorimager screen for 48 hrs and then detecting and quantifying the resulting phosphorimage using a Molecular Dynamics STORM™ system. Percent conversion of substrate to product was then calculated from the upper and lower spot values.

Figure 13:
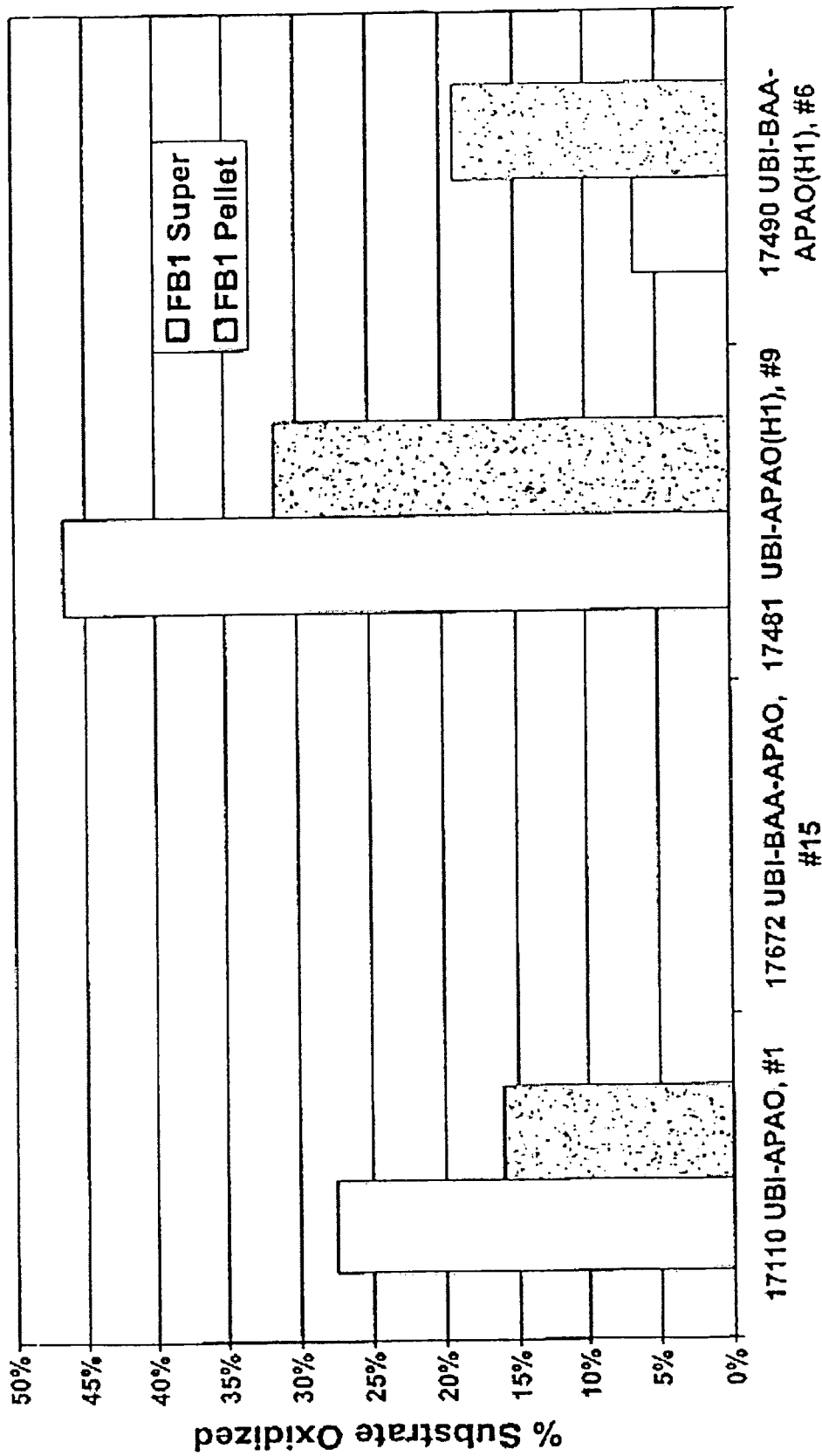
FIG. 13: In planta activity of exemplary homologues of the invention in stably transformed maize callus lines.

FIG. 13 illustrates the fumonisin degrading activity in stably-transformed callus lines. Percent substrate oxidized was measured in a standard "APAO" assay utilizing $^{14}$C-labeled FB1. The reaction mixture pH was optimized for the construct being evaluated, i.e., pH 7.0 for PHP17110 and PHP17672 (wild-type APAO), and pH 5.5 for PHP17481 and PHP17490 (R3H1). The supernatant activity (solid bars) and pellet activity (hatched bars) was determined separately for each extract. See, FIG. 13.

FB1-oxidizing activity of calli transformed with R3H1 was higher than corresponding wild type APAO constructs, even when measured at the optimum pH for that enzyme (pH 7.5 for wild type; pH 5.5 for R3H1). Wild type APAO had undetectable activity when fused to a BAA signal sequence (construct PHP17672), which is in line with the low ELISA values for this callus line. The callus expressing R3H1 fused to BAA (PHP17490) had twice as much ELISA protein as wild type (PHP17672) (170 ppm), and it had much greater enzyme activity, particularly in the pellet fraction. While these data are from a single callus line in each case, they appear to represent the upper end of expression for each construct, since the highest expressing callus line in each case was chosen for evaluation. Therefore, maize-expressed shuffling variant R3H1 is active versus FB1, and retains significant activity on secretion, unlike the wild type APAO enzyme.

Example VI

APAO Assay of T0 Plants Transformed with clone 6e9 (SEQ ID NO: 71) for In Vitro and In Vivo APAO Activity Sample Preparation APAO variants 6e9 (SEQ ID NO:68) and 2e8 (SEQ ID NO:67), as fill length open reading frames linked to barley alpha amylase signal sequence (BAA) (SEQ ID NO:80) were cloned into *Agrobacterium* expression vectors for maize transformation and used to transform GS3×elite inbred F1 embryos. As a negative control, non-secreted, wild type APAO transformants were also generated. Transformation resulted in a total of 60 and 58 transformation events for 6e9 (SEQ ID NO:68) and 2e8 (SEQ ID NO:67), respectively.

For in vitro evaluation of transgene expression in the T0 generation, all T0 plants and 10 negative controls were processed and sampled for in vitro APAO activity. At the V5 to V6 plant stage (6 leaves, 4-5 completely unfurled), five leaf punches were taken from the uppermost, completely unfurled leaf, transferred to megatiter tubes, and retained on ice. The leaf puncher was rinsed with 95% ethanol between samples. Extraction buffer (100 mM PBST, pH7.5+10 μM FAD+Complete (Roche) protease inhibitor cocktail) was added to each sample in a 400 ρL aliquot, along with two 5/32" steel bearings. The tubes were capped tightly and chilled on ice for 15 to 30 minutes. Samples were disrupted with a Geno/Grinder 2000 (SPEX CertiPrep, Metuchen, N.J.) at 650 strokes/min for 15 seconds then chilled in ice water for 5 to 10 minutes. This process was repeated three more times. Extracts were spun down at 5000 g at 4° C. for 10 minutes.

TLC Assay of Extracts for APAO Activity

Nine microliters of each supernatant and one microliter of 14C-FB1 (10 mg/mL, dH2O) were mixed in V-bottom microtiter plates such that [14C-FB1]=1 μg/μL, and wells were capped tightly. Samples were incubated overnight at room temperature. One microliter of each reaction was spotted onto TLC plates (Whatman KC18 Silica Gel 60A). Also ~1 ug of 14C-FB1 and 14C-oxoFB1 (diluted in Extraction Buffer) was spotted on the ends of each plate. The plates were developed in MeOH:4% KCl (8:2) and air-dried. The plates were then exposed to a phosphor-screen overnight, and a Storm phosphorimager was used to obtain TLC images.

A total of 53 of the 60 T0 plants transformed with 6e9 were positive for APAO activity in this assay. A total of 54 of 58 T0 plants transformed with 2e8 were also positive for APAO activity.

Sampling and Processing of Leaf Tips for In Vivo Conversion Studies

Three of the positive plants (28421745, 28421778, 28421777) at stage V7 (7 leaves, 5-6 completely unfurled) and one negative control (28421798) were selected. The terminal ~10 cm was removed from the tip of the most recently fully-opened (6th) leaf and transferred to a 50 mL falcon tube containing ~10 mL of dH20. Leaf tips were rinsed under dH2O to remove debris, pollen, etc. The bottom of each leaf tip was re-cut underneath dH2O (to prevent cavitation) to ~5-6 cm, and transferred to new tubes containing ~10 ML dH2O. Leaves were soaked for ~15 minutes, the dH2O was changed, and the process was repeated two more times (to remove any enzyme that may have leaked out of injury site). Leaf tips were then transferred to 7 mL scintillation vials containing 450 µL of dH2O. 50 µL of 14C-FB1 (10 mg/mL, dH2O) was added to each sample such that final [14C-FB1] =1 ug/uL. Each vial was partially sealed with parafilm and the vials were placed in a rack in a crisper lined with moist paper towels, ensuring a tight lid. Samples were incubated for 72 hours on the lab bench at room temperature, 4 to 6 inches below 24-hour fluorescent lights.

Toxin solutions were transferred to new tubes at t=72 hours and 1 µL and 2 µL of the $^{14}$C-FB1 solutions were spotted onto TLC plates (Whatman KC18 Silica Gel 60A). Also ~1 ug of $^{14}$C-FB1 and $^{14}$C-oxoFB1 were spotted on the ends of each plate. Plates were developed in MeOH:4% KCl (8:2) and air-dried. Plates were exposed to phosphor-screen overnight, and a Storm phosphorimager was used to get TLC images.

Leaf tips were rinsed three times in dH$_2$O. The bottom ~1 cm of each leaf that was dipped in the toxin solution was removed. Leaf tips were then transferred to 13 mm glass tubes, frozen in liquid nitrogen and ground to a powder with a glass rod. 500 µL of 50% ACN (in dH$_2$O) was added to each powdered sample and ground further with a glass rod. Grindates were transferred to 2mL tubes, and the glass tubes were rinsed with another 500 µL of 50% ACN (in dH$_2$O), and pooled with the first grindate. Tubes holding the samples were then sonicated in a water bath for 15 minutes and spun down at 10,000 g at 4° C. for 10 minutes to pellet any debris. Supernatant was transferred to new tubes. The powder was re-extracted (sonicated) with another 500 uL of 50% ACN (in dH$_2$O) as before, and supernatant was pooled with first supernatant. Supernatants were then filtered through 0.2 µM nylon SpinX units.

Determination of DPM's (Disintegrations per Minute)

20 uL of each extract supernatant was mixed with ~6 mL scintillation fluid. External standard quench correction was used to determine dpm's in each sample. The concentration of $^{14}$C-label in each sample was estimated based on the activity of $^{14}$C-FB1 (~946 dpm/ug $^{14}$C-FB1). The volume of each extract that would yield ~20 ug of $^{14}$C-label (to make 20 uL of ~1 ug/uL stocks for TLC assays) was determined. The calculated volumes were then dried down in the SpeedVac. Residues were dissolved in 20 µL of MeOH to get ~1 ug/uL of $^{14}$C-label.

1 µL and 2 µL of each ~1 ug/uL sample were spotted onto TLC plates (Whatman KC18 Silica Gel 60A). Also ~1 ug of $^{14}$C-FB1 and $^{14}$C-oxoFB1 were spotted on the ends of each plate. The plates were developed in MeOH:4% KCl (8:2) and air-dried. Plates were exposed to phosphor-screen overnight, and a Storm phosphorimager was used to get TLC images.

ImageQuant software was used to determine the volume of counts for each spot, and % conversion of FB1 to oxoFB1 was estimated in each sample.

All three APAO-expressing T0 generation plants expressing 6e9 (SEQ ID NO: 68) which were tested showed significant conversion of labeled FB1 to oxo-FB1 (estimated at 50% to 60% conversion). The three APAO-expressing T0 generation plants expressing 2e8 (SEQ ID NO: 70) which were tested showed conversion ranging from 67% to 80% of FB1 to oxo-FB1. The non-transformed control extracts showed no detectable oxo-FB1. Only trace amounts of oxo-FB1 were detected in the remaining leaf imbibition buffer, indicating that conversion occurred in vivo and not as a result of enzyme leakage into the imbibition solution followed by uptake of oxidized FB1.

Example VII

*Agrobacterium*-Mediated Transformation

For *Agrobacterium*-mediated transformation of maize with an FD/FDD nucleotide sequence of the invention, operably linked to a promoter, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the DNA construct containing the nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

Example VIII

Soybean Embryo Transformation

Soybean embryos are bombarded with a plasmid containing an FD/FDD nucleotide sequence of the instant invention operably linked to a ubiquitin promoter as follows. To induce somatic embryos, cotyledons, 3-5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188), and the 3' region of the nopaline synthase gene from the T-DNA of the Ti plasmid of Agrobacterium tumefaciens. The expression cassette comprising the FD/FDD sequence operably linked to the ubiquitin promoter can be isolated as a restriction fragment. This fragment can then be inserted into a unique restriction site of the vector carrying the marker gene.

To 50 µl of a 60 mg/ml 1 µm gold particle suspension is added (in order): 5 µl DNA (1 µg/µl), 20 µl spermidine (0.1 M), and 50 µl CaCl$_2$ (2.5 M). The particle preparation is then agitated for three minutes, spun in a microfuge for 10 seconds and the supernatant removed. The DNA-coated particles are then washed once in 400 µl 70% ethanol and resuspended in 40 µl of anhydrous ethanol. The DNA/particle suspension can be sonicated three times for one second each. Five microliters of the DNA-coated gold particles are then loaded on each macro carrier disk.

Approximately 300-400 mg of a two-week-old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example IX

Transformation and Regeneration of Transgenic Plants

Immature maize embryos from greenhouse donor plants are bombarded with a plasmid containing the FD/FDD sequences of the present invention operably linked to a ubiquitin promoter and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

This plasmid DNA plus plasmid DNA containing a PAT selectable marker is precipitated onto 1.1 µm (average diameter) tungsten pellets using a CaCl$_2$ precipitation procedure as follows:

100 µl prepared tungsten particles in water
10 µl(1 µg) DNA in Tris EDTA buffer (1 µg total DNA)
100 µl 2.5 M CaCl$_2$
10 µl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 µl 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity.

Bombardment and Culture Media

Bombardment medium (560Y) comprises 4.0 g/l N6 basal salts (SIGMA C-1416), 1.0 ml/l Eriksson's Vitamin Mix (1000×SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000×SIGMA-1511), 0.5 mg/l thiamine HCl, 30.0 g/l sucrose, and 2.0 mg/l 2,4-D (brought to volume with D-I H$_2$O following adjustment to pH 5.8 with KOH); 3.0 g/l Gelrite (added after bringing to volume with D-I H$_2$O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated or recombinant nucleic acid comprising a polynucleotide sequence that encodes a polypeptide that is at least 97% identical to the entire length of SEQ ID NO:50 or a fully complementary polynucleotide sequence thereof, wherein at pH 5.5 said polypeptide has a fumonisin detoxification activity or a fumonisin derivative detoxification activity that is at least 1.5-fold greater than any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:5 land SEQ ID NO:52.

2. The nucleic acid of claim 1, wherein said polypeptide has a fumonisin detoxification activity that is at least 1.5-fold greater than any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52.

3. The nucleic acid of claim 2, wherein said polypeptide has a fumonisin detoxification activity that is at least 20-fold greater than any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52.

4. The nucleic acid of claim 2, wherein said nucleic acid is selected from the group consisting of:
   (a) a nucleic acid encoding a polypeptide, wherein said polypeptide is at least 97% identical to the entire length of SEQ ID NO:50;
   (b) a nucleic acid encoding a polypeptide, wherein said polypeptide is at least 97% identical to the entire length of a sequence selected from the group consisting of SEQ ID NOs: and 47 and 47;
   (c) a nucleic acid encoding a polypeptide wherein said polypeptide is at least 97% identical to the entire length of a sequence selected from the group consisting of SEQ ID NOs: 48-49, 71, and SEQ ID NOs: 85, 87, 89, 91, 93, 95, 97, 99, 101, 103, 105, 107, 109, 111, 113, 115, 117, 119, 121, 123, 125, and 127; and
   (d) a nucleic acid that is fully complementary to the nucleic acid of (a), (b) or (c);
wherein the nucleic acid in (b) and (c) encodes a polypeptide having at least 97% identical to SEQ ID NO: 50.

5. An isolated or recombinant nucleic acid comprising a polynucleotide sequence selected from the group consisting of:
   (a) a polynucleotide sequence selected from the group consisting of SEQ ID NOs: 21-25, SEQ ID NOs: 67-68, and SEQ ID NOs: 84, 86, 88, 90, 92, 94, 96, 98, 100, 102, 104, 106, 108, 110, 112, 114, 116, 118, 120, 122, 124, and 126;
   (b) a polynucleotide sequence encoding a polypeptide selected from the group consisting of SEQ ID NOs: 46-50, SEQ ID NO: 71, and SEQ ID NOs: 85, 87, 89, 91, 93, 95, 97, 99, 101, 103, 105, 107, 109, 111, 113, 115, 117, 119, 121, 123, 125, and 127;
   wherein at pH 5.5 said polypeptide has a fumonisin detoxification activity or a fumonisin derivative detoxification activity that is at least 1.5-fold greater than any of the polypeptides selected from the group consisting of: SEQ ID NO: 54; SEQ ID NO: 56; SEQ ID NO: 58; SEQ ID NO: 60; SEQ ID NO: 62; SEQ ID NO: 64; SEQ ID NO: 51 and SEQ ID NO: 52; and
   (c) a polynucleotide sequence fully complementary to the polynucleotide of (a) or (b).

6. The nucleic acid of claim 1, wherein the polynucleotide encodes a fumonisin amine oxidase.

7. The nucleic acid of claim 1, wherein said nucleic acid comprises a characteristic selected from the group consisting of:
   (a) wherein the optimum pH of said fumonisin detoxification activity is lower for said polypeptide than for any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52; and
   (b) wherein the thermostability of said fumonisin detoxification activity is higher for said polypeptide than for any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52.

8. The nucleic acid of claim 1, wherein said polypeptide comprises a leader sequence that directs the secretion of the polypeptide from a plant cell.

9. The nucleic acid of claim 1, wherein said nucleic acid comprises a characteristic selected from the group consisting of:
   (a) wherein at pH 5.5, the $k_{cat}$ of the fumonisin detoxification reaction catalyzed by the polypeptide is higher than the $k_{cat}$ of the fumonisin detoxification reaction catalyzed by any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52;
   (b) wherein at pH 5.5, the fumonisin $K_M$ for the fumonisin detoxification reaction catalyzed by the polypeptide is lower than the fumonisin $K_M$ for the fumonisin detoxification reaction catalyzed by the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52; and
   (c) wherein at pH 5.5, the fumonisin $k_{cat}/K_M$ of the fumonisin detoxification reaction catalyzed by the polypeptide is higher than the fumonisin $k_{cat}/K_M$ of the fumonisin detoxification reaction catalyzed by any of the polypeptides selected from the group consisting of: SEQ ID NO:54; SEQ ID NO:56; SEQ ID NO:58; SEQ ID NO:60; SEQ ID NO:62; SEQ ID NO:64; SEQ ID NO:51 and SEQ ID NO:52.

10. The nucleic acid of claim 1, operably linked to a promoter.

11. A nucleic acid construct comprising a promoter operably linked to the polynucleotide of claim 1.

12. The nucleic acid construct of claim 11, wherein the promoter is heterologous with respect to the polynucleotide and effective to cause sufficient expression of the encoded polypeptide to cause the detoxification of fumonisin.

13. The nucleic acid construct of claim 12, wherein the polynucleotide functions as a selectable marker.

14. The nucleic acid construct of claim 12, wherein a parental codon of the polynucleotide has been replaced by a synonymous codon that is preferentially used in a plant relative to the parental codon.

15. The nucleic acid construct of claim 11, wherein the construct is a vector.

16. A vector comprising a first polynucleotide sequence comprising a promoter operably linked to the polynucleotide of claim 1 and a second polynucleotide sequence encoding a second polypeptide that confers a detectable phenotypic trait upon a cell or organism expressing the second polypeptide at an effective level.

17. The vector of claim 16, wherein the detectable phenotypic trait consists of one or more traits selected from the group consisting of: herbicide resistance; pesticide resistance; and a visible marker.

18. The vector of claim 15, wherein the vector is a plant transformation vector.

19. An isolated host cell comprising the vector of claim 15, wherein the vector has been stably incorporated into the genome of the host cell.

20. The cell of claim 19, wherein the polynucleotide is operably linked to a regulatory sequence.

21. The cell of claim 19, wherein the cell is a transgenic plant cell.

22. The transgenic plant cell of claim 21, wherein the plant cell expresses an exogenous polypeptide with fumonisin detoxification activity.

23. An isolated transformed cell comprising the nucleic acid of claim 1.

24. A composition comprising at least two different nucleic acids of claim 1.

25. The composition of claim 24 comprising at least ten different nucleic acids

UNITED STATES PATENT AND TRADEMARK OFFICE
CERTIFICATE OF CORRECTION

| | | |
|---|---|---|
| PATENT NO. | : 7,611,897 B2 | Page 1 of 1 |
| APPLICATION NO. | : 10/872750 | |
| DATED | : November 3, 2009 | |
| INVENTOR(S) | : Chatterjee et al. | |

It is certified that error appears in the above-identified patent and that said Letters Patent is hereby corrected as shown below:

Col. 395, Claim 1, Line 18:

DELETE after NO: "5 1and"
ADD after NO: --51 and--

Col. 395, Claim 4, Line 39:

DELETE after NOs: "and 47 and 47"
ADD after NOs: --46 and 47--

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,611,897 B2  Page 1 of 1
APPLICATION NO. : 10/872750
DATED : November 3, 2009
INVENTOR(S) : Chatterjee et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1531 days.

Signed and Sealed this

Twelfth Day of October, 2010

David J. Kappos
*Director of the United States Patent and Trademark Office*

SEQUENCE LISTING

```
<160> NUMBER OF SEQ ID NOS: 127

<210> SEQ ID NO 1
<211> LENGTH: 1803
<212> TYPE: DNA
<213> ORGANISM: Artificial Sequence
<220> FEATURE:
<223> OTHER INFORMATION: Synthetic Construct Clone A5

<400> SEQUENCE: 1
atggcacttg caccgagcta catcaatccc ccaaacgtcg cctccccagc agggtattct     60
cacgtcggcg taggcccaga cggagggagg tatgtgacaa tagctggaca gattggacaa    120
gacgctttgg gcgtgacaga ccctgcctac gagaaacagg ttgcccaagc attcgccaat    180
ctgcgagctt gtcttgctgc agttggagcc acttcaaacg acgtcaccaa gctcaattac    240
tacatcgtcg actacgcccc gagcaaactc accgcaattg gagatgggct gaaggctacc    300
tttgcccttg acaggctccc tccttgcacg ctggtgccag tgccggccct ggcttcacct    360
gaatacctct ttgaggttga tgccacggcg ctggtgccgg gacacacgac cccagacaac    420
gttgcggacg tggtcgtggt gggcgctggc ttgagcggtt tggagacggc acgcaaagtc    480
caggctgccg ggctgtcctg cctcgttctt gaggcgatgg atcgtgtggg gggaaagact    540
ctgagcgtac aatcgggtcc cggcaggacg actatcaacg acctcggcgc tgcgtggatc    600
aatgacagca accaaagcga agtatccaga ttgtttgaaa gatttcatct ggagggcgag    660
ctccagagga cgatcggaaa ttcaatccat caagcacaag acgtacaac cactacagct    720 ccttatggtg attccttgct gagcgaggag gttgcaagtg cacttgcgga actcctcccc    780
gtatggtctc agctgatcga agagcatagt cttgaagacc ccaaggcgag ccctcaggcg    840
aagcggctcg acagtgtgag cttcgcgcac tactgtgaga aggacctaaa cttgcctgct    900
gttctcggcg tggcaaacca gatcacacgc gctctgctcg gtgtggaagc ccacgagatc    960
agcatgcttt ttctcaccga ctacgtcaag agtgccaccg gtctcagtaa tattttctcg   1020
```

```
gacaagaaag acggcgggca gtatatgcga tgcaaaacag gtatgcagtc gctttgccat    1080
gccatgtcaa aggaacttgt tccaggctca gtgcacctca acaccccgt cgctgaaatt    1140 gagcagtcgg catccggctg tacagtacga tcggcctagg gcgccgtgtt ccgaagcaaa    1200
aaggtggtgg tttcgttacc gacaaccttg tatcccacct tgacattttc accacctctt    1260
cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380
tgtgacccca tctcatttgc cagagatacc agcatcgaag tcgatcggca atggtccatt    1440
acctgtttca tggtcggaga cccgggacgg aagtggtccc aacagtccaa gcaggtacga    1500
caaaagtctg tctgggacca actccgcgca gcctacgaga acgccggggc ccaagtccca    1560
gagccggcca acgtgctcga gatcgagtgg tcgaagcagc agtatttcca aggagctccg    1620
agcgccgtct atgggctgaa cgatctcatc acactgggtt cggcgctcag aacgccgttc    1680
aagggtgttc atttcgttgg aacggagacg tctttagttt ggaaagggta tatggaaggg    1740
gccatacgat cgggtcaacg aggtgctgca gaagttgtgg ctagcctggt gccagcagca    1800
tag                                                                  1803

<210> SEQ ID NO 2
<211> LENGTH: 1803
<212> TYPE: DNA
<213> ORGANISM: Artificial Sequence
<220> FEATURE:
<223> OTHER INFORMATION: Synthetic Construct Clone D5

<400> SEQUENCE: 2
atggcacttg caccgagcta catcaatccc ccaaacctcg cctccccagc agggtattcc     60
cacgtcggcg taggcccaaa cggagggagg tatgtgacaa tagctggaca gattggacaa    120
gacgctttgg gcgtgacaga ccctgcctac gagaaacagg ttgcccaagc attcgccaac    180
ctgcgagctt gccttgctgc agttggagcc acttcaaacg acgtcaccaa gctcaattac    240
tacatcgtcg actacgcccc gagcaaactc accgcaattg gagatgggct gaaggctacc    300
tttgccctgg acaggctccc tccttgcacg ctggtgccag tgccggccct ggcttcacct    360
gaatacctct ttgaggttga tgccacggcg ctggttccag acactcaac cccagacaat    420 gttgcggacg tggttgtggt gggcgctggc ttgagcggtt tggagacggc acgcaaagtc    480
caggctgccg gctgtcctg cctcgttctt gaggcgatgg atcgtgtagg gggaaagact    540
ctgagcgtac aatcgggtcc cggcaggacg actatcaatg acctcggcgc tgcgtggatc    600
aatgacagca ccaaagcgaa gtattcaaa ttatttgaaa gatttcattt ggagggcgag    660
ctccagagga cgactggaaa ttcaatccat caagcacaag acggtacaac cactacagct    720
ccttatggtg actccttgct gagcgaggag gttgcaagtg cactcgcgga actccttccc    780
gcatggtctc agctgatcga agagcatagt cttgaagacc caaggcgag ccctcaggcg    840 aagcggctcg acagtgtgag cttcgcgcac tactgtgaga aggacctaaa cttgcctgct    900
gttctcggcg tggcaaacca gatcacacgc gctctgctcg gtgtggaagc ccacgagatc    960
agcatgcttt ttctcaccga ctacatcaag agtgccaccg gtctcagtaa tattgtctcg   1020
gacaagaaag acggtgggca gtatatgcga tgcaaaacag gtatgcagtc gatttgccat   1080
gccatgtcaa aggaacttgt tccaggctca gtgcacctca acaccccgt cgccgaaatt   1140 gagcagtcgg catccggctg tacagtacga tcggcctcgg gcgccgtgtt ccgaagtaaa   1200
aaggtggtgg tttcgttacc gacaaccttg tatcccacct tgacattttc accacctctt   1260
```

```
cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380 tgtgaccccca tctcatttgc cagagatacc agcatcgaag tcgatcggca atggtccatt   1440
acctgtttca tggtcggaga cccgggacgg aagtggtccc aacagtccaa gcaggtacga    1500
caaaagtctg tctgggacca actccgcgca gcctacgaga acgccgggc ccaagtccca     1560 gagccggcca acgtgctcga aatcgagtgg tcgaagcagc agtatttcca aggagcgccg    1620
agcgccgtct atgggctgaa cgatctcatc acactgggtt cggcgctcag aacgccgttc    1680
aagggtgttc atttcgttgg aacggagacg tctttggttt ggaaagggta tatggaaggg    1740
gccatacgat cgggtcaacg aggtgctgca gaagttgtgg ctagcctggt gccagcagca    1800
tag                                                                  1803

<210> SEQ ID NO 3
<211> LENGTH: 1803
<212> TYPE: DNA
<213> ORGANISM: Artificial Sequence
<220> FEATURE:
<223> OTHER INFORMATION: Synthetic Construct Clone F7

<400> SEQUENCE: 3
atggcacttg caccgagcta catcaatccc ccaaacgtcg cctccccagc agggtattct     60
cacgtcggcg taggcccaga cggagggagg tatgtgacaa tagctggaca gattggacaa    120
gacgcttcgg ccgtgacaga ccctgcctac gagaaacagg ttgcccaagc attcgccaac    180
ctgcgagctt gccttgctgc agttggagcc acttcaaacg acgtcaccaa gctcaattac    240
tacatcgtcg actacgcccc gagcaaactc accgcaattg gagatgggct gaaggctacc    300
tttgcccttg acaggctccc tccttgcacg ctggtgccag tgtcggcctt ggcttcacct    360
gaatacctct ttgaggttga tgccacgcg ctggttccag acactcaac cccagacaac      420 gttgcggacg tggtcgtggt gggcgctggc ttgagcggtt tggagacggc acgcaaagtc    480
caggctgccg gctgtcctg cctcgttctt gaggcgatgg atcgtgtagg gggaaagact     540
ctgagcgtac aatcgggtcc cggcaggacg actatcaacg acctcggcgc tgcgtggatc    600
aatgacagca accaaagcga agtattcaaa ttatttgaaa gatttcattt ggagggcgag    660
ctccagagga cgactggaaa ttcaatccat caagcacaag acggtacaac cactacagct    720
ccttatggtg actccttgct gagcgaggag gttgcaagtg cactcgcgga actccttccc    780
gcatggtctc agctgatcga agagcatagt cttgaagacc ccaaggcgag ccctcaggcg    840
aagcggctcg acagtgtgag cttcgcacac tactgtgaga aggatctaaa cttgcctgct    900
gttctcagcg tggcaaacca gatcacacgc gctctgctcg gtgtggaagc ccacgagatc    960
agcatgcttt ttctcaccga ctacatcaag agtgccaccg gtctcagtaa tattttctcg    1020
gacaagaaag acggcgggca gtatatgcga tgcaaaacag gtatgcagtc gatttgccat    1080
gccatgtcaa aggaacttgt tccaggctca gtgcacctca acaccccgt cgccgaaatt     1140 gagcagtcgg catccggctg tacagtacga tcggcctcgg gcgccgtgtt ccgaagcaaa    1200
aaggtggtgg tttcgttacc gacaaccttg tatcccacct tgatattttc accacctctc    1260
cccgccgaga agcaagcatt ggctgaaaaa tccatcctgg gctactatag caagatagtc    1320
ttcgtatggg acaagccgtg gtggcgcgaa caaggcttct cgggcgtcct tcaatcgagc    1380 tgtgaccccca tcttatttgc cagagatacc agcatcgaag tcgatcggca atggtccatt   1440
```

-continued

```
acctgtttca tggtcggaga cccgggacgg aagtggtccc aacagtccaa gcaggtacga    1500
caaaagtctg tctgggacca actccgcgca gcctacgaga acgccgggc  ccaagtccca    1560 gagccggcca acgtgctcga gatcgagtgg tcgaagcagc agtatttcca aggagctccg    1620
agcgccgtct atgggctgaa cgatctcatc acactgggtt cggcgctcag aacgccgttc    1680
aagggtgttc atttcgttgg aacggagacg tctttggttt ggaaagggta tatggaaggg    1740
gccatacgat cgggtcaacg aggcgctgca gaagttgtgg ctagcctggt gccagcagca    1800
tag                                                                  1803
```

<210> SEQ ID NO 4
<211> LENGTH: 1803
<212> TYPE: DNA
<213> ORGANISM: Artificial Sequence
<220> FEATURE:
<223> OTHER INFORMATION: Synthetic Construct Clone F12

<400> SEQUENCE: 4

```
atggcacttg caccgagcta catcaatccc ccaaacgtcg cctccccagc agggtattcc      60
cacgtcggcg taggcccaga cggagggagg tatgcgacaa tagctggaca gattggacaa     120
gacgcttcgg ccgtgacaga ccctgcctac gagaaacagg ttgcccaagc attcgccaac     180
ctgcgagctt gccttgctgc agttggagcc tcttcaaacg acgtcaccaa gctcaattac     240
tacatcgtcg actacgcccc gagcaaactc accgcaattg agatgggct  gaaggctacc     300 tttgcccttg acaggctccc tccttgcacg ctggtgccag tgtcggcctt gtcttcacct     360
gaatacctct ttgaggttga tgctacggcg ctggttccag acactcaac  cccagacaat     420 gttgcggacg tggtcgtggt gggcgctggc ttgagcggtt tggagacggc acgcaaagtc     480
caggccgccg gtctgtcctg cctcgttctt gaggcgatgg atcgtgtggg gggaaagact     540
ctgagcgtac aatcgggtcc cggcaggacg actatcaatg acctcggcgc tgcgtggatc     600
aatgacagca accaaagcga agtattcaaa ttatttgaaa gatttcattt ggagggcgag     660
ctccagagga cgaccggaaa ttcaatccat caagcacaag acgtacaat  cactacagct     720 ccttatggtg actccttgct gagcgaggag gttgcaagtg cactcgcgga actccttccc     780
gcatggtctc agctgatcga agagcatagc cttcaagacc ccaaggcgag ccctcaggcg     840
aagcagctcg acagtgtgag cttcgcgcac tactgtgaga aggaactaaa cttgcctgct     900
gttctcggcg tagcaaacca gatcacacgc gctctgctcg gtgtggaagc ccacgagatc     960
agcatgcttt ttctcaccga ctacatcaag agtgccaccg gtctcagtaa tattgtctcg    1020
gataagaaag acggtgggca gtatatgcga tgcaaaacag gtatgcagtc gctttgccat    1080
gccatgtcaa aggaacttgt tccacgctca gtgcacctca caccccccgt cgctgaaatt    1140
gagcagtctg catccggctg tacagtacga tcggcctcgg gcgccgtgtt ccgaagcaaa    1200
aaggtggtgg tttcgttacc gacaaccttg tatcccacct tgacattttc accacctctc    1260
cccgccgaga agcaagcatt ggcggaaaat tctatcctgg gctactatag caagatagtc    1320
ttcgtatggg acaacccgtg gtggcgcgaa caaggcttct cgggcgtcct ccaatcgagc    1380
tgtgaccccc tctcatttgc cagagatacc agcatcgaag tcgatcggca atggtccatt    1440
acctgtttca tggtcggaga cccgggacgg aagtggtccc aacagtccaa gcaggtacga    1500
cagaagtctg tctggaacca actccgcgca gcctacgaga acgccgggc  ccaagtccca    1560 gagccggcca acgtgctcga aatcgagtgg tcgaagcagc agtatttcca aggagctccg    1620
agcgccgtct atgggctgaa cgatctcatc acactgggtt cggcgctcag aacgccgttc    1680
```

| | |
|---|---:|
| aagtgtgttc atttcgttgg aacggagacg tctttagttt ggaaagggta tatggaaggg | 1740 |
| gccatacgat cgggtcagcg aggcgctgca gaagttgtgg ctagcctggt gccagcagca | 1800 |
| tag | 1803 |

<210> SEQ ID NO 5
<211> LENGTH: 1803
<212> TYPE: DNA
<213> ORGANISM: Artificial Sequence
<220> FEATURE:
<223> OTHER INFORMATION: Synthetic Construct Clone G11

<400> SEQUENCE: 5

| | |
|---|---:|
| atggcacttg caccgagcta catcaatccc ccaaacgtcg cctccccagc agggtattct | 60 |
| cacgtcggcg taggcccaaa cggagggagg tatgtgacaa tagctggaca gattggacaa | 120 |
| gacgcttcgg gcgtgacaga ccctgcctac gagaaacagg ttgcccaagc attcgccaat | 180 |
| ctgcgagctt gccttgctgc agttggagcc acttcaaacg acattaccaa gctcaattac | 240 |
| tacatcgtcg actacaaccc gagcaaactc accgcaattg agatgggct gaaggctacc | 300 |
| tttgcccttg acaggctccc tccttgcacg ctggtgccag tgccggccct ggcttcacct | 360 |
| gaatacctct ttgaggttga tgccacggcg ctggttccag acactcaac cccagacaat | 420 |
| gttgcggacg tggtcgtggt gggcgctggc ttgagcggtt ggagacggc acgcaaagtc | 480 |
| caggctgccg gctgtcctg cctcgttctt gaggcgatgg atcgtgtggg gggaaagact | 540 |
| ctgagcgtac aatcgggtcc cggcaggacg gctatcaatg acctcggcgc tgcgtggatc | 600 |
| aatgacagca ccaaagcga agtattcaaa ttatttgaaa gattccattt ggagggcgag | 660 |
| ctccaggga cgaccggaaa ttcaatccat caagcacaag acgtacaac cactacagct | 720 |
| ccttatggtg actccttgct gagcgaggag gttgcaagtg cactcgcgga actccttccc | 780 |
| gcatggtctc agctgatcga agagcatagt cttgaagacc caaggcgag ccctcaggcg | 840 |
| aagcggctcg acagtgtgag cttcgcgcac tactgtgaga aggacctaaa cttgcctgct | 900 |
| gttctcagcg tggcaaacca gatcacacgc gctctgctcg gtgtggaagc ccacgagatc | 960 |
| agcatgcttt ttctcaccga ctacatcaag agtgccaccg gtctcagtaa tattttctcg | 1020 |
| gacaagaaag acgcgggca gtatatgcga tgcaaaacag gtatgcagtc gctttgccat | 1080 |
| gccatgtcaa aggaacttgt tccaggctca gtgcacctca caccccgt cgccgaaatt | 1140 |
| gagcagtcgg cgtccggctg tatagtacga tcggcctcgg gcggcgtgtt ccgaagtaaa | 1200 |
| aaggtggtgg tttcgttacc gacaaccttg tatcccacct tgatattttc accacctctt | 1260 |
| cccgccgaga agcaagcatt ggcggaaaat tctatcctgg gctactatag caagatagtc | 1320 |
| ttcgtatggg acaacccgtg gtggcgcgaa caaggcttct cgggcgttct ccaatcgagc | 1380 |
| tgtgacccca tctcatttgc cagagatacc agcatcgaag tcgatcggca atggtccatt | 1440 |
| acctgtttca tggtcggaga cccgggacgg aagtggtccc aacagtccaa gcaggtacga | 1500 |
| caaaagtctg tctgggacca actccgcgca gcctacgaga acgccggggc ccaagtccca | 1560 |
| gagccggcca acgtgctcga gatcgagtgg tcgaagcagc agtatttcca aggagctccg | 1620 |
| agcgccgtct atgggctgaa cgatctcatc acactgggtt cggcgctcag aacgccgttc | 1680 |
| aagtgtgttc atttcgttgg aacggagacg tctttggttt ggaaagggta tatggaaggg | 1740 |
| gccatacgat cgggtcaacg aggtgctgca gaagttgtgg ctagcctggt gccagcagca | 1800 |
| tag | 1803 |

<210> SEQ ID NO 6
<211> LENGTH: 1803
<212> TYPE: DNA
<213> ORGANISM: Artificial Sequence
<220> FEATURE:
<223> OTHER INFORMATION: Synthetic Construct Clone R3H1

<400> SEQUENCE: 6

```
atggcacttg caccgagcta catcaatccc ccaaacgtcg cctccccagc agggtattct    60
cacgtcggcg taggcccaaa cgaagcgagg tatgtgacaa tagctggaca gattggacaa   120
gacgcttcgg gcgtgacaga ccctgcctac gagaaacagg ttgcccaagc attcgccaat   180
ctgcgagctt gccttgctgc agttggagcc tcttcaaacg acgtcaccaa gctcaattac   240
tacatcgtcg actacgcccc gagcaaactc accgcaattg agatgggct gaagtctacc    300
tttgccttg acaggctccc tccttgcacg ctggtgccag tgccggccct ggcttcacct    360
gaatacctct ttgaggttga tgccacgcg ctggtgccgg acacacgac cccagacaat     420
gttgcggacg tggtaatggt gggcgctggc ttgagcggtt ggagacggc acgcaaagtc    480
caggctgccg gctgtcctg cctcgttctt gaggcgatgg atcgtgtagg gggaaagact    540
ctgagcgtac aatcgggtcc cggcaggacg actatcaacg acctcggcgc tgcgtggatc    600
aatgacagca accaaagcga agtattcaaa ttatttgaaa gatttcattt ggagggcgag    660
ctccagagga cgaccggaaa ttcaatccat caagcacaag acggtacaat cactacagct    720
ccttatggtg actccttgct gagcgaggag gttgcaagtg cacttgcgga actcctcccc    780
gtatggtctc agctgatcga agagcatagt cttgaagacc caaggcgag ccctcaggcg     840
aagcacctcg acagtgtgag cttcgcacac tactgtgaga aggacctaaa cttgcctgct    900
gttctcagcg tggcaaacca gatcacacgc gctctgctcg gtgtggaagc ccacgagatc    960
agcatgcttt ttctcaccga ctacatcaag agtgccaccg gtctcagtaa tattgtctcg   1020
gacaagaaag acggcgggca gtatatgcga tgcaaaacag gtatgcagtc gatttgccat   1080
gccatgtcaa aggaacttgt tccaggctca gtgcacctca caccccgt cgctggaatt    1140
gagcagtcgg cgtccggctg tatagtacga tcggcctcgg gcggcgtgtt ccgaagcaaa   1200
aaggtggtgg tttcgttacc gacaaccttg tatcccacct tgacatttt accacctctt   1260
tccgccgaga agcaagcatt ggcggaaaat tctatcctgg gctactatag caagatagtc   1320
ttcgtatggg acaagccgtg gtggcgcgaa caaggcttct cgggcgtcct ccaatcgagc   1380
tgtgaccca tctcatttgc cagagatacc agcatcgaag tcgatcggca atggtccatt    1440
acctgtttca tggtcggaga cccgggacgg aagtggtccc aacagtccaa gcaggtacga   1500
caaaagtctg tctggaacca actccgcgca gcctacgaga cgctggggc caagtccca     1560
gagccggcca acgtgctcga gatcgagtgg tcgaagcagc agtatttcca aggagctccg   1620
agcgccgtct atgggctgaa cgatctcatc acactgggtt cggcgctcag aacgccgttc   1680
aagagtgttc atttcgttgg aacggagacg tctttagttt ggaaagggta tatggaaggg   1740
gccatacgat cgggtcaacg aggtgctgca gaagttgtgg ctagcctggt gccagcagca   1800
tag                                                                1803
```

<210> SEQ ID NO 7
<211> LENGTH: 1803
<212> TYPE: DNA
<213> ORGANISM: Artificial Sequence
<220> FEATURE:
<223> OTHER INFORMATION: Synthetic Construct Clone 3B12

<400> SEQUENCE: 7

```
atggcacctg caccgagcta catcaatccc ccaaacgtcg cctccccagc agggtattct      60
cacgtcggcg taggcccaaa cgaagcgagg tatgtgacaa tagctggaca gattggacaa     120
gacgcttcgg ccgtgacaga ccctgcctac gagaaacagg ttgcccaagc attcgccaac    180
ctgcgagctt gtcttgctgc agttggagcc tcttcaaacg acgtcaccaa gctcaattac    240
tacatcgtcg actacgcccc gagcaaactc accgcaattg gagatgggct gaagtctacc    300
tttgcccttg acaggctccc tccttgcacg ctggtgccag tgtcggcctt ggcttcacct    360
gaatacctct ttgaggttga tgctacggcg ctggttccag acactcaac cccagacaat     420
gttgcggacg tggtcgtggt gggcgctggc ttgagcggtt tggagacggc acgcaaagtc    480
caggccgccg ggctgtcctg cctcgttctt gaggcgatgg atcgtgtagg gggaaagact    540
ctgagtgtac aatcgggtcc cggcaggacg actatcaacg acctcggcgc tgcgtggatc    600
aatgacagca accaaagcga agtattcaaa ttatttgaaa gattccattt ggagggcgag    660
ctccagagga cgaccggaaa ttcaatccat caagcacaag acgtacaat cactacagct      720
ccttatggtg actccttgct gagcgaggag gttgcaagtg cacttgcgga actcctcccc    780
gtatggtctc agctgatcga agagcatagt cttgaagacc ccaaggcgag ccctcaggcg    840
aagcggctcg acagtgtgag cttcgcgcac tactgtgaga aggaactaaa cttgcctgct    900
gttctcggcg tggcaaacca gatcacacgc gctctgctcg gtgtggaagc ccacgagatc    960
agcatgcttt ttctcaccga ctacgtcaag agtgccaccg gtctcagtaa tattttctcg   1020
gacaagaaag acggcgggca gtatatgcga tgcaaaacag gtatgcagtc gatttgccat   1080
gccatgtcaa aggaacttgt tccaggctca gtgcacctca acaccccgt cgccgaaatt    1140
gagcagtcgg cgtccggctg tacagtacga tcggcctcgg gcgccgtgtt ccgaagcaaa   1200
aaggtggtgg tttcgttacc gacaaccttg tatcccacct tgacattttc accacctctt   1260
cccgccgaga agcaagcatt ggcggaaaat tctatcctgg gctactatag caagatagtc    1320
ttcgtatggg acaagccgtg gtggcgcgaa caaggcttct cgggcgttct ccaatcgagc    1380
tgtgacccca tctcatttgc cagagatacc agcatcgaag tcgatcggca atggtccatt   1440
acctgtttca tggtcggaga cccgggacgg aagtggtccc aacagtccaa gcaggtacga   1500
caaaagtctg tctgggacca actccgcgca gcctacgaga acgccggggc ccaagtccca   1560
gagccggcca acgtgctcga aatcgagtgg tcgaagcagc agtatttcca aggagctccg   1620
agcgccgtct atgggctgaa cgatctcatc acactgggtt cggcgctcag aacgccgttc   1680
aagggtgttc atttcgttgg aacggagacg tcttttggttt ggaaagggta tatggaaggg  1740
gccatacgat cgggtcaacg aggtgctgca gaagttgtgg ctagcctggt gccagcagca   1800
tag                                                                 1803
```

<210> SEQ ID NO 8
<211> LENGTH: 1803
<212> TYPE: DNA
<213> ORGANISM: Artificial Sequence
<220> FEATURE:
<223> OTHER INFORMATION: Synthetic Construct Clone 4F13G12

<400> SEQUENCE: 8

```
atggcacttg caccgagcta catcaatccc ccaaacgtcg cctccccagc agggtattct      60
cacgtcggcg taggcccaaa cgaagcgagg tatgtgacaa tagctggaca gattggacaa    120
```

| | |
|---|---:|
| gacgcttcgg ccgtgacaga ccctgcctac gagaaacagg ttgcccaagc attcgccaac | 180 |
| ctgcgagctt gccttgctgc agttggagcc acttcaaacg acgtcaccaa gctcaattac | 240 |
| tacatcgtcg actacaaccc gagcaaactc accgcaattg agatgggct gaaggctacc | 300 |
| tttgcccttg acaggctccc tccttgcacg ctggtgccag tgtcggcctt ggcttcacct | 360 |
| gaatacctct ttgaggttaa tgccacggcg ctggttccag dacactcaac cccagacaat | 420 |
| gttgcggacg tggtagtggt gggcgctggc ttgagcggtt tggagacggc acgcaaagtc | 480 |
| caggccgccg gtctgtcctg cctcgttctt gaggcgatgg atcgtgtggg gggaaagact | 540 |
| ctgagcgtac aatcgggtcc cggcaggacg actatcaacg acctcggcgc tgcgtggatc | 600 |
| aatgacagca accaaagcga agtattcaaa ttatttgaaa gatttcatct ggagggcgag | 660 |
| ctccagagga cgactggaaa ttcaatccat caagcacaag acggtacaac cactacagct | 720 |
| ccttatggtg actccttgct gagcgaggag gttgcaagtg cacttgcgga actcctcccc | 780 |
| gcatggtctc agctgatcga agagcatagt cttgaagacc ccaaggcgag ccctcaggcg | 840 |
| aagcggctcg acagtgtgag cttcgcgcac tactgtgaga aggaactaaa cttgcctgct | 900 |
| gttctcggcg tggcaaacca gatcacacgc gctctgctcg gtgtggaagc ccacgagatc | 960 |
| agcatgcttt ttctcaccga ctacatcaag agtgccaccg gtctcagtaa tattttctcg | 1020 |
| gataagaaag acgtgggca gtatatgcga tgcaaaacag gtatgcagtc gctttgccat | 1080 |
| gccatgtcaa aggaacttgt tccaggctca gtgcacctca cacccccgt cgctgaaatt | 1140 |
| gagcagtcgg catccggctg tacagtacgg tcggcctcgg gcgccgtgtt ccgaagcaaa | 1200 |
| aaggtggtgg tttcgttacc gacaaccttg tatcccacct tgacattttc accacccctt | 1260 |
| cccgccgaga agcaagcatt ggcggaaaat tctatcctgg gctactatag caagatagtc | 1320 |
| ttcgtatggg acaagccgtg gtggcgcgaa caaggcttct cgggcgtcct ccaatcgagc | 1380 |
| tgtgaccca tctcatttgc cacagatacc agcatcgaag tcgatcggca atggtccatt | 1440 |
| acctgtttca tggtcggaga cccgggacgg aagtggtccc aacagtccaa gcaggtacga | 1500 |
| caaaagtctg tctgggacca actccgcgca gcctacgaga acgccggggc caagtcccca | 1560 |
| gagccggcca acgtgctcga aatcgagtgg tcgaagcagc agtatttcca aggagctccg | 1620 |
| agcgccgtct atgggctgaa cgatctcatc acactgggtt cggcgctcag aacgccgttc | 1680 |
| aagagtgttc atttcgttgg aacggagacg tctttggttt ggaaagggta tatggaaggg | 1740 |
| gccatacgat cgggtcaacg aggtgctgca gaagttgtgg ctagcctggt gccagcagca | 1800 |
| tag | 1803 |

<210> SEQ ID NO 9
<211> LENGTH: 1620
<212> TYPE: DNA
<213> ORGANISM: Artificial Sequence
<220> FEATURE:
<223> OTHER INFORMATION: Synthetic Construct Clone 4F15A11

<400> SEQUENCE: 9

| | |
|---|---:|
| atggcacttg caccgagcta catcaatccc ccaaacgacg tcaccaagct caattactac | 60 |
| atcgtcgact acgccccgag caaactcacc gcaattggag atgggctgaa ggctaccttt | 120 |
| gcccttgaca ggctccctcc ttgcacgctg tgccagtgt cggccttggc ttcacctgaa | 180 |
| tacctctttg aggttgatgc cacggcgctg gttccaggac actcaacccc agacaatgtt | 240 |
| gcggacgtg tcgtggtggg cgctggcttg agcggtttgg agacggcacg caaagtccag | 300 |
| gctgccgggc tgtcctgcct cgttcttgag gcgatggatc gtgtagggg aaagactctg | 360 |

```
agcgtacaat cgggtcccgg caggacgact atcaacgacc tcggcgctgc gtggatcaat    420
gacagcaacc aaagcgaagt attcaaatta tttgaaagat tccatttgga gggcgagctc    480
cagaggacga ccggaaattc aatccatcaa gcacaagacg gtacaaccac tacagctcct    540
tatggtgact ccttgctgag cgaggaggtt gcaagtgcac tcgcggaact ccttcccgca    600
tggtctcagc tgatcgaaga gcatagtctt gaagacccca aggcgagccc tcaggcgaag    660
cggctcgaca gtgtgagctt cgcgcactac tgtgagaagg aactaaactt gcctgctgtt    720
ctcggcgtag caaaccagat cacacgcgct ctgctcggtg tggaagccca cgagatcagc    780 atgcttttc tcaccgacta cgtcaagagt gccaccggtc tcagtaatat tttctcggat     840
aagaaagacg gcgggcagta tatgcgatgc aaaacaggta tgcagtcgat ttgccacgcc    900
atgtcaaagg aacttgttcc aggctcagtg cacctcaaca ccccgtcgc cgaaattgag     960 cagtcggcgt ccggctgtac agtacgatcg gcctcgggcg ccgtgttccg aagcaaaaag   1020
gtggtggttt cgttaccgac aaccttgtat cccaccttga cattttcacc acctctttcc   1080
gccgagaagc aagcattggc ggaaaatctt atcttgggca tctatagcaa gatagtcttc   1140
gtatggagca acgcgtgtgg gcgcgaacaa ggcttctgcg gcgtcctcca tcagagctgt   1200
ggccccatct catttgccag agataccagc atcgaagtcg atcggcaatg gtccattacc   1260
tgtttcatgg tcgcagaccc gggacggaag tggtcccaac agtccaagca ggtacgacag   1320
aagtctgtct gggaccaact ccgcgcagcc tacgagaacg ccggggccca agtcccagag   1380
ccggccaacg tgctcgagat cgagtggtcg aagcagcagt atttccaagg agcgccgagc   1440
gccgtctatg ggctgaacga tctcatcaca ctgggttcgg cgctcagaac gccgttcaag   1500
ggtgttcatt tcgttggaac ggagacgtct ttagtttgga aagggtatat ggaaggggcc   1560
atacgatcgg gtcaacgagg tgctgcagaa gttgtggcta gcctggtgcc agcagcatag   1620
```

<210> SEQ ID NO 10
<211> LENGTH: 1803
<212> TYPE: DNA
<213> ORGANISM: Artificial Sequence
<220> FEATURE:
<223> OTHER INFORMATION: Synthetic Construct Clone 4F15C3

<400> SEQUENCE: 10

```
atggcacttg caccgagcta catcaatccc ccaaacgtcg cctccccagc agggtattct     60
cacgtcggcg taggcccaga cggagggagg tatgtggcaa tagctggaca gattggacaa    120
gacgcttcgg gcgtgacaga ccctgcctac gagaaacagg ttgcccaagc attcgccaat    180
ctgcgagctt gccttgctgc agttggagcc acttcaaacg acgtcaccaa gctcaactac    240
tacatcgtcg actacgcccc gagcaaactc accgcaattg gagatgggct gaaggctacc    300
tttgcccttg acaggctccc tccttgcacg ctggtgccag tgccgccct ggcttcacct     360 gaatacctct ttgaggttga tgccacggcg ctggttccag acactcaac cccagacaat    420 gttgcggacg tggtcgtggt gggcgctggc ttgagcggtt tggagacggc acgcaaagtc    480
caggccgccg ggctgtcctg cctcgttctt gaggcgatgg atcgtgtagg gggaaagact    540
ctgagcgtac aatcgggtcc cggcaggacg actatcaacg acctcggcgc tgcgtggatc    600
aatgacagca accaaagcga agtattcaaa ttatttgaaa gatttcattt ggagggcgag    660
ctccagagga cgaccggaaa ttcaatccat caagcacaag acgtacaat cactacagct    720 ccttatggtg actccttgct gagcgaggag gttgcaagtg cactcgcgga actccttccc    780
```

| | |
|---|---:|
| gcatggtctc agctgatcga agagcatagt cttgaagacc ccaaggcgag ccctcaggcg | 840 |
| aagcggctcg acagtgtgag cttcgcgcac tactgtgaga aggacctaaa cttgcctgct | 900 |
| gttctcggcg tggcaaacca gatcacacgc gctctgctcg gtgtggaagc ccacgagatc | 960 |
| agcatgcttt ttctcaccga ctacatcaag agtgccaccg gtctcagtaa tattgtctcg | 1020 |
| gacaagaaag acggtgggca gtatatgcga tgcaaaacag gtatgcagtc gctttgccat | 1080 |
| gccatgtcaa aggaacttgt tccaggctca gtgcacctca cacccccgt cgccgaaatt | 1140 |
| gagcagtcgg cgtccggctg tatagtacga tcggcctcgg cggcgtgtt ccgaagtaaa | 1200 |
| aaggtggtgg tttcgttacc gacaaccttg tatcccacct tgatattttc accacctctc | 1260 |
| cccgccgaga agcaagcatt ggctgaaaaa tccatcctgg gctactatag caagatagtc | 1320 |
| ttcgtatggg acaagccgtg gtggcgcgaa caaggcttct cgggcgtcct ccaatcgagc | 1380 |
| tgtgacccca tctcatttgc cagagatacc aacatcgaag tcgatcggca atggtccatt | 1440 |
| acctgtttca tggtcggaga cccgggacgg aagtggtccc aacagtccaa gcaggtacga | 1500 |
| cagaagtctg tctggaacca actccgcgca gcctacgaga acgccggggc ccaagtccca | 1560 |
| gagccggcca acgtgctcga aatcgagtgg tcgaagcagc agtatttcca aggagctccg | 1620 |
| agcgccgtct atgggctgaa cgatctcatc acactgggtt cggcgctcag aacgccgttc | 1680 |
| aagtgtgttc atttcgttgg aacggagacg tctttggttt ggaaagggta tatggaaggg | 1740 |
| gccatacgat cgggtcaacg aggtgctgca gaagttgtgg ccagcctggt gccagcagca | 1800 |
| tag | 1803 |

<210> SEQ ID NO 11
<211> LENGTH: 1803
<212> TYPE: DNA
<213> ORGANISM: Artificial Sequence
<220> FEATURE:
<223> OTHER INFORMATION: Synthetic Construct Clone 4F16C6

<400> SEQUENCE: 11

| | |
|---|---:|
| atggcacttg caccgagcta catcaatccc ccaaacgtcg cctccccagc agggtattct | 60 |
| cacgtcggcg taggcccaaa cggagggagg tatgtgacaa tagctggaca gattggacaa | 120 |
| gacgctttgg gcgtgacaga ccctgcctac gagaaacagg ttgcccaagc attcgccaat | 180 |
| ctgcgagctt gtcttgctgc agttggagcc acttcaaacg acgtcaccaa gctcaattac | 240 |
| tacatcgtcg actacgcccc gagcaaactc accgcaattg agatgggct gaaggctacc | 300 |
| tttgcccttg acaggctccc tccttgcacg ctggtgccag tgccggccct ggcttcacct | 360 |
| gaatacctct ttgaggttga tgccacggcg ctggttccag acacacaac cccagacaat | 420 |
| gttgcggacg tggtcgtggt gggcgctggc ttgagcggtt tggagacggc acgcaaagtc | 480 |
| caggctgctg gctgtcctg cctcgttctt gaggcgatgg atcgtgtggg gggaaagact | 540 |
| ctgagcgtac aatcgggtcc cggcaggacg actatcaacg acctcggcgc tgcgtggatc | 600 |
| aatgacagca accaaagcga agtattcaaa ttatttgaaa gatttcatt ggagggcgag | 660 |
| ctccagagga cgaccggaaa ttcaatccat caagcacaag acgtacaac cactacagct | 720 |
| ccttatggtg attccttgct gagcgaggag gttgcaagtg cactcgcgga actccttccc | 780 |
| gcatggtctc agctgatcga agagcatagt cttgaagacc ccaaggcgag ccctcaggcg | 840 |
| aagcggctcg acagtgtgag cttcgcacac tactgtgaga aggacctaaa cttgcctgct | 900 |
| gttctcagcg tggcaaacca gatcacacgc gctctgctcg gtgtggaagc ccacgagatc | 960 |
| agcatgcttt ttctcaccga ctacatcaag agtgccaccg gtctcagtaa tattgtctcg | 1020 |

```
gataagaaag acggtgggca gtatatgcga tgcaaaacag gtatgcagtc gatttgccat    1080
gccatgtcaa aggaacttgt tccaggctca gtgcacctca acaccccgt  cgccgaaatt    1140
gagcagtcgg catccggctg tacagtacga tcggcctcgg gcgccgtgta ccgaagtaaa    1200
aaggtggtgg tttcgttacc gacaaccttg tatcccacct tgacattttc accacctctc    1260
cccgccgaga agcaagcatt ggcggaaaat tctatcctgg ctactatag  caagatagtc    1320
ttcgtatggg acaagccgtg gtggcgcgaa caaggcttct cgggcgttct ccaatcgagc    1380
tgtgaccccca tctcatttgc cagagatacc agcatcgaag tcgatcggca atggtccatt    1440
acctgtttca tggtcggaga cccgggacgg aagtggtccc aacagtccaa gcaggtacga    1500
caaaagtctg tctggaacca actccgcgca gcctacgaga acgctggggc ccaagtccca    1560
gagccggcca acgtgctcga gatcgagtgg tcgaagcagc agtatttcca aggagctccg    1620
agcgccgtct atgggctgaa cgatctcatc acactgggtt cggcgctcag aacgccgttc    1680
aagtgtgttc atttcgttgg aacggagacg tctttggttt ggaaagggta tatggaaggg    1740
gccatacgat cgggtcaacg aggcgctgca gaagttgtgg ctagcctggt gccagcagca    1800
tag                                                                  1803

<210> SEQ ID NO 12
<211> LENGTH: 1803
<212> TYPE: DNA
<213> ORGANISM: Artificial Sequence
<220> FEATURE:
<223> OTHER INFORMATION: Synthetic Construct Clone 4F19F2

<400> SEQUENCE: 12
atggcacttg caccgagcta catcaatccc ccaaacgtcg cctccccagc agggtattct      60
cacgtcggcg taggcccaaa cggagggagg tatgtgacaa tagctggaca gattggacaa     120
gacgcttcgg gcgtgacaga ccctgcctac gagaaacagg ttgcccaagc attcgccaac     180
ctgcgagctt gccttgctgc agttggagcc acttcaaacg acattaccaa gctcaattac     240
tacatcgtcg actacgcccc gagcaaactc accgcaattg agatgggct  gaaggctacc     300
tttgcccttg acaggctccc tccttgcacg ctggtgccag tgccggccct ggcttcacct     360
gaatacctct ttgaggttga tgccacggcg ctggttccag acactcgac  cccagacaat     420
gttgcggacg tggtcgtggt gggcgctggc ttgagcggtt tggagacggc acgcaaagtc     480
caggctgccg gctgtcctg  cctcgttctt gaggcgatgg atcgtgtagg gggaaagact     540
ctgagcgtac aatcaggtcc cggcaggacg accatcaatg acctcggcgc cgcgtggatc     600
aatgacagca ccaaagcga  agtattcaaa ttatttgaaa gatttcattt ggagggcgag     660
ctccagagga cgactggaaa ttcaatccat caagcacaag acggtacaac cactacagct     720
ccttatggtg actccttgct gagcgaggag gttgcaagtg cactgcggga actcctcccc     780
gtatggtctc agctgatcga agagtatagt cttgaagacc ccaaggcgag ccctcaggcg     840
aagcagctcg acagtgtgag cttcgcgcac tactgtgaga aggacctaaa cttgcctgct     900
gttctcggcg cggcaaacca gatcacacgc gctctgctcg gtgtggaagc ccacgagatc     960
agcatgcttt ttctcaccga ctacatcaag agtgccaccg gtctcagtaa tattttctcg    1020
gacaagaaag acggcgggca gtatatgcga tgcaaaacag gtatgcagtc gctttgccat    1080
gccatgtcaa aggaacttgt tccaggctca gtgcacctca acaccccgt  cgccgaaatt    1140
gagcagtcgg catccggctg tacagtacga tcggcctcgg gcgccgtgtt ccgaagcaaa    1200
```

```
aaggtggtgg tttcgttacc gacaaccttg tatcccacct tgatattttc accacctctt    1260
cccgccgaga agcaagcatt ggcggaaaat tctatcctgg gctactatag caagatagtc    1320
ttcgtatggg acaacccgtg gtggcgcgaa caaggcttct cgggcgtcct ccaatcgagc    1380
tgtgacccca tctcatttgc cagagatacc agcatcgaag tcgatcggca atggtccatt    1440
acctgtttca tggtcggaga cccgggacgg aagtggtccc aacagtccaa gcaggtacga    1500
caaaagtctg tctgggacca actccgcgca gcctacgaga acgccgggc  ccaagtccca    1560 gagccggcca acgtgctcga aatcgagtgg tcgaagcagc agtatttcca aggagctccg    1620
ggcgccgtct atgggctgaa cgatctcatc acactgggtt cggcgctcag aacgccgttc    1680
aagtgtgttc atttcgttgg aacggagacg tctttggttt ggaaagggta tatggaaggg    1740
gccatacgat cgggtcaacg aggtgctgca gaagttgtgg ctagcctggt gccagcagca    1800
tag                                                                 1803
```

<210> SEQ ID NO 13
<211> LENGTH: 1803
<212> TYPE: DNA
<213> ORGANISM: Artificial Sequence
<220> FEATURE:
<223> OTHER INFORMATION: Synthetic Construct Clone 4F21C8

<400> SEQUENCE: 13

```
atggcacttg caccgagcta catcaatccc ccaaacgtcg cctccccagc agggtattct      60
cacgtcggcg taggcccaga cggagggagg tatgtgacaa tagctggaca gattggacaa     120
gacgctttgg gcgtgacaga ccctgcctac gagaaacagg ttgcccaagc attcgccaat     180
ctgcgagctt gtcttgctgc agttggagcc acttcaaacg acgtcaccaa gctcaattac     240
tacatcgtcg actacgcccc gagcaaactc accgcaattg gagatgggct gaagtctacc     300
tttgcccttg acaggctccc tccttgcacg ctggtgccag tgccggcctt gtcttcacct     360
gaatacctct ttgaggttga tgctacggcg ctggttccag acactcaac  cccagacaat     420 gttgcggacg tggtcgtggt gggcgctggc ttgagcggtt tggagacggc acgcaaagtc     480
caggctgccg ggctgtcctg cctcgttctt gaggcgatgg atcgtgtggg gggaaagact     540
ctgagcgtac aatcgggccc cggcaggacg actatcaacg acctcggcgc tgcgtggatc     600
aatgacagca accaaagcga agtattcaaa ttatttgaaa gatttcattt ggagggcgag     660
ctccagagga cgaccggaaa ttcaatccat caagcacaag acggtacaac cactacagct     720
ccttatggtg actccttgct gagcgaggag gttgcaagtg cactcgcgga actccttccc     780
gcatggtctc agctgatcga agagcatagt cttgaagacc ccaaggcgag ccctcaggcg     840
aagcggctcg acagtgtgag cttcgcacac tactgtgaga aggatctaaa cttgcctgct     900
gttctcagcg tggcaaacca gatcacacgc gctctgctcg gtgtggaagc ccacgagatc     960
agcatgcttt ttctcaccga ctacatcaag agtgccaccg gtctcagtaa tattttctcg    1020
gacaagaaag acggcgggca gtatgtgcga tgcaaaacag gtatgcagtc gatttgccat    1080
gccatgtcaa aggaacttgt tccaggctca gtgcacctca acacccccgt cgccggaatt    1140
gagcagtcgg cgtccggctg tacagtacga tcggcctcgg gcgccgtgtt ccgaagcaaa    1200
aagtggtgtg tttcgttacc gacaaccctg tatcccacct tgacatttc accacctctt    1260 cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380
tgtgacccca tctcatttgc cagagatacc agcatcgaag tcgatcggca atggtccatt    1440
```

```
acctgtttca tggtcggaga cccgggacgg aagtggtccc aacagtccaa gcaggtacga    1500
caaaagtctg tctggaacca actccgcgca gcctacgaga acgctggggc ccaagtccca    1560
gagccggcca acgtgctcga gatcgagtgg tcgaagcagc agtatttcca aggagctccg    1620
agcgccgtct atgggctgaa cgatctcatc acactgggtt cggcgctcag aacgccgttc    1680
aagagtgttc atttcgttgg aacggagacg tctttagttt ggaaagggta tatgaaggg     1740 gccatacgat cgggtcagcg aggcgctgca gaagttgtgg ctagcctggt gccagcagca    1800
tag                                                                  1803

<210> SEQ ID NO 14
<211> LENGTH: 1803
<212> TYPE: DNA
<213> ORGANISM: Artificial Sequence
<220> FEATURE:
<223> OTHER INFORMATION: Synthetic Construct Clone 4F22B2

<400> SEQUENCE: 14
atggcacttg caccgagcta catcaatccc ccaaacgccg cctccccagc agggtattcc      60
cacgtcggcg taggcccaga cggagggagg tatgtgacaa tagctggaca gattggacaa    120
gacgctttgg gcgtgacaga ccctgcctac gagaaacagg ttgcccaagc attcgccaac    180
ctgcgagctt gccttgctgc agttggagcc tcttcaaacg acgtcaccaa gctcaattac    240
tacatcgtcg actacgcctc gagcaaactc accgcaattg agatgggct gaaggctacc     300 tttgccctg acaggctccc tccttgcacg ctggtgccag tgtcggcctt ggcttcacct      360
gaatacctct ttgaggttga tgccacggcg ctggtgccgg acacacaac cccagacaat     420 gttgcggacg tggtcgtggt gggcgctggc ttgagcggtt tggagacggc acgcaaagtc    480
caggctgccg gctgtcctg cctcgttctt gaggcgacgg atcgtgtagg gggaaagact    540
ctgagcgtac aatcgggtcc cggcaggacg actatcaatg acctcggcgc tgcgtggatc    600
aatgacagca accaaagcga agtattcaaa ttatttgaaa gatttcatct ggagggcgag    660
ctccagagga cgaccggaaa ttcaatccat caagcacaag acgtacaat cactacagct     720 ccttatggtg actccttgct gagcgaggaa gttgcaagtg cactcgcgga actccttccc    780
gcatggtctc agctgatcga agagcatagt cttgaaaacc ccaaggagag ccctcaggcg    840
aagcggctcg acagtgtgag cttcgcgcac tactgtgaga aggacctaaa cttgcctgct    900
gttctcggcg tggcaaacca gatcacacgc gctctgctcg gtgtggaagc ccacgagatc    960
agcatgcttt ttctcaccga ctacatcaag agtgccaccg gtctcagtaa tattttctcg   1020
gacaagaaag acggcgggca gtatatgcga tgcaaaacag gtatgcagtc gctttgccat   1080
gccatgtcaa aggaacttgt tccaggctca gtgcgcctca cacccccgt cgctgaaatt    1140 gagcagtcgg catccggctg tacagtacga tcggcctcgg gcgccgtgtt ccgaagcaaa   1200
aaggtggtgg tttcattacc ggcaaccttt tctcccacct tgacatttc accacctctc    1260 cccgccgaga agcaagcatt ggcggaaaat tctatcctgg gctactatag caagatagtc   1320
ttcgtatggg acaagccgtg gtggcgcgaa caaggcttct cgggcgttct ccaatcgagc   1380
tgtgacccca tctcatttgc cagagatacc agcatcgaag tcgatcggca atggtccatt   1440
acctgtttca tggtcggaga cccgggacgg aagtggtccc aacagtccaa gcaggtacga   1500
caaaagtctg tctgggacca actccgcgca gcctacgaga acgccggggc ccaagtccca   1560
gagccgccga acgtgctcga gatcggtagg tcgaagcagc agtatttcca aggagctccg   1620
```

-continued

| | |
|---|---|
| agcgccgtct atgggctgaa cgatctcatc acactgggtt cggcgctcag aacgccgttc | 1680 |
| aagtgtgttc atttcgttgg aacggagacg tctttagttt ggaaagggta tatggaaggg | 1740 |
| gccatacgat cgggtcaacg aggtgctgca gaagttgtgg ctagcctggt gccagcagca | 1800 |
| tag | 1803 |

<210> SEQ ID NO 15
<211> LENGTH: 1803
<212> TYPE: DNA
<213> ORGANISM: Artificial Sequence
<220> FEATURE:
<223> OTHER INFORMATION: Synthetic Construct Clone 4F24F2

<400> SEQUENCE: 15

| | |
|---|---|
| atggcacttg caccgagcta catcaatccc ccaaacgtcg cctccccagc agggtattct | 60 |
| cacgtcggcg taggcccaaa cgaagcgagg tatgtgacaa tagctggaca gattggacaa | 120 |
| gacgcttcgg gcgtgacaga ccctgcctac gagaaacagg ttgcccaagc attcgccaac | 180 |
| ctgcgagctt gccttgctgc agttggagcc acttcaaacg acgtcaccaa gctcaattac | 240 |
| tacatcgtcg actacgcccc gagcaaactc accccaattg gagatgggct gaaggctacc | 300 |
| tttgcccttg acaggctccc ttcttgcacg ctggtgccag tgtcggcctt ggcttcacct | 360 |
| gaatacctct ttgaggttga tgccacggcg ctggttccag acactcaac cccagacaac | 420 |
| gttgcggacg tggtcgtggt gggcgctggc ttgagcggtt tggagacggc acgcaaagtc | 480 |
| caggctgccg ggctgtcctg cctcgttctt gaggcgatgg atcgtgtggg gggaaagact | 540 |
| ctgagcgtac aatcgggtcc cggcaggacg actatcaatg acctcggcgc tgcgtggatc | 600 |
| aatgacagca ccaaagcga agtattcaaa ttatttgaaa gatttcattt ggagggcgag | 660 |
| ctccagagga cgaccggaaa ttcaatccat caagcacaag acggtacaat cactactgct | 720 |
| ccttatggtg actccttgct gagcgaggag gttgcaagtg cactcgcgga actcctcccc | 780 |
| gtatggtctc agctgatcga agagcatagt cttgaagacc caaggcgag ccctcaggcg | 840 |
| aagcggctcg acagtgtgag cttcgcgcac tactgtgaga aggaactaaa cttgcctgct | 900 |
| gttctcggcg tagcaaacca gatcacacgc gctctgctcg gtgtggaagc ccacgagatc | 960 |
| agcatgcttt ttctcaccga ctacatcaag agtgccaccg gtctcagtaa tattttctcg | 1020 |
| gacaagaaag acggcgggca gtatatgcga tgcaaaacag gtatgcagtc gatttgccat | 1080 |
| gccatgtcaa aggaacttgt tccaggctca gtgcacctca acaccccgt cgccgaaatt | 1140 |
| gagcagtcgg catccggctg tatagtacga tcggcctcgg gcgccgtgtt ccgaagtaaa | 1200 |
| aaggtggtgg tttcgttacc gacaaccttg tatcccacct tgatatttc accaccttt | 1260 |
| cccgccgaga agcaagcatt ggcggaaaat tctatcctgg gctactatag caagatagtc | 1320 |
| ttcgtatggg acaagccgtg gtggcgcgaa caaggcttct cgggcgttct ccaatcgagc | 1380 |
| tgtgacccca tctcatttgc cagagatacc agcatcgaag tcgatcggca atggtccatt | 1440 |
| acctgtttca tggtcggaga cccgggacgg aagtggtccc aacagtccaa gcaggtacga | 1500 |
| caaaagtctg tctggaacca actccgcgca gcctacgaga acgccgggc caagtccca | 1560 |
| gagccggcca acgtgctcga gatcgagtgg tcgaagcagc agtatttcca aggagctccg | 1620 |
| agcgccgtct atgggctgaa cgatctcatc acactgggtt cggcgctcag aacgccgttc | 1680 |
| aagagtgttc atttcgttgg aacggagacg tctttggttt ggaaagggta tatggaaggg | 1740 |
| gccatacgat cgggtcaacg aggcgctgca gaagttgtgg ctagcctggt gccagcagca | 1800 |
| tag | 1803 |

<210> SEQ ID NO 16
<211> LENGTH: 1803
<212> TYPE: DNA
<213> ORGANISM: Artificial Sequence
<220> FEATURE:
<223> OTHER INFORMATION: Synthetic Construct Clone 4F28G1

<400> SEQUENCE: 16

```
atggcacttg cgccgagcta catcaatccc ccaaacgtcg cctccccagc agggtattct      60
cacgtcggcg taggcccaga cggagggagg tatgtgacaa tagctggaca gattggacaa     120
gacgctttgg gcgtgacaga ccctgcctac gagaaacagg ttgcccaagc attcgccaat     180
ctgcgagctt gccttgctgc agttggagcc acttcaaacg acgtcaccaa gctcaattac     240
tacatcgtcg actacgcccc gagcaaactc accgcaattg agatgggct gaaggctacc      300
tttgcccttg acaggctccc tccttgcacg ctggtgccag tgtcggcctt gtcctcacct     360
gaatacctct ttgaggttga tgccacggcg ctggtgccgg acacacgac cccagacaac      420
gttgcggacg tggtcgtggt gggcgctggc ttgagcggtt tggagacggc acgcaaagtc     480
caggctgccg ggctgtcctg cctcgttctt gaggcgatgg atcgtgtagg gggaaagact     540
ctgagcgtac aatcgggtcc cggcaggacg actatcaatg acctcggcgc tgcgtggatc     600
aatgacagca accaaagcga agtattcaaa ttatttgaaa gatttcattt ggagggcgag     660
ctccagagga cgaccggaaa ttcaatccat caagcacaag acgtacaac cactacagct      720
ccttatggtg actccttgct gagcgaggag gttgcaagtg cactcgcgga actccttccc     780
gcatggtctc agctgatcga agagcatagt cttgaagacc ccaaggcgag ccctcaggcg     840
aagcggctcg acagtgtgag cttcgcgcac tactgtgaga aggacctaaa cttgcctgct     900
gttctcggcg tagcaaacca gatcacacgc gctctgctcg tgtggaagc ccacgagatc      960
agcatgcttt ttctcaccga ctacatcaag agtgccaccg gtctcagtaa tattttctcg    1020
gacaagaaag acggcgggca gtatatgcga tgcaaaacag gtatgcagtc gctttgccat    1080
gccatgtcaa ggaacttgt tccaggctca gtgcacctca caccccccgt cgctgaaatt     1140
gagcagtcgg catccggctg tacagtacga tcggcctcgg gcgccgtgtt ccgaagcaaa    1200
aaggtggtgg tttcgttacc gacaaccttg tatcccacct tgacattttc accacctctc    1260
cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380
tgtgaccca tctcatttgc cagagatacc agcatcgaag tcgatcggca atggtccatt     1440
acctgtttca tggtcggaga cccgggacgg aagtggtccc aacagtccaa gcaggtacga    1500
caaaagtctg tctgggacca actccgcgca gcctacgaga acgccggggc ccaagtccca    1560
gagccggcca acgtgctcga gatcgagtgg tcgaagcagc agtatttcca aggagcgccg    1620
agcgccgtct atgggctgaa cgatctcatc acactgggtt cggcgctcag aacgccgttc    1680
aagggtgttc atttcgttgg aacggagacg tctttagttt ggaaagggta tatgaagggg    1740
gccatacgat cgggtcaacg aggtgctgca gaagttgtgg ctagcctggt gccagcagca    1800
tag                                                                  1803
```

<210> SEQ ID NO 17
<211> LENGTH: 1803
<212> TYPE: DNA
<213> ORGANISM: Artificial Sequence
<220> FEATURE:

<223> OTHER INFORMATION: Synthetic Construct Clone 4F2G10

<400> SEQUENCE: 17

```
atggcacttg caccgagcca catcaatccc ccaaacgtcg cctccccagc agggtattcc      60
cacgtcggcg taggcccaaa cggagggagg tatgtgacaa tagccggaca gattggacaa     120
gacgctttgg gcgtgacaga ccctgcctac gagaaacagg ttgcccaagc attcgccaac     180
ctgcgagctt gccttgctgc agttggagcc acttcaaacg acgtcaccaa gctcaattac     240
tacatcgtcg actacaaccc gagcaaactc accgcaattg agatgggct gaaggctacc      300
tttgcccttg acaggctccc tccttgcacg ctggtgccag tgccggccct ggcttcacct     360
gaatacctct ttgaggttga tgccacggcg ctggtgccgg acacacgac cccagacaac      420
gttgcggacg tggtcgtggt gggcgctggc ttgagcggtt tggagacggc acgcaaagtc     480
caggctgccg gtctgtcctg cctcgttctt gaggcgatgg atcgtgtagg gggaaagact     540
ctgagcgtac aatcgggtcc cggcaggacg actatcaatg acctcggcgc tgcgtggatc     600
aatgacagca accaaagcga agtattcaaa ttatttgaaa ggttccattt ggagggcgag     660
ctccagagga cgactggaaa ttcaatccat caagcacaag acgtacaac cactacagct      720
ccttatggtg actccttgct gagcgaggag gttgcaagtg cactcgcgga actccttccc     780
gcatggtctc agctgatcga agagcatagt cttgaagacc caaggcgag ccctcaggcg      840
aagcggctcg acagtgtgag cttcgcgcac tactgtgaga aggacctaaa cttgcctgct     900
gttctcggcg tggcaaacca gatcacacgc gctctgctcg gtgtggaagc ccacgagatc     960
agcatgcttt ttctcaccga ctacatcaag agtgccaccg gtctcagtaa tattgtctcg    1020
gacaagaaag acgcgggca gtatatgcga tgcaaaacag gtatgcagtc gctttgccat     1080
gccatgtcaa aggaacttgt tccaggctca gtgcacctca caccccgt cgctgaaatt      1140
gagcagtcgg cgtccggctg tacagtacga tcggcctcgg gcgccgtgtt ccgaagcaaa    1200
aaggtggtgg tttcgttacc gacaaccttg tatcccacct tgacattttc accacctctt    1260
cccgccgaga agcaagcatt ggctgaaaaa tccatcctgg gctactatag caagatagtc    1320
ttcgtatggg acaagccgtg gtggcgcgaa caaggcttct cgggcgtcct ccaatcgagc    1380
tgtgacccca tctcattagc cagagatacc agcatcgaag tcgatcggga atggtccatt    1440
acctgtttca tggtcggaga cccggacgg aagtggtccc aacagtccaa gcaggtacga     1500
cagaagtctg tctggaacca actccgcgca gcctacgaga acgccggggc ccaagtccca    1560
gagccggcca acgtgctcga gatcgagtgg tcgaagcagc agtatttcca aggagctccg    1620
agcgccgtct atgggctgaa cgatctcatc acactggtt cggcgctcag aacgccgttc     1680
aagggtgttc atttcgtcgg aacggagacg tctttggttt ggaaagggta tatggaaggg    1740
gccatacgat cgggtcaacg aggtgctgca gaagttgtgg ctagcctggt gccagcagca    1800
tag                                                                  1803
```

<210> SEQ ID NO 18
<211> LENGTH: 1803
<212> TYPE: DNA
<213> ORGANISM: Artificial Sequence
<220> FEATURE:
<223> OTHER INFORMATION: Synthetic Construct Clone 4F3B5

<400> SEQUENCE: 18

```
atggcacttg caccgagcca catcaatccc ccaaacgtcg cctccccagc agggtattcc      60
cacgtcggcg taggcccaaa cggagggagg tatgtgacaa tagctggaca gattggacaa    120
```

```
gacgcttcgg gcgtgacaga ccctgcctac gagaaacagg ttgcccaagc attcgccaat      180
ctgcgagctt gccttgctgc agttggagcc acttcaaacg acgtcaccaa gctcaattac      240
tacatcgtcg actacgcccc gagcaaactc accgcaattg agatgggct gaaggctacc       300 tttgcccttg acaggctccc tccttgcacg ctggtgccag tgtcggcctt ggcttcacct      360
gaatacctct ttgaggttga tgccacggcg ctggttccag acactcaac cccagacaac       420 gttgcggacg tggtcgtggt gggcgctggc ttgagcggtt tggagacggc acgcaaagtc      480
caggctgccg ggctgtcctg cctcgttctt gaggcgatgg atcgtgtagg gggaaagact      540
ctgagcgtac aatcgggtcc cggcaggacg actatcaacg acctcggcgc tgcgtggatc      600
aatgacagca accaaagcga agtattcaaa ttatttgaaa gatttcattt ggagggcgag      660
ctccagagga cgaccggaaa ttcaatccat caagcacaag acggtacaac cactacagct      720
ccttatggtg actccttgct gagcgaggag gttgcaagtg cactcgcgga actccttccc      780
gcatggtctc agctgatcga agagcatagt cttgaagacc caaggcgag ccctcaggcg       840 aagcggctcg acagtgtgag cttcgcacac tactgtgaga aggacctaaa cttgcctgct      900
gttctcagcg tggcaaacca gatcacacgc gctctgctcg gtgtggaagc ccacgagatc      960
agcatgcttt ttctcaccga ctacatcaag agtgccaccg gtctcagtaa tattttctcg     1020
gacaagaaag acggcgggca gtatatgcga tgcaaaacag gtatgcagtc gctttgccat     1080
gccatgtcaa aggaacttgt tccaggctca gtgcacctca acacccccgt cgctgaaatt     1140
gagcagtcgg catccggctg tacagtacga tcggcctcgg gcgccgtgtt ccgaagtaaa     1200
aaggtggtgg tttcgttacc gacaaccttg tatcccacct tgatattttc accacctctt     1260
cccgccgaga agcaagcatt ggcggaaaat tctatcctgg gctactatag caagatagtc     1320
ttcgtatggg acaagccgtg gtggcgcgaa caaggcttct cgggcgtcct ccaatcgagc     1380 tgtgaccccca tctcatttgc cagagatacc agcatcgaag tcgatcggca atggtccatt     1440
acctgtttca tggtcgggga cccgggacgg aagtggtccc aacagtccaa gcaggtacga     1500
caaaagtctg tctgggacca actccgcgca gcctacgaga acgccgggc ccaagtccca      1560 gagccggcca acgtgctcga aatcgagtgg tcgaagcagc agtatttcca aggagctccg     1620
agcgccgtct atgggctgaa cgatctcatc acactgggtt cggcgctcag aacgccgttc     1680
aagggtgttc atttcgttgg aacggagacg tctttggttt ggaaagggta tatggaaggg     1740
gccatacgat cgggtcagcg aggtgctgca gaagttgtgg ctagcctggt gccagcagca     1800
tag                                                                   1803

<210> SEQ ID NO 19
<211> LENGTH: 1803
<212> TYPE: DNA
<213> ORGANISM: Artificial Sequence
<220> FEATURE:
<223> OTHER INFORMATION: Synthetic Construct Clone 4F6A11

<400> SEQUENCE: 19
atggcacttg caccgagcta catcaatccc ccaaacgtcg cctccccagc agggtattct       60
cacgtcggcg taggcccaga cggagggagg tatgtgacaa tagctggaca gattggacaa      120
gacgcttcgg ccgtgacaga cccgcctac gagaaacagg ttgcccaac attcgccaac       180 ctgcgagctt gtcttgctgc agttggagcc tcttcaaacg acgtcaccaa gctcaattac      240
tacatcgtcg actacgcccc gagcaaactc accgcaattg agatgggct gaaggctacc       300
```

-continued

```
tttgcccttg acaggctccc tccttgcacg ctggtgccag tgtcggcctt gtcttcacct    360
gaatacctct ttgaggttga tgccacggcg ctggttccag gacactcaac cccagacaat    420
gttgcggacg tggtagtggt gggcgctggc ttgagcggtt tggagacggc acgcaaagtc    480
caggccgccg gtctgtcctg cctcgttctt gaggcgatgg atcgtgtagg gggaaagact    540
ctgagcgtac aatcgggtcc cggcaggacg actatcaatg acctcggcgc tgcgtggatc    600
aatgacagca accaaagcga agtattcaaa ttatttgaaa gatttcattt ggagggcgag    660
ctccagagga cgaccggaaa ttcaatccat caagcacaag acggtacaat cactacagct    720
ccttatggtg actccttgct gagcgaggag gttgcaagtg cactcgcgga actccttccc    780
gcatggtctc agctgatcga agagcatagc cttcaagacc ccaaggcgag ccctcaggcg    840
aagcagctcg acagtgtgag cttcgcgcac tactgtgaga aggaactaaa cttgcctgct    900
gttctcggcg tggcaaacca gatcacacgc gctctgctcg gtgtggaagc ccacgaggtc    960
agcatgcttt tcctcaccga ctacatcaag agtgccaccg gtctcagtaa tattgtctcg   1020
gataagaaag acggtgggca gtatatgcga tgcaaaacag gtatgcagtc gctttgccat   1080
gccatgtcaa aggaacttgt tccaggctca gtgcacctca acaccccgt cgctgaaatt    1140
gagcagtcgg catccggctg tacagtacga tcggcctcgg gcgccgtgtt ccgaagcaaa   1200
aaggtggtgt tttcgttacc gacaaccttg tatcccacct tgacattttc accacctctc   1260
cccgccgaga agcaagcatt ggcggaaaat tctatcctgg gctactatag caagatagtc   1320
ttcgtatggg acaacccgtg gtggcgcgaa caaggcttct cgggcgttct ccaatcgagc   1380
tgtgaccccA tctcatttgc cagagatacc agcatcgaag ccgatcggca atggtccatt   1440
acctgtttca tggtcggaga cccgggacgg aagtggtccc aacagtccaa gcaggtacga   1500
caaaagtctg tctggaacca actccgcgca gcctacgaga acgccggggc ccgagtccca   1560
gagccggcca acgtgctaga gatcgagtgg tcgaagcagc agtatttccc aagagcgccg   1620
agcgccgtct atgggctgaa cgatctcatc acactgggtt cggcgctcag aacgccgttc   1680
aagtgtgttc atttcgtcgg aacggagacg tctttagttt ggaaagggta tatgaaggg    1740
gccatacgat cgggtcaacg aggtgctgca gaagttgtgg ctagcctggt gccagcagca   1800
tag                                                                 1803
```

<210> SEQ ID NO 20
<211> LENGTH: 1803
<212> TYPE: DNA
<213> ORGANISM: Artificial Sequence
<220> FEATURE:
<223> OTHER INFORMATION: Synthetic Construct Clone 6F2J12

<400> SEQUENCE: 20

```
atggcacttg caccgagcta catcaatccc ccaaacgtcg cctccccagc agggtattcc     60
cacgtcggcg taggcccaga cggagggagg tatgtgacaa tagctggaca gattggacaa   120
gacgcttcgg gcgtgacaga ccctgcctac gagaaacagg ttgcccaagc attcgccaat   180
ctgcgagctt gccttgctgc agttggagcc acttcaaacg acgtcaccaa gctcaattac   240
tacatcgtcg actacaaccc gagcaaactc accgcaattg agatgggct gaaggctacc    300
tttgcccttg acaggctccc tccttgcacg ctggtgccag tgtcggcctt ggcttcacct   360
gaatacctct ttgaggttga tgccacggcg ctggttccag gacactcaac cccagacaat   420
gttgcggacg tggtagtggt gggcgctggc ttgagcggtt tggagacggc acgcaaagtc   480
caggccgccg gtctgtcctg cctcgttctt gaggcgatgg atcgtgtagg gggaaagact   540
```

```
ctgagcgtac aatcgggtcc cggcaggacg actatcgacg acctcggcgc tgcgtggatc    600
aatgacagca accaaagcga agtattcaaa ttatttgaaa gatttcattt ggagggcgag    660
ctccagagga cgaccggaaa ttcaatccat caagcacaag acggtacaat cactacagct    720
ccttatggtg actccttgct gagcgaggag gttgcaagtg cacttgcgga actcctcccc    780
gcatggtctc agctgatcga agagcatagt cttgaagacc caaggcgag ccctcaggcg     840 aagcagctcg acagtgtgag cttcgcacac tactgtgaga aggacctaaa cttgcctgct    900
gttctcggcg tggcaaacca gatcacacgc gctctgctcg gtgtggaagc ccacgaggtc    960
agcatgcttt ttctcaccga ctacatcaag agtgccaccg gtctcagtaa tattttctcg   1020
gataagaaag atggcgggca gtatatgcga tgcaaaacag gtatgcagtc gctttgccat   1080
gccatgtcaa aggaacttgt tccaggctca gtgcgcctca cacccccgt cgctgaaatt    1140 gagcagtcgg cgtccggctg tacagtacga tcggcctcgg gcgccgtgtt ccgaagcaaa   1200
aaggtggtgg tttcgttacc gacaaccttg tatcccacct tgacattttc accacctctt   1260
cccgccgaga agcaagcatt ggcggaaaat tctatcctgg gctactatag caagatagtc   1320
ttcgtatggg acaagccgtg gtggcgcgaa caaggcttct cgggcgtcct ccaatcgagc   1380
tgtgacccca tctcatttgc cagagatacc agcatcgaag ccgatcggca atggtccatt   1440
acctgtttca tggtcggaga cccgggacgg aagtggtccc aacagtccaa gcaggtacga   1500
caaaagtctg tctgggacca actccgcgca gcctacgaga cgctggggc ccaagtccca    1560 gagccggcca acgtgctcga aatcgagtgg tcgaagcagc agtatttcca aggagctccg   1620
agcgccgtct atgggctgaa cgatctcatc acactgggtt cggcgctcag aacgccgttc   1680
aagagtgttc atttcgttgg aacggagacg tctttagttt ggaaagggta tatggaaggg   1740
gccatacgat cgggtcaacg aggtgctgca gaagttgtgg ctagcctggt gccagcagca   1800
tag                                                                1803
```

<210> SEQ ID NO 21
<211> LENGTH: 1392
<212> TYPE: DNA
<213> ORGANISM: Artificial Sequence
<220> FEATURE:
<223> OTHER INFORMATION: Synthetic Construct Clone TrR3H1

<400> SEQUENCE: 21

```
aaagacaatg ttgcggacgt ggtagtggtg ggcgctggct tgagcggttt ggagacggca     60
cgcaaagtcc aggccgccgg tctgtcctgc ctcgttcttg aggcgatgga tcgtgtaggg    120
ggaaagactc tgagcgtaca atcgggtccc ggcaggacga ctatcgacga cctcggcgct    180
gcgtggatca atgacagcaa ccaaagcgaa gtattcaaat tatttgaaag atttcatttg    240
gagggcgagc tccagaggac gaccggaaat tcaatccatc aagcacaaga cggtacaatc    300
actacagctc cttatggtga ctccttgctg agcgaggagg ttgcaagtgc actcgcggaa    360
ctccttcccg catggtctca gctgatcgaa gagcatagtc ttgaagaccc aaggcgagc    420 cctcaggcga agcagctcga cagtgtgagc ttcgcacact actgtgagaa ggacctaaac    480
ttgcctgctg ttctcggcgt ggcaaaccag atcacacgcg ctctgctcgg tgtggaagcc    540
cacgaggtca gcatgctttt tctcaccgac tacatcaaga gtgccaccgg tctcagtaat    600
attttctcgg ataagaaaga cggtgggcag tatatgcgat gcaaaacagg tatgcagtcg    660
ctttgccatg ccatgtcaaa ggaacttgtt ccaggctcag tgcgcctcaa cacccccgtc    720
```

```
gctgaaattg agcagtcggc gtccggctgt acagtacgat cggcctcggg cgccgtgttc    780
cgaagcaaaa aggtggtggt ttcgttaccg acaaccttgt atcccacctt gacattttca    840
ccacctcttc ccgccgagaa gcaagcattg gcggaaaatt ctatcctggg ctactatagc    900
aagatagtct tcgtatggga caagccgtgg tggcgcgaac aaggcttctc gggcgtcctc    960
caatcgagct gtggccccat ctcatttgcc agagatacca gcatcgaagc cgatcggcaa   1020
tggtccatta cctgtttcat ggtcggagac ccggacggaa gtggtccca acagtccaag    1080 caggtacgac aaaagtctgt ctgggaccaa ctccgcgcag cctacgagaa cgctggggcc   1140
caagtcccag agccggccaa cgtgctcgaa atcgagtggt cgaagcagca gtatttccaa   1200
ggagctccga gcgccgtcta tgggctgaac gatctcatca cactgggttc ggcgctcaga   1260
acgccgttca agtgtgttca tttcgtcgga acggagacgt ctttagtttg gaaagggtat   1320
atggaagggg ccatacgatc gggtcaacga ggtgctgcag aagttgtggc tagcctggtg   1380
ccagcagcat ag                                                       1392

<210> SEQ ID NO 22
<211> LENGTH: 1392
<212> TYPE: DNA
<213> ORGANISM: Artificial Sequence
<220> FEATURE:
<223> OTHER INFORMATION: Synthetic Construct Clone G6

<400> SEQUENCE: 22
aaagacaatg ttgcggacgt ggtagtggtg ggcgctggct tgagcggttt ggagacggca     60
cgcaaagtcc aggccgccgg tctgtcctgc ctcgttcttg aggcgttgga tcgtgtaggg    120
ggaaagactc tgagcgtaca atcgggtccc ggcaggacga ctatcgacga cctcggcgct    180
gcgtggatca atgacagcaa ccaaagcgaa gtattcaaat tatttgaaag atttcatttg    240
gagggcgagc tccagaggac gaccggaaat tcaatccatc aagcacaaga cggtacaatc    300
actacagctc cttatggtga ctccttgctg agcgaggagg ttgcaagcgc actcgcggaa    360
ctccttcccg catggtctca gctgatcgaa gagcatagtc ttgaagaccc caaggcgagc    420
cctcaggcga agcagctcga cagtgtgagc ttcgcacact actgtgagaa ggacctaaac    480
ttgcctgctg ttctcggcgt ggcaaaccag atcacacgcg ctctgctcgg tgtggaagcc    540
cacgaggtca gcatgctttt tctcaccgac tacatcaaga gtgccaccgg tctcagtaat    600
attttctcgg ataagaaaga cggtgggcag tatatgcgat gcaaaacagg tatgcagtcg    660 cttttgccatg ccatgtcaaa ggaacttgtt ccaggctcag tgcgcctcaa cacccccgtc    720
gctgaaattg agcagtcggc gtccggctgt acagtacgat cggcctcggg cgccgtgttc    780
cgaagcaaaa aggtggtggt ttcgttaccg acaaccttgt atcccacctt gacattttca    840
ccacctcttc ccgccgagaa gcaagcattg gcggaaaatt ctatcctggg ctactatagc    900
aagatagtct tcgtatggga caagccgtgg tggcgcgaac aaggcttctc gggcgtcctc    960
caatcgagct gtggccccat ctcatttgcc agagatacca gcatcgaagc cgatcggcaa   1020
tggtccatta cctgtttcat ggtcggagac ccggacggaa gtggtccca acagtccaag    1080 caggtacgac aaaagtctgt ctgggaccaa ctccgcgcag cctacgagaa cgctggggcc   1140
caagtcccag agccggccaa cgtgctcgaa atcgagtggt cgaagcagca gtatttccaa   1200
ggagctccga gcgccgtcta tgggctgaac gatctcatca cactgggttc ggcgctcaga   1260
acgccgttca agtgtgttca tttcgtcgga acggagacgt ctttagtttg gaaagggtat   1320
atggaagggg ccatacgatc gggtcaacga ggtgctgcag aagttgtggc tagcctggtg   1380
```

```
ccagcagcat ag                                                       1392

<210> SEQ ID NO 23
<211> LENGTH: 1392
<212> TYPE: DNA
<213> ORGANISM: Artificial Sequence
<220> FEATURE:
<223> OTHER INFORMATION: Synthetic Construct Clone H8

<400> SEQUENCE: 23
aaagacaatg ttgcggacgt ggtagtggtg ggcgctggct tgagcggttt ggagacggca     60
cgcaaagtcc aggccgccgg tctgtcctgc ctcgttcttg aggcgatgga tcgtgtaggg    120
ggaaagactc tgagcgtaca atcgggtccc ggcaggacga ctatcgacga cctcggcgct    180
gcgtggatca atgacagcaa ccaaagcgaa gtattcaaat tatttgaaag atttcatttg    240
gagggcgagc tccagaggac gaccggaaat tcaatccatc aagcacaaga cggtacaatc    300
actacagctc cttatggtga ctccttgctg agcgaggagg ttgcaagtgc actcgcggaa    360
ctccttcccg catggtctca gctgatcgaa gagcatagtc ttgaagaccc caaggcgagc    420
cctcaggcga agcagctcga cagtgtgagc ttcgcacact actgtgagaa ggacctaaac    480
ttgcctgctg ttctcggcgt ggcaaaccag atcacgcgcg ctctgctcgg tgtggaagcc    540
cacgaggtca gcatgctttt tctcaccgac tacatcaaga gtgccaccgg tctcagtaat    600
attttctcgg ataagaaaga cggtgggcag tatatgcgat gcaaaacagg tatgcagtcg    660
ctttgccatg ccatgtcaaa ggaacttgtt ccaggctcag tgcgcctcaa cacccccgtc    720
gctgaaattg agcagtcggc gtccggctgt acagtacgat cggcctcggg cgccgtgttc    780
cgaagcaaaa aggtggtggt ttcgttaccg acaaccttgt atcccaccct tgacattttca    840 ccacctcttc ccgccgagaa gcaagcattg gcggaaaatt ctatcctggg ctactatagc    900
aagatagtct tcgtatggga caagccgtgg tggcgcgaac aaggcttctc gggcgtcctc    960
caatcgagct gtggccccat ctcatttgcc agagatacca gcatcgaagc cgatcagcaa   1020
tggtccatta cctgtttcat ggtcggagac ccggacgga agtggtccca acagtccaag    1080
caggtacgac aaaagtctgt ctgggaccaa ctccgcgcag cctacgagag cgctggggcc    1140
caagtcccag agccggccaa cgtgctcgaa atcgagtggc gaagcagca gtatttccaa    1200 ggagctccga gcgccgtcta tggctgaac gatctcgtca cactgggttc ggcgctcaga    1260
acgccgttca gtgtgttca tttcgtcgga acggagacgt ctttagtttg gaaagggtat    1320
atggaagggg ccatacgatc gggtcaacga ggtgctacag aagttgtggc tagcctggtg    1380
ccagcagcat ag                                                       1392

<210> SEQ ID NO 24
<211> LENGTH: 1392
<212> TYPE: DNA
<213> ORGANISM: Artificial Sequence
<220> FEATURE:
<223> OTHER INFORMATION: Synthetic Construct Clone E7

<400> SEQUENCE: 24
aaagacaatg ttgcggacgt ggtagtggtg ggcgctggct tgagcggttt ggagacggca     60
cgcaaagtcc aggccgccgg tctgtcctgc ctcgttcttg aggcgatgga ccgtgtaggg    120
gggaagactc tgagcgtaca atcgggtccc ggcaggacga ctatcgacga cctcggcgct    180
gcgtggatca atgacagcaa ccaaagcgaa gtattcaaat tatttgaaag atttcatttg    240
```

```
gagggcgagc tccagaggac gaccggaaat tcaatccatc aagcacaaga cggtacaatc      300
actacagctc cttatggtga ctccttgctg agcgaggagg ttgcaagtgc actcgcggaa      360
ctccttcccg catggtctca gctgatcgaa gagcatagtc ttgaagaccc caaggcgagc      420
cctcaggcga agcagctcga cagtgtgagc ttcgcacact actgtgagaa ggacctaaac      480
ttgcctgctg ttctcggcgt ggcaaaccag atcacacgcg ctctgctcgg tgtggaagcc      540
cacgaggtca gcatgctttt tctcaccgac tacatcaaga gtgccaccgg tctcagtaat      600
attttctcgg agaagaaaga cggtgggcag tatatgcgat gcaaaacagg tatgcagtcg      660
ctttgccatg ccatgtcaaa ggaacttgtt ccaggctcag tgcgcctcaa caccccgtc      720 gctgaaattg agcagtcggc gtccggctgt acagtacgat cggcctcggg cgccgtgttc      780
cgaagcaaaa aggtggtggt ttcgttaccg acaaccttgt atccctcctt gacattttca      840
ccgcctcttc ccgccgagaa gcaagcattg gcggaaaatt ctatcctggg ctactatagc      900
aagatagtct tcgtatggga caagccgtgg tggcgcgaac aaggcttctc gggcgtcctc      960
caatcgagct gtggccccat ctcatttgcc agagatacca gcatcgaagc cgatcggcaa     1020
tggtccatta cctgtttcat ggtcggagac ccggacgaga gtggtccca acagtccaag     1080 caggtacgac aaaagtctgt ctgggaccaa ctccgcgcag cctacgagaa cgctggggcc     1140
caagtcccag agccggccaa cgtgctcgaa atcgagtggc gaagcagca gtatttccaa     1200 ggagctccga gcgccgtcta tgggctgaac gatctcatca cactgggttc ggcgctcaga     1260
acgccgttca gtgtgttca tttcgtcgga acggagacgt ctttagtttg gaaagggtat     1320
atggaagggg ccatacgatc gggtcaacga ggtgctgcag aagttgtggc tagcctggtg     1380
ccagcagcct ag                                                         1392

<210> SEQ ID NO 25
<211> LENGTH: 1392
<212> TYPE: DNA
<213> ORGANISM: Artificial Sequence
<220> FEATURE:
<223> OTHER INFORMATION: Synthetic Construct Clone B6

<400> SEQUENCE: 25
aaagacaatg ttgcggacgt ggtagtggtg ggcgctggct tgagcggttt ggagacggca       60
cgcaaagtcc aggccgccgg tctgtcctgc ctcgttcttg aggcgatgga tcgtgtaggg      120
ggaaagactc tgagcgtaca atcgggtccc ggcaggacga ctatcgacga cctcggcgct      180
gcgtggatca atgacagcaa ccaaagcgaa gtattcaaat tatttgaaag atttcatttg      240
gagggcgagc tccagaggac gaccggaaat tcaatccatc aagcacaaga cggtacaatc      300
actacagctc cttatggtga ctccttgctg agcgaggagg ttgcaagtgc actcgcggaa      360
ctccttcccg catggtctca gctgatcgaa gagcatagtc ttgaagaccc caaggcgagc      420
cctcaggcga agcagctcga cagtgtgagc ttcgcacact actgtgagaa ggacctaaac      480
ttgcctgctg ttctcggcgt ggcaaaccag atcacacgcg ctctgctcgg tgtggaagcc      540
cacgaggtca gcatgctttt tctcaccgac tacatcaaga gtgccaccgg tctcagtaat      600
attttctcgg ataagaaaga cggtgggcag tatatgcgat gcaaaacagg tatgcagtcg      660
cttagccatg ccatgtcaaa ggaacttgtt ccaggctcag tgcgcctcaa caccccgtc      720 gctgaaattg agcagtcggc gtccggctgt acagtacgat cggcctcggg cgccgtgttc      780
cgaagcaaaa aggtggtggt ttcgttaccg acaaccttgt atcccaccttt gacattttca     840 ccgcctcttc ccgccgagaa gcaagcattg gcggaaaatt ctatcctggg ctactatagc      900
```

-continued

```
aagatagtct tcgtatggga caagccgtgg tggcgcgaac aaggcttctc gggcgtcctc    960
caatcgagcg gtggccccat ctcatttgcc agagatacca gcatcgaagc cgatcggcaa   1020
tggtccatta cctgtttcat ggtcggagac ccgggacgga agtggtccca acagtccaag   1080
caggtacgac aaaagtctgt ctgggaccaa ctccgcgcag cctacgagaa cgctggggcc   1140
caagtcccag agccggccaa cgtgctcgaa atcgagtggt cgaagcagca gtatttccaa   1200
ggagctccga gcgccgtcta tgggctgaac gatctcatca cactgggttc ggcgctcaga   1260
acgccgttca gtgtgttca tttcgtcgga acggagacgc ctttagtttg gaaagggtat    1320
atggaagggg ccatacgatc gggtcaacga ggtgctgcag aagttgtggc tagcctggtg   1380
ccagcagcat ag                                                       1392
```

<210> SEQ ID NO 26
<211> LENGTH: 600
<212> TYPE: PRT
<213> ORGANISM: Artificial Sequence
<220> FEATURE:
<223> OTHER INFORMATION: Translation of Synthetic Construct Clone A5

<400> SEQUENCE: 26

```
Met Ala Leu Ala Pro Ser Tyr Ile Asn Pro Asn Val Ala Ser Pro
  1               5                  10                  15

Ala Gly Tyr Ser His Val Gly Val Gly Pro Asp Gly Gly Arg Tyr Val
                 20                  25                  30

Thr Ile Ala Gly Gln Ile Gly Gln Asp Ala Leu Gly Val Thr Asp Pro
             35                  40                  45

Ala Tyr Glu Lys Gln Val Ala Gln Ala Phe Ala Asn Leu Arg Ala Cys
         50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                     85                  90                  95

Leu Lys Ala Thr Phe Ala Leu Asp Arg Leu Pro Pro Cys Thr Leu Val
                100                 105                 110

Pro Val Pro Ala Leu Ala Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
            195                 200                 205

Ser Arg Leu Phe Glu Arg Phe His Leu Glu Gly Glu Leu Gln Arg Thr
        210                 215                 220

Ile Gly Asn Ser Ile His Gln Ala Gln Asp Gly Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu Glu His Ser Leu Glu
                260                 265                 270
```

```
Asp Pro Lys Ala Ser Pro Gln Ala Lys Arg Leu Asp Ser Val Ser Phe
            275                 280                 285

Ala His Tyr Cys Glu Lys Asp Leu Asn Leu Pro Ala Val Leu Gly Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Val Lys Ser Ala Thr Gly Leu Ser
                325                 330                 335

Asn Ile Phe Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
            355                 360                 365

Gly Ser Val His Leu Asn Thr Pro Val Ala Glu Ile Glu Gln Ser Ala
            370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
            450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
            530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 27
<211> LENGTH: 600
<212> TYPE: PRT
<213> ORGANISM: Artificial Sequence
<220> FEATURE:
<223> OTHER INFORMATION: Translation of Synthetic Construct Clone D5

<400> SEQUENCE: 27

Met Ala Leu Ala Pro Ser Tyr Ile Asn Pro Pro Asn Leu Ala Ser Pro
1               5                   10                  15

Ala Gly Tyr Ser His Val Gly Val Gly Pro Asn Gly Gly Arg Tyr Val
            20                  25                  30
```

```
Thr Ile Ala Gly Gln Ile Gly Gln Asp Ala Leu Gly Val Thr Asp Pro
     35                  40                  45

Ala Tyr Glu Lys Gln Val Ala Gln Ala Phe Ala Asn Leu Arg Ala Cys
 50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                 85                  90                  95

Leu Lys Ala Thr Phe Ala Leu Asp Arg Leu Pro Pro Cys Thr Leu Val
                100                 105                 110

Pro Val Pro Ala Leu Ala Ser Pro Glu Tyr Leu Phe Glu Val Asp Ala
            115                 120                 125

Thr Ala Leu Val Pro Gly His Ser Thr Pro Asp Asn Val Ala Asp Val
            130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
            195                 200                 205

Phe Lys Leu Phe Glu Arg Phe His Leu Glu Gly Glu Leu Gln Arg Thr
210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Arg Leu Asp Ser Val Ser Phe
            275                 280                 285

Ala His Tyr Cys Glu Lys Asp Leu Asn Leu Pro Ala Val Leu Gly Val
            290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
            355                 360                 365

Gly Ser Val His Leu Asn Thr Pro Val Ala Glu Ile Glu Gln Ser Ala
            370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
            435                 440                 445
```

```
Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 28
<211> LENGTH: 600
<212> TYPE: PRT
<213> ORGANISM: Artificial Sequence
<220> FEATURE:
<223> OTHER INFORMATION: Translation of Synthetic Construct Clone F7

<400> SEQUENCE: 28

Met Ala Leu Ala Pro Ser Tyr Ile Asn Pro Asn Val Ala Ser Pro
 1                5                  10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205
```

```
Phe Lys Leu Phe Glu Arg Phe His Leu Glu Gly Glu Leu Gln Arg Thr
    210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Val Ala Ser Ala Leu Ala
                245                 250                 255
Glu Leu Leu Pro Ala Trp Ser Gln Leu Ile Glu Glu His Ser Leu Glu
                260                 265                 270
Asp Pro Lys Ala Ser Pro Gln Ala Lys Arg Leu Asp Ser Val Ser Phe
            275                 280                 285
Ala His Tyr Cys Glu Lys Asp Leu Asn Leu Pro Ala Val Leu Ser Val
    290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Phe Ser Asp Lys Lys Asp Gly Gly Gln Tyr Met Arg Cys Lys
                340                 345                 350
Thr Gly Met Gln Ser Ile Cys His Ala Met Ser Lys Glu Leu Val Pro
            355                 360                 365
Gly Ser Val His Leu Asn Thr Pro Val Ala Glu Ile Glu Gln Ser Ala
    370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Ile Phe
                405                 410                 415
Ser Pro Pro Leu Pro Ala Glu Lys Gln Ala Leu Ala Glu Lys Ser Ile
                420                 425                 430
Leu Gly Tyr Tyr Ser Lys Ile Val Phe Val Trp Asp Lys Pro Trp Trp
            435                 440                 445
Arg Glu Gln Gly Phe Ser Gly Val Leu Gln Ser Ser Cys Asp Pro Ile
    450                 455                 460
Leu Phe Ala Arg Asp Thr Ser Ile Glu Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
    515                 520                 525
Glu Trp Ser Lys Gln Gln Tyr Phe Gln Gly Ala Pro Ser Ala Val Tyr
530                 535                 540
Gly Leu Asn Asp Leu Ile Thr Leu Gly Ser Ala Leu Arg Thr Pro Phe
545                 550                 555                 560
Lys Gly Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
        595                 600

<210> SEQ ID NO 29
<211> LENGTH: 600
<212> TYPE: PRT
```

```
<213> ORGANISM: Artificial Sequence
<220> FEATURE:
<223> OTHER INFORMATION: Translation of Synthetic Construct Clone F12

<400> SEQUENCE: 29

Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Ala
             20                  25                  30

Thr Ile Ala Gly Gln Ile Gly Gln Asp Ala Ser Ala Val Thr Asp Pro
         35                  40                  45

Ala Tyr Glu Lys Gln Val Ala Gln Ala Phe Ala Asn Leu Arg Ala Cys
 50                  55                  60

Leu Ala Ala Val Gly Ala Ser Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                 85                  90                  95

Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
                115                 120                 125

Thr Ala Leu Val Pro Gly His Ser Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
                195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Gln
                260                 265                 270

Asp Pro Lys Ala Ser Pro Gln Ala Lys Gln Leu Asp Ser Val Ser Phe
    275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
                340                 345                 350

Thr Gly Met Gln Ser Leu Cys His Ala Met Ser Lys Glu Leu Val Pro
            355                 360                 365

Arg Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
```

```
                385                 390                 395                 400
Lys Val Val Val Ser Leu Pro Thr Thr Leu Tyr Pro Thr Leu Thr Phe
                    405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Asn Pro Trp Trp
            435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 30
<211> LENGTH: 600
<212> TYPE: PRT
<213> ORGANISM: Artificial Sequence
<220> FEATURE:
<223> OTHER INFORMATION: Translation of Synthetic Construct Clone G11

<400> SEQUENCE: 30

Met Ala Leu Ala Pro Ser Tyr Ile Asn Pro Asn Val Ala Ser Pro
 1               5                  10                  15

Ala Gly Tyr Ser His Val Gly Val Gly Pro Asn Gly Gly Arg Tyr Val
            20                  25                  30

Thr Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
```

-continued

```
                145                 150                 155                 160
           Gln Ala Ala Gly Leu Ser Cys Leu Val Leu Glu Ala Met Asp Arg Val
                        165                 170                 175
           Gly Gly Lys Thr Leu Ser Val Gln Ser Gly Pro Gly Arg Thr Ala Ile
                        180                 185                 190
           Asn Asp Leu Gly Ala Ala Trp Ile Asn Asp Ser Asn Gln Ser Glu Val
                        195                 200                 205
           Phe Lys Leu Phe Glu Arg Phe His Leu Glu Gly Glu Leu Gln Arg Thr
                        210                 215                 220
           Thr Gly Asn Ser Ile His Gln Ala Gln Asp Gly Thr Thr Thr Thr Ala
           225                 230                 235                 240
           Pro Tyr Gly Asp Ser Leu Leu Ser Glu Val Ala Ser Ala Leu Ala
                        245                 250                 255
           Glu Leu Leu Pro Ala Trp Ser Gln Leu Ile Glu Glu His Ser Leu Glu
                        260                 265                 270
           Asp Pro Lys Ala Ser Pro Gln Ala Lys Arg Leu Asp Ser Val Ser Phe
                        275                 280                 285
           Ala His Tyr Cys Glu Lys Asp Leu Asn Leu Pro Ala Val Leu Ser Val
                        290                 295                 300
           Ala Asn Gln Ile Thr Arg Ala Leu Leu Gly Val Glu Ala His Glu Ile
           305                 310                 315                 320
           Ser Met Leu Phe Leu Thr Asp Tyr Ile Lys Ser Ala Thr Gly Leu Ser
                        325                 330                 335
           Asn Ile Phe Ser Asp Lys Lys Asp Gly Gly Gln Tyr Met Arg Cys Lys
                        340                 345                 350
           Thr Gly Met Gln Ser Leu Cys His Ala Met Ser Lys Glu Leu Val Pro
                        355                 360                 365
           Gly Ser Val His Leu Asn Thr Pro Val Ala Glu Ile Glu Gln Ser Ala
                        370                 375                 380
           Ser Gly Cys Ile Val Arg Ser Ala Ser Gly Gly Val Phe Arg Ser Lys
           385                 390                 395                 400
           Lys Val Val Val Ser Leu Pro Thr Thr Leu Tyr Pro Thr Leu Ile Phe
                        405                 410                 415
           Ser Pro Pro Leu Pro Ala Glu Lys Gln Ala Leu Ala Glu Asn Ser Ile
                        420                 425                 430
           Leu Gly Tyr Tyr Ser Lys Ile Val Phe Val Trp Asp Asn Pro Trp Trp
                        435                 440                 445
           Arg Glu Gln Gly Phe Ser Gly Val Leu Gln Ser Ser Cys Asp Pro Ile
                        450                 455                 460
           Ser Phe Ala Arg Asp Thr Ser Ile Glu Val Asp Arg Gln Trp Ser Ile
           465                 470                 475                 480
           Thr Cys Phe Met Val Gly Asp Pro Gly Arg Lys Trp Ser Gln Gln Ser
                        485                 490                 495
           Lys Gln Val Arg Gln Lys Ser Val Trp Asp Gln Leu Arg Ala Ala Tyr
                        500                 505                 510
           Glu Asn Ala Gly Ala Gln Val Pro Glu Pro Ala Asn Val Leu Glu Ile
                        515                 520                 525
           Glu Trp Ser Lys Gln Gln Tyr Phe Gln Gly Ala Pro Ser Ala Val Tyr
                        530                 535                 540
           Gly Leu Asn Asp Leu Ile Thr Leu Gly Ser Ala Leu Arg Thr Pro Phe
           545                 550                 555                 560
           Lys Cys Val His Phe Val Gly Thr Glu Thr Ser Leu Val Trp Lys Gly
                        565                 570                 575
```

```
Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 31
<211> LENGTH: 600
<212> TYPE: PRT
<213> ORGANISM: Artificial Sequence
<220> FEATURE:
<223> OTHER INFORMATION: Translation of Synthetic Construct Clone R3H1

<400> SEQUENCE: 31

Met Ala Leu Ala Pro Ser Tyr Ile Asn Pro Asn Val Ala Ser Pro
 1               5                  10                  15

Ala Gly Tyr Ser His Val Gly Val Gly Pro Asn Glu Ala Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
 50                  55                  60

Leu Ala Ala Val Gly Ala Ser Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Met Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu His Ser Leu Glu
            260                 265                 270

Asp Pro Lys Ala Ser Pro Gln Ala Lys His Leu Asp Ser Val Ser Phe
        275                 280                 285

Ala His Tyr Cys Glu Lys Asp Leu Asn Leu Pro Ala Val Leu Ser Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335
```

```
Asn Ile Val Ser Asp Lys Lys Asp Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
    370                 375                 380

Ser Gly Cys Ile Val Arg Ser Ala Ser Gly Gly Val Phe Arg Ser Lys
385                 390                 395                 400

Lys Val Val Val Ser Leu Pro Thr Thr Leu Tyr Pro Thr Leu Thr Phe
                405                 410                 415

Leu Pro Pro Leu Ser Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 32
<211> LENGTH: 600
<212> TYPE: PRT
<213> ORGANISM: Artificial Sequence
<220> FEATURE:
<223> OTHER INFORMATION: Translation of Synthetic Construct Clone 3B12

<400> SEQUENCE: 32

Met Ala Pro Ala Pro Ser Tyr Ile Asn Pro Pro Asn Val Ala Ser Pro
1               5                   10                  15

Ala Gly Tyr Ser His Val Gly Val Gly Pro Asn Glu Ala Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95
```

-continued

```
Leu Lys Ser Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu His Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Val Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510
```

-continued

```
Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 33
<211> LENGTH: 600
<212> TYPE: PRT
<213> ORGANISM: Artificial Sequence
<220> FEATURE:
<223> OTHER INFORMATION: Translation of Synthetic Construct Clone
      4F13G12

<400> SEQUENCE: 33

Met Ala Leu Ala Pro Ser Tyr Ile Asn Pro Asn Val Ala Ser Pro
 1               5                  10                  15

Ala Gly Tyr Ser His Val Gly Val Gly Pro Asn Glu Ala Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asn Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270
```

```
Asp Pro Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
            325                 330                 335

Asn Ile Phe Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
            405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
    450                 455                 460

Ser Phe Ala Thr Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
            485                 490                 495

Lys Gln Val Arg Gln Lys Ser Val Trp Asp Gln Leu Arg Ala Ala Tyr
        500                 505                 510

Glu Asn Ala Gly Ala Gln Val Pro Glu Pro Ala Asn Val Leu Glu Ile
    515                 520                 525

Glu Trp Ser Lys Gln Gln Tyr Phe Gln Gly Ala Pro Ser Ala Val Tyr
530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
            565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 34
<211> LENGTH: 539
<212> TYPE: PRT
<213> ORGANISM: Artificial Sequence
<220> FEATURE:
<223> OTHER INFORMATION: Translation of Synthetic Construct Clone
      4F15A11

<400> SEQUENCE: 34

Met Ala Leu Ala Pro Ser Tyr Ile Asn Pro Pro Asn Asp Val Thr Lys
1               5                   10                  15

Leu Asn Tyr Tyr Ile Val Asp Tyr Ala Pro Ser Lys Leu Thr Ala Ile
```

-continued

```
                20                  25                  30
Gly Asp Gly Leu Lys Ala Thr Phe Ala Leu Asp Arg Leu Pro Pro Cys
            35                  40                  45

Thr Leu Pro Val Ser Ala Leu Ala Ser Pro Glu Tyr Leu Phe Glu
    50                  55                  60

Val Asp Ala Thr Ala Leu Val Pro Gly His Ser Thr Pro Asp Asn Val
65                  70                  75                  80

Ala Asp Val Val Val Gly Ala Gly Leu Ser Gly Leu Glu Thr Ala
                85                  90                  95

Arg Lys Val Gln Ala Ala Gly Leu Ser Cys Leu Val Leu Glu Ala Met
                100                 105                 110

Asp Arg Val Gly Gly Lys Thr Leu Ser Val Gln Ser Gly Pro Gly Arg
                115                 120                 125

Thr Thr Ile Asn Asp Leu Gly Ala Ala Trp Ile Asn Asp Ser Asn Gln
            130                 135                 140

Ser Glu Val Phe Lys Leu Phe Glu Arg Phe His Leu Glu Gly Glu Leu
145                 150                 155                 160

Gln Arg Thr Thr Gly Asn Ser Ile His Gln Ala Gln Asp Gly Thr Thr
                165                 170                 175

Thr Thr Ala Pro Tyr Gly Asp Ser Leu Leu Ser Glu Glu Val Ala Ser
                180                 185                 190

Ala Leu Ala Glu Leu Leu Pro Ala Trp Ser Gln Leu Ile Glu Glu His
            195                 200                 205

Ser Leu Glu Asp Pro Lys Ala Ser Pro Gln Ala Lys Arg Leu Asp Ser
    210                 215                 220

Val Ser Phe Ala His Tyr Cys Glu Lys Glu Leu Asn Leu Pro Ala Val
225                 230                 235                 240

Leu Gly Val Ala Asn Gln Ile Thr Arg Ala Leu Leu Gly Val Glu Ala
                245                 250                 255

His Glu Ile Ser Met Leu Phe Leu Thr Asp Tyr Val Lys Ser Ala Thr
                260                 265                 270

Gly Leu Ser Asn Ile Phe Ser Asp Lys Lys Asp Gly Gly Gln Tyr Met
            275                 280                 285

Arg Cys Lys Thr Gly Met Gln Ser Ile Cys His Ala Met Ser Lys Glu
    290                 295                 300

Leu Val Pro Gly Ser Val His Leu Asn Thr Pro Val Ala Glu Ile Glu
305                 310                 315                 320

Gln Ser Ala Ser Gly Cys Thr Val Arg Ser Ala Ser Gly Ala Val Phe
                325                 330                 335

Arg Ser Lys Lys Val Val Val Ser Leu Pro Thr Thr Leu Tyr Pro Thr
                340                 345                 350

Leu Thr Phe Ser Pro Pro Leu Ser Ala Glu Lys Gln Ala Leu Ala Glu
            355                 360                 365

Asn Leu Ile Leu Gly Ile Tyr Ser Lys Ile Val Phe Val Trp Ser Asn
            370                 375                 380

Ala Cys Gly Arg Glu Gln Gly Phe Cys Gly Val Leu His Gln Ser Cys
385                 390                 395                 400

Gly Pro Ile Ser Phe Ala Arg Asp Thr Ser Ile Glu Val Asp Arg Gln
                405                 410                 415

Trp Ser Ile Thr Cys Phe Met Val Ala Asp Pro Gly Arg Lys Trp Ser
            420                 425                 430

Gln Gln Ser Lys Gln Val Arg Gln Lys Ser Val Trp Asp Gln Leu Arg
            435                 440                 445
```

```
Ala Ala Tyr Glu Asn Ala Gly Ala Gln Val Pro Glu Pro Ala Asn Val
        450                 455                 460

Leu Glu Ile Glu Trp Ser Lys Gln Gln Tyr Phe Gln Gly Ala Pro Ser
465                 470                 475                 480

Ala Val Tyr Gly Leu Asn Asp Leu Ile Thr Leu Gly Ser Ala Leu Arg
                485                 490                 495

Thr Pro Phe Lys Gly Val His Phe Val Gly Thr Glu Thr Ser Leu Val
            500                 505                 510

Trp Lys Gly Tyr Met Glu Gly Ala Ile Arg Ser Gly Gln Arg Gly Ala
        515                 520                 525

Ala Glu Val Val Ala Ser Leu Val Pro Ala Ala
530                 535

<210> SEQ ID NO 35
<211> LENGTH: 600
<212> TYPE: PRT
<213> ORGANISM: Artificial Sequence
<220> FEATURE:
<223> OTHER INFORMATION: Translation of Synthetic Construct Clone 4F15C3

<400> SEQUENCE: 35

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
            20                  25                  30

Ala Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270
```

```
Asp Pro Lys Ala Ser Pro Gln Ala Lys Arg Leu Asp Ser Val Ser Phe
            275                 280                 285

Ala His Tyr Cys Glu Lys Asp Leu Asn Leu Pro Ala Val Leu Gly Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
            355                 360                 365

Gly Ser Val His Leu Asn Thr Pro Val Ala Glu Ile Glu Gln Ser Ala
            370                 375                 380

Ser Gly Cys Ile Val Arg Ser Ala Ser Gly Gly Val Phe Arg Ser Lys
385                 390                 395                 400

Lys Val Val Val Ser Leu Pro Thr Thr Leu Tyr Pro Thr Leu Ile Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
            450                 455                 460

Ser Phe Ala Arg Asp Thr Asn Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
            530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 36
<211> LENGTH: 600
<212> TYPE: PRT
<213> ORGANISM: Artificial Sequence
<220> FEATURE:
<223> OTHER INFORMATION: Translation of Synthetic Construct Clone 4F16C6

<400> SEQUENCE: 36

Met Ala Leu Ala Pro Ser Tyr Ile Asn Pro Pro Asn Val Ala Ser Pro
1               5                   10                  15

Ala Gly Tyr Ser His Val Gly Val Gly Pro Asn Gly Gly Arg Tyr Val
            20                  25                  30
```

-continued

```
Thr Ile Ala Gly Gln Ile Gly Gln Asp Ala Leu Gly Val Thr Asp Pro
         35                  40                  45
Ala Tyr Glu Lys Gln Val Ala Gln Ala Phe Ala Asn Leu Arg Ala Cys
 50                  55                  60
Leu Ala Ala Val Gly Ala Thr Ser Asn Asp Val Thr Lys Leu Asn Tyr
 65                  70                  75                  80
Tyr Ile Val Asp Tyr Ala Pro Ser Lys Leu Thr Ala Ile Gly Asp Gly
                 85                  90                  95
Leu Lys Ala Thr Phe Ala Leu Asp Arg Leu Pro Pro Cys Thr Leu Val
                100                 105                 110
Pro Val Pro Ala Leu Ala Ser Pro Glu Tyr Leu Phe Glu Val Asp Ala
            115                 120                 125
Thr Ala Leu Val Pro Gly His Thr Thr Pro Asp Asn Val Ala Asp Val
            130                 135                 140
Val Val Val Gly Ala Gly Leu Ser Gly Leu Glu Thr Ala Arg Lys Val
145                 150                 155                 160
Gln Ala Ala Gly Leu Ser Cys Leu Val Leu Glu Ala Met Asp Arg Val
                165                 170                 175
Gly Gly Lys Thr Leu Ser Val Gln Ser Gly Pro Gly Arg Thr Thr Ile
                180                 185                 190
Asn Asp Leu Gly Ala Ala Trp Ile Asn Asp Ser Asn Gln Ser Glu Val
            195                 200                 205
Phe Lys Leu Phe Glu Arg Phe His Leu Glu Gly Glu Leu Gln Arg Thr
        210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Glu Val Ala Ser Ala Leu Ala
                245                 250                 255
Glu Leu Leu Pro Ala Trp Ser Gln Leu Ile Glu His Ser Leu Glu
                260                 265                 270
Asp Pro Lys Ala Ser Pro Gln Ala Lys Arg Leu Asp Ser Val Ser Phe
        275                 280                 285
Ala His Tyr Cys Glu Lys Asp Leu Asn Leu Pro Ala Val Leu Ser Val
    290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Val Ser Asp Lys Lys Asp Gly Gly Gln Tyr Met Arg Cys Lys
            340                 345                 350
Thr Gly Met Gln Ser Ile Cys His Ala Met Ser Lys Glu Leu Val Pro
        355                 360                 365
Gly Ser Val His Leu Asn Thr Pro Val Ala Glu Ile Glu Gln Ser Ala
    370                 375                 380
Ser Gly Cys Thr Val Arg Ser Ala Ser Gly Ala Val Tyr Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
            420                 425                 430
Leu Gly Tyr Tyr Ser Lys Ile Val Phe Val Trp Asp Lys Pro Trp Trp
        435                 440                 445
```

```
Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 37
<211> LENGTH: 600
<212> TYPE: PRT
<213> ORGANISM: Artificial Sequence
<220> FEATURE:
<223> OTHER INFORMATION: Translation of Synthetic Construct Clone 4F19F2

<400> SEQUENCE: 37

Met Ala Leu Ala Pro Ser Tyr Ile Asn Pro Asn Val Ala Ser Pro
1               5                   10                  15

Ala Gly Tyr Ser His Val Gly Val Gly Pro Asn Gly Gly Arg Tyr Val
            20                  25                  30

Thr Ile Ala Gly Gln Ile Gly Gln Asp Ala Ser Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Ile Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205
```

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Asp Leu Asn Leu Pro Ala Val Leu Gly Ala
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Ile Phe
                405                 410                 415

Ser Pro Pro Leu Pro Ala Glu Lys Gln Ala Leu Ala Gly Asn Ser Ile
            420                 425                 430

Leu Gly Tyr Tyr Ser Lys Ile Val Phe Val Trp Asp Asn Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Gly Ala Val Tyr
    530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 38
<211> LENGTH: 600
<212> TYPE: PRT

<213> ORGANISM: Artificial Sequence
<220> FEATURE:
<223> OTHER INFORMATION: Translation of Synthetic Construct Clone 4F21C8

<400> SEQUENCE: 38

```
Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Leu Gly Val Thr Asp Pro
            35                  40                  45

Ala Tyr Glu Lys Gln Val Ala Gln Ala Phe Ala Asn Leu Arg Ala Cys
 50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ser Ser Pro Glu Tyr Leu Phe Glu Val Asp Ala
            115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
            195                 200                 205

Phe Lys Leu Phe Glu Arg Phe His Leu Glu Gly Glu Leu Gln Arg Thr
210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Arg Leu Asp Ser Val Ser Phe
            275                 280                 285

Ala His Tyr Cys Glu Lys Asp Leu Asn Leu Pro Ala Val Leu Ser Val
290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Val Arg Cys Lys
            340                 345                 350

Thr Gly Met Gln Ser Ile Cys His Ala Met Ser Lys Glu Leu Val Pro
            355                 360                 365

Gly Ser Val His Leu Asn Thr Pro Val Ala Gly Ile Glu Gln Ser Ala
            370                 375                 380

Ser Gly Cys Thr Val Arg Ser Ala Ser Gly Ala Val Phe Arg Ser Lys
```

```
                385                 390                 395                 400
Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
                420                 425                 430

Leu Gly Tyr Tyr Ser Lys Ile Val Phe Val Trp Asp Lys Pro Trp Trp
                435                 440                 445

Arg Glu Gln Gly Phe Ser Gly Val Leu Gln Ser Ser Cys Asp Pro Ile
                450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
                500                 505                 510

Glu Asn Ala Gly Ala Gln Val Pro Glu Pro Ala Asn Val Leu Glu Ile
                515                 520                 525

Glu Trp Ser Lys Gln Gln Tyr Phe Gln Gly Ala Pro Ser Ala Val Tyr
                530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Ala Ser Leu Val Pro Ala Ala
                595                 600

<210> SEQ ID NO 39
<211> LENGTH: 600
<212> TYPE: PRT
<213> ORGANISM: Artificial Sequence
<220> FEATURE:
<223> OTHER INFORMATION: Translation of Synthetic Construct Clone 4F22B2

<400> SEQUENCE: 39

Met Ala Leu Ala Pro Ser Tyr Ile Asn Pro Asn Ala Ala Ser Pro
  1                 5                  10                  15

Ala Gly Tyr Ser His Val Gly Val Gly Pro Asp Gly Gly Arg Tyr Val
                 20                  25                  30

Thr Ile Ala Gly Gln Ile Gly Gln Asp Ala Leu Gly Val Thr Asp Pro
                 35                  40                  45

Ala Tyr Glu Lys Gln Val Ala Gln Ala Phe Ala Asn Leu Arg Ala Cys
         50                  55                  60

Leu Ala Ala Val Gly Ala Ser Ser Asn Asp Val Thr Lys Leu Asn Tyr
 65                  70                  75                  80

Tyr Ile Val Asp Tyr Ala Ser Ser Lys Leu Thr Ala Ile Gly Asp Gly
                 85                  90                  95

Leu Lys Ala Thr Phe Ala Leu Asp Arg Leu Pro Pro Cys Thr Leu Val
                100                 105                 110

Pro Val Ser Ala Leu Ala Ser Pro Glu Tyr Leu Phe Glu Val Asp Ala
                115                 120                 125

Thr Ala Leu Val Pro Gly His Thr Thr Pro Asp Asn Val Ala Asp Val
                130                 135                 140

Val Val Val Gly Ala Gly Leu Ser Gly Leu Glu Thr Ala Arg Lys Val
```

```
                      -continued
  145               150               155               160
Gln Ala Ala Gly Leu Ser Cys Leu Val Leu Glu Ala Thr Asp Arg Val
              165                 170                 175
Gly Gly Lys Thr Leu Ser Val Gln Ser Gly Pro Gly Arg Thr Thr Ile
              180                 185                 190
Asn Asp Leu Gly Ala Ala Trp Ile Asn Asp Ser Asn Gln Ser Glu Val
              195                 200                 205
Phe Lys Leu Phe Glu Arg Phe His Leu Glu Gly Leu Gln Arg Thr
              210                 215                 220
Thr Gly Asn Ser Ile His Gln Ala Gln Asp Gly Thr Ile Thr Thr Ala
225               230                 235                 240
Pro Tyr Gly Asp Ser Leu Leu Ser Glu Val Ala Ser Ala Leu Ala
              245                 250                 255
Glu Leu Leu Pro Ala Trp Ser Gln Leu Ile Glu Glu His Ser Leu Glu
              260                 265                 270
Asn Pro Lys Glu Ser Pro Gln Ala Lys Arg Leu Asp Ser Val Ser Phe
              275                 280                 285
Ala His Tyr Cys Glu Lys Asp Leu Asn Leu Pro Ala Val Leu Gly Val
              290                 295                 300
Ala Asn Gln Ile Thr Arg Ala Leu Leu Gly Val Glu Ala His Glu Ile
305               310                 315                 320
Ser Met Leu Phe Leu Thr Asp Tyr Ile Lys Ser Ala Thr Gly Leu Ser
              325                 330                 335
Asn Ile Phe Ser Asp Lys Lys Asp Gly Gln Tyr Met Arg Cys Lys
              340                 345                 350
Thr Gly Met Gln Ser Leu Cys His Ala Met Ser Lys Glu Leu Val Pro
              355                 360                 365
Gly Ser Val Arg Leu Asn Thr Pro Val Ala Glu Ile Glu Gln Ser Ala
              370                 375                 380
Ser Gly Cys Thr Val Arg Ser Ala Ser Gly Ala Val Phe Arg Ser Lys
385               390                 395                 400
Lys Val Val Val Ser Leu Pro Ala Thr Phe Ser Pro Thr Leu Thr Phe
              405                 410                 415
Ser Pro Pro Leu Pro Ala Glu Lys Gln Ala Leu Ala Glu Asn Ser Ile
              420                 425                 430
Leu Gly Tyr Tyr Ser Lys Ile Val Phe Val Trp Asp Lys Pro Trp Trp
              435                 440                 445
Arg Glu Gln Gly Phe Ser Gly Val Leu Gln Ser Ser Cys Asp Pro Ile
              450                 455                 460
Ser Phe Ala Arg Asp Thr Ser Ile Glu Val Asp Arg Gln Trp Ser Ile
465               470                 475                 480
Thr Cys Phe Met Val Gly Asp Pro Gly Arg Lys Trp Ser Gln Gln Ser
              485                 490                 495
Lys Gln Val Arg Gln Lys Ser Val Trp Asp Gln Leu Arg Ala Ala Tyr
              500                 505                 510
Glu Asn Ala Gly Ala Gln Val Pro Glu Pro Asn Val Leu Glu Ile
              515                 520                 525
Gly Arg Ser Lys Gln Gln Tyr Phe Gln Gly Ala Pro Ser Ala Val Tyr
              530                 535                 540
Gly Leu Asn Asp Leu Ile Thr Leu Gly Ser Ala Leu Arg Thr Pro Phe
545               550                 555                 560
Lys Cys Val His Phe Val Gly Thr Glu Thr Ser Leu Val Trp Lys Gly
              565                 570                 575
```

-continued

```
Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 40
<211> LENGTH: 600
<212> TYPE: PRT
<213> ORGANISM: Artificial Sequence
<220> FEATURE:
<223> OTHER INFORMATION: Translation of Synthetic Construct Clone 4F24F2

<400> SEQUENCE: 40

Met Ala Leu Ala Pro Ser Tyr Ile Asn Pro Asn Val Ala Ser Pro
  1               5                  10                  15

Ala Gly Tyr Ser His Val Gly Val Gly Pro Asn Glu Ala Arg Tyr Val
             20                  25                  30

Thr Ile Ala Gly Gln Ile Gly Gln Asp Ala Ser Gly Val Thr Asp Pro
         35                  40                  45

Ala Tyr Glu Lys Gln Val Ala Gln Ala Phe Ala Asn Leu Arg Ala Cys
 50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Pro Ile Gly Asp Gly
                 85                  90                  95

Leu Lys Ala Thr Phe Ala Leu Asp Arg Leu Pro Ser Cys Thr Leu Val
            100                 105                 110

Pro Val Ser Ala Leu Ala Ser Pro Glu Tyr Leu Phe Glu Val Asp Ala
            115                 120                 125

Thr Ala Leu Val Pro Gly His Ser Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu His Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335
```

```
Asn Ile Phe Ser Asp Lys Lys Asp Gly Gln Tyr Met Arg Cys Lys
            340                 345                 350
Thr Gly Met Gln Ser Ile Cys His Ala Met Ser Lys Glu Leu Val Pro
        355                 360                 365
Gly Ser Val His Leu Asn Thr Pro Val Ala Glu Ile Glu Gln Ser Ala
    370                 375                 380
Ser Gly Cys Ile Val Arg Ser Ala Ser Gly Ala Val Phe Arg Ser Lys
385                 390                 395                 400
Lys Val Val Ser Leu Pro Thr Thr Leu Tyr Pro Thr Leu Ile Phe
            405                 410                 415
Ser Pro Pro Phe Pro Ala Glu Lys Gln Ala Leu Ala Glu Asn Ser Ile
            420                 425                 430
Leu Gly Tyr Tyr Ser Lys Ile Val Phe Val Trp Asp Lys Pro Trp Trp
        435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Glu Val Asp Arg Gln Trp Ser Ile
465                 470                 475                 480
Thr Cys Phe Met Val Gly Asp Pro Gly Arg Lys Trp Ser Gln Gln Ser
            485                 490                 495
Lys Gln Val Arg Gln Lys Ser Val Trp Asn Gln Leu Arg Ala Ala Tyr
        500                 505                 510
Glu Asn Ala Gly Ala Gln Val Pro Glu Pro Ala Asn Val Leu Glu Ile
    515                 520                 525
Glu Trp Ser Lys Gln Gln Tyr Phe Gln Gly Ala Pro Ser Ala Val Tyr
    530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
            565                 570                 575
Tyr Met Glu Gly Ala Ile Arg Ser Gly Gln Arg Gly Ala Ala Glu Val
        580                 585                 590
Val Ala Ser Leu Val Pro Ala Ala
        595                 600

<210> SEQ ID NO 41
<211> LENGTH: 600
<212> TYPE: PRT
<213> ORGANISM: Artificial Sequence
<220> FEATURE:
<223> OTHER INFORMATION: Translation of Synthetic Construct Clone 4F28G1

<400> SEQUENCE: 41

Met Ala Leu Ala Pro Ser Tyr Ile Asn Pro Pro Asn Val Ala Ser Pro
1               5                   10                  15
Ala Gly Tyr Ser His Val Gly Val Gly Pro Asp Gly Gly Arg Tyr Val
            20                  25                  30
Thr Ile Ala Gly Gln Ile Gly Gln Asp Ala Leu Gly Val Thr Asp Pro
        35                  40                  45
Ala Tyr Glu Lys Gln Val Gln Ala Phe Ala Asn Leu Arg Ala Cys
    50                  55                  60
Leu Ala Ala Val Gly Ala Thr Ser Asn Asp Val Thr Lys Leu Asn Tyr
65                  70                  75                  80
Tyr Ile Val Asp Tyr Ala Pro Ser Lys Leu Thr Ala Ile Gly Asp Gly
            85                  90                  95
```

-continued

```
Leu Lys Ala Thr Phe Ala Leu Asp Arg Leu Pro Pro Cys Thr Leu Val
                100                 105                 110

Pro Val Ser Ala Leu Ser Ser Pro Glu Tyr Leu Phe Glu Val Asp Ala
            115                 120                 125

Thr Ala Leu Val Pro Gly His Thr Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510
```

```
Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 42
<211> LENGTH: 600
<212> TYPE: PRT
<213> ORGANISM: Artificial Sequence
<220> FEATURE:
<223> OTHER INFORMATION: Translation of Synthetic Construct Clone 4F2G10

<400> SEQUENCE: 42

Met Ala Leu Ala Pro Ser His Ile Asn Pro Asn Val Ala Ser Pro
1               5                   10                  15

Ala Gly Tyr Ser His Val Gly Val Gly Pro Asn Gly Gly Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270
```

```
Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
            355                 360                 365

Gly Ser Val His Leu Asn Thr Pro Val Ala Glu Ile Glu Gln Ser Ala
        370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Leu Ala Arg Asp Thr Ser Ile Glu Val Asp Arg Glu Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 43
<211> LENGTH: 600
<212> TYPE: PRT
<213> ORGANISM: Artificial Sequence
<220> FEATURE:
<223> OTHER INFORMATION: Translation of Synthetic Construct Clone 4F3B5

<400> SEQUENCE: 43

Met Ala Leu Ala Pro Ser His Ile Asn Pro Pro Asn Val Ala Ser Pro
 1               5                  10                  15

Ala Gly Tyr Ser His Val Gly Val Gly Pro Asn Gly Gly Arg Tyr Val
            20                  25                  30
```

-continued

```
Thr Ile Ala Gly Gln Ile Gly Gln Asp Ala Ser Gly Val Thr Asp Pro
         35                  40                  45

Ala Tyr Glu Lys Gln Val Ala Gln Ala Phe Ala Asn Leu Arg Ala Cys
         50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                     85                  90                  95

Leu Lys Ala Thr Phe Ala Leu Asp Arg Leu Pro Pro Cys Thr Leu Val
                100                 105                 110

Pro Val Ser Ala Leu Ala Ser Pro Glu Tyr Leu Phe Glu Val Asp Ala
                115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190

Asn Asp Leu Gly Ala Ala Trp Ile Asn Asp Ser Asn Gln Ser Glu Val
                195                 200                 205

Phe Lys Leu Phe Glu Arg Phe His Leu Glu Gly Glu Leu Gln Arg Thr
                210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
                260                 265                 270

Asp Pro Lys Ala Ser Pro Gln Ala Lys Arg Leu Asp Ser Val Ser Phe
                275                 280                 285

Ala His Tyr Cys Glu Lys Asp Leu Asn Leu Pro Ala Val Leu Ser Val
                290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
                340                 345                 350

Thr Gly Met Gln Ser Leu Cys His Ala Met Ser Lys Glu Leu Val Pro
                355                 360                 365

Gly Ser Val His Leu Asn Thr Pro Val Ala Glu Ile Glu Gln Ser Ala
370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Ile Phe
                405                 410                 415

Ser Pro Pro Leu Pro Ala Glu Lys Gln Ala Leu Ala Glu Asn Ser Ile
                420                 425                 430

Leu Gly Tyr Tyr Ser Lys Ile Val Phe Val Trp Asp Lys Pro Trp Trp
                435                 440                 445

Arg Glu Gln Gly Phe Ser Gly Val Leu Gln Ser Ser Cys Asp Pro Ile
```

```
                450                 455                 460
Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Gly Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
        595                 600

<210> SEQ ID NO 44
<211> LENGTH: 600
<212> TYPE: PRT
<213> ORGANISM: Artificial Sequence
<220> FEATURE:
<223> OTHER INFORMATION: Translation of Synthetic Construct Clone 4F6A11

<400> SEQUENCE: 44

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
```

```
                210                 215                 220
Thr Gly Asn Ser Ile His Gln Ala Gln Asp Gly Thr Ile Thr Thr Ala
225                 230                 235                 240
Pro Tyr Gly Asp Ser Leu Leu Ser Glu Glu Val Ala Ser Ala Leu Ala
                245                 250                 255
Glu Leu Leu Pro Ala Trp Ser Gln Leu Ile Glu Glu His Ser Leu Gln
                260                 265                 270
Asp Pro Lys Ala Ser Pro Gln Ala Lys Gln Leu Asp Ser Val Ser Phe
            275                 280                 285
Ala His Tyr Cys Glu Lys Glu Leu Asn Leu Pro Ala Val Leu Gly Val
        290                 295                 300
Ala Asn Gln Ile Thr Arg Ala Leu Leu Gly Val Glu Ala His Glu Val
305                 310                 315                 320
Ser Met Leu Phe Leu Thr Asp Tyr Ile Lys Ser Ala Thr Gly Leu Ser
                325                 330                 335
Asn Ile Val Ser Asp Lys Lys Asp Gly Gln Tyr Met Arg Cys Lys
                340                 345                 350
Thr Gly Met Gln Ser Leu Cys His Ala Met Ser Lys Glu Leu Val Pro
            355                 360                 365
Gly Ser Val His Leu Asn Thr Pro Val Ala Glu Ile Glu Gln Ser Ala
        370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
            420                 425                 430
Leu Gly Tyr Tyr Ser Lys Ile Val Phe Val Trp Asp Asn Pro Trp Trp
        435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Glu Ala Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asn Gln Leu Arg Ala Ala Tyr
            500                 505                 510
Glu Asn Ala Gly Ala Arg Val Pro Glu Pro Ala Asn Val Leu Glu Ile
        515                 520                 525
Glu Trp Ser Lys Gln Gln Tyr Phe Pro Arg Ala Pro Ser Ala Val Tyr
    530                 535                 540
Gly Leu Asn Asp Leu Ile Thr Leu Gly Ser Ala Leu Arg Thr Pro Phe
545                 550                 555                 560
Lys Cys Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
        595                 600

<210> SEQ ID NO 45
<211> LENGTH: 600
<212> TYPE: PRT
<213> ORGANISM: Artificial Sequence
```

<220> FEATURE:
<223> OTHER INFORMATION: Translation of Synthetic Construct Clone 6F2J12

<400> SEQUENCE: 45

```
Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
50                  55                  60

Leu Ala Ala Val Gly Ala Thr Ser Asn Asp Val Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asp Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Asp Leu Asn Leu Pro Ala Val Leu Gly Val
    290                 295                 300

Ala Asn Gln Ile Thr Arg Ala Leu Leu Gly Val Glu Ala His Glu Val
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val Arg Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400
```

```
Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
            435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Glu Ala Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 46
<211> LENGTH: 463
<212> TYPE: PRT
<213> ORGANISM: Artificial Sequence
<220> FEATURE:
<223> OTHER INFORMATION: Translation of Synthetic Construct Clone TrR3H1

<400> SEQUENCE: 46

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160
```

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 47
<211> LENGTH: 463
<212> TYPE: PRT
<213> ORGANISM: Artificial Sequence
<220> FEATURE:
<223> OTHER INFORMATION: Translation of Synthetic Construct Clone G6

<400> SEQUENCE: 47

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Leu Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

```
Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 48
<211> LENGTH: 463
```

<212> TYPE: PRT
<213> ORGANISM: Artificial Sequence
<220> FEATURE:
<223> OTHER INFORMATION: Translation of Synthetic Construct Clone H8

<400> SEQUENCE: 48

```
Lys Asp Asn Val Ala Asp Val Val Val Gly Ala Gly Leu Ser Gly
 1               5                  10                  15

Leu Glu Thr Ala Arg Lys Val Gln Ala Ala Gly Leu Ser Cys Leu Val
             20                  25                  30

Leu Glu Ala Met Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
     50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Gln Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Ser Ala Gly Ala Gln Val Pro Glu
    370                 375                 380
```

-continued

```
Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Val Thr Leu Gly
            405                 410                 415

Ser Ala Leu Arg Thr Pro Phe Lys Cys Val His Phe Val Gly Thr Glu
        420                 425                 430

Thr Ser Leu Val Trp Lys Gly Tyr Met Glu Gly Ala Ile Arg Ser Gly
    435                 440                 445

Gln Arg Gly Ala Thr Glu Val Val Ala Ser Leu Val Pro Ala Ala
    450                 455                 460

<210> SEQ ID NO 49
<211> LENGTH: 463
<212> TYPE: PRT
<213> ORGANISM: Artificial Sequence
<220> FEATURE:
<223> OTHER INFORMATION: Translation of Synthetic Construct Clone E7

<400> SEQUENCE: 49

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Ser Leu Thr Phe Ser Pro Pro Leu Pro Ala Glu Lys Gln
        275                 280                 285
```

```
Ala Leu Ala Glu Asn Ser Ile Leu Gly Tyr Tyr Ser Lys Ile Val Phe
    290                 295                 300

Val Trp Asp Lys Pro Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 50
<211> LENGTH: 463
<212> TYPE: PRT
<213> ORGANISM: Artificial Sequence
<220> FEATURE:
<223> OTHER INFORMATION: Translation of Synthetic Construct Clone B6

<400> SEQUENCE: 50

Lys Asp Asn Val Ala Asp Val Val Val Gly Ala Gly Leu Ser Gly
1               5                  10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190
```

```
Lys Ser Ala Thr Gly Leu Ser Asn Ile Phe Ser Asp Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 51
<211> LENGTH: 1803
<212> TYPE: DNA
<213> ORGANISM: Exophiala spinifera

<400> SEQUENCE: 51
atggcacttg caccgagcta catcaatccc ccaaacgtcg cctccccagc agggtattct    60
cacgtcggcg taggcccaga cggagggagg tatgtgacaa tagctggaca gattggacaa   120
gacgcttcgg gcgtgacaga ccctgcctac gagaaacagg ttgcccaagc attcgccaat   180
ctgcgagctt gccttgctgc agttggagcc acttcaaacg acgtcaccaa gctcaattac   240
tacatcgtcg actacgcccc gagcaaactc accgcaattg agatgggct gaaggctacc   300 tttgcccttg acaggctccc tccttgcacg ctggtgccag tgtcggcctt gtcttcacct   360
gaatacctct tgaggttga tgccacggcg ctggtgccgg acacacgac cccagacaac   420 gttgcggacg tggtagtggt gggcgctggc ttgagcggtt tggagacggc acgcaaagtc   480
caggccgccg gtctgtcctg cctcgttctt gaggcgatgg atcgtgtagg gggaaagact   540
ctgagcgtac aatcgggtcc cggcaggacg actatcaacg acctcggcgc tgcgtggatc   600
```

```
aatgacagca accaaagcga agtatccaga ttgtttgaaa gatttcattt ggagggcgag    660
ctccagagga cgactggaaa ttcaatccat caagcacaag acggtacaac cactacagct    720
ccttatggtg actccttgct gagcgaggag gttgcaagtg cacttgcgga actcctcccc    780
gtatggtctc agctgatcga agagcatagc cttcaagacc tcaaggcgag ccctcaggcg    840
aagcggctcg acagtgtgag cttcgcgcac tactgtgaga aggaactaaa cttgcctgct    900
gttctcggcg tagcaaacca gatcacacgc gctctgctcg gtgtggaagc ccacgagatc    960
agcatgcttt ttctcaccga ctacatcaag agtgccaccg gtctcagtaa tattttctcg   1020
gacaagaaag acggcgggca gtatatgcga tgcaaaacag gtatgcagtc gatttgccat   1080
gccatgtcaa aggaacttgt tccaggctca gtgcacctca caccccccgt cgctgaaatt   1140
gagcagtcgc atccggctg tacagtacga tcggcctcgg gcgccgtgtt ccgaagcaaa    1200
aaggtggtgg tttcgttacc gacaaccttg tatcccacct tgacattttc accacctctt   1260
cccgccgaga agcaagcatt ggcggaaaat tctatcctgg gctactatag caagatagtc   1320
ttcgtatggg acaagccgtg gtggcgcgaa caaggcttct cgggcgtcct ccaatcgagc   1380
tgtgaccca tctcatttgc cagagatacc agcatcgacg tcgatcgaca atggtccatt    1440
acctgtttca tggtcggaga cccgggacgg aagtggtccc aacagtccaa gcaggtacga   1500
caaaagtctg tctgggacca actccgcgca gcctacgaga acgccgggc ccaagtccca    1560
gagccggcca acgtgctcga aatcgagtgg tcgaagcagc agtatttcca aggagctccg   1620
agcgccgtct atgggctgaa cgatctcatc cactctgggtt cggcgctcag aacgccgttc   1680
aagagtgttc atttcgttgg aacggagacg tctttagttt ggaaagggta tatggaaggg   1740
gccatacgat cgggtcaacg aggtgctgca gaagttgtgg ctagcctggt gccagcagca   1800
tag                                                                 1803
```

<210> SEQ ID NO 52
<211> LENGTH: 600
<212> TYPE: PRT
<213> ORGANISM: Exophiala spinifera

<400> SEQUENCE: 52

Met Ala Leu Ala Pro Ser Tyr Ile Asn Pro Asn Val Ala Ser Pro
1               5                   10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
        50                  55                  60

Leu Ala Ala Val Gly Ala Thr Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Val Val Gly Ala Gly Leu Ser Gly Leu Glu Thr Ala Arg Lys Val
145                 150                 155                 160

```
Gln Ala Ala Gly Leu Ser Cys Leu Val Leu Glu Ala Met Asp Arg Val
                165                 170                 175
Gly Gly Lys Thr Leu Ser Val Gln Ser Gly Pro Gly Arg Thr Thr Ile
            180                 185                 190
Asn Asp Leu Gly Ala Ala Trp Ile Asn Asp Ser Asn Gln Ser Glu Val
        195                 200                 205
Ser Arg Leu Phe Glu Arg Phe His Leu Glu Gly Glu Leu Gln Arg Thr
    210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Glu Val Ala Ser Ala Leu Ala
                245                 250                 255
Glu Leu Leu Pro Val Trp Ser Gln Leu Ile Glu His Ser Leu Gln
            260                 265                 270
Asp Leu Lys Ala Ser Pro Gln Ala Lys Arg Leu Asp Ser Val Ser Phe
        275                 280                 285
Ala His Tyr Cys Glu Lys Glu Leu Asn Leu Pro Ala Val Leu Gly Val
    290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Phe Ser Asp Lys Lys Asp Gly Gly Gln Tyr Met Arg Cys Lys
            340                 345                 350
Thr Gly Met Gln Ser Ile Cys His Ala Met Ser Lys Glu Leu Val Pro
        355                 360                 365
Gly Ser Val His Leu Asn Thr Pro Val Ala Glu Ile Glu Gln Ser Ala
    370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Glu Asn Ser Ile
            420                 425                 430
Leu Gly Tyr Tyr Ser Lys Ile Val Phe Val Trp Asp Lys Pro Trp Trp
        435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Asp Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
        515                 520                 525
Glu Trp Ser Lys Gln Gln Tyr Phe Gln Gly Ala Pro Ser Ala Val Tyr
    530                 535                 540
Gly Leu Asn Asp Leu Ile Thr Leu Gly Ser Ala Leu Arg Thr Pro Phe
545                 550                 555                 560
Lys Ser Val His Phe Val Gly Thr Glu Thr Ser Leu Val Trp Lys Gly
                565                 570                 575
```

```
Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 53
<211> LENGTH: 1803
<212> TYPE: DNA
<213> ORGANISM: Exophiala spinifera

<400> SEQUENCE: 53
atggcacttg caccgagcta catcaatccc ccaaacgtcg cctccccagc agggtattcc      60
cacatcggcg taggcccaaa cgaagcgagg tatgtgacaa tagctggaca gattggacaa     120
gacgctttgg gcgtgacaga cccagcctac gagaaacagg ttgcccaagc attcgccaat     180
ctgcgagctt gccttgctgc agttggagcc tcttcaaacg acgtcaccaa gctcaattac     240
tacatcgtcg actacgcccc gagcaaactc accgcaattg agatgggct gaagtctacc      300 tttgcccttg acaggctccc tccttgcacg ctggtgccag taccggcctt ggcttcacct     360
gaatacctct tgaggttga tgccacggcg ctggtgccag acactcgac cccagacaac       420 gttgcggacg tggtagtggt gggcgctggc ttgagcggtt tggagacggc acgcaaagtc     480
caagccgccg tctgtcctg cctcgttctt gaggcgatgg atcgtgtagg gggaaagact      540
ctgagcgtac aatcgggtcc cggcaggacg actatcaacg acctcggcgc tgcgtggatc     600
aatgacagca ccaaagcga gtatccaga ttgtttgaaa gatttcattt ggagggcgag        660
ctccagagga cgaccggaaa ttcaatccat caagcacaag acggtacaac cactacagct     720
ccttatggtg actccccgct gagcgaggag gttgcaagtg cacttgcgga actcctcccc     780
gtatggtctc agctgatcga gagtatagc cttgaagacc ccaaggcgag ccctcaggcg      840
aagcggctcg acagtgtgag cttcgcgcac tactgtgaga aggacctaaa cttgcctgct     900
gttctcagcg tggcaaacca gatcacacgc gctctgctcg gtgtggaagc ccacgagatc     960
agcatgcttt ttctcaccga ctacatcaag agtgccaccg gtctcagtaa tattgtctcg    1020
gacaagaaag acggcgggca gtatatgcga tgcaaaacag gtatgcagtc gatttgccat    1080
gccatgtcaa aggaacttgt tccaggctca gtgcacctca caccccgt cgctggaatt       1140 gagcagtcgg cgtccggctg tatagtacga tcggcctcgg gcgccgtgtt ccgaagcaaa    1200
aaggtggtgg tttcgttacc gacaacattg tatcccacct tgacattttc accacctctt    1260
cccgccgaga agcaagcatt ggcggaaaaa tctatcctcg gctactatag caagatagtc    1320
ttcgtatggg acaacccgtg gtggcgcgaa caaggcttct cgggcgtcct ccaatcgagc    1380
tgtgacccca tctcatttgc cagagatacc agcatcgaag tcgatcggca atggtccatt    1440
acctgtttca tggtcggaga cccgggacgg aagtggtccc aacagtccaa gcaggtacga    1500
caaaagtctg tctgggacca actccgcgca gcctacgaga cgccgggc ccaagtccca       1560 gagccggcca cgtgctcga atcgagtgg tcgaagcagc agtatttcca aggagctccg       1620
agcgccgtct atgggctgaa cgatctcatc acactgggtt cggcgctcag aacgccgttc    1680
aagtgtgttc atttcgttgg aacggagacg tctttagttt ggaaagggta tatggaaggg    1740
gccatacgat cgggtcaacg aggtgctgca gaagttgtgg ctagcctggt gccagcagca    1800
tag                                                                  1803

<210> SEQ ID NO 54
<211> LENGTH: 600
```

<212> TYPE: PRT
<213> ORGANISM: Exophiala spinifera

<400> SEQUENCE: 54

```
Met Ala Leu Ala Pro Ser Tyr Ile Asn Pro Asn Val Ala Ser Pro
 1               5                  10                  15

Ala Gly Tyr Ser His Ile Gly Val Gly Pro Asn Glu Ala Arg Tyr Val
            20                  25                  30

Thr Ile Ala Gly Gln Ile Gly Gln Asp Ala Leu Gly Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Ser Ser Asn Asp Val Thr Lys Leu Asn Tyr
65                  70                  75                  80

Tyr Ile Val Asp Tyr Ala Pro Ser Lys Leu Thr Ala Ile Gly Asp Gly
                85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Leu Gln Arg Thr
    210                 215                 220

Thr Gly Asn Ser Ile His Gln Ala Gln Asp Gly Thr Thr Thr Ala
225                 230                 235                 240

Pro Tyr Gly Asp Ser Pro Leu Ser Glu Glu Val Ala Ser Ala Leu Ala
                245                 250                 255

Glu Leu Leu Pro Val Trp Ser Gln Leu Ile Glu Glu Tyr Ser Leu Glu
            260                 265                 270

Asp Pro Lys Ala Ser Pro Gln Ala Lys Arg Leu Asp Ser Val Ser Phe
        275                 280                 285

Ala His Tyr Cys Glu Lys Asp Leu Asn Leu Pro Ala Val Leu Ser Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Gly Ile Glu Gln Ser Ala
    370                 375                 380

Ser Gly Cys Ile Val Arg Ser Ala Ser Gly Ala Val Phe Arg Ser Lys
385                 390                 395                 400
```

```
Lys Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Asn Pro Trp Trp
                435                 440                 445

Arg Glu Gln Gly Phe Ser Gly Val Leu Gln Ser Cys Asp Pro Ile
        450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
                500                 505                 510

Glu Asn Ala Gly Ala Gln Val Pro Glu Pro Ala Asn Val Leu Glu Ile
            515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Ala Ser Leu Val Pro Ala Ala
            595                 600

<210> SEQ ID NO 55
<211> LENGTH: 1803
<212> TYPE: DNA
<213> ORGANISM: Exophiala spinifera

<400> SEQUENCE: 55
atggcacttg caccgagcta catcaatccc ccaaacgtcg cctccccagc agggtattcc      60
cacatcggcg taggcccaaa cgaagcgagg tatgtgacaa tagctggaca gattggacaa     120
gacgctttgg gcgtgacaga cccagcctac gagaaacagg ttgcccaagc attcgccaat     180
ctgcgagctt gccttgctgc agttggagcc tcttcaaacg acgtcaccaa gctcaattac     240
tacatcgtcg actacgcccc gagcaaactc accgcaattg agatgggct gaagtctacc     300 tttgcccttg acaggctccc tccttgcacg ctggtgccag taccggcctt ggcttcacct     360
gaatacctct ttgaggttga cgccacggcg ctggtgccag acactcgac cccagacaac     420 gttgcggacg tggtagtggt gggcgctggc ttgagcggct ggagacggc acgcaaagtc     480 caggccgccg tctgtcctg cctcgttctt gaggcgatgg atcgtgtagg gggaaagact     540
ctgagcgtac aatcgggtcc cggcaggacg actatcaacg acctcggcgc tgcgtggatc     600
aatgacagca accaaagcga agtatccaga ttgtttgaaa gatttcattt ggagggcgag     660
ctccagagga cgaccggaaa ttcaatccat caagcacaag acggtacaac cactacagct     720
ccttatggtg actccccgct gagcgaggag gttgcaagtg cacttgcgga actcctcccc     780
gtatggtctc agctgatcga agagtatagc cttgaagacc caaggcgag ccctcaggcg     840 aagcggctcg acagtgtgag cttcgcgcac tactgtgaga aggacctaaa cttgcctgct     900
gttctcagcg tggcaaacca gatcacacgc gctctgctcg gtgtggaagc ccacgagatc     960
```

```
agcatgcttt ttctcaccga ctacatcaag agtgccaccg gtctcagtaa tattgtctcg    1020
gacaagaaag acggcgggca gtatatgcga tgcaaaacag gtatgcagtc gatttgccat    1080
gccatgtcaa aggaacttgt tccaggctca gtgcacctca acaccccgt cgctggaatt     1140 gagcagtcgg cgtccggctg tatagtacga tcggcctcgg gcgccgtgtt ccgaagcaaa    1200
aaggtggtgg tttcgttacc gacaacattg tatcccacct tgacattttc accacctctt    1260
cccgccgaga agcaagcatt ggcggaaaaa tctatcctcg gctactatag caagatagtc    1320
ttcgtatggg acaacccgtg gtggcgcgaa caaggcttct cgggcgtcct ccaatcgagc    1380 tgtgaccca tctcatttgc cagagatacc agcatcgaag tcgatcggca atggtccatt     1440
acctgtttca tggtcggaga cccgggacgg aagtggtccc aacagtccaa gcaggtacga    1500
caaaagtctg tctgggacca actccgcgca gcctacgaga acgccggggc ccaagtccca    1560
gagccggcca acgtgctcga aatcgagtgg tcgaagcagc agtatttcca aggagctccg    1620
agcgccgtct atgggctgaa cgatctcatc acactgggtt cggcgctcag aacgccgttc    1680
aagtgtgttc atttcgttgg aacggagacg tctttagttt ggaaagggta tatggaaggg    1740
gccatacgat cgggtcaacg aggtgctgca gaagttgtgg ctagcctggt gccagcagca    1800
tag                                                                  1803

<210> SEQ ID NO 56
<211> LENGTH: 600
<212> TYPE: PRT
<213> ORGANISM: Exophiala spinifera

<400> SEQUENCE: 56

Met Ala Leu Ala Pro Ser Tyr Ile Asn Pro Asn Val Ala Ser Pro
  1               5                  10                  15

Ala Gly Tyr Ser His Ile Gly Val Gly Pro Asn Glu Ala Arg Tyr Val
                 20                  25                  30

Thr Ile Ala Gly Gln Ile Gly Gln Asp Ala Leu Gly Val Thr Asp Pro
             35                  40                  45

Ala Tyr Glu Lys Gln Val Ala Gln Ala Phe Ala Asn Leu Arg Ala Cys
         50                  55                  60

Leu Ala Ala Val Gly Ala Ser Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                 85                  90                  95

Leu Lys Ser Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
            115                 120                 125

Thr Ala Leu Val Pro Gly His Ser Thr Pro Asp Asn Val Ala Asp Val
        130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Leu Glu Gly Glu Leu Gln Arg Thr
```

```
            210                 215                 220
Thr Gly Asn Ser Ile His Gln Ala Gln Asp Gly Thr Thr Thr Ala
225                 230                 235                 240

Pro Tyr Gly Asp Ser Pro Leu Ser Glu Val Ala Ser Ala Leu Ala
                245                 250                 255

Glu Leu Leu Pro Val Trp Ser Gln Leu Ile Glu Glu Tyr Ser Leu Glu
                260                 265                 270

Asp Pro Lys Ala Ser Pro Gln Ala Lys Arg Leu Asp Ser Val Ser Phe
                275                 280                 285

Ala His Tyr Cys Glu Lys Asp Leu Asn Leu Pro Ala Val Leu Ser Val
        290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gln Tyr Met Arg Cys Lys
                340                 345                 350

Thr Gly Met Gln Ser Ile Cys His Ala Met Ser Lys Glu Leu Val Pro
                355                 360                 365

Gly Ser Val His Leu Asn Thr Pro Val Ala Gly Ile Glu Gln Ser Ala
        370                 375                 380

Ser Gly Cys Ile Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Lys Ser Ile
                420                 425                 430

Leu Gly Tyr Tyr Ser Lys Ile Val Phe Val Trp Asp Asn Pro Trp Trp
        435                 440                 445

Arg Glu Gln Gly Phe Ser Gly Val Leu Gln Ser Ser Cys Asp Pro Ile
        450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asp Gln Leu Arg Ala Ala Tyr
                500                 505                 510

Glu Asn Ala Gly Ala Gln Val Pro Glu Pro Ala Asn Val Leu Glu Ile
                515                 520                 525

Glu Trp Ser Lys Gln Gln Tyr Phe Gln Gly Ala Pro Ser Ala Val Tyr
        530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
                580                 585                 590

Val Ala Ser Leu Val Pro Ala Ala
            595                 600

<210> SEQ ID NO 57
<211> LENGTH: 1803
<212> TYPE: DNA
<213> ORGANISM: Exophiala spinifera
```

<220> FEATURE:
<221> NAME/KEY: unsure
<222> LOCATION: 649
<223> OTHER INFORMATION: n = a, c, g or t

<400> SEQUENCE: 57

```
atggcacttg caccgagcta catcaatccc ccaaacgtcg cctccccagc agggtattct      60
cacgtcggcg taggcccaga cggagggagg tatgtgacaa tagctggaca gattggacaa     120
gacgcttcgg gcgtgacaga ccctgcctac gagaaacagg ttgcccaagc attcgccaat     180
ctgcgagctt gccttgctgc agttggagcc acttcaaacg acgtcaccaa gctcaattac     240
tacatcgtcg actacgcccc gagcaaactc accgcaattg gagatgggct gaaggctacc     300
tttgcccttg acaggctccc tccttgcacg ctggtgccag tgtcggcctt gtcttcacct     360
gaatacctct ttgaggttga tgccacggcg ctggtgccgg acacacgac cccagacaac      420
gttgcggacg tggtaatggt gggcgctggc ttgagcggtt tggagacggc acgcaaagtc     480
caagccgccg gtctgtcctg cctcgttctt gaggcgatgg atcgtgtagg gggaaagact     540
ctgagcgtac aatcgggtcc cggcaggacg actatcaacg acctcggcgc tgcgtggatc     600
aatgacagca accaaagcga agtatccaga ttgtttgaaa gatttcatnt ggagggcgag     660
ctccagagga cgactggaaa ttcaatccat caagcacaag acgtacaac cactacagct      720
ccttatggtg actccttgct gagcgaggag gttgcaagtg cacttgcgga actcctcccc     780
gtatggtctc agctgatcga agagcatagc cttcaagacc tcaaggcgag ccctcaggcg     840
aagcggctcg acagtgtgag cttcgcgcac tactgtgaga aggaactaaa cttgcctgct     900
gttctcggcg taacaaacca gatcacacgc gctctgctcg gtgtggaagc ccacgagatc     960
agcatgcttt ttctcaccga ctacatcaag agtgccaccg gtctcagtaa tattttctcg    1020
gacaagaaag acggcgggca gtatatgcga tgcaaaacag gtatgcagtc gatttgccat    1080
gccatgtcaa aggaacttgt tccaggctca gtgcacctca acaccccgt cgctgaaatt     1140
gagcagtcgg catccggctg tacagtacga tcggcctcgg gcgccgtgtt ccgaagcaaa    1200
aaggtggtgg tttcgttacc gacaaccttg tatcccacct tgacattttc accacctctc    1260
cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380
tgtgacccca tctcatttgc cagagatacc agcatcgacg tcgatcgaca atggtccatt    1440
acctgtttca tggtcggaga cccgggacgg aagtggtccc aacagtccaa gcaggtacga    1500
caaaagtctg tctgggacca actccgcgca gcctacgaga acgccggggc ccaagtccca    1560
gagccggcca acgtgctcga aatcgagtgg tcgaagcagc agtatttcca aggagctccg    1620
agcgccgtct atgggctgaa cgatctcatc acactgggtt cggcgctcag aacgccgttc    1680
aagagtgttc atttcgttgg tacggagacg tctttagttt ggaaagggta tatgaagggg    1740
gccatacgat cgggtcaacg aggtgctgca gaagttgtgg ctagcctggt gccagcagca    1800
tag                                                                  1803
```

<210> SEQ ID NO 58
<211> LENGTH: 600
<212> TYPE: PRT
<213> ORGANISM: Exophiala spinifera
<220> FEATURE:
<221> NAME/KEY: UNSURE
<222> LOCATION: 217
<223> OTHER INFORMATION: Xaa = Val, Leu or Met

<400> SEQUENCE: 58

```
Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
             20                  25                  30

Thr Ile Ala Gly Gln Ile Gly Gln Asp Ala Ser Gly Val Thr Asp Pro
         35                  40                  45

Ala Tyr Glu Lys Gln Val Ala Gln Ala Phe Ala Asn Leu Arg Ala Cys
     50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                 85                  90                  95

Leu Lys Ala Thr Phe Ala Leu Asp Arg Leu Pro Pro Cys Thr Leu Val
            100                 105                 110

Pro Val Ser Ala Leu Ser Ser Pro Glu Tyr Leu Phe Glu Val Asp Ala
        115                 120                 125

Thr Ala Leu Val Pro Gly His Thr Thr Pro Asp Asn Val Ala Asp Val
    130                 135                 140

Val Met Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asn Asp Leu Gly Ala Ala Trp Ile Asn Asp Ser Asn Gln Ser Glu Val
        195                 200                 205

Ser Arg Leu Phe Glu Arg Phe His Xaa Glu Gly Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Val Trp Ser Gln Leu Ile Glu Glu His Ser Leu Gln
            260                 265                 270

Asp Leu Lys Ala Ser Pro Gln Ala Lys Arg Leu Asp Ser Val Ser Phe
        275                 280                 285

Ala His Tyr Cys Glu Lys Glu Leu Asn Leu Pro Ala Val Leu Gly Val
    290                 295                 300

Thr Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gln Tyr Met Arg Cys Lys
            340                 345                 350

Thr Gly Met Gln Ser Ile Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415
```

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Asp Val Asp Arg Gln Trp Ser Ile
465                 470                 475                 480

Thr Cys Phe Met Val Gly Asp Pro Gly Arg Lys Trp Ser Gln Ser
                485                 490                 495

Lys Gln Val Arg Gln Lys Ser Val Trp Asp Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
    530                 535                 540

Gly Leu Asn Asp Leu Ile Thr Leu Gly Ser Ala Leu Arg Thr Pro Phe
545                 550                 555                 560

Lys Ser Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
            580                 585                 590

Val Ala Ser Leu Val Pro Ala Ala
            595                 600

<210> SEQ ID NO 59
<211> LENGTH: 1803
<212> TYPE: DNA
<213> ORGANISM: Rhinocladiella atrovirens
<220> FEATURE:
<221> NAME/KEY: unsure
<222> LOCATION: 643
<223> OTHER INFORMATION: n = a, c, g or t
<220> FEATURE:
<221> NAME/KEY: unsure
<222> LOCATION: 648
<223> OTHER INFORMATION: n = a, c, g or t

<400> SEQUENCE: 59
atggcacttg caccgagcta catcaatccc ccaaacctcg cctccccagc agggtattcc      60
cacgtcggcg taggcccaaa cggagggagg tatgcgacaa tagctggaca gattggacaa     120
gacgcttcgg ccgtgacaga ccctgcctac gagaaacagg ttgcccaagc attcgccaac     180
ctgcgagctt gtcttgctgc agttggagcc acttcaaacg acattaccaa gctcaattac     240
tacatcgtcg actacaaccc gagcaaactc accgcaattg agatgggct gaaggctacc     300 tttgcccttg acaggctccc tccttgcacg ctggtgccag tgccggccct ggcttcacct     360 gaataccct ttgaggttga tgccacggcg ctggttccag acactcaac cccagacaat      420 gttgcggacg tggtcgtggt gggcgctggc ttgagcggtt tggagacggc acgcaaagtc     480
caggctgccg gctgtcctg cctcgttctt gaggcgatgg atcgtgtggg gggaaagact     540
ctgagcgtac aatcgggtcc cggcaggacg gctatcaatg acctcggcgc tgcgtggatc     600
aatgacagca accaaagcga agtattcaaa ttatttgaaa ganttcantt ggagggcgag     660
ctccagagga cgaccggaaa ttcaatccat caagcacaag acggtacaac cactacagct     720
ccttatggtg attccctgct gagcgaggag gttgcaagtg cactcgcgga actccttccc     780

-continued

```
gcatggtctc agctgatcga agagcatagt cttgaagacc ccaaggcgag ccctcaagcg      840
aagcagctcg acagtgtgag cttcgcacac tactgtgaga aggatctaag cttgcctgct      900
gttctcggcg tggcaaacca gatcacacgc gctctgctcg gtgtggaagc cacgagatc      960 agcatgcttt ttctcaccga ctacatcaag agtgccaccg gtctcagtaa tattgtctcg     1020
gataagaaag acggtgggca gtatatgcga tgcaaaacag gtatgcagtc gctttgccat     1080
gccatgtcaa aggaacttgt tccaggctca gtgcacctca caccccccgt cgccgaaatt     1140
gagcagtcgg catccggctg tacagtacga tcggcctcgg gcggcgtgtt ccgaagtaaa     1200
aaggtggtgg tttcgttacc gacaaccttg tatcccacct tgatattttc accacctctt     1260
cccgccgaga agcaagcatt ggctgaaaaa tccatcctgg gctactatag caagatagtc     1320
ttcgtatggg acaagccgtg gtggcgcgaa caaggcttct cgggcgtcct ccaatcgagc     1380 tgtgaccca tctcatttgc cagagatacc agcatcgaag tcgatcggca atggtccatt     1440
acctgtttca tggtcggaga cccgggacgg aagtggtccc aacagtccaa gcaggtacga     1500
cagaagtctg tctggaacca actccgcgca gcctacgaga acgccggggc ccaagtccca     1560
gagccggcca acgtgctcga gatcgagtgg tcgaagcagc agtatttcca aggagcgccg     1620
agcgtcgtct atgggctgaa ctgtctcaac acactgggtt cggcgctcag aacgccgttc     1680
aagggtgttc atttcgttgg aacggagacg tctttggttt ggaaagggta tatggaaggg     1740
gccatacgat cgggtcagcg aggcgctgca gaagttgtgg ctagcctggt gccagcagca     1800
tag                                                                   1803
```

```
<210> SEQ ID NO 60
<211> LENGTH: 600
<212> TYPE: PRT
<213> ORGANISM: Rhinocladiella atrovirens
<220> FEATURE:
<221> NAME/KEY: UNSURE
<222> LOCATION: 215
<223> OTHER INFORMATION: Xaa = Ile, Val, Leu or Phe
<220> FEATURE:
<221> NAME/KEY: UNSURE
<222> LOCATION: 216
<223> OTHER INFORMATION: Xaa = Gln or His

<400> SEQUENCE: 60

Met Ala Leu Ala Pro Ser Tyr Ile Asn Pro Asn Leu Ala Ser Pro
  1               5                  10                  15

Ala Gly Tyr Ser His Val Gly Val Gly Pro Asn Gly Gly Arg Tyr Ala
             20                  25                  30

Thr Ile Ala Gly Gln Ile Gly Gln Asp Ala Ser Ala Val Thr Asp Pro
         35                  40                  45

Ala Tyr Glu Lys Gln Val Ala Gln Ala Phe Ala Asn Leu Arg Ala Cys
     50                  55                  60

Leu Ala Ala Val Gly Ala Thr Ser Asn Asp Ile Thr Lys Leu Asn Tyr
 65                  70                  75                  80

Tyr Ile Val Asp Tyr Asn Pro Ser Lys Leu Thr Ala Ile Gly Asp Gly
                 85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Pro Phe Glu Val Asp Ala
        115                 120                 125

Thr Ala Leu Val Pro Gly His Ser Thr Pro Asp Asn Val Ala Asp Val
    130                 135                 140
```

-continued

```
Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Ala Ile
            180                 185                 190

Asn Asp Leu Gly Ala Ala Trp Ile Asn Asp Ser Asn Gln Ser Glu Val
        195                 200                 205

Phe Lys Leu Phe Glu Arg Xaa Xaa Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Asp Leu Ser Leu Pro Ala Val Leu Gly Val
    290                 295                 300

Ala Asn Gln Ile Thr Arg Ala Leu Leu Gly Val Glu Ala His Glu Ile
305                 310                 315                 320

Ser Met Leu Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Leu Cys His Ala Met Ser Lys Glu Leu Val Pro
        355                 360                 365

Gly Ser Val His Leu Asn Thr Pro Val Ala Glu Ile Glu Gln Ser Ala
    370                 375                 380

Ser Gly Cys Thr Val Arg Ser Ala Ser Gly Gly Val Phe Arg Ser Lys
385                 390                 395                 400

Lys Val Val Val Ser Leu Pro Thr Thr Leu Tyr Pro Thr Leu Ile Phe
                405                 410                 415

Ser Pro Pro Leu Pro Ala Glu Lys Gln Ala Leu Ala Glu Lys Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Asp Pro Ile
    450                 455                 460

Ser Phe Ala Arg Asp Thr Ser Ile Glu Val Asp Arg Gln Trp Ser Ile
465                 470                 475                 480

Thr Cys Phe Met Val Gly Asp Pro Gly Arg Lys Trp Ser Gln Gln Ser
                485                 490                 495

Lys Gln Val Arg Gln Lys Ser Val Trp Asn Gln Leu Arg Ala Ala Tyr
            500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Val Val Tyr
    530                 535                 540

Gly Leu Asn Cys Leu Asn Thr Leu Gly Ser Ala Leu Arg Thr Pro Phe
545                 550                 555                 560

Lys Gly Val His Phe Val Gly Thr Glu Thr Ser Leu Val Trp Lys Gly
```

-continued

```
                    565                 570                 575
Tyr Met Glu Gly Ala Ile Arg Ser Gly Gln Arg Gly Ala Ala Glu Val
                580                 585                 590
Val Ala Ser Leu Val Pro Ala Ala
        595                 600

<210> SEQ ID NO 61
<211> LENGTH: 1803
<212> TYPE: DNA
<213> ORGANISM: Rhinocladiella atrovirens
<220> FEATURE:
<221> NAME/KEY: unsure
<222> LOCATION: 555
<223> OTHER INFORMATION: n = a, c, g or t
<220> FEATURE:
<221> NAME/KEY: unsure
<222> LOCATION: 560
<223> OTHER INFORMATION: n = a, c, g or t
<220> FEATURE:
<221> NAME/KEY: unsure
<222> LOCATION: 625
<223> OTHER INFORMATION: n = a, c, g or t
<220> FEATURE:
<221> NAME/KEY: unsure
<222> LOCATION: 732
<223> OTHER INFORMATION: n = a, c, g or t
<220> FEATURE:
<221> NAME/KEY: unsure
<222> LOCATION: 786
<223> OTHER INFORMATION: n = a, c, g or t
<220> FEATURE:
<221> NAME/KEY: unsure
<222> LOCATION: 883
<223> OTHER INFORMATION: n = a, c, g or t
<220> FEATURE:
<221> NAME/KEY: unsure
<222> LOCATION: (896)...(896)
<223> OTHER INFORMATION: n = a, c, g or t
<220> FEATURE:
<221> NAME/KEY: unsure
<222> LOCATION: (1134)...(1134)
<223> OTHER INFORMATION: n = a, c, g or t
<220> FEATURE:
<221> NAME/KEY: unsure
<222> LOCATION: (1207)...(1207)
<223> OTHER INFORMATION: n = a, c, g or t
<220> FEATURE:
<221> NAME/KEY: unsure
<222> LOCATION: (1213)...(1213)
<223> OTHER INFORMATION: n = a, c, g or t
<220> FEATURE:
<221> NAME/KEY: unsure
<222> LOCATION: (1225)...(1225)
<223> OTHER INFORMATION: n = a, c, g or t
<220> FEATURE:
<221> NAME/KEY: unsure
<222> LOCATION: (1227)...(1227)
<223> OTHER INFORMATION: n = a, c, g or t

<400> SEQUENCE: 61
atggcacttg caccgagcta catcaatccc ccaaacctcg cctccccagc agggtattcc     60
tacgtcggcg taggcccaaa cggagggagg tatgtgacaa tagctggaca gattggacaa    120
gacgcttcgg ccgtgacaga ccctgcctac gagaaacagg ttgcccaagc attcgccaac    180
ctgcgagctt gtcttgctgc agttggagcc acttcaaacg acattaccaa gctcaattac    240
tacatcgtcg actacaaccc gagcaaactc accgcaattg agatgggct gaaggctacc    300 tttgcccttg acaggctccc tccttgcacg ctggtgccag tgccggccct ggcttcacct    360
gaatacctct ttgaggttga tgccacggcg ctggttccag acactcaac cccagacaat    420 gttgcggacg tggtcgtggt gggcgctggc ttgagcggtt tggagacggc acgcaaagtc    480
```

```
caggctgccg ggctgtcctg cctcgttctt gaggcgatgg atcgtgtggg gggaaagact    540
ctgagcgtac aatcnggtcn cggcaggacg actatcaatg acctcggcgc tgcgtggatc    600
aatgacagca accaaagcga agtantcaaa ttatttgaaa gatttcattt ggagggcgag    660
ctccagagga cgaccggaaa ttcaatccat caagcacaag acggtacaac cactacagct    720
ccttatggtg antccctgct gagcgaggag gttgcaagtg cactcgcgga actccttccc    780
gcatgntctc agctgatcga agagcatagt cttgaagacc ccaaggcgag ccctcaagcg    840
aagcagctcg acagtgtgag cttcgcacac tactgtgaga agnatctaaa cttgcntgct    900
gttctcggcg tggcaaacca gatcacacgc gctctgctcg gtgtggaagc ccacgagatc    960
agcatgtttt ttctcaccga ctacatcaag agtgccaccg gtctcagtaa tattgtctcg   1020
gataagaaag acggtgggca gtatatgcga tgcaaaacag gtatgcagtc gctttgccat   1080
gccatgtcaa aggaacttgt tccaggctca gtgcacctca acccccgt cgcngaaatt     1140 gagcagtcgg catccggctg tacagtacga tcggcctcgg gcggcgtgtt ccgaagtaaa   1200
aaggtgntgg ttncgttacc gacancnttg tatcccacct tgatattttc accacctctt   1260
cccgccgaga agcaagcatt ggctgaaaaa tccatcctgg gctactatag caagatagtc   1320
ttcgtatggg acaagccgtg gtggcgcgaa caaggcttct cgggcgtcct ccaatcgagc   1380 tgtgaccca tctcatttgc cagagatacc agcatcgaag tcgatcggca atggtccatt    1440
acctgtttca tggtcggaga cccgggacgg aagtggtccc aacagtccaa gcaggtacga   1500
cagaagtctg tctggaacca actccgcgca gcctacgaga cgccggggc ccaagtccca    1560 gagccggcca acgtgctcga gatcgagtgg tcgaagcagc agtatttcca aggagcgccg   1620
agcgccgtct atgggctgaa ctgtctcaac acactgggtt cggcgctcag aacgccgttc   1680
aagggtgttc atttcgttgg aacggagacg tctttggttt ggaaagggta tatggaaggg   1740
gccatacgat cgggtcagcg aggcgctgca gaagttgtgg ctagcctggt gccagcagca   1800
tag                                                                 1803
```

<210> SEQ ID NO 62
<211> LENGTH: 600
<212> TYPE: PRT
<213> ORGANISM: Rhinocladiella atrovirens
<220> FEATURE:
<221> NAME/KEY: UNSURE
<222> LOCATION: 187
<223> OTHER INFORMATION: Xaa = Leu, Arg, Pro or His
<220> FEATURE:
<221> NAME/KEY: UNSURE
<222> LOCATION: 209
<223> OTHER INFORMATION: Xaa = Ile, Val, Leu or Phe
<220> FEATURE:
<221> NAME/KEY: UNSURE
<222> LOCATION: 244
<223> OTHER INFORMATION: Xaa = Glu or Asp
<220> FEATURE:
<221> NAME/KEY: UNSURE
<222> LOCATION: 262
<223> OTHER INFORMATION: Xaa = Ter, Cys or Trp
<220> FEATURE:
<221> NAME/KEY: UNSURE
<222> LOCATION: 295
<223> OTHER INFORMATION: Xaa = Tyr, Asn, Asp or His
<220> FEATURE:
<221> NAME/KEY: UNSURE
<222> LOCATION: 299
<223> OTHER INFORMATION: Xaa = Leu, Arg, Pro or His
<220> FEATURE:
<221> NAME/KEY: UNSURE
<222> LOCATION: (403)...(403)

<223> OTHER INFORMATION: Xaa = Val, Leu or Met
<220> FEATURE:
<221> NAME/KEY: UNSURE
<222> LOCATION: (405)...(405)
<223> OTHER INFORMATION: Xaa = Ala, Thr, Pro or Ser
<220> FEATURE:
<221> NAME/KEY: UNSURE
<222> LOCATION: (409)...(409)
<223> OTHER INFORMATION: Xaa = Ala, Thr, Pro or Ser

<400> SEQUENCE: 62

```
Met Ala Leu Ala Pro Ser Tyr Ile Asn Pro Pro Asn Leu Ala Ser Pro
 1               5                  10                  15

Ala Gly Tyr Ser Tyr Val Gly Val Gly Pro Asn Gly Gly Arg Tyr Val
            20                  25                  30

Thr Ile Ala Gly Gln Ile Gly Gln Asp Ala Ser Ala Val Thr Asp Pro
        35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Ile Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Xaa Gly Arg Thr Thr Ile
            180                 185                 190

Asn Asp Leu Gly Ala Ala Trp Ile Asn Asp Ser Asn Gln Ser Glu Val
        195                 200                 205

Xaa Lys Leu Phe Glu Arg Phe His Leu Glu Gly Glu Leu Gln Arg Thr
    210                 215                 220

Thr Gly Asn Ser Ile His Gln Ala Gln Asp Gly Thr Thr Thr Thr Ala
225                 230                 235                 240

Pro Tyr Gly Xaa Ser Leu Leu Ser Glu Glu Val Ala Ser Ala Leu Ala
                245                 250                 255

Glu Leu Leu Pro Ala Xaa Ser Gln Leu Ile Glu Glu His Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Xaa Leu Asn Leu Xaa Ala Val Leu Gly Val
    290                 295                 300

Ala Asn Gln Ile Thr Arg Ala Leu Leu Gly Val Glu Ala His Glu Ile
305                 310                 315                 320

Ser Met Phe Phe Leu Thr Asp Tyr Ile Lys Ser Ala Thr Gly Leu Ser
                325                 330                 335

Asn Ile Val Ser Asp Lys Lys Asp Gly Gly Gln Tyr Met Arg Cys Lys
            340                 345                 350

Thr Gly Met Gln Ser Leu Cys His Ala Met Ser Lys Glu Leu Val Pro
```

-continued

```
            355                 360                 365
Gly Ser Val His Leu Asn Thr Pro Val Ala Glu Ile Glu Gln Ser Ala
        370                 375                 380
Ser Gly Cys Thr Val Arg Ser Ala Ser Gly Gly Val Phe Arg Ser Lys
385                 390                 395                 400
Lys Val Xaa Val Xaa Leu Pro Thr Xaa Leu Tyr Pro Thr Leu Ile Phe
                405                 410                 415
Ser Pro Pro Leu Pro Ala Glu Lys Gln Ala Leu Ala Glu Lys Ser Ile
            420                 425                 430
Leu Gly Tyr Tyr Ser Lys Ile Val Phe Val Trp Asp Lys Pro Trp Trp
        435                 440                 445
Arg Glu Gln Gly Phe Ser Gly Val Leu Gln Ser Ser Cys Asp Pro Ile
    450                 455                 460
Ser Phe Ala Arg Asp Thr Ser Ile Glu Val Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asn Gln Leu Arg Ala Ala Tyr
            500                 505                 510
Glu Asn Ala Gly Ala Gln Val Pro Glu Pro Ala Asn Val Leu Glu Ile
        515                 520                 525
Glu Trp Ser Lys Gln Gln Tyr Phe Gln Gly Ala Pro Ser Ala Val Tyr
    530                 535                 540
Gly Leu Asn Cys Leu Asn Thr Leu Gly Ser Ala Leu Arg Thr Pro Phe
545                 550                 555                 560
Lys Gly Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
        595                 600

<210> SEQ ID NO 63
<211> LENGTH: 1803
<212> TYPE: DNA
<213> ORGANISM: Rhinocladiella atrovirens
<220> FEATURE:
<221> NAME/KEY: unsure
<222> LOCATION: 37
<223> OTHER INFORMATION: n = a, c, g or t
<220> FEATURE:
<221> NAME/KEY: unsure
<222> LOCATION: 1134
<223> OTHER INFORMATION: n = a, c, g or t
<220> FEATURE:
<221> NAME/KEY: unsure
<222> LOCATION: 1207
<223> OTHER INFORMATION: n = a, c, g or t
<220> FEATURE:
<221> NAME/KEY: unsure
<222> LOCATION: 1210
<223> OTHER INFORMATION: n = a, c, g or t
<220> FEATURE:
<221> NAME/KEY: unsure
<222> LOCATION: 1256
<223> OTHER INFORMATION: n = a, c, g or t
<220> FEATURE:
<221> NAME/KEY: unsure
<222> LOCATION: 1297
<223> OTHER INFORMATION: n = a, c, g or t
<220> FEATURE:
<221> NAME/KEY: unsure
<222> LOCATION: (1329)...(1329)
```

```
<223> OTHER INFORMATION: n = a, c, g or t
<220> FEATURE:
<221> NAME/KEY: unsure
<222> LOCATION: (1433)...(1433)
<223> OTHER INFORMATION: n = a, c, g or t
<220> FEATURE:
<221> NAME/KEY: unsure
<222> LOCATION: (1465)...(1465)
<223> OTHER INFORMATION: n = a, c, g or t
<220> FEATURE:
<221> NAME/KEY: unsure
<222> LOCATION: (1512)...(1512)
<223> OTHER INFORMATION: n = a, c, g or t
<220> FEATURE:
<221> NAME/KEY: unsure
<222> LOCATION: (1533)...(1533)
<223> OTHER INFORMATION: n = a, c, g or t
<220> FEATURE:
<221> NAME/KEY: unsure
<222> LOCATION: (1612)...(1612)
<223> OTHER INFORMATION: n = a, c, g or t

<400> SEQUENCE: 63
atggcacttg caccgagcta catcaatccc ccaaacntcg cctccccagc agggtattcc      60
cacgtcggcg taggcccaaa cggagggagg tatgtgacaa tagctggaca gattggacaa     120
gacgcttcgg ccgtgacaga ccctgcctac gagaaacagg ttgcccaagc attcgccaac     180
ctgcgagctt gtcttgctgc agttggagcc acttcaaacg acattaccaa gctcaattac     240
tacatcgtcg actacaaccc gagcaaactc accgcaattg agatgggct gaaggctacc      300
tttgcccttg acaggctccc tccttgcacg ctggtgccag tgccggccct ggcttcacct     360
gaatacctct ttgaggttga tgctacggcg ctggttccag acactcaac cccagacaat      420
gttgcggacg tggtcgtggt gggcgctggc ttgagcggtt tggagacggc acgcaaagtc     480
caggctgccg ggctgtcctg cctcgttctt gaggcgatgg atcgtgtggg gggaaagact     540
ctgagcgtac aatcgggtcc cggcaggacg actatcaatg acctcggcgc tgcgtggatc     600
aatgacagca accaaagcga agtattcaaa ttatttgaaa gatttcatt ggagggcgag      660
ctccaggaga cgaccggaaa ttcaatccat caagcacaag acgtacaac cactacagct      720
ccttatggtg attccctgct gagcgaggag gttgcaagtg cactcgcgga actccttccc     780
gcatggtctc agctgatcga agagcatagt cttgaagacc caaggcgag ccctcaagcg      840
aagcagctcg acagtgtgag cttcgcacac tactgtgaga aggatctaaa cttgcctgct     900
gttctcggcg tggcaaacca gatcacacgc gctctgctcg gtgtggaagc ccacgagatc     960
agcatgcttt ttctcaccga ctacatcaag agtgccaccg gtctcagtaa tattgtctcg    1020
gataagaaag acggtgggca gtatatgcga tgcaaaacag gtatgcagtc gctttgccat    1080
gccatgtcaa aggaacttgt tccaggctca gtgcacctca cacccccgt cgcngaaatt     1140
gagcagtcgg catccggctg tacagtacga tcggcctcgg cggcgtgtt ccgaagtaaa     1200
aaggtgntgn tttcgttacc gacaaccttg tatcccacct tgatattttc accacntctt    1260
cccgccgaga agcaagcatt ggctgaaaaa tccatcntgg gctactatag caagatagtc    1320
ttcgtatgng acaagctgtg gtggcgcgaa caaggcttct cgggcgtcct ccaatcgagc    1380
tgtgaccccca tctcatttgc cagagatacc agcatcgaag tcgatcggca atngtccatt    1440
acctgtttca tggtcggaga cccgngacgc aagtggtccc aacagtccaa gcaggtacga    1500
cagaagtctg tntggaacca actccgcgca gcntacgaga acgccggggc ccaagtccca    1560
gagccggcca acgtgctcga gatcgagtgg tcgaagcagc agtatttcca angagcgccg    1620
agcgccgtct atgggctgaa ctgtctcaac acactgggtt cggcgctcag aacgccgttc    1680
```

```
aagggtgttc atttcgttgg aacggagacg tctttggttt ggaaagggta tatggaaggg    1740
gccatacgat cgggtcagcg aggcgctgca gaagttgtgc ctagcctggt gccagcagca    1800
tag                                                                  1803
```

```
<210> SEQ ID NO 64
<211> LENGTH: 600
<212> TYPE: PRT
<213> ORGANISM: Rhinocladiella atrovirens
<220> FEATURE:
<221> NAME/KEY: UNSURE
<222> LOCATION: 13
<223> OTHER INFORMATION: Xaa = Ile, Val, Leu or Phe
<220> FEATURE:
<221> NAME/KEY: UNSURE
<222> LOCATION: 403
<223> OTHER INFORMATION: Xaa = Val, Leu or Met
<220> FEATURE:
<221> NAME/KEY: UNSURE
<222> LOCATION: 404
<223> OTHER INFORMATION: Xaa = Ile, Val, Leu or Phe
<220> FEATURE:
<221> NAME/KEY: UNSURE
<222> LOCATION: 419
<223> OTHER INFORMATION: Xaa = Leu, Arg, Pro or His
<220> FEATURE:
<221> NAME/KEY: UNSURE
<222> LOCATION: 433
<223> OTHER INFORMATION: Xaa = Val, Leu or Met
<220> FEATURE:
<221> NAME/KEY: UNSURE
<222> LOCATION: 443
<223> OTHER INFORMATION: Xaa = Ter, Cys or Trp
<220> FEATURE:
<221> NAME/KEY: UNSURE
<222> LOCATION: (478)...(478)
<223> OTHER INFORMATION: Xaa = Leu, Ter, Ser or Trp
<220> FEATURE:
<221> NAME/KEY: UNSURE
<222> LOCATION: (489)...(489)
<223> OTHER INFORMATION: Xaa = Ter, Arg, or Gly
<220> FEATURE:
<221> NAME/KEY: UNSURE
<222> LOCATION: (538)...(538)
<223> OTHER INFORMATION: Xaa = Ter, Arg or Gly

<400> SEQUENCE: 64

Met Ala Leu Ala Pro Ser Tyr Ile Asn Pro Asn Xaa Ala Ser Pro
  1               5                  10                  15

Ala Gly Tyr Ser His Val Gly Val Gly Pro Asn Gly Gly Arg Tyr Val
             20                  25                  30

Thr Ile Ala Gly Gln Ile Gly Gln Asp Ala Ser Ala Val Thr Asp Pro
         35                  40                  45

Ala Tyr Glu Lys Gln Val Ala Gln Ala Phe Ala Asn Leu Arg Ala Cys
     50                  55                  60

Leu Ala Ala Val Gly Ala Thr Ser Asn Asp Ile Thr Lys Leu Asn Tyr
 65                  70                  75                  80

Tyr Ile Val Asp Tyr Asn Pro Ser Lys Leu Thr Ala Ile Gly Asp Gly
                 85                  90                  95

Leu Lys Ala Thr Phe Ala Leu Asp Arg Leu Pro Pro Cys Thr Leu Val
            100                 105                 110

Pro Val Pro Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
```

```
                145                 150                 155                 160
Gln Ala Ala Gly Leu Ser Cys Leu Val Leu Glu Ala Met Asp Arg Val
                165                 170                 175
Gly Gly Lys Thr Leu Ser Val Gln Ser Gly Pro Gly Arg Thr Thr Ile
                180                 185                 190
Asn Asp Leu Gly Ala Ala Trp Ile Asn Asp Ser Asn Gln Ser Glu Val
                195                 200                 205
Phe Lys Leu Phe Glu Arg Phe His Leu Glu Gly Glu Leu Gln Arg Thr
                210                 215                 220
Thr Gly Asn Ser Ile His Gln Ala Gln Asp Gly Thr Thr Thr Thr Ala
225                 230                 235                 240
Pro Tyr Gly Asp Ser Leu Leu Ser Glu Val Ala Ser Ala Leu Ala
                245                 250                 255
Glu Leu Leu Pro Ala Trp Ser Gln Leu Ile Glu Glu His Ser Leu Glu
                260                 265                 270
Asp Pro Lys Ala Ser Pro Gln Ala Lys Gln Leu Asp Ser Val Ser Phe
                275                 280                 285
Ala His Tyr Cys Glu Lys Asp Leu Asn Leu Pro Ala Val Leu Gly Val
                290                 295                 300
Ala Asn Gln Ile Thr Arg Ala Leu Leu Gly Val Glu Ala His Glu Ile
305                 310                 315                 320
Ser Met Leu Phe Leu Thr Asp Tyr Ile Lys Ser Ala Thr Gly Leu Ser
                325                 330                 335
Asn Ile Val Ser Asp Lys Lys Asp Gly Gly Gln Tyr Met Arg Cys Lys
                340                 345                 350
Thr Gly Met Gln Ser Leu Cys His Ala Met Ser Lys Glu Leu Val Pro
                355                 360                 365
Gly Ser Val His Leu Asn Thr Pro Val Xaa Glu Ile Glu Gln Ser Ala
                370                 375                 380
Ser Gly Cys Thr Val Arg Ser Ala Ser Gly Gly Val Phe Arg Ser Lys
385                 390                 395                 400
Lys Val Xaa Xaa Ser Leu Pro Thr Thr Leu Tyr Pro Thr Leu Ile Phe
                405                 410                 415
Ser Pro Xaa Leu Pro Ala Glu Lys Gln Ala Leu Ala Glu Lys Ser Ile
                420                 425                 430
Xaa Gly Tyr Tyr Ser Lys Ile Val Phe Val Xaa Asp Lys Leu Trp Trp
                435                 440                 445
Arg Glu Gln Gly Phe Ser Gly Val Leu Gln Ser Cys Asp Pro Ile
                450                 455                 460
Ser Phe Ala Arg Asp Thr Ser Ile Glu Val Asp Arg Gln Xaa Ser Ile
465                 470                 475                 480
Thr Cys Phe Met Val Gly Asp Pro Xaa Arg Lys Trp Ser Gln Gln Ser
                485                 490                 495
Lys Gln Val Arg Gln Lys Ser Xaa Trp Asn Gln Leu Arg Ala Xaa Tyr
                500                 505                 510
Glu Asn Ala Gly Ala Gln Val Pro Glu Pro Ala Asn Val Leu Glu Ile
                515                 520                 525
Glu Trp Ser Lys Gln Gln Tyr Phe Gln Xaa Ala Pro Ser Ala Val Tyr
                530                 535                 540
Gly Leu Asn Cys Leu Asn Thr Leu Gly Ser Ala Leu Arg Thr Pro Phe
545                 550                 555                 560
Lys Gly Val His Phe Val Gly Thr Glu Thr Ser Leu Val Trp Lys Gly
                565                 570                 575
```

Tyr Met Glu Gly Ala Ile Arg Ser Gly Gln Arg Gly Ala Ala Glu Val
            580                 585                 590

Val Pro Ser Leu Val Pro Ala Ala
        595                 600

<210> SEQ ID NO 65
<211> LENGTH: 1803
<212> TYPE: DNA
<213> ORGANISM: Artificial Sequence
<220> FEATURE:
<223> OTHER INFORMATION: Synthetic Construct Clone APAO(B6) Glyc-

<400> SEQUENCE: 65

| | | | | | |
|---|---|---|---|---|---|
| atggcacttg | caccgagcta | catcaatccc | ccaaacgtcg | cctccccagc | agggtattct | 60 |
| cacgtcggcg | taggcccaga | cggagggagg | tatgtgacaa | tagctggaca | gattggacaa | 120 |
| gacgcttcgg | gcgtgacaga | ccctgcctac | gagaaacagg | ttgcccaagc | attcgccaat | 180 |
| ctgcgagctt | gccttgctgc | agttggagcc | acttcaaacg | acgtcaccaa | gctcaattac | 240 |
| tacatcgtcg | actacgcccc | gagcaaactc | accgcaattg | gagatgggct | gaaggctacc | 300 |
| tttgcccttg | acaggctccc | tccttgcacg | ctggtgccag | tgtcggcctt | ggcttcacct | 360 |
| gaatacctct | ttgaggttga | tgccacggcg | ctggttccag | acactcaac | cccagacaat | 420 |
| gttgcggacg | tggtagtggt | gggcgctggc | ttgagcggtt | tggagacggc | acgcaaagtc | 480 |
| caggccgccg | tctgtcctg | cctcgttctt | gaggcgatgg | atcgtgtagg | gggaaagact | 540 |
| ctgagcgtac | aatcgggtcc | cggcaggacg | actatcgacg | acctcggcgc | tgcgtggatc | 600 |
| aatgacagca | accaggcgga | ggtgttcaag | ctcttcgaaa | gatttcattt | ggagggcgag | 660 |
| ctccagagga | cgaccggaaa | ttcaatccat | caagcacaag | acgtacaat | cactacagct | 720 |
| ccttatggtg | actccttgct | gagcgaggag | gttgcaagtg | cactcgcgga | actccttccc | 780 |
| gcatggtctc | agctgatcga | agagcatagt | cttgaagacc | ccaaggcgag | ccctcaggcg | 840 |
| aagcagctcg | acagtgtgag | cttcgcacac | tactgtgaga | aggacctaaa | cttgcctgct | 900 |
| gttctcggcg | tggcaaacca | gatcacacgc | gctctgctcg | gtgtggaagc | ccacgaggtc | 960 |
| agcatgcttt | ttctcaccga | ctacatcaag | agtgccaccg | gtctcagtaa | tattttctcg | 1020 |
| gataagaaag | acgtgggca | gtatatgcga | tgcaaaacag | gtatgcagtc | gcttagccat | 1080 |
| gccatgtcaa | aggaacttgt | tccaggctca | gtgcgcctca | caccccgt | cgctgaaatt | 1140 |
| gagcagtcgc | cgtccggctg | tacagtacga | tcggcctcgg | gcgccgtgtt | ccgaagcaaa | 1200 |
| aaggtggtgg | tttcgttacc | gacaaccttg | tatcccacct | tgacattttc | accgcctctt | 1260 |
| cccgccgaga | agcaagcatt | ggcggaaaat | tctatcctgg | gctactatag | caagatagtc | 1320 |
| ttcgtatggg | acaagccgtg | gtggcgcgaa | caaggcttct | cgggcgtcct | ccaatcgagc | 1380 |
| ggtggcccca | tctcatttgc | cagagatacc | agcatcgaag | ccgatcggca | atggtccatt | 1440 |
| acctgtttca | tggtcggaga | cccgggacgg | aagtggtccc | aacagtccaa | gcaggtacga | 1500 |
| caaaagtctg | tctgggacca | actccgcgca | gcctacgaga | acgctgggc | ccaagtccca | 1560 |
| gagccggcca | acgtgctcga | aatcgagtgg | tcgaagcagc | agtatttcca | aggagctccg | 1620 |
| agcgccgtct | atgggctgaa | cgatctcatc | acactgggtt | cggcgctcag | aacgccgttc | 1680 |
| aagtgtgttc | atttcgtcgg | aacggagacg | tctttagttt | ggaaagggta | tatggaaggg | 1740 |
| gccatacgat | cgggtcaacg | aggtgctgca | gaagttgtgg | ctagcctggt | gccagcagca | 1800 |
| tag | | | | | | 1803 |

<210> SEQ ID NO 66
<211> LENGTH: 600
<212> TYPE: PRT
<213> ORGANISM: Artificial Sequence
<220> FEATURE:
<223> OTHER INFORMATION: Translation of Synthetic Construct Clone APAO(B6) Glyc-

<400> SEQUENCE: 66

```
Met Ala Leu Ala Pro Ser Tyr Ile Asn Pro Asn Val Ala Ser Pro
 1               5                  10                  15

Ala Gly Tyr Ser His Val Gly Val Gly Pro Asp Gly Gly Arg Tyr Val
             20                  25                  30

Thr Ile Ala Gly Gln Ile Gly Gln Asp Ala Ser Gly Val Thr Asp Pro
         35                  40                  45

Ala Tyr Glu Lys Gln Val Ala Gln Ala Phe Ala Asn Leu Arg Ala Cys
     50                  55                  60

Leu Ala Ala Val Gly Ala Thr Ser Asn Asp Val Thr Lys Leu Asn Tyr
 65                  70                  75                  80

Tyr Ile Val Asp Tyr Ala Pro Ser Lys Leu Thr Ala Ile Gly Asp Gly
                 85                  90                  95

Leu Lys Ala Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asp Ala
        115                 120                 125

Thr Ala Leu Val Pro Gly His Ser Thr Pro Asp Asn Val Ala Asp Val
    130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
            180                 185                 190

Asp Asp Leu Gly Ala Ala Trp Ile Asn Asp Ser Asn Gln Ala Glu Val
        195                 200                 205

Phe Lys Leu Phe Glu Arg Phe His Leu Glu Gly Glu Leu Gln Arg Thr
    210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Asp Leu Asn Leu Pro Ala Val Leu Gly Val
    290                 295                 300

Ala Asn Gln Ile Thr Arg Ala Leu Leu Gly Val Glu Ala His Glu Val
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gly Gln Tyr Met Arg Cys Lys
            340                 345                 350

Thr Gly Met Gln Ser Leu Ser His Ala Met Ser Lys Glu Leu Val Pro
        355                 360                 365
```

```
Gly Ser Val Arg Leu Asn Thr Pro Val Ala Glu Ile Glu Gln Ser Ala
        370                 375                 380
Ser Gly Cys Thr Val Arg Ser Ala Ser Gly Ala Val Phe Arg Ser Lys
385                 390                 395                 400
Lys Val Val Val Ser Leu Pro Thr Thr Leu Tyr Pro Thr Leu Thr Phe
                405                 410                 415
Ser Pro Pro Leu Pro Ala Glu Lys Gln Ala Leu Ala Gly Asn Ser Ile
            420                 425                 430
Leu Gly Tyr Tyr Ser Lys Ile Val Phe Val Trp Asp Lys Pro Trp Trp
        435                 440                 445
Arg Glu Gln Gly Phe Ser Gly Val Leu Gln Ser Ser Gly Pro Ile
    450                 455                 460
Ser Phe Ala Arg Asp Thr Ser Ile Glu Ala Asp Arg Gln Trp Ser Ile
465                 470                 475                 480
Thr Cys Phe Met Val Gly Asp Pro Gly Arg Lys Trp Ser Gln Gln Ser
                485                 490                 495
Lys Gln Val Arg Gln Lys Ser Val Trp Asp Gln Leu Arg Ala Ala Tyr
            500                 505                 510
Glu Asn Ala Gly Ala Gln Val Pro Glu Pro Ala Asn Val Leu Glu Ile
        515                 520                 525
Glu Trp Ser Lys Gln Gln Tyr Phe Gln Gly Ala Pro Ser Ala Val Tyr
    530                 535                 540
Gly Leu Asn Asp Leu Ile Thr Leu Gly Ser Ala Leu Arg Thr Pro Phe
545                 550                 555                 560
Lys Cys Val His Phe Val Gly Thr Glu Thr Ser Leu Val Trp Lys Gly
                565                 570                 575
Tyr Met Glu Gly Ala Ile Arg Ser Gly Gln Arg Gly Ala Ala Glu Val
            580                 585                 590
Val Ala Ser Leu Val Pro Ala Ala
        595                 600

<210> SEQ ID NO 67
<211> LENGTH: 1392
<212> TYPE: DNA
<213> ORGANISM: Artificial Sequence
<220> FEATURE:
<223> OTHER INFORMATION: Synthetic Construct Clone 2E8

<400> SEQUENCE: 67
aaagacaatg ttgcggacgt ggtagtggtg ggcgctggct tgagcggttt ggagacggca      60
cgcaaagtcc aggccgccgg tctgtcctgc ctcgttcttg aggcgatgga ccgtgtaggg     120
gggaagactc tgagcgtaca atcgggtccc ggcaggacga ctatcgacga cctcggcgct     180
gcgtggatca atgacagcaa ccaaagcgaa gtattcaaat tatttgaaag atttcatttg     240
gagggcgagc tccagaggac gaccggaaat tcaatccatc aagcacaaga cggtacaatc     300
actacagctc cttatggtga ctccttgctg agcgaggagg ttgcaagtgc actcgcggaa     360
ctccttcccg catggtctca gctgatcgaa gagcatagtc ttgaagaccc caaggcgagc     420
cctcaggcga agcagctcga cagtgtgagc ttcgcacact actgtgagaa ggacctaaac     480
ttgcctgctg ttctcggcgt ggcaaaccag atcacgcgg ctctgctcgg tgtggaagcc     540
cacgaggtca gcatgctttt tctcaccgac tacatcaaga gtgccaccgg tctcagtaat     600
attttctcgg agaagaaaga cggtgggcag tatatgcgat gcaaaacagg tatgcagtcg     660
cttagccatg ccatgtcaaa ggaacttgtt ccaggctcag tgcgcctcaa cacccccgtc     720
```

```
gctgaaattg agcagtcggc gtccggctgt acagtacgat cggcctcggg cgccgtgttc    780
cgaagcaaaa aggtggtggt ttcgttaccg acaaccttgt atcccacctt gacattttca    840
ccgcctcttc ccgccgagaa gcaagcattg gcggaaaatt ctatcctggg ctactatagc    900
aagatagtct tcgtatggga caagccgtgg tggcgcgaac aaggcttctc gggcgtcctc    960
caatcgagcc gtggcccat ctcatttgcc agagatacca gcatcgaagc cgatcggcaa    1020
tggtccatta cctgtttcat ggtcggagac ccgggacgga agtggtccca acagtccaag   1080
caggtacgac aaaagtctgt ctgggaccaa ctccgcgcag cctacgagaa cgctggggcc    1140
caagtcccag ggccggccaa cgtgctcgaa atcgagtggt cgaagcagca gtatttccaa    1200
ggagctccga gcgccgtcta tgggctgaac gatctcatca cactgggttc ggcgctcaga    1260
acgccgttca agtgtgttca tttcgtcgga acggagacgt ctttagtttg gaaagggtat    1320
atggaagggg ccatacgatc gggtcaacga ggtgctgcag aagttgtggc tagcctggtg    1380
ccagcagcat ag                                                        1392
```

<210> SEQ ID NO 68
<211> LENGTH: 1392
<212> TYPE: DNA
<213> ORGANISM: Artificial Sequence
<220> FEATURE:
<223> OTHER INFORMATION: Synthetic Construct Clone 6E9

<400> SEQUENCE: 68

```
aaagacaatg ttgcggacgt ggtagtggtg ggcgctggct tgagcggttt ggagacggca     60
cgcaaagtcc aggccgccgg tctgtcctgc ctcgttcttg aggcgatgga tcgtgtaggg    120
ggaaagactc tgagcgtaca atcgggtccc ggcaggacga ctatcgacga cctcggcgct    180
gcgtggatca atgacagcaa ccaaagcgaa gtattcaaat tatttgaaag atttcatttg    240
gagggcgagc tccagaggac gaccggaaat tcaatccacc aagcacaaga cggtacaatc    300
actacagctc cttatggtga ctccttgctg agcgaggagg ttgcaagtgc actcgcggaa    360
ctccttcccg catggtctca gctgatcgaa gagcatagtc ttgaagaccc caaggcgagc    420
cctcaggcga agcagctcga cagtgtgagc ttcgcacact actgtgagaa ggacctaaac    480
ttgcccgctg ttctcggcgt ggcaaaccag atcacacgcg ctctgctcgg tgtggaagcc    540
cacgaggtca gcatgctttt tctcaccgac tacatcaaga gtgccaccgg tctcagtaat    600
attttctcgg agaagaaaga cggtgggcag tatatgcgat gcaaaacagg tatgcagtcg    660
cttagccatg ccatgtcaaa ggaacttgtt ccaggctcag tgcgcctcaa cacccccgtc    720
gctgaaattg agcagtcggc gtccggctgt acagtacgat cggcctcggg cgccgtgttc    780
cgaagcaaaa aggtggtggt ttcgttaccg acaaccttgt atcccacctt gacattttca    840
ccgcctcttc ccgccgagaa gcaagcattg gcggaaaatt ctatcctggg ctactatagc    900
aagatagtct tcgtatggga caagccgtgg tggcgcgaac aaggcttctc gggcgtcctc    960
caatcgagcg gtggcccat ctcatttgcc agagatacca gcatcgaagc cgatcagcaa    1020
tggtccatta cctgtttcat ggtcggagac ccgggacgga agtggtccca acagtccaag   1080
caggtacgac aaaagtctgt ctgggaccaa ctccgcgcag cctacgagaa cgctggggcc    1140
caagtcccag agccggccaa cgtgctcgaa atcgagtggt cgaagcagca gtatttccaa    1200
ggagctccga gcgccgtcta tgggctgaac gatctcatca cactgggttc ggcgctcaga    1260
acgccgttca agcgtgttca tttcgtcgga acggagacgt ctttagtttg gaaagggtat    1320
```

```
atggaagggg ccatacgatc gggtcaacga ggtgctacag aagttgtggc tagcctggtg    1380
ccagcagcat ag                                                        1392

<210> SEQ ID NO 69
<211> LENGTH: 1803
<212> TYPE: DNA
<213> ORGANISM: Artificial Sequence
<220> FEATURE:
<223> OTHER INFORMATION: Synthetic Construct Clone R3H1F

<400> SEQUENCE: 69
atggcacttg caccgagcta catcaatccc ccaaacgtcg cctccccagc agggtattcc      60
cacgtcggcg taggcccaga cggagggagg tatgtgacaa tagctggaca gattggacaa     120
gacgcttcgg gcgtgacaga ccctgcctac gagaaacagg ttgcccaagc attcgccaac     180
ctgcgagctt gccttgctgc agttggagcc acctcaaacg acgtcaccaa gctcaattac     240
tacatcgtcg actacaaccc gagcaaactc accgcaattg gagatgggct gaaggctacc     300
tttgcccttg acaggctccc tccttgcacg ctggtgccag tgtcggcctt ggcttcacct     360
gaatacctct ttgaggttga tgccacggcg ctggttccag acactcaac cccagacaat      420 gttgcggacg tggtagtggt gggcgctggc ttgagcggtt tggagacggc acgcaaagtc     480
caggccgccg tctgtcctg cctcgttctt gaggcgatgg atcgtgtagg gggaaagact     540
ctgagcgtac aatcgggtcc cggcaggacg actatcgacg acctcggcgc tgcgtggatc     600
aatgacagca ccaaagcga agtattcaaa ttatttgaaa gatttcattt ggagggcgag     660
ctccagagga cgaccggaaa ttcaatccat caagcacaag acggtacaat cactacagct     720
ccttatggtg actccttgct gagcgaggag gttgcaagtg cactcgcgga actccttccc     780
gcatggtctc agctgatcga agagcatagt cttgaagacc ccaaggcgag ccctcaggcg     840
aagcagctcg acagtgtgag cttcgcacac tactgtgaga aggacctaaa cttgcctgct     900
gttctcggcg tggcaaacca gatcacacgc gctctgctcg gtgtggaagc ccacgaggtc     960
agcatgcttt ttctcaccga ctacatcaag agtgccaccg gtctcagtaa tattttctcg    1020
gataagaaag acggtgggca gtatatgcga tgcaaaacag gtatgcagtc gctttgccat    1080
gccatgtcaa aggaacttgt tccaggctca gtgcgcctca cacccccgt cgctgaaatt    1140 gagcagtcgg cgtccggctg tacagtacga tcggcctcgg gcgccgtgtt ccgaagcaaa    1200
aaggtggtgg tttcgttacc gacaaccttg tatcccacct tgacattttc accacctctt    1260
cccgccgaga agcaagcatt ggcggaaaat tctatcctgg gctactatag caagatagtc    1320
ttcgtatggg acaagccgtg gtggcgcgaa caaggcttct cgggcgtcct ccaatcgagc    1380
tgtggcccca tctcatttgc cagagatacc agcatcgaag ccgatcggca atggtccatt    1440
acctgtttca tggtcggaga cccgggacgg aagtggtccc aacagtccaa gcaggtacga    1500
caaaagtctg tctgggacca actccgcgca gcctacgaga acgctggggc ccaagtccca    1560
gagccggcca acgtgctcga aatcgagtgg tcgaagcagc agtatttcca aggagctccg    1620
agcgccgtct atgggctgaa cgatctcatc acactgggtt cggcgctcag aacgccgttc    1680
aagtgtgttc atttcgtcgg aacggagacg tctttagttt ggaaagggta tatggaaggg    1740
gccatacgat cgggtcaacg aggtgctgca gaagttgtgg ctagcctggt gccagcagca    1800
tag                                                                 1803

<210> SEQ ID NO 70
<211> LENGTH: 463
```

```
<212> TYPE: PRT
<213> ORGANISM: Artificial Sequence
<220> FEATURE:
<223> OTHER INFORMATION: Translation of Synthetic Construct Clone 2E8

<400> SEQUENCE: 70
```

Lys Asp Asn Val Ala Asp Val Val Val Gly Ala Gly Leu Ser Gly
 1               5                  10                  15

Leu Glu Thr Ala Arg Lys Val Gln Ala Ala Gly Leu Ser Cys Leu Val
             20                  25                  30

Leu Glu Ala Met Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
 50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
             100                 105                 110

Glu Val Ala Ser Ala Leu Ala Glu Leu Leu Pro Ala Trp Ser Gln Leu
             115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                 165                 170                 175

Gly Val Glu Ala His Glu Val Ser Met Leu Phe Leu Thr Asp Tyr Ile
             180                 185                 190

Lys Ser Ala Thr Gly Leu Ser Asn Ile Phe Ser Glu Lys Lys Asp Gly
             195                 200                 205

Gly Gln Tyr Met Arg Cys Lys Thr Gly Met Gln Ser Leu Ser His Ala
210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                 245                 250                 255

Gly Ala Val Phe Arg Ser Lys Lys Val Val Ser Leu Pro Thr Thr
             260                 265                 270

Leu Tyr Pro Thr Leu Thr Phe Ser Pro Pro Leu Pro Ala Glu Lys Gln
             275                 280                 285

Ala Leu Ala Glu Asn Ser Ile Leu Gly Tyr Tyr Ser Lys Ile Val Phe
290                 295                 300

Val Trp Asp Lys Pro Trp Trp Arg Glu Gln Gly Phe Ser Gly Val Leu
305                 310                 315                 320

Gln Ser Ser Arg Gly Pro Ile Ser Phe Ala Arg Asp Thr Ser Ile Glu
                 325                 330                 335

Ala Asp Arg Gln Trp Ser Ile Thr Cys Phe Met Val Gly Asp Pro Gly
             340                 345                 350

Arg Lys Trp Ser Gln Gln Ser Lys Gln Val Arg Gln Lys Ser Val Trp
             355                 360                 365

Asp Gln Leu Arg Ala Ala Tyr Glu Asn Ala Gly Ala Gln Val Pro Gly
             370                 375                 380

```
Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 71
<211> LENGTH: 463
<212> TYPE: PRT
<213> ORGANISM: Artificial Sequence
<220> FEATURE:
<223> OTHER INFORMATION: Translation of Synthetic Construct Clone 6E9

<400> SEQUENCE: 71

Lys Asp Asn Val Ala Asp Val Val Val Gly Ala Gly Leu Ser Gly
1                5                  10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285
```

```
Ala Leu Ala Glu Asn Ser Ile Leu Gly Tyr Tyr Ser Lys Ile Val Phe
    290                 295                 300

Val Trp Asp Lys Pro Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Gln Gln Trp Ser Ile Thr Cys Phe Met Val Gly Asp Pro Gly
                340                 345                 350

Arg Lys Trp Ser Gln Gln Ser Lys Gln Val Arg Gln Lys Ser Val Trp
                355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Arg Val His Phe Val Gly Thr Glu
                420                 425                 430

Thr Ser Leu Val Trp Lys Gly Tyr Met Glu Gly Ala Ile Arg Ser Gly
                435                 440                 445

Gln Arg Gly Ala Thr Glu Val Val Ala Ser Leu Val Pro Ala Ala
    450                 455                 460

<210> SEQ ID NO 72
<211> LENGTH: 600
<212> TYPE: PRT
<213> ORGANISM: Artificial Sequence
<220> FEATURE:
<223> OTHER INFORMATION: Translation of Synthetic Construct Clone R3H1F

<400> SEQUENCE: 72

Met Ala Leu Ala Pro Ser Tyr Ile Asn Pro Pro Asn Val Ala Ser Pro
1               5                   10                  15

Ala Gly Tyr Ser His Val Gly Val Gly Pro Asp Gly Gly Arg Tyr Val
                20                  25                  30

Thr Ile Ala Gly Gln Ile Gly Gln Asp Ala Ser Gly Val Thr Asp Pro
            35                  40                  45

Ala Tyr Glu Lys Gln Val Ala Gln Ala Phe Ala Asn Leu Arg Ala Cys
    50                  55                  60

Leu Ala Ala Val Gly Ala Thr Ser Asn Asp Val Thr Lys Leu Asn Tyr
65                  70                  75                  80

Tyr Ile Val Asp Tyr Asn Pro Ser Lys Leu Thr Ala Ile Gly Asp Gly
                85                  90                  95

Leu Lys Ala Thr Phe Ala Leu Asp Arg Leu Pro Pro Cys Thr Leu Val
            100                 105                 110

Pro Val Ser Ala Leu Ala Ser Pro Glu Tyr Leu Phe Glu Val Asp Ala
            115                 120                 125

Thr Ala Leu Val Pro Gly His Ser Thr Pro Asp Asn Val Ala Asp Val
130                 135                 140

Val Val Val Gly Ala Gly Leu Ser Gly Leu Glu Thr Ala Arg Lys Val
145                 150                 155                 160

Gln Ala Ala Gly Leu Ser Cys Leu Val Leu Glu Ala Met Asp Arg Val
                165                 170                 175

Gly Gly Lys Thr Leu Ser Val Gln Ser Gly Pro Gly Arg Thr Thr Ile
                180                 185                 190
```

```
Asp Asp Leu Gly Ala Ala Trp Ile Asn Asp Ser Asn Gln Ser Glu Val
        195                 200                 205

Phe Lys Leu Phe Glu Arg Phe His Leu Glu Gly Glu Leu Gln Arg Thr
210                 215                 220

Thr Gly Asn Ser Ile His Gln Ala Gln Asp Gly Thr Ile Thr Thr Ala
225                 230                 235                 240

Pro Tyr Gly Asp Ser Leu Leu Ser Glu Val Ala Ser Ala Leu Ala
                245                 250                 255

Glu Leu Leu Pro Ala Trp Ser Gln Leu Ile Glu Glu His Ser Leu Glu
            260                 265                 270

Asp Pro Lys Ala Ser Pro Gln Ala Lys Gln Leu Asp Ser Val Ser Phe
        275                 280                 285

Ala His Tyr Cys Glu Lys Asp Leu Asn Leu Pro Ala Val Leu Gly Val
        290                 295                 300

Ala Asn Gln Ile Thr Arg Ala Leu Leu Gly Val Glu Ala His Glu Val
305                 310                 315                 320

Ser Met Leu Phe Leu Thr Asp Tyr Ile Lys Ser Ala Thr Gly Leu Ser
                325                 330                 335

Asn Ile Phe Ser Asp Lys Lys Asp Gly Gln Tyr Met Arg Cys Lys
            340                 345                 350

Thr Gly Met Gln Ser Leu Cys His Ala Met Ser Lys Glu Leu Val Pro
            355                 360                 365

Gly Ser Val Arg Leu Asn Thr Pro Val Ala Glu Ile Glu Gln Ser Ala
        370                 375                 380

Ser Gly Cys Thr Val Arg Ser Ala Ser Gly Ala Val Phe Arg Ser Lys
385                 390                 395                 400

Lys Val Val Val Ser Leu Pro Thr Thr Leu Tyr Pro Thr Leu Thr Phe
                405                 410                 415

Ser Pro Pro Leu Pro Ala Glu Lys Gln Ala Leu Ala Glu Asn Ser Ile
            420                 425                 430

Leu Gly Tyr Tyr Ser Lys Ile Val Phe Val Trp Asp Lys Pro Trp Trp
        435                 440                 445

Arg Glu Gln Gly Phe Ser Gly Val Leu Gln Ser Ser Cys Gly Pro Ile
450                 455                 460

Ser Phe Ala Arg Asp Thr Ser Ile Glu Ala Asp Arg Gln Trp Ser Ile
465                 470                 475                 480

Thr Cys Phe Met Val Gly Asp Pro Gly Arg Lys Trp Ser Gln Ser
                485                 490                 495

Lys Gln Val Arg Gln Lys Ser Val Trp Asp Gln Leu Arg Ala Ala Tyr
        500                 505                 510

Glu Asn Ala Gly Ala Gln Val Pro Glu Pro Ala Asn Val Leu Glu Ile
        515                 520                 525

Glu Trp Ser Lys Gln Gln Tyr Phe Gln Gly Ala Pro Ser Ala Val Tyr
530                 535                 540

Gly Leu Asn Asp Leu Ile Thr Leu Gly Ser Ala Leu Arg Thr Pro Phe
545                 550                 555                 560

Lys Cys Val His Phe Val Gly Thr Glu Thr Ser Leu Val Trp Lys Gly
                565                 570                 575

Tyr Met Glu Gly Ala Ile Arg Ser Gly Gln Arg Gly Ala Ala Glu Val
        580                 585                 590

Val Ala Ser Leu Val Pro Ala Ala
        595                 600
```

```
<210> SEQ ID NO 73
<211> LENGTH: 6
<212> TYPE: PRT
<213> ORGANISM: Artificial Sequence
<220> FEATURE:
<223> OTHER INFORMATION: Glycosylation site at amino acids 201-206 of
      SEQ ID NO:52

<400> SEQUENCE: 73

Asn Asp Ser Asn Gln Ser
 1               5

<210> SEQ ID NO 74
<211> LENGTH: 15
<212> TYPE: DNA
<213> ORGANISM: Artificial Sequence
<220> FEATURE:
<223> OTHER INFORMATION: Nucleotides 1-15 of SEQ ID NO:1

<400> SEQUENCE: 74
atggcacttg caccg                                                    15

<210> SEQ ID NO 75
<211> LENGTH: 15
<212> TYPE: DNA
<213> ORGANISM: Artificial Sequence
<220> FEATURE:
<223> OTHER INFORMATION: Silent variation of nucleotides 1-15 of SEQ ID
      NO:1

<400> SEQUENCE: 75
atggccttag cgcca                                                    15

<210> SEQ ID NO 76
<211> LENGTH: 5
<212> TYPE: PRT
<213> ORGANISM: Artificial Sequence
<220> FEATURE:
<223> OTHER INFORMATION: Amino acids 1-5 of SEQ ID NO:26

<400> SEQUENCE: 76

Met Ala Leu Ala Pro
 1               5

<210> SEQ ID NO 77
<211> LENGTH: 26
<212> TYPE: PRT
<213> ORGANISM: Artificial Sequence
<220> FEATURE:
<223> OTHER INFORMATION: Amino acids 1-26 of SEQ ID NO:26

<400> SEQUENCE: 77

Met Ala Leu Ala Pro Ser Tyr Ile Asn Pro Pro Asn Val Ala Ser Pro
 1               5                  10                  15

Ala Gly Tyr Ser His Val Gly Val Gly Pro
             20                  25

<210> SEQ ID NO 78
<211> LENGTH: 26
<212> TYPE: PRT
<213> ORGANISM: Artificial Sequence
<220> FEATURE:
<223> OTHER INFORMATION: Conservative variant of amino acids 1-26 of SEQ
      ID NO: 26

<400> SEQUENCE: 78

Met Ala Val Ala Pro Ser Tyr Ile Asn Pro Pro Gln Val Ala Ser Pro
```

```
                    1               5                  10                 15
Ala Gly Tyr Ala His Leu Gly Val Gly Pro
            20              25

<210> SEQ ID NO 79
<211> LENGTH: 26
<212> TYPE: PRT
<213> ORGANISM: Artificial Sequence
<220> FEATURE:
<223> OTHER INFORMATION: Conservative variant of amino acids 1-26 of SEQ
      ID NO: 26

<400> SEQUENCE: 79

Met Ser Leu Ala Pro Ser Trp Ile Asn Pro Pro Asn Val Ala Ala Pro
1               5                   10                  15

Ala Gly Trp Ser His Val Gly Val Gly Pro
            20              25

<210> SEQ ID NO 80
<211> LENGTH: 72
<212> TYPE: DNA
<213> ORGANISM: Artificial Sequence
<220> FEATURE:
<223> OTHER INFORMATION: Barley alpha amylase signal sequence based on
      published sequence of GenBank accession K02638

<400> SEQUENCE: 80
atggccaaca agcacctgtc cctctcsctc ttcctcgtgc tcctcggcct ctccgcctcc      60
ctcgcctccg gc                                                         72

<210> SEQ ID NO 81
<211> LENGTH: 72
<212> TYPE: DNA
<213> ORGANISM: Artificial Sequence
<220> FEATURE:
<223> OTHER INFORMATION:
      Barley alpha-amylase type B isozyme sequence based
      on published sequence of accession K02638

<400> SEQUENCE: 81
atggcgaaca aacacttgtc cctctcsctc ttcctcgtcc tccttggcct gtcggccagc      60
ttggcctccg gg                                                         72

<210> SEQ ID NO 82
<211> LENGTH: 24
<212> TYPE: PRT
<213> ORGANISM: Artificial Sequence
<220> FEATURE:
<223> OTHER INFORMATION: Translation of barley alpha amylase signal
      sequence

<400> SEQUENCE: 82

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 83
<211> LENGTH: 24
<212> TYPE: PRT
<213> ORGANISM: Artificial Sequence
<220> FEATURE:
<223> OTHER INFORMATION: Translation of barley alpha-amylase type B
      isozyme sequence
```

<400> SEQUENCE: 83

```
Met Ala Asn Lys His Leu Ser Leu Ser Leu Phe Leu Val Leu Leu Gly
 1               5                  10                  15

Leu Ser Ala Ser Leu Ala Ser Gly
            20
```

<210> SEQ ID NO 84
<211> LENGTH: 1392
<212> TYPE: DNA
<213> ORGANISM: Artificial Sequence
<220> FEATURE:
<223> OTHER INFORMATION: Synthetic Construct Clone 1B5
<220> FEATURE:
<221> NAME/KEY: CDS
<222> LOCATION: (1)...(1392)

<400> SEQUENCE: 84

```
aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat    192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg    240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa    288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag    336
Asp Gly Thr Ile Thr Thr Ala Pro Tyr Gly Asp Ser Leu Leu Ser Glu
            100                 105                 110 gag gtt gca agc gca ctc gcg gaa ctc ctt ccc gca tgg tct cag ctg    384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag    432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac    480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc    528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc    576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt    624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt agc cat gcc    672
Gly Gln Tyr Met Arg Cys Lys Thr Gly Met Gln Ser Leu Ser His Ala
    210                 215                 220 atg tca aag gaa ctt gtt cca ggc tca gtg cgc ctc aac acc ccc gtc    720
Met Ser Lys Glu Leu Val Pro Gly Ser Val Arg Leu Asn Thr Pro Val
```

```
                225                 230                 235                 240
gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa      864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                325                 330                 335 gcc gat cag caa tgg tcc att acc tgt ttc atg gtc gga gac ccg gga     1056
Ala Asp Gln Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag     1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala *
    450                 455                 460

<210> SEQ ID NO 85
<211> LENGTH: 463
<212> TYPE: PRT
<213> ORGANISM: Artificial Sequence
<220> FEATURE:
<223> OTHER INFORMATION: Translation of Synthetic Construct Clone 1B5

<400> SEQUENCE: 85

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60
```

-continued

```
Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
            260                 265                 270

Leu Tyr Pro Thr Leu Thr Phe Ser Pro Leu Pro Ala Glu Lys Gln
        275                 280                 285

Ala Leu Ala Glu Asn Ser Ile Leu Gly Tyr Tyr Ser Lys Ile Val Phe
290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Gln Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460
```

<210> SEQ ID NO 86
<211> LENGTH: 1392

<212> TYPE: DNA
<213> ORGANISM: Artificial Sequence
<220> FEATURE:
<223> OTHER INFORMATION: Synthetic Construct Clone 4A9
<220> FEATURE:
<221> NAME/KEY: CDS
<222> LOCATION: (1)...(1392)

<400> SEQUENCE: 86

```
aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat    192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg    240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa    288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag    336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg    384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag    432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac    480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc    528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc    576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt    624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt agc cat gcc    672
Gly Gln Tyr Met Arg Cys Lys Thr Gly Met Gln Ser Leu Ser His Ala
    210                 215                 220 atg tca aag gaa ctt gtt cca ggc tca gtg cgc ctc aac acc ccc gtc    720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg    768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc    816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa    864
```

```
Leu Tyr Pro Thr Leu Thr Phe Ser Pro Pro Leu Pro Ala Glu Lys Gln
            275                 280                 285 gca ttg gcg gaa aat tct atc ctg ggc tac tat agc aag ata gtc ttc       912
Ala Leu Ala Glu Asn Ser Ile Leu Gly Tyr Tyr Ser Lys Ile Val Phe
        290                 295                 300 gta tgg gac aag ccg tgg tgg cgc gaa caa ggc ttc tcg ggc gtc ctc       960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa      1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga      1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg      1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag      1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
        435                 440                 445 caa cgt ggt gct gca gaa gtt gtg gct agc ctg gtg cca gca gca tag      1392
Gln Arg Gly Ala Ala Glu Val Val Ala Ser Leu Val Pro Ala Ala  *
    450                 455                 460

<210> SEQ ID NO 87
<211> LENGTH: 463
<212> TYPE: PRT
<213> ORGANISM: Artificial Sequence
<220> FEATURE:
<223> OTHER INFORMATION: Translation of Synthetic Construct Clone 4A9

<400> SEQUENCE: 87

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
```

-continued

```
                    115                 120                 125
Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460
```

<210> SEQ ID NO 88
<211> LENGTH: 1392
<212> TYPE: DNA
<213> ORGANISM: Artificial Sequence
<220> FEATURE:
<223> OTHER INFORMATION: Synthetic Construct Clone 4B11
<220> FEATURE:
<221> NAME/KEY: CDS
<222> LOCATION: (1)...(1392)

<400> SEQUENCE: 88 aaa gac aat gtt gcg gac gtg gta gtg gtg ggc gct ggc ttg agc ggt        48

```
                                                                -continued

Lys Asp Asn Val Ala Asp Val Val Val Gly Ala Gly Leu Ser Gly
 1               5                  10                  15 ttg gag acg gca cgc aaa gtc cag gcc gcc ggt ctg tcc tgc ctc gtt         96
Leu Glu Thr Ala Arg Lys Val Gln Ala Ala Gly Leu Ser Cys Leu Val
             20                  25                  30 ctt gag gcg atg gac cgt gta ggg ggg aag act ctg agc gta caa tcg        144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat        192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg        240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa        288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag        336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg        384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag        432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac        480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc        528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc        576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt        624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc        672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc        720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg        768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc        816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa        864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc        912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc        960
Val Trp Asp Lys Pro Trp Trp Arg Glu Gln Gly Phe Ser Gly Val Leu
305                 310                 315                 320
```

-continued

```
caa tcg agc ggt ggc ccc atc tca ttt gcc aga gat acc agc atc gaa      1008
Gln Ser Ser Gly Gly Pro Ile Ser Phe Ala Arg Asp Thr Ser Ile Glu
            325                 330                 335 gcc gat cgg caa tgg tcc att acc tgt ttc atg gtc gga gac ccg gga      1056
Ala Asp Arg Gln Trp Ser Ile Thr Cys Phe Met Val Gly Asp Pro Gly
        340                 345                 350 cgg aag tgg tcc caa cag tcc aag cag gta cga caa aag tct gtc tgg      1104
Arg Lys Trp Ser Gln Gln Ser Lys Gln Val Arg Gln Lys Ser Val Trp
    355                 360                 365 gac caa ctc cgc gca gcc tac gag agc gct ggg gcc caa gtc cca gag      1152
Asp Gln Leu Arg Ala Ala Tyr Glu Ser Ala Gly Ala Gln Val Pro Glu
370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
            405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala *
450                 455                 460
```

<210> SEQ ID NO 89
<211> LENGTH: 463
<212> TYPE: PRT
<213> ORGANISM: Artificial Sequence
<220> FEATURE:
<223> OTHER INFORMATION: Translation of Synthetic Construct Clone 4B11

<400> SEQUENCE: 89

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
            85                  90                  95

Asp Gly Thr Ile Thr Thr Ala Pro Tyr Gly Asp Ser Leu Leu Ser Glu
        100                 105                 110

Glu Val Ala Ser Ala Leu Ala Glu Leu Leu Pro Ala Trp Ser Gln Leu
    115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
            165                 170                 175
```

```
Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Ser Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 90
<211> LENGTH: 1392
<212> TYPE: DNA
<213> ORGANISM: Artificial Sequence
<220> FEATURE:
<223> OTHER INFORMATION: Synthetic Construct Clone 4D11
<220> FEATURE:
<221> NAME/KEY: CDS
<222> LOCATION: (1)...(1392)

<400> SEQUENCE: 90 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg ttg gat cgt gta ggg gga aag act ctg agc gta caa tcg     144
Leu Glu Ala Leu Asp Arg Val Gly Gly Lys Thr Leu Ser Val Gln Ser
         35                  40                  45
```

```
ggt ccc ggc agg acg act atc gac gac ctc ggc gct gcg tgg atc aat      192
Gly Pro Gly Arg Thr Thr Ile Asp Asp Leu Gly Ala Ala Trp Ile Asn
 50                  55                  60 gac agc aac caa agc gaa gta ttc aaa tta ttt gaa aga ttt cat ttg      240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
             100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
         115                 120                 125 atc gaa gag cat agt ctt gaa gac ccc aag gcg agc cct cag gcg aag      432
Ile Glu Glu His Ser Leu Glu Asp Pro Lys Ala Ser Pro Gln Ala Lys
130                 135                 140 cag ctc gac agt gtg agc ttc gca cac tac tgt gag aag gac cta aac      480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
                 165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
             180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
         195                 200                 205 ggg cag tat atg cga tgc aaa aca ggt atg cag tcg ctt tgc cat gcc      672
Gly Gln Tyr Met Arg Cys Lys Thr Gly Met Gln Ser Leu Cys His Ala
210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                 245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
             260                 265                 270 ttg tat ccc act ttg aca ttt tca cca cct ctt ccc gcc gag aag caa      864
Leu Tyr Pro Thr Leu Thr Phe Ser Pro Pro Leu Pro Ala Glu Lys Gln
         275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                 325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
             340                 345                 350 cgg aag tgg tcc caa cag tcc aag cag gta cga caa aag tcc gtc tgg     1104
Arg Lys Trp Ser Gln Gln Ser Lys Gln Val Arg Gln Lys Ser Val Trp
         355                 360                 365
```

```
gac caa ctc cgc gca gcc tac gag aac gct ggg gcc caa gtc cca gag    1152
Asp Gln Leu Arg Ala Ala Tyr Glu Asn Ala Gly Ala Gln Val Pro Glu
        370                 375                 380 ccg gcc aac gtg ctc gaa atc gag tgg tcg aag cag cag tat ttc caa    1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag    1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala  *
        450                 455                 460

<210> SEQ ID NO 91
<211> LENGTH: 463
<212> TYPE: PRT
<213> ORGANISM: Artificial Sequence
<220> FEATURE:
<223> OTHER INFORMATION: Translation of Synthetic Construct Clone 4D11

<400> SEQUENCE: 91

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Leu Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240
```

```
Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 92
<211> LENGTH: 1392
<212> TYPE: DNA
<213> ORGANISM: Artificial Sequence
<220> FEATURE:
<223> OTHER INFORMATION: Synthetic Construct Clone 5A3
<220> FEATURE:
<221> NAME/KEY: CDS
<222> LOCATION: (1)...(1392)

<400> SEQUENCE: 92 aaa gac aat gtt gcg gac gtg gta gtg gtg ggc gct ggc ttg agc ggt       48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt       96
Leu Glu Thr Ala Arg Lys Val Gln Ala Ala Gly Leu Ser Cys Leu Val
             20                  25                  30 ctt gag gcg atg gat cgt gta ggg ggg aag act ctg agc gta caa tcg      144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat      192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg      240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                 85                  90                  95
```

-continued

| | | |
|---|---|---|
| gac ggt aca atc act aca gct cct tat ggt gac tcc ttg ctg agc gag<br>Asp Gly Thr Ile Thr Thr Ala Pro Tyr Gly Asp Ser Leu Leu Ser Glu<br>100            105            110 | | 336 |
| gag gtt gca agt gca ctc gcg gaa ctc ctt ccc gca tgg tct cag ctg<br>Glu Val Ala Ser Ala Leu Ala Glu Leu Leu Pro Ala Trp Ser Gln Leu<br>     115            120            125 | | 384 |
| atc gaa gag cat agt ctt gaa gac ccc aag gcg agc cct cag gcg aag<br>Ile Glu Glu His Ser Leu Glu Asp Pro Lys Ala Ser Pro Gln Ala Lys<br>130            135            140 | | 432 |
| cag ctc gac agt gtg agc ttc gca cac tac tgt gag aag gac cta aac<br>Gln Leu Asp Ser Val Ser Phe Ala His Tyr Cys Glu Lys Asp Leu Asn<br>145            150            155            160 | | 480 |
| ttg cct gct gtt ctc ggc gtg gca aac cag atc aca cgc gct ctg ctc<br>Leu Pro Ala Val Leu Gly Val Ala Asn Gln Ile Thr Arg Ala Leu Leu<br>           165            170            175 | | 528 |
| ggt gtg gaa gcc cac gag gtc agc atg ctt ttt ctc acc gac tac atc<br>Gly Val Glu Ala His Glu Val Ser Met Leu Phe Leu Thr Asp Tyr Ile<br>           180            185            190 | | 576 |
| aag agt gcc acc ggt ctc agt aat att ttc tcg gag aag aaa gac ggt<br>Lys Ser Ala Thr Gly Leu Ser Asn Ile Phe Ser Glu Lys Lys Asp Gly<br>           195            200            205 | | 624 |
| ggg cag tat atg cga tgc aaa aca ggt atg cag tcg ctt tgc cat gcc<br>Gly Gln Tyr Met Arg Cys Lys Thr Gly Met Gln Ser Leu Cys His Ala<br>210            215            220 | | 672 |
| atg tca aag gaa ctt gtt cca ggc tca gtg cgc ctc aac acc ccc gtc<br>Met Ser Lys Glu Leu Val Pro Gly Ser Val Arg Leu Asn Thr Pro Val<br>225            230            235            240 | | 720 |
| gct gaa att gag cag tcg gcg tcc ggc tgt aca gta cga tcg gcc tcg<br>Ala Glu Ile Glu Gln Ser Ala Ser Gly Cys Thr Val Arg Ser Ala Ser<br>           245            250            255 | | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>           260            265            270 | | 816 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>           275            280            285 | | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>290            295            300 | | 912 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>305            310            315            320 | | 960 |
| caa tcg agc ggt ggc ccc atc tca ttt gcc aga gat acc agc atc gaa<br>Gln Ser Ser Gly Gly Pro Ile Ser Phe Ala Arg Asp Thr Ser Ile Glu<br>           325            330            335 | | 1008 |
| gcc gat cgg caa tgg tcc att acc tgt ttc atg gtc gga gac ccg gga<br>Ala Asp Arg Gln Trp Ser Ile Thr Cys Phe Met Val Gly Asp Pro Gly<br>           340            345            350 | | 1056 |
| cgg aag tgg tcc caa cag tcc aag cag gta cga caa aag tct gtc tgg<br>Arg Lys Trp Ser Gln Gln Ser Lys Gln Val Arg Gln Lys Ser Val Trp<br>           355            360            365 | | 1104 |
| gac caa ctc cgc gca gcc tac gag aac gct ggg gcc caa gtc cca gag<br>Asp Gln Leu Arg Ala Ala Tyr Glu Asn Ala Gly Ala Gln Val Pro Glu<br>370            375            380 | | 1152 |
| ccg gcc aac gtg ctc gaa atc gag tgg tcg aag cag cag tat ttc caa<br>Pro Ala Asn Val Leu Glu Ile Glu Trp Ser Lys Gln Gln Tyr Phe Gln<br>385            390            395            400 | | 1200 |
| gga gct ccg agc gcc gtc tat ggg ctg aac gat ctc atc aca ctg ggt<br>Gly Ala Pro Ser Ala Val Tyr Gly Leu Asn Asp Leu Ile Thr Leu Gly | | 1248 |

```
                         405                 410                 415
tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
                         420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
                         435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala   *
        450                 455                 460
```

<210> SEQ ID NO 93
<211> LENGTH: 463
<212> TYPE: PRT
<213> ORGANISM: Artificial Sequence
<220> FEATURE:
<223> OTHER INFORMATION: Translation of Synthetic Construct Clone 5A3

<400> SEQUENCE: 93

```
Lys Asp Asn Val Ala Asp Val Val Val Gly Ala Gly Leu Ser Gly
 1               5                  10                  15

Leu Glu Thr Ala Arg Lys Val Gln Ala Ala Gly Leu Ser Cys Leu Val
                 20                  25                  30

Leu Glu Ala Met Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
         50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
```

```
                290             295             300
Val Trp Asp Lys Pro Trp Trp Arg Glu Gln Gly Phe Ser Gly Val Leu
305             310             315             320

Gln Ser Ser Gly Gly Pro Ile Ser Phe Ala Arg Asp Thr Ser Ile Glu
            325             330             335

Ala Asp Arg Gln Trp Ser Ile Thr Cys Phe Met Val Gly Asp Pro Gly
            340             345             350

Arg Lys Trp Ser Gln Gln Ser Lys Gln Val Arg Gln Lys Ser Val Trp
            355             360             365

Asp Gln Leu Arg Ala Ala Tyr Glu Asn Ala Gly Ala Gln Val Pro Glu
        370             375             380

Pro Ala Asn Val Leu Glu Ile Glu Trp Ser Lys Gln Gln Tyr Phe Gln
385             390             395             400

Gly Ala Pro Ser Ala Val Tyr Gly Leu Asn Asp Leu Ile Thr Leu Gly
            405             410             415

Ser Ala Leu Arg Thr Pro Phe Lys Cys Val His Phe Val Gly Thr Glu
            420             425             430

Thr Ser Leu Val Trp Lys Gly Tyr Met Glu Gly Ala Ile Arg Ser Gly
            435             440             445

Gln Arg Gly Ala Ala Glu Val Val Ala Ser Leu Val Pro Ala Ala
        450             455             460

<210> SEQ ID NO 94
<211> LENGTH: 1392
<212> TYPE: DNA
<213> ORGANISM: Artificial Sequence
<220> FEATURE:
<223> OTHER INFORMATION: Synthetic Construct Clone 5G10
<220> FEATURE:
<221> NAME/KEY: CDS
<222> LOCATION: (1)...(1392)

<400> SEQUENCE: 94 aaa gac aat gtt gcg gac gtg gta gtg gtg ggc gct ggc ttg agc ggt        48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt        96
Leu Glu Thr Ala Arg Lys Val Gln Ala Ala Gly Leu Ser Cys Leu Val
                20                  25                  30 ctt gag gcg ttg gat cgt gta ggg gga aag act ctg agc gta caa tcg       144
Leu Glu Ala Leu Asp Arg Val Gly Gly Lys Thr Leu Ser Val Gln Ser
            35                  40                  45 ggt ccc ggc agg acg act atc gac gac ctc ggc gct gcg tgg atc aat       192
Gly Pro Gly Arg Thr Thr Ile Asp Asp Leu Gly Ala Ala Trp Ile Asn
        50                  55                  60 gac agc aac caa agc gaa gta ttc aaa tta ttt gaa aga ttt cat ttg       240
Asp Ser Asn Gln Ser Glu Val Phe Lys Leu Phe Glu Arg Phe His Leu
65                  70                  75                  80 gag ggc gag ctc cag agg acg acc gga aat tca atc cat caa gca caa       288
Glu Gly Glu Leu Gln Arg Thr Thr Gly Asn Ser Ile His Gln Ala Gln
                85                  90                  95 gac ggt aca atc act aca gct cct tat ggt gac tcc ttg ctg ggc gag       336
Asp Gly Thr Ile Thr Thr Ala Pro Tyr Gly Asp Ser Leu Leu Gly Glu
            100                 105                 110 gag gtt gca agc gca ctc gcg gaa ctc ctt ccc gca tgg tct cag ctg       384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag       432
Ile Glu Glu His Ser Leu Glu Asp Pro Lys Ala Ser Pro Gln Ala Lys
```

-continued

```
                130                 135                 140
cag ctc gac agt gtg agc ttc gca cac tac tgt gag aag gac cta aac    480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc    528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc    576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt    624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc    672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc    720
Met Ser Lys Glu Leu Val Pro Gly Ser Val Arg Leu Asn Thr Pro Val
225                 230                 235                 240 gct gaa att gag cag tcg gcg tcc ggc tgt aca gta cgg tcg gcc tcg    768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc    816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa    864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc    912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc    960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa   1008
Gln Ser Ser Gly Gly Pro Ile Ser Phe Ala Arg Asp Thr Ser Ile Glu
                325                 330                 335 gcc gat cag caa tgg tcc att acc tgt ttc atg gtc gga gac ccg gga   1056
Ala Asp Gln Gln Trp Ser Ile Thr Cys Phe Met Val Gly Asp Pro Gly
            340                 345                 350 cgg aag tgg tcc caa cag tcc aag cag gta cga caa aag tct gtc tgg   1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag   1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa   1200
Pro Ala Asn Val Leu Glu Ile Glu Trp Ser Lys Gln Gln Tyr Phe Gln
385                 390                 395                 400 gga gct ccg agc gcc gtc tat ggg ttg aac gat ctc atc aca ctg ggt   1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag   1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt   1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag   1392
```

Gln Arg Gly Ala Ala Glu Val Val Ala Ser Leu Val Pro Ala Ala *
    450                 455                 460

<210> SEQ ID NO 95
<211> LENGTH: 463
<212> TYPE: PRT
<213> ORGANISM: Artificial Sequence
<220> FEATURE:
<223> OTHER INFORMATION: Translation of Synthetic Construct Clone 5G10

<400> SEQUENCE: 95

Lys Asp Asn Val Ala Asp Val Val Val Gly Ala Gly Leu Ser Gly
  1               5                  10                  15

Leu Glu Thr Ala Arg Lys Val Gln Ala Ala Gly Leu Ser Cys Leu Val
                 20                  25                  30

Leu Glu Ala Leu Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
     50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Gly Glu
            100                 105                 110

Glu Val Ala Ser Ala Leu Ala Glu Leu Leu Pro Ala Trp Ser Gln Leu
            115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Gln Gln Trp Ser Ile Thr Cys Phe Met Val Gly Asp Pro Gly
            340                 345                 350

```
Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
        370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 96
<211> LENGTH: 1392
<212> TYPE: DNA
<213> ORGANISM: Artificial Sequence
<220> FEATURE:
<223> OTHER INFORMATION: Synthetic Construct Clone 6B11
<220> FEATURE:
<221> NAME/KEY: CDS
<222> LOCATION: (1)...(1392)

<400> SEQUENCE: 96 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt     96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
        35                  40                  45 ggt ccc ggc agg acg act atc gac gac ctc ggc gct gcg tgg atc aat    192
Gly Pro Gly Arg Thr Thr Ile Asp Asp Leu Gly Ala Ala Trp Ile Asn
    50                  55                  60 gac agc aac caa agc gaa gta ttc aaa tta ttt gaa aga ttt cat ttg    240
Asp Ser Asn Gln Ser Glu Val Phe Lys Leu Phe Glu Arg Phe His Leu
65                  70                  75                  80 gag ggc gag ctc cag agg acg acc gga aat tca atc cac caa gca caa    288
Glu Gly Glu Leu Gln Arg Thr Thr Gly Asn Ser Ile His Gln Ala Gln
                85                  90                  95 gac ggt aca atc act aca gct cct tat ggt gac tcc ttg ctg agc gag    336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg    384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag    432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac    480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc    528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac gtc    576
```

```
                Gly Val Glu Ala His Glu Val Ser Met Leu Phe Leu Thr Asp Tyr Val
                            180                 185                 190 aag agt gcc acc ggt ctc agt aat att ttc tcg gag aag aaa gac ggt        624
Lys Ser Ala Thr Gly Leu Ser Asn Ile Phe Ser Glu Lys Lys Asp Gly
            195                 200                 205 ggg cag tat atg cga tgc aaa aca ggt atg cag tcg ctt tgc cat gcc        672
Gly Gln Tyr Met Arg Cys Lys Thr Gly Met Gln Ser Leu Cys His Ala
        210                 215                 220 atg tca aag gaa ctt gtt cca ggc tca gtg cgc ctc aac acc ccc gtc        720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg        768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc        816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa        864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc        912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc        960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa       1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga       1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg       1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag       1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa       1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt       1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag       1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt       1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag       1392
Gln Arg Gly Ala Ala Glu Val Val Ala Ser Leu Val Pro Ala Ala *
    450                 455                 460

<210> SEQ ID NO 97
<211> LENGTH: 463
<212> TYPE: PRT
<213> ORGANISM: Artificial Sequence
<220> FEATURE:
<223> OTHER INFORMATION: Translation of Synthetic Construct Clone 6B11
```

<400> SEQUENCE: 97

```
Lys Asp Asn Val Ala Asp Val Val Val Gly Ala Gly Leu Ser Gly
  1               5                  10                  15

Leu Glu Thr Ala Arg Lys Val Gln Ala Ala Gly Leu Ser Cys Leu Val
             20                  25                  30

Leu Glu Ala Met Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
         50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
             100                 105                 110

Glu Val Ala Ser Ala Leu Ala Glu Leu Leu Pro Ala Trp Ser Gln Leu
             115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                 165                 170                 175

Gly Val Glu Ala His Glu Val Ser Met Leu Phe Leu Thr Asp Tyr Val
             180                 185                 190

Lys Ser Ala Thr Gly Leu Ser Asn Ile Phe Ser Glu Lys Lys Asp Gly
             195                 200                 205

Gly Gln Tyr Met Arg Cys Lys Thr Gly Met Gln Ser Leu Cys His Ala
         210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                 245                 250                 255

Gly Ala Val Phe Arg Ser Lys Lys Val Val Val Ser Leu Pro Thr Thr
             260                 265                 270

Leu Tyr Pro Thr Leu Thr Phe Ser Pro Pro Leu Pro Ala Glu Lys Gln
             275                 280                 285

Ala Leu Ala Glu Asn Ser Ile Leu Gly Tyr Tyr Ser Lys Ile Val Phe
         290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                 325                 330                 335

Ala Asp Arg Gln Trp Ser Ile Thr Cys Phe Met Val Gly Asp Pro Gly
             340                 345                 350

Arg Lys Trp Ser Gln Gln Ser Lys Gln Val Arg Gln Lys Ser Val Trp
             355                 360                 365

Asp Gln Leu Arg Ala Ala Tyr Glu Asn Ala Gly Ala Gln Val Pro Glu
         370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                 405                 410                 415
```

```
Ser Ala Leu Arg Thr Pro Phe Lys Cys Val His Phe Val Gly Thr Glu
        420                 425                 430
Thr Ser Leu Val Trp Lys Gly Tyr Met Glu Gly Ala Ile Arg Ser Gly
        435                 440                 445
Gln Arg Gly Ala Ala Glu Val Val Ala Ser Leu Val Pro Ala Ala
        450                 455                 460

<210> SEQ ID NO 98
<211> LENGTH: 1392
<212> TYPE: DNA
<213> ORGANISM: Artificial Sequence
<220> FEATURE:
<223> OTHER INFORMATION: Synthetic Construct Clone 6B3
<220> FEATURE:
<221> NAME/KEY: CDS
<222> LOCATION: (1)...(1392)

<400> SEQUENCE: 98 aaa gac aat gtt gcg gac gtg gta gtg gtg ggc gct ggc ttg agc ggt        48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt       96
Leu Glu Thr Ala Arg Lys Val Gln Ala Ala Gly Leu Ser Cys Leu Val
             20                  25                  30 ctt gag gcg ttg gat cgt gta ggg gga aag act ctg agc gta caa tcg      144
Leu Glu Ala Leu Asp Arg Val Gly Gly Lys Thr Leu Ser Val Gln Ser
         35                  40                  45 ggt ccc ggc agg acg act atc gac gac ctc ggc gct gcg tgg atc aat      192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg      240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag      432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac      480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc      672
Gly Gln Tyr Met Arg Cys Lys Thr Gly Met Gln Ser Leu Cys His Ala
    210                 215                 220
```

```
atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgc aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa      864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
            340                 345                 350 cgg aag tgg tcc caa cag tcc aag cag gta cga caa gag tct gtc tgg     1104
Arg Lys Trp Ser Gln Gln Ser Lys Gln Val Arg Gln Glu Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag     1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala *
    450                 455                 460

<210> SEQ ID NO 99
<211> LENGTH: 463
<212> TYPE: PRT
<213> ORGANISM: Artificial Sequence
<220> FEATURE:
<223> OTHER INFORMATION: Translation of Synthetic Construct Clone 6B3

<400> SEQUENCE: 99

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Leu Asp Arg Val Gly Gly Lys Thr Leu Ser Val Gln Ser
            35                  40                  45
```

-continued

```
Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Glu Ser Val Trp
        355                 360                 365

Asp Gln Leu Arg Ala Ala Tyr Glu Asn Ala Gly Ala Gln Val Pro Glu
370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460
```

```
<210> SEQ ID NO 100
<211> LENGTH: 1392
<212> TYPE: DNA
<213> ORGANISM: Artificial Sequence
<220> FEATURE:
<223> OTHER INFORMATION: Synthetic Construct Clone 7A5
<220> FEATURE:
<221> NAME/KEY: CDS
<222> LOCATION: (1)...(1392)

<400> SEQUENCE: 100 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg ttg gat cgt gta ggg gga aag act ctg agc gta caa tcg     144
Leu Glu Ala Leu Asp Arg Val Gly Gly Lys Thr Leu Ser Val Gln Ser
         35                  40                  45 ggt ccc ggc agg acg act atc gac gac ctc ggc gct gcg tgg atc aat     192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg     240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa     288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag     336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg     384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag     432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac     480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc     528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc     576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt     624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc     672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc     720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg     768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc     816
Gly Ala Val Phe Arg Ser Lys Lys Val Val Val Ser Leu Pro Thr Thr
            260                 265                 270
```

```
ttg tat ccc tcc ttg aca ttt tca cca cct ctt ccc gcc gag aag caa       864
Leu Tyr Pro Ser Leu Thr Phe Ser Pro Pro Leu Pro Ala Glu Lys Gln
    275                 280                 285 gca ttg gcg gaa aat tct atc ctg ggc tac tat agc aag ata gtc ttc       912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc       960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa      1008
Gln Ser Ser Gly Gly Pro Ile Ser Phe Ala Arg Asp Thr Ser Ile Glu
            325                 330                 335 gcc gat cgg caa tgg tcc att acc tgt ttc atg gtc gga gac ccg gga      1056
Ala Asp Arg Gln Trp Ser Ile Thr Cys Phe Met Val Gly Asp Pro Gly
        340                 345                 350 cgg aag tgg tcc caa cag tcc aag cag gta cga caa aag tct gtc tgg      1104
Arg Lys Trp Ser Gln Gln Ser Lys Gln Val Arg Gln Lys Ser Val Trp
    355                 360                 365 gac caa ctc cgc gca gcc tac gag aac gct ggg gcc caa gtc cca gag      1152
Asp Gln Leu Arg Ala Ala Tyr Glu Asn Ala Gly Ala Gln Val Pro Glu
370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc gtc aca ctg ggt      1248
Gly Ala Pro Ser Ala Val Tyr Gly Leu Asn Asp Leu Val Thr Leu Gly
            405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala  *
450                 455                 460

<210> SEQ ID NO 101
<211> LENGTH: 463
<212> TYPE: PRT
<213> ORGANISM: Artificial Sequence
<220> FEATURE:
<223> OTHER INFORMATION: Translation of Synthetic Construct Clone 7A5

<400> SEQUENCE: 101

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Leu Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110
```

```
Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
                180                 185                 190

Lys Ser Ala Thr Gly Leu Ser Asn Ile Phe Ser Glu Lys Lys Asp Gly
            195                 200                 205

Gly Gln Tyr Met Arg Cys Lys Thr Gly Met Gln Ser Leu Cys His Ala
            210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
                260                 265                 270

Leu Tyr Pro Ser Leu Thr Phe Ser Pro Pro Leu Pro Ala Glu Lys Gln
            275                 280                 285

Ala Leu Ala Glu Asn Ser Ile Leu Gly Tyr Tyr Ser Lys Ile Val Phe
            290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Asn Ala Gly Ala Gln Val Pro Glu
            370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Val Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
            450                 455                 460

<210> SEQ ID NO 102
<211> LENGTH: 1392
<212> TYPE: DNA
<213> ORGANISM: Artificial Sequence
<220> FEATURE:
<223> OTHER INFORMATION: Synthetic Construct Clone 7B8
<220> FEATURE:
<221> NAME/KEY: CDS
<222> LOCATION: (1)...(1392)

<400> SEQUENCE: 102
```

-continued

```
aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat     192
Gly Pro Gly Arg Thr Thr Ile Asp Asp Leu Gly Ala Ala Trp Ile Asn
 50                  55                  60 gac agc aac caa agc gaa gta ttc aaa tta ttt gaa aga ttt cat ttg     240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa     288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag     336
Asp Gly Thr Ile Thr Thr Ala Pro Tyr Gly Asp Ser Leu Leu Ser Glu
            100                 105                 110 gag gtt gca agc gca ctc gcg gaa ctc cct ccc gca tgg tct cag ctg     384
Glu Val Ala Ser Ala Leu Ala Glu Leu Pro Pro Ala Trp Ser Gln Leu
        115                 120                 125 atc gaa gag cat agt ctt gaa gac ccc aag gcg agc cct cag gcg aag     432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac     480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc     528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc     576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt     624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc     672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc     720
Met Ser Lys Glu Leu Val Pro Gly Ser Val Arg Leu Asn Thr Pro Val
225                 230                 235                 240 gct gaa att gag cag tcg gcg tcc ggc tgt acg gta cga tcg gcc tcg     768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc     816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa     864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc     912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc     960
Val Trp Asp Lys Pro Trp Trp Arg Glu Gln Gly Phe Ser Gly Val Leu
```

-continued

```
               305                 310                 315                 320
caa tcg agc ggt ggc ccc atc tca ttt gcc aga gat acc agc atc gaa        1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga        1056
Ala Asp Arg Gln Trp Ser Ile Thr Cys Phe Met Val Gly Asp Pro Gly
                340                 345                 350 cgg aag tgg tcc caa cag tcc aag cag gta cga caa aag tct gtc tgg       1104
Arg Lys Trp Ser Gln Gln Ser Lys Gln Val Arg Gln Lys Ser Val Trp
                355                 360                 365 gac caa ctc cgc gca gcc tac gag aac gct ggg gcc caa gtc cca gag       1152
Asp Gln Leu Arg Ala Ala Tyr Glu Asn Ala Gly Ala Gln Val Pro Glu
                370                 375                 380 ccg gcc aac gtg ctc gaa atc gag tgg tcg aag cag cag tat ttc caa       1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc gtc aca ctg ggt       1248
Gly Ala Pro Ser Ala Val Tyr Gly Leu Asn Asp Leu Val Thr Leu Gly
                405                 410                 415 tcg gcg ctc aga acg ccg ttc aag tgt gtt cat ttc gtc gga acg gag       1296
Ser Ala Leu Arg Thr Pro Phe Lys Cys Val His Phe Val Gly Thr Glu
                420                 425                 430 acg tct tta gtt tgg aaa ggg tat atg gaa ggg gcc ata cga tcg ggt       1344
Thr Ser Leu Val Trp Lys Gly Tyr Met Glu Gly Ala Ile Arg Ser Gly
                435                 440                 445 caa cga ggt gct aca gaa gtt gtg gct agc ctg gtg cca gca gca tag       1392
Gln Arg Gly Ala Thr Glu Val Val Ala Ser Leu Val Pro Ala Ala  *
                450                 455                 460
```

<210> SEQ ID NO 103
<211> LENGTH: 463
<212> TYPE: PRT
<213> ORGANISM: Artificial Sequence
<220> FEATURE:
<223> OTHER INFORMATION: Translation of Synthetic Construct Clone 7B8

<400> SEQUENCE: 103

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Met Asp Arg Val Gly Gly Lys Thr Leu Ser Val Gln Ser
                35                  40                  45

Gly Pro Gly Arg Thr Thr Ile Asp Asp Leu Gly Ala Ala Trp Ile Asn
                50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
                100                 105                 110

Glu Val Ala Ser Ala Leu Ala Leu Pro Pro Ala Trp Ser Gln Leu
                115                 120                 125

Ile Glu Glu His Ser Leu Glu Asp Pro Lys Ala Ser Pro Gln Ala Lys
                130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
```

```
                        165                 170                 175
Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Val Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Thr Glu Val Val Ala Ser Leu Val Pro Ala Ala
    450                 455                 460

<210> SEQ ID NO 104
<211> LENGTH: 1392
<212> TYPE: DNA
<213> ORGANISM: Artificial Sequence
<220> FEATURE:
<223> OTHER INFORMATION: Synthetic Construct Clone 7C10
<220> FEATURE:
<221> NAME/KEY: CDS
<222> LOCATION: (1)...(1392)

<400> SEQUENCE: 104 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
        35                  40                  45
```

```
                     35                    40                       45
ggt ccc ggc agg acg act atc gac gac ctc ggc gct gcg tgg atc aat       192
Gly Pro Gly Arg Thr Thr Ile Asp Asp Leu Gly Ala Ala Trp Ile Asn
 50                     55                    60 gac agc aac caa agc gaa gta ttc aaa tta ttt gaa aga ttt cat ttg       240
Asp Ser Asn Gln Ser Glu Val Phe Lys Leu Phe Glu Arg Phe His Leu
 65                     70                    75                 80 gag ggc gag ctc cag agg acg acc gga aat tca atc cat caa gca caa       288
Glu Gly Glu Leu Gln Arg Thr Thr Gly Asn Ser Ile His Gln Ala Gln
                    85                    90                    95 gac ggt aca atc act aca gct cct tat ggt gac tcc ttg ctg agc gag       336
Asp Gly Thr Ile Thr Thr Ala Pro Tyr Gly Asp Ser Leu Leu Ser Glu
                100                   105                   110 gag gtt gca agt gca ctc gcg gaa ctc ctt ccc gca tgg tct cag ctg       384
Glu Val Ala Ser Ala Leu Ala Glu Leu Leu Pro Ala Trp Ser Gln Leu
            115                   120                   125 atc gaa gag cat agt ctt gaa gac ccc aag gcg agc cct cag gcg aag       432
Ile Glu Glu His Ser Leu Glu Asp Pro Lys Ala Ser Pro Gln Ala Lys
130                   135                   140 cag ctc gac agt gtg agc ttc gca cac tac tgt gag aag gac cta aac       480
Gln Leu Asp Ser Val Ser Phe Ala His Tyr Cys Glu Lys Asp Leu Asn
145                   150                   155                   160 ttg cct gct gtt ctc ggc gtg gca aac cag atc aca cgc gct ctg ctc       528
Leu Pro Ala Val Leu Gly Val Ala Asn Gln Ile Thr Arg Ala Leu Leu
                    165                   170                   175 ggt gtg gaa gcc cgc gag gtc agc atg ctt ttt ctc acc gac tac atc       576
Gly Val Glu Ala Arg Glu Val Ser Met Leu Phe Leu Thr Asp Tyr Ile
                180                   185                   190 aag agt gcc acc ggt ctc agt aat att ttc tcg gag aag aaa gac ggt       624
Lys Ser Ala Thr Gly Leu Ser Asn Ile Phe Ser Glu Lys Lys Asp Gly
            195                   200                   205 ggg cag tat atg cga tgc aaa aca ggt atg cag tcg ctt agc cat gcc       672
Gly Gln Tyr Met Arg Cys Lys Thr Gly Met Gln Ser Leu Ser His Ala
        210                   215                   220 atg tca aag gaa ctt gtt cca ggc tca gtg cgc ctc aac acc ccc gtc       720
Met Ser Lys Glu Leu Val Pro Gly Ser Val Arg Leu Asn Thr Pro Val
225                   230                   235                   240 gct gaa att gag cag tcg gcg tcc ggc tgt aca gta cga tcg gcc tcg       768
Ala Glu Ile Glu Gln Ser Ala Ser Gly Cys Thr Val Arg Ser Ala Ser
                    245                   250                   255 ggc gcc gtg ttc cga agc aaa aag gtg gtg gtt tcg tta ccg aca acc       816
Gly Ala Val Phe Arg Ser Lys Lys Val Val Val Ser Leu Pro Thr Thr
                260                   265                   270 ttg tat ccc acc ttg aca ttt tca ccg cct ctt ccc gcc gag aag caa       864
Leu Tyr Pro Thr Leu Thr Phe Ser Pro Pro Leu Pro Ala Glu Lys Gln
            275                   280                   285 gca ttg gcg gaa aat tct atc ctg ggc tac tat agc aag ata gtc ttc       912
Ala Leu Ala Glu Asn Ser Ile Leu Gly Tyr Tyr Ser Lys Ile Val Phe
        290                   295                   300 gta tgg gac aag ccg tgg tgg cgc gaa caa ggc ttc tcg ggc gtc ctc       960
Val Trp Asp Lys Pro Trp Trp Arg Glu Gln Gly Phe Ser Gly Val Leu
305                   310                   315                   320 caa tcg agc ggt ggc ccc atc tca ttt gcc aga gat acc agc atc gaa      1008
Gln Ser Ser Gly Gly Pro Ile Ser Phe Ala Arg Asp Thr Ser Ile Glu
                    325                   330                   335 gcc gat cgg caa tgg tcc att acc tgt ttc atg gtc gga gac ccg gga      1056
Ala Asp Arg Gln Trp Ser Ile Thr Cys Phe Met Val Gly Asp Pro Gly
                340                   345                   350 cgg aag tgg tcc caa cag tcc aag cag gta cga caa aag tct gtc tgg      1104
```

```
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag      1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala *
    450                 455                 460

<210> SEQ ID NO 105
<211> LENGTH: 463
<212> TYPE: PRT
<213> ORGANISM: Artificial Sequence
<220> FEATURE:
<223> OTHER INFORMATION: Translation of Synthetic Construct Clone 7C10

<400> SEQUENCE: 105

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Met Asp Arg Val Gly Gly Lys Thr Leu Ser Val Gln Ser
            35                  40                  45

Gly Pro Gly Arg Thr Thr Ile Asp Asp Leu Gly Ala Ala Trp Ile Asn
        50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala Arg Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220
```

```
Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
            245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
290                 295                 300

Val Trp Asp Lys Pro Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 106
<211> LENGTH: 1392
<212> TYPE: DNA
<213> ORGANISM: Artificial Sequence
<220> FEATURE:
<223> OTHER INFORMATION: Synthetic Construct Clone 7E9
<220> FEATURE:
<221> NAME/KEY: CDS
<222> LOCATION: (1)...(1392)

<400> SEQUENCE: 106 aaa gac aat gtt gcg gac gtg gta gtg gtg ggc gct ggc ttg agc ggt     48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt     96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
        35                  40                  45 ggt ccc ggc agg acg act atc gac gac ctc ggc gct gcg tgg atc aat    192
Gly Pro Gly Arg Thr Thr Ile Asp Asp Leu Gly Ala Ala Trp Ile Asn
    50                  55                  60 gac agc aac caa agc gaa gta ttc aaa tta ttt gaa aga ttt cat ttg    240
Asp Ser Asn Gln Ser Glu Val Phe Lys Leu Phe Glu Arg Phe His Leu
65                  70                  75                  80
```

```
gag ggc gag ctc cag agg acg acc gga aat tca atc cat caa gca caa      288
Glu Gly Glu Leu Gln Arg Thr Thr Gly Asn Ser Ile His Gln Ala Gln
                85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag      432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac      480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt agc cat gcc      672
Gly Gln Tyr Met Arg Cys Lys Thr Gly Met Gln Ser Leu Ser His Ala
    210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa      864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc tgt ggc ccc atc tca ttt gcc aga gat acc agc atc gaa     1008
Gln Ser Ser Cys Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400
```

```
gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
            405                 410                 415 tcg gcg ctc aga acg ccg ttc aag tgt gtt cat ttc gtc gga acg gag    1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
            435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala *
        450                 455                 460

<210> SEQ ID NO 107
<211> LENGTH: 463
<212> TYPE: PRT
<213> ORGANISM: Artificial Sequence
<220> FEATURE:
<223> OTHER INFORMATION: Translation of Synthetic Construct Clone 7E9

<400> SEQUENCE: 107

Lys Asp Asn Val Ala Asp Val Val Val Gly Ala Gly Leu Ser Gly
 1               5                  10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Val Ser Leu Pro Thr Thr
            260                 265                 270

Leu Tyr Pro Thr Leu Thr Phe Ser Pro Pro Leu Pro Ala Glu Lys Gln
```

-continued

```
                275                 280                 285
Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
                340                 345                 350

Arg Lys Trp Ser Gln Gln Ser Lys Gln Val Arg Gln Lys Ser Val Trp
                355                 360                 365

Asp Gln Leu Arg Ala Ala Tyr Glu Asn Ala Gly Ala Gln Val Pro Glu
                370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
                420                 425                 430

Thr Ser Leu Val Trp Lys Gly Tyr Met Glu Gly Ala Ile Arg Ser Gly
                435                 440                 445

Gln Arg Gly Ala Ala Glu Val Val Ala Ser Leu Val Pro Ala Ala
                450                 455                 460

<210> SEQ ID NO 108
<211> LENGTH: 1392
<212> TYPE: DNA
<213> ORGANISM: Artificial Sequence
<220> FEATURE:
<223> OTHER INFORMATION: Synthetic Construct Clone 9A2
<220> FEATURE:
<221> NAME/KEY: CDS
<222> LOCATION: (1)...(1392)

<400> SEQUENCE: 108 aaa gac aat gtt gcg gac gtg gta gtg gtg ggc gct ggc ttg agc ggt       48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt       96
Leu Glu Thr Ala Arg Lys Val Gln Ala Ala Gly Leu Ser Cys Leu Val
                20                  25                  30 ctt gag gcg atg gat cgt gta ggg gga aag act ctg agc gta caa tcg      144
Leu Glu Ala Met Asp Arg Val Gly Gly Lys Thr Leu Ser Val Gln Ser
            35                  40                  45 ggt ccc ggc agg acg act atc gac gac ctc ggc gct gcg tgg atc aat      192
Gly Pro Gly Arg Thr Thr Ile Asp Asp Leu Gly Ala Ala Trp Ile Asn
        50                  55                  60 gac agc aac caa agc gaa gta ttc aaa tta ttt gaa aga ttt cat ttg      240
Asp Ser Asn Gln Ser Glu Val Phe Lys Leu Phe Glu Arg Phe His Leu
65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
                100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
            115                 120                 125
```

-continued

| | |
|---|---|
| atc gaa gag cat agt ctt gaa gat ccc aag gcg agc cct cag gcg aag<br>Ile Glu Glu His Ser Leu Glu Asp Pro Lys Ala Ser Pro Gln Ala Lys<br>130                        135                         140 | 432 |
| cag ctc gac agt gtg agc ttc gca cac tac tgt gag aag gac cta aac<br>Gln Leu Asp Ser Val Ser Phe Ala His Tyr Cys Glu Lys Asp Leu Asn<br>145                       150                       155                  160 | 480 |
| ttg cct gct gtt ctc ggc gtg gca aac cag atc aca cgc gct ctg ctc<br>Leu Pro Ala Val Leu Gly Val Ala Asn Gln Ile Thr Arg Ala Leu Leu<br>                 165                       170                       175 | 528 |
| ggt gtg gaa gcc cac gag gtc agc atg ctt ttt ctc acc gac tac atc<br>Gly Val Glu Ala His Glu Val Ser Met Leu Phe Leu Thr Asp Tyr Ile<br>                      180                       185                  190 | 576 |
| aag agt gcc acc ggt ctc agt aat att ttc tcg gag aag aaa gac ggt<br>Lys Ser Ala Thr Gly Leu Ser Asn Ile Phe Ser Glu Lys Lys Asp Gly<br>        195                       200                       205 | 624 |
| ggg cag tat atg cga tgc aaa aca ggt atg cag tcg ctt agc cat gcc<br>Gly Gln Tyr Met Arg Cys Lys Thr Gly Met Gln Ser Leu Ser His Ala<br>210                        215                        220 | 672 |
| atg tca aag gaa ctt gtt cca ggc tca gtg cgc ctc aac acc ccc gtc<br>Met Ser Lys Glu Leu Val Pro Gly Ser Val Arg Leu Asn Thr Pro Val<br>225                        230                       235                  240 | 720 |
| gct gaa att gag cag tcg gcg tcc ggc tgt aca gta cga tcg gcc tcg<br>Ala Glu Ile Glu Gln Ser Ala Ser Gly Cys Thr Val Arg Ser Ala Ser<br>                         245                       250                     255 | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>        260                       265                       270 | 816 |
| ttg tat ccc acc ttg aca ttt tca cca cct ctt ccc gcc gag aag caa<br>Leu Tyr Pro Thr Leu Thr Phe Ser Pro Pro Leu Pro Ala Glu Lys Gln<br>               275                       280                       285 | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>290                        295                        300 | 912 |
| gta tgg gac aag ccg tgg tgg cgc gaa caa ggc ttc tcg ggc gtc ctc<br>Val Trp Asp Lys Pro Trp Trp Arg Glu Gln Gly Phe Ser Gly Val Leu<br>305                        310                       315                  320 | 960 |
| caa tcg agc ggt ggc ccc atc tca ttt gcc aga gat acc agc atc gaa<br>Gln Ser Ser Gly Gly Pro Ile Ser Phe Ala Arg Asp Thr Ser Ile Glu<br>                         325                       330                     335 | 1008 |
| gcc gat cgg caa tgg tcc att acc tgt ttc atg gtc gga gac ccg gga<br>Ala Asp Arg Gln Trp Ser Ile Thr Cys Phe Met Val Gly Asp Pro Gly<br>                      340                       345                     350 | 1056 |
| cgg aag tgg tcc caa cag tcc aag cag gta cga caa aag tct gtc tgg<br>Arg Lys Trp Ser Gln Gln Ser Lys Gln Val Arg Gln Lys Ser Val Trp<br>        355                       360                       365 | 1104 |
| gac caa ctc cgc gca gcc tac gag agc gct ggg gcc caa gtc cca gag<br>Asp Gln Leu Arg Ala Ala Tyr Glu Ser Ala Gly Ala Gln Val Pro Glu<br>370                        375                        380 | 1152 |
| ccg gcc aac gtg ctc gaa atc gag tgg tcg aag cag cag tat ttc caa<br>Pro Ala Asn Val Leu Glu Ile Glu Trp Ser Lys Gln Gln Tyr Phe Gln<br>385                        390                       395                  400 | 1200 |
| gga gct ccg agc gcc gtc tat ggg ctg aac gat ctc atc aca ctg ggt<br>Gly Ala Pro Ser Ala Val Tyr Gly Leu Asn Asp Leu Ile Thr Leu Gly<br>                      405                       410                   415 | 1248 |
| tcg gcg ctc aga acg ccg ttc aag tgt gtt cat ttc gtc gga acg gag<br>Ser Ala Leu Arg Thr Pro Phe Lys Cys Val His Phe Val Gly Thr Glu<br>                  420                       425                     430 | 1296 |
| acg tct tta gtt tgg aaa ggg tat atg gaa ggg gcc ata cga tcg ggt<br>Thr Ser Leu Val Trp Lys Gly Tyr Met Glu Gly Ala Ile Arg Ser Gly | 1344 |

```
                   435                 440                 445
caa cga ggt gct gca gaa gtt gtg gct agc ctg gtg cca gca gca tag    1392
Gln Arg Gly Ala Ala Glu Val Val Ala Ser Leu Val Pro Ala Ala  *
    450                 455                 460
```

<210> SEQ ID NO 109
<211> LENGTH: 463
<212> TYPE: PRT
<213> ORGANISM: Artificial Sequence
<220> FEATURE:
<223> OTHER INFORMATION: Translation of Synthetic Construct Clone 9A2

<400> SEQUENCE: 109

```
Lys Asp Asn Val Ala Asp Val Val Val Gly Ala Gly Leu Ser Gly
  1               5                  10                  15

Leu Glu Thr Ala Arg Lys Val Gln Ala Ala Gly Leu Ser Cys Leu Val
                 20                  25                  30

Leu Glu Ala Met Asp Arg Val Gly Gly Lys Thr Leu Ser Val Gln Ser
                 35                  40                  45

Gly Pro Gly Arg Thr Thr Ile Asp Asp Leu Gly Ala Ala Trp Ile Asn
 50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
                100                 105                 110

Glu Val Ala Ser Ala Leu Ala Glu Leu Leu Pro Ala Trp Ser Gln Leu
                115                 120                 125

Ile Glu Glu His Ser Leu Glu Asp Pro Lys Ala Ser Pro Gln Ala Lys
                130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
                180                 185                 190

Lys Ser Ala Thr Gly Leu Ser Asn Ile Phe Ser Glu Lys Lys Asp Gly
                195                 200                 205

Gly Gln Tyr Met Arg Cys Lys Thr Gly Met Gln Ser Leu Ser His Ala
                210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
                260                 265                 270

Leu Tyr Pro Thr Leu Thr Phe Ser Pro Pro Leu Pro Ala Glu Lys Gln
                275                 280                 285

Ala Leu Ala Glu Asn Ser Ile Leu Gly Tyr Tyr Ser Lys Ile Val Phe
                290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335
```

```
Ala Asp Arg Gln Trp Ser Ile Thr Cys Phe Met Val Gly Asp Pro Gly
            340                 345                 350

Arg Lys Trp Ser Gln Ser Lys Gln Val Arg Gln Lys Ser Val Trp
        355                 360                 365

Asp Gln Leu Arg Ala Ala Tyr Glu Ser Ala Gly Ala Gln Val Pro Glu
            370                 375                 380

Pro Ala Asn Val Leu Glu Ile Glu Trp Ser Lys Gln Tyr Phe Gln
385                 390                 395                 400

Gly Ala Pro Ser Ala Val Tyr Gly Leu Asn Asp Leu Ile Thr Leu Gly
            405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
            435                 440                 445

Gln Arg Gly Ala Ala Glu Val Val Ala Ser Leu Val Pro Ala Ala
        450                 455                 460

<210> SEQ ID NO 110
<211> LENGTH: 1392
<212> TYPE: DNA
<213> ORGANISM: Artificial Sequence
<220> FEATURE:
<223> OTHER INFORMATION: Synthetic Construct Clone 9B10
<220> FEATURE:
<221> NAME/KEY: CDS
<222> LOCATION: (1)...(1392)

<400> SEQUENCE: 110 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
                 20                  25                  30 ctt gag gcg atg gat cgt gta ggg gga aag act ctg agc gta caa tcg     144
Leu Glu Ala Met Asp Arg Val Gly Gly Lys Thr Leu Ser Val Gln Ser
             35                  40                  45 ggt ccc ggc agg acg act atc gac gac ctc ggc gct gcg tgg atc aat     192
Gly Pro Gly Arg Thr Thr Ile Asp Asp Leu Gly Ala Ala Trp Ile Asn
         50                  55                  60 gac agc aac caa agc gaa gta ttc aaa tta ttt gaa aga ttt cat ttg     240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa     288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag     336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg     384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag     432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac     480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc     528
Leu Pro Ala Val Leu Gly Val Ala Asn Gln Ile Thr Arg Ala Leu Leu
```

-continued

```
                165                 170                 175
ggt gtg gaa gcc cac gag gtc agc atg ctt ttt ctc acc gac tac atc      576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt agc cat gcc      672
Gly Gln Tyr Met Arg Cys Lys Thr Gly Met Gln Ser Leu Ser His Ala
    210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa      864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc tgt ggc ccc atc tca ttt gcc aga gat acc agc atc gaa     1008
Gln Ser Ser Cys Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag     1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala  *
    450                 455                 460
```

<210> SEQ ID NO 111
<211> LENGTH: 463
<212> TYPE: PRT
<213> ORGANISM: Artificial Sequence -continued

```
<220> FEATURE:
<223> OTHER INFORMATION: Translation of Synthetic Construct Clone 9B10

<400> SEQUENCE: 111

Lys Asp Asn Val Ala Asp Val Val Val Gly Ala Gly Leu Ser Gly
  1               5                  10                  15

Leu Glu Thr Ala Arg Lys Val Gln Ala Ala Gly Leu Ser Cys Leu Val
             20                  25                  30

Leu Glu Ala Met Asp Arg Val Gly Gly Lys Thr Leu Ser Val Gln Ser
         35                  40                  45

Gly Pro Gly Arg Thr Thr Ile Asp Asp Leu Gly Ala Ala Trp Ile Asn
     50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400
```

```
Gly Ala Pro Ser Ala Val Tyr Gly Leu Asn Asp Leu Ile Thr Leu Gly
            405                 410                 415

Ser Ala Leu Arg Thr Pro Phe Lys Cys Val His Phe Val Gly Thr Glu
        420                 425                 430

Thr Ser Leu Val Trp Lys Gly Tyr Met Glu Gly Ala Ile Arg Ser Gly
    435                 440                 445

Gln Arg Gly Ala Ala Glu Val Val Ala Ser Leu Val Pro Ala Ala
450                 455                 460

<210> SEQ ID NO 112
<211> LENGTH: 1392
<212> TYPE: DNA
<213> ORGANISM: Artificial Sequence
<220> FEATURE:
<223> OTHER INFORMATION: Synthetic Construct Clone 9B8
<220> FEATURE:
<221> NAME/KEY: CDS
<222> LOCATION: (1)...(1392)

<400> SEQUENCE: 112
```

| | | |
|---|---|---|
| aaa gac aat gtt gcg gac gtg gta gtg gtg ggc gct ggc ttg agc ggt<br>Lys Asp Asn Val Ala Asp Val Val Val Val Gly Ala Gly Leu Ser Gly<br>1               5                   10                  15 | | 48 |
| ttg gag acg gca cgc aaa gtc cag gcc gcc ggt ctg tcc tgc ctc gtt<br>Leu Glu Thr Ala Arg Lys Val Gln Ala Ala Gly Leu Ser Cys Leu Val<br>            20                  25                  30 | | 96 |
| ctt gag gcg atg gat cgt gta ggg gga aag act ctg agc gta caa tcg<br>Leu Glu Ala Met Asp Arg Val Gly Gly Lys Thr Leu Ser Val Gln Ser<br>        35                  40                  45 | | 144 |
| ggt ccc ggc agg acg act atc gac gac ctc ggc gct gcg tgg atc aat<br>Gly Pro Gly Arg Thr Thr Ile Asp Asp Leu Gly Ala Ala Trp Ile Asn<br>    50                  55                  60 | | 192 |
| gac agc aac caa agc gaa gta ttc aaa tta ttt gaa aga ttt cat ttg<br>Asp Ser Asn Gln Ser Glu Val Phe Lys Leu Phe Glu Arg Phe His Leu<br>65                  70                  75                  80 | | 240 |
| gag ggc gag ctc cag agg acg acc gga aat tca atc cat caa gca caa<br>Glu Gly Glu Leu Gln Arg Thr Thr Gly Asn Ser Ile His Gln Ala Gln<br>                85                  90                  95 | | 288 |
| gac ggt aca atc act aca gct cct tat ggt gac tcc ttg ctg agc gag<br>Asp Gly Thr Ile Thr Thr Ala Pro Tyr Gly Asp Ser Leu Leu Ser Glu<br>            100                 105                 110 | | 336 |
| gag gtt gca agt gca ctc gcg gaa ctc ctt ccc gca tgg tct cag ctg<br>Glu Val Ala Ser Ala Leu Ala Glu Leu Leu Pro Ala Trp Ser Gln Leu<br>        115                 120                 125 | | 384 |
| atc gaa gag cat agt ctt gaa gac ccc aag gcg agc cct cag gcg aag<br>Ile Glu Glu His Ser Leu Glu Asp Pro Lys Ala Ser Pro Gln Ala Lys<br>    130                 135                 140 | | 432 |
| cag ctc gac agt gtg agc ttc gca cac tac tgt gag aag gac cta aac<br>Gln Leu Asp Ser Val Ser Phe Ala His Tyr Cys Glu Lys Asp Leu Asn<br>145                 150                 155                 160 | | 480 |
| ttg cct gct gtt ctc ggc gtg gca aac cag atc aca cgc gct ctg ctc<br>Leu Pro Ala Val Leu Gly Val Ala Asn Gln Ile Thr Arg Ala Leu Leu<br>                165                 170                 175 | | 528 |
| ggt gtg gaa gcc cac gag gtc agc atg ctt ttt ctc acc gac tac atc<br>Gly Val Glu Ala His Glu Val Ser Met Leu Phe Leu Thr Asp Tyr Ile<br>            180                 185                 190 | | 576 |
| aag agt gcc acc ggt ctc agt aat att ttc tcg gag aag aaa gac ggt<br>Lys Ser Ala Thr Gly Leu Ser Asn Ile Phe Ser Glu Lys Lys Asp Gly<br>        195                 200                 205 | | 624 |
| ggg cag tat atg cga tgc aaa aca ggt atg cag tcg ctt agc cat gcc | | 672 |

```
Gly Gln Tyr Met Arg Cys Lys Thr Gly Met Gln Ser Leu Ser His Ala
        210                 215                 220 atg tca aag gaa ctt gtt cca ggc tca gtg cgc ctc aac acc ccc gtc       720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg       768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc       816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa       864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc       912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc       960
Val Trp Asp Lys Pro Trp Trp Arg Glu Gln Gly Phe Ser Gly Val Leu
305                 310                 315                 320 caa tcg agc tgt ggc ccc atc tca ttt gcc aga gat acc agc atc gaa      1008
Gln Ser Ser Cys Gly Pro Ile Ser Phe Ala Arg Asp Thr Ser Ile Glu
                325                 330                 335 gcc gat cgg caa tgg tcc att acc tgt ttc atg gtc gga gac ccg gga      1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg      1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag      1152
Asp Gln Leu Arg Ala Ala Tyr Glu Asn Ala Gly Ala Gln Val Pro Glu
370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt      1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala  *
450                 455                 460

<210> SEQ ID NO 113
<211> LENGTH: 463
<212> TYPE: PRT
<213> ORGANISM: Artificial Sequence
<220> FEATURE:
<223> OTHER INFORMATION: Translation of Synthetic Construct Clone 9B8

<400> SEQUENCE: 113

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30
```

-continued

```
Leu Glu Ala Met Asp Arg Val Gly Gly Lys Thr Leu Ser Val Gln Ser
            35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Ser His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Cys Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
```

<210> SEQ ID NO 114
<211> LENGTH: 1392
<212> TYPE: DNA
<213> ORGANISM: Artificial Sequence
<220> FEATURE:
<223> OTHER INFORMATION: Synthetic Construct Clone 9C5
<220> FEATURE:
<221> NAME/KEY: CDS
<222> LOCATION: (1)...(1392)

<400> SEQUENCE: 114

| | | | | | | | | | | | | | | | | |
|---|---|---|---|---|---|---|---|---|---|---|---|---|---|---|---|---|
| aaa | gac | aat | gtt | gcg | gac | gtg | gta | gtg | gtg | ggc | gct | ggc | ttg | agc | ggt | 48 |
| Lys | Asp | Asn | Val | Ala | Asp | Val | Val | Val | Val | Gly | Ala | Gly | Leu | Ser | Gly | |
| 1 | | | | 5 | | | | | 10 | | | | | 15 | | |
| ttg | gag | acg | gca | cgc | aaa | gtc | cag | gcc | gcc | ggt | ctg | tcc | tgc | ctc | gtt | 96 |
| Leu | Glu | Thr | Ala | Arg | Lys | Val | Gln | Ala | Ala | Gly | Leu | Ser | Cys | Leu | Val | |
| | | | 20 | | | | | 25 | | | | | 30 | | | |
| ctt | gag | gcg | atg | gat | cgt | gta | ggg | ggg | aag | act | ctg | agc | gta | caa | tcg | 144 |
| Leu | Glu | Ala | Met | Asp | Arg | Val | Gly | Gly | Lys | Thr | Leu | Ser | Val | Gln | Ser | |
| | | 35 | | | | | 40 | | | | | 45 | | | | |
| ggt | ccc | ggc | agg | acg | act | atc | gac | gac | ctc | ggc | gct | gcg | tgg | atc | aat | 192 |
| Gly | Pro | Gly | Arg | Thr | Thr | Ile | Asp | Asp | Leu | Gly | Ala | Ala | Trp | Ile | Asn | |
| 50 | | | | | 55 | | | | | 60 | | | | | | |
| gac | agc | aac | caa | agc | gaa | gta | ttc | aaa | tta | ttt | gaa | aga | ttt | cat | ttg | 240 |
| Asp | Ser | Asn | Gln | Ser | Glu | Val | Phe | Lys | Leu | Phe | Glu | Arg | Phe | His | Leu | |
| 65 | | | | | 70 | | | | | 75 | | | | | 80 | |
| gag | ggc | gag | ctc | cag | agg | acg | acc | gga | aat | tca | atc | cat | caa | gca | caa | 288 |
| Glu | Gly | Glu | Leu | Gln | Arg | Thr | Thr | Gly | Asn | Ser | Ile | His | Gln | Ala | Gln | |
| | | | | 85 | | | | | 90 | | | | | 95 | | |
| gac | ggt | aca | atc | act | aca | gct | cct | tat | ggt | gac | tcc | ttg | ctg | agc | gag | 336 |
| Asp | Gly | Thr | Ile | Thr | Thr | Ala | Pro | Tyr | Gly | Asp | Ser | Leu | Leu | Ser | Glu | |
| | | | 100 | | | | | 105 | | | | | 110 | | | |
| gag | gtt | gca | agt | gca | ctc | gcg | gaa | ctc | ctt | ccc | gca | tgg | tct | cag | ctg | 384 |
| Glu | Val | Ala | Ser | Ala | Leu | Ala | Glu | Leu | Leu | Pro | Ala | Trp | Ser | Gln | Leu | |
| | | 115 | | | | | 120 | | | | | 125 | | | | |
| atc | gaa | gag | cat | agt | ctt | gaa | gac | ccc | aag | gcg | agc | cct | cag | gcg | aag | 432 |
| Ile | Glu | Glu | His | Ser | Leu | Glu | Asp | Pro | Lys | Ala | Ser | Pro | Gln | Ala | Lys | |
| | 130 | | | | | 135 | | | | | 140 | | | | | |
| cag | ctc | gac | agt | gtg | agc | ttc | gca | cac | tac | tgt | gag | aag | gac | cta | aac | 480 |
| Gln | Leu | Asp | Ser | Val | Ser | Phe | Ala | His | Tyr | Cys | Glu | Lys | Asp | Leu | Asn | |
| 145 | | | | | 150 | | | | | 155 | | | | | 160 | |
| ttg | cct | gct | gtt | ctc | ggc | gtg | gca | aac | cag | atc | aca | cgc | gct | ctg | ctc | 528 |
| Leu | Pro | Ala | Val | Leu | Gly | Val | Ala | Asn | Gln | Ile | Thr | Arg | Ala | Leu | Leu | |
| | | | | 165 | | | | | 170 | | | | | 175 | | |
| ggt | gtg | gaa | gcc | cac | gag | gtc | agc | atg | ctt | ttt | ctc | acc | gac | tac | atc | 576 |
| Gly | Val | Glu | Ala | His | Glu | Val | Ser | Met | Leu | Phe | Leu | Thr | Asp | Tyr | Ile | |
| | | | 180 | | | | | 185 | | | | | 190 | | | |
| aag | agt | gcc | acc | ggt | ctc | agt | aat | att | ttc | tcg | gag | aag | aaa | gac | ggt | 624 |
| Lys | Ser | Ala | Thr | Gly | Leu | Ser | Asn | Ile | Phe | Ser | Glu | Lys | Lys | Asp | Gly | |
| | | 195 | | | | | 200 | | | | | 205 | | | | |
| ggg | cag | tat | atg | cga | tgc | aaa | aca | ggt | atg | cag | tcg | ctt | tgc | cat | gcc | 672 |
| Gly | Gln | Tyr | Met | Arg | Cys | Lys | Thr | Gly | Met | Gln | Ser | Leu | Cys | His | Ala | |
| | 210 | | | | | 215 | | | | | 220 | | | | | |
| atg | tca | aag | gaa | ctt | gtt | cca | ggc | tca | gtg | cgc | ctc | aac | acc | ccc | gtc | 720 |
| Met | Ser | Lys | Glu | Leu | Val | Pro | Gly | Ser | Val | Arg | Leu | Asn | Thr | Pro | Val | |
| 225 | | | | | 230 | | | | | 235 | | | | | 240 | |
| gct | gaa | att | gag | cag | tcg | gcg | tcc | ggc | tgt | aca | gta | cga | tcg | gcc | tcg | 768 |
| Ala | Glu | Ile | Glu | Gln | Ser | Ala | Ser | Gly | Cys | Thr | Val | Arg | Ser | Ala | Ser | |
| | | | | 245 | | | | | 250 | | | | | 255 | | |

-continued

```
ggc gcc gtg ttc cga agc aaa aag gtg gtg gtt tcg tta ccg acg acc      816
Gly Ala Val Phe Arg Ser Lys Lys Val Val Val Ser Leu Pro Thr Thr
        260                 265                 270 ttg tat ccc acc ttg aca ttt tca ccg cct ctt ccc gcc gag aag caa      864
Leu Tyr Pro Thr Leu Thr Phe Ser Pro Pro Leu Pro Ala Glu Lys Gln
    275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
                405                 410                 415 tcg gcg ctc aga acg ccg ttc agg tgt gtt cat ttc gtc gga acg gag     1296
Ser Ala Leu Arg Thr Pro Phe Arg Cys Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala  *
    450                 455                 460
```

<210> SEQ ID NO 115
<211> LENGTH: 463
<212> TYPE: PRT
<213> ORGANISM: Artificial Sequence
<220> FEATURE:
<223> OTHER INFORMATION: Translation of Synthetic Construct Clone 9C5

<400> SEQUENCE: 115

```
Lys Asp Asn Val Ala Asp Val Val Val Gly Ala Gly Leu Ser Gly
  1               5                  10                  15

Leu Glu Thr Ala Arg Lys Val Gln Ala Ala Gly Leu Ser Cys Leu Val
                 20                  25                  30

Leu Glu Ala Met Asp Arg Val Gly Gly Lys Thr Leu Ser Val Gln Ser
             35                  40                  45

Gly Pro Gly Arg Thr Thr Ile Asp Asp Leu Gly Ala Ala Trp Ile Asn
         50                  55                  60

Asp Ser Asn Gln Ser Glu Val Phe Lys Leu Phe Glu Arg Phe His Leu
 65                  70                  75                  80

Glu Gly Glu Leu Gln Arg Thr Thr Gly Asn Ser Ile His Gln Ala Gln
                 85                  90                  95
```

```
Asp Gly Thr Ile Thr Thr Ala Pro Tyr Gly Asp Ser Leu Leu Ser Glu
            100                 105                 110
Glu Val Ala Ser Ala Leu Ala Glu Leu Leu Pro Ala Trp Ser Gln Leu
        115                 120                 125
Ile Glu Glu His Ser Leu Glu Asp Pro Lys Ala Ser Pro Gln Ala Lys
    130                 135                 140
Gln Leu Asp Ser Val Ser Phe Ala His Tyr Cys Glu Lys Asp Leu Asn
145                 150                 155                 160
Leu Pro Ala Val Leu Gly Val Ala Asn Gln Ile Thr Arg Ala Leu Leu
                165                 170                 175
Gly Val Glu Ala His Glu Val Ser Met Leu Phe Leu Thr Asp Tyr Ile
            180                 185                 190
Lys Ser Ala Thr Gly Leu Ser Asn Ile Phe Ser Glu Lys Lys Asp Gly
        195                 200                 205
Gly Gln Tyr Met Arg Cys Lys Thr Gly Met Gln Ser Leu Cys His Ala
    210                 215                 220
Met Ser Lys Glu Leu Val Pro Gly Ser Val Arg Leu Asn Thr Pro Val
225                 230                 235                 240
Ala Glu Ile Glu Gln Ser Ala Ser Gly Cys Thr Val Arg Ser Ala Ser
                245                 250                 255
Gly Ala Val Phe Arg Ser Lys Lys Val Val Ser Leu Pro Thr Thr
            260                 265                 270
Leu Tyr Pro Thr Leu Thr Phe Ser Pro Pro Leu Pro Ala Glu Lys Gln
        275                 280                 285
Ala Leu Ala Glu Asn Ser Ile Leu Gly Tyr Tyr Ser Lys Ile Val Phe
    290                 295                 300
Val Trp Asp Lys Pro Trp Arg Glu Gln Gly Phe Ser Gly Val Leu
305                 310                 315                 320
Gln Ser Ser Gly Gly Pro Ile Ser Phe Ala Arg Asp Thr Ser Ile Glu
                325                 330                 335
Ala Asp Arg Gln Trp Ser Ile Thr Cys Phe Met Val Gly Asp Pro Gly
            340                 345                 350
Arg Lys Trp Ser Gln Gln Ser Lys Gln Val Arg Gln Lys Ser Val Trp
        355                 360                 365
Asp Gln Leu Arg Ala Ala Tyr Glu Asn Ala Gly Ala Gln Val Pro Glu
    370                 375                 380
Pro Ala Asn Val Leu Glu Ile Glu Trp Ser Lys Gln Gln Tyr Phe Gln
385                 390                 395                 400
Gly Ala Pro Ser Ala Val Tyr Gly Leu Asn Asp Leu Ile Thr Leu Gly
                405                 410                 415
Ser Ala Leu Arg Thr Pro Phe Arg Cys Val His Phe Val Gly Thr Glu
            420                 425                 430
Thr Ser Leu Val Trp Lys Gly Tyr Met Glu Gly Ala Ile Arg Ser Gly
        435                 440                 445
Gln Arg Gly Ala Ala Glu Val Val Ala Ser Leu Val Pro Ala Ala
    450                 455                 460

<210> SEQ ID NO 116
<211> LENGTH: 1392
<212> TYPE: DNA
<213> ORGANISM: Artificial Sequence
<220> FEATURE:
<223> OTHER INFORMATION: Synthetic Construct Clone 9C7
<220> FEATURE:
<221> NAME/KEY: CDS
```

<222> LOCATION: (1)...(1392)

<400> SEQUENCE: 116

| | | |
|---|---|---|
| aaa gac aat gtt gcg gac gtg gta gtg gtg ggc gct ggc ttg agc ggt<br>Lys Asp Asn Val Ala Asp Val Val Val Val Gly Ala Gly Leu Ser Gly<br>1                     5                      10                  15 | 48 |
| ttg gag acg gca cgc aaa gtc cag gcc gcc ggt ctg tcc tgc ctc gtt<br>Leu Glu Thr Ala Arg Lys Val Gln Ala Ala Gly Leu Ser Cys Leu Val<br>            20                    25                    30 | 96 |
| ctt gag gcg ttg gat cgt gta ggg gga aag act ctg agc gta caa tcg<br>Leu Glu Ala Leu Asp Arg Val Gly Gly Lys Thr Leu Ser Val Gln Ser<br>      35                    40                    45 | 144 |
| ggt ccc ggc agg acg act atc gac gac ctc ggc gct gcg tgg atc aat<br>Gly Pro Gly Arg Thr Thr Ile Asp Asp Leu Gly Ala Ala Trp Ile Asn<br>50                      55                    60 | 192 |
| gac agc aac caa agc gaa gta ttc aaa tta ttt gaa aga ttt cat ttg<br>Asp Ser Asn Gln Ser Glu Val Phe Lys Leu Phe Glu Arg Phe His Leu<br>65                      70                    75                  80 | 240 |
| gag ggc gag ctc cag agg acg acc gga aat tca atc cat caa gca caa<br>Glu Gly Glu Leu Gln Arg Thr Thr Gly Asn Ser Ile His Gln Ala Gln<br>                  85                    90                    95 | 288 |
| gac ggt aca atc act aca gct cct tat ggt gac tcc ttg ctg agc gag<br>Asp Gly Thr Ile Thr Thr Ala Pro Tyr Gly Asp Ser Leu Leu Ser Glu<br>            100                    105                  110 | 336 |
| gag gtt gca agt gca ctc gcg gaa ctc ctt ccc gca tgg tct cag ctg<br>Glu Val Ala Ser Ala Leu Ala Glu Leu Leu Pro Ala Trp Ser Gln Leu<br>            115                    120                  125 | 384 |
| atc gaa gag cat agt ctt gaa gac ccc aag gcg agc cct cag gcg aag<br>Ile Glu Glu His Ser Leu Glu Asp Pro Lys Ala Ser Pro Gln Ala Lys<br>130                      135                    140 | 432 |
| cag ctc gac agt gtg agc ttc gca cac tac tgt gag aag gac cta aac<br>Gln Leu Asp Ser Val Ser Phe Ala His Tyr Cys Glu Lys Asp Leu Asn<br>145                      150                    155                  160 | 480 |
| ttg cct gct gtt ctc ggc gtg gca aac cag atc aca cgc gct ctg ctc<br>Leu Pro Ala Val Leu Gly Val Ala Asn Gln Ile Thr Arg Ala Leu Leu<br>            165                    170                  175 | 528 |
| ggt gtg gaa gcc cac gag gtc agc atg ctt ttt ctc acc gac tac atc<br>Gly Val Glu Ala His Glu Val Ser Met Leu Phe Leu Thr Asp Tyr Ile<br>            180                    185                  190 | 576 |
| aag agt gcc acc ggt ctc agt aat att ttc tcg gag aag aaa gac ggt<br>Lys Ser Ala Thr Gly Leu Ser Asn Ile Phe Ser Glu Lys Lys Asp Gly<br>            195                    200                  205 | 624 |
| ggg cag tat atg cga tgc aaa aca ggt atg cag tcg ctt tgc cat gcc<br>Gly Gln Tyr Met Arg Cys Lys Thr Gly Met Gln Ser Leu Cys His Ala<br>210                      215                    220 | 672 |
| atg tca aag gaa ctt gtt cca ggc tca gtg cgc ctc aac acc ccc gtc<br>Met Ser Lys Glu Leu Val Pro Gly Ser Val Arg Leu Asn Thr Pro Val<br>225                      230                    235                  240 | 720 |
| gct gaa att gag cag tcg gcg tcc ggc tgt aca gta cga tcg gcc tcg<br>Ala Glu Ile Glu Gln Ser Ala Ser Gly Cys Thr Val Arg Ser Ala Ser<br>                  245                    250                  255 | 768 |
| ggc gcc gtg ttc cga agc aaa aag gtg gtg gtt tcg tta ccg aca acc<br>Gly Ala Val Phe Arg Ser Lys Lys Val Val Val Ser Leu Pro Thr Thr<br>            260                    265                  270 | 816 |
| ttg tat ccc act ttg aca ttt tca cca cct ctt ccc gcc gag aag caa<br>Leu Tyr Pro Thr Leu Thr Phe Ser Pro Pro Leu Pro Ala Glu Lys Gln<br>            275                    280                  285 | 864 |
| gca ttg gcg gaa aat tct atc ctg ggc tac tat agc aag ata gtc ttc<br>Ala Leu Ala Glu Asn Ser Ile Leu Gly Tyr Tyr Ser Lys Ile Val Phe<br>290                      295                    300 | 912 |

```
gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
            340                 345                 350 cgg aag tgg tcc caa cag tcc aag cag gta cga caa aag tcc gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag     1296
Ser Ala Leu Arg Thr Pro Phe Lys Cys Val His Phe Val Gly Thr Glu
            420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala  *
450                 455                 460
```

<210> SEQ ID NO 117
<211> LENGTH: 463
<212> TYPE: PRT
<213> ORGANISM: Artificial Sequence
<220> FEATURE:
<223> OTHER INFORMATION: Translation of Synthetic Construct Clone 9C7

<400> SEQUENCE: 117

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
                20                  25                  30

Leu Glu Ala Leu Asp Arg Val Gly Gly Lys Thr Leu Ser Val Gln Ser
            35                  40                  45

Gly Pro Gly Arg Thr Thr Ile Asp Asp Leu Gly Ala Ala Trp Ile Asn
        50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
```

```
                145                 150                 155                 160
Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
            195                 200                 205

Gly Gln Tyr Met Arg Cys Lys Thr Gly Met Gln Ser Leu Cys His Ala
        210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Val Val Ser Leu Pro Thr Thr
                260                 265                 270

Leu Tyr Pro Thr Leu Thr Phe Ser Pro Pro Leu Pro Ala Glu Lys Gln
            275                 280                 285

Ala Leu Ala Glu Asn Ser Ile Leu Gly Tyr Tyr Ser Lys Ile Val Phe
        290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 118
<211> LENGTH: 1392
<212> TYPE: DNA
<213> ORGANISM: Artificial Sequence
<220> FEATURE:
<223> OTHER INFORMATION: Synthetic Construct Clone 9D3
<220> FEATURE:
<221> NAME/KEY: CDS
<222> LOCATION: (1)...(1392)

<400> SEQUENCE: 118 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
 1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
            20                  25                  30
```

```
ctt gag gcg atg gat cgt gta ggg gga aag act ctg agc gta caa tcg      144
Leu Glu Ala Met Asp Arg Val Gly Gly Lys Thr Leu Ser Val Gln Ser
         35                  40                  45 ggt ccc ggc agg acg act atc gac gac ctc ggc gct gcg tgg atc aat      192
Gly Pro Gly Arg Thr Thr Ile Asp Asp Leu Gly Ala Ala Trp Ile Asn
 50                  55                  60 gac agc aac caa agc gaa gta ttc aaa tta ttt gaa aga ttt cat ttg      240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
            115                 120                 125 atc gaa gag cat agt ctt gaa gac ccc aag gcg agc cct cag gcg aag      432
Ile Glu Glu His Ser Leu Glu Asp Pro Lys Ala Ser Pro Gln Ala Lys
130                 135                 140 cag ctc gac agt gtg agc ttc gca cac tac tgt gag aag gac cta aac      480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
            195                 200                 205 ggg cag tat atg cga tgc aaa aca ggt atg cag tcg ctt tgc cat gcc      672
Gly Gln Tyr Met Arg Cys Lys Thr Gly Met Gln Ser Leu Cys His Ala
            210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa      864
Leu Tyr Pro Thr Leu Thr Phe Ser Pro Pro Leu Pro Ala Glu Lys Gln
            275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
            290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc tgt ggc ccc atc tca ttt gcc aga gat acc agc atc gaa     1008
Gln Ser Ser Cys Gly Pro Ile Ser Phe Ala Arg Asp Thr Ser Ile Glu
                325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
```

```
                      340                 345                 350
cgg aag tgg tcc caa cag tcc aag cag gta cga caa aag tct gtc tgg      1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag      1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa      1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc gtc aca ctg ggt      1248
Gly Ala Pro Ser Ala Val Tyr Gly Leu Asn Asp Leu Val Thr Leu Gly
            405                 410                 415 tcg gcg ctc aga acg ccg ttc aag tgt gtt cat ttc gtc gga acg gag      1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt      1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag      1392
Gln Arg Gly Ala Ala Glu Val Val Ala Ser Leu Val Pro Ala Ala  *
450                 455                 460

<210> SEQ ID NO 119
<211> LENGTH: 463
<212> TYPE: PRT
<213> ORGANISM: Artificial Sequence
<220> FEATURE:
<223> OTHER INFORMATION: Translation of Synthetic Construct Clone 9D3

<400> SEQUENCE: 119

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
            85                  90                  95

Asp Gly Thr Ile Thr Thr Ala Pro Tyr Gly Asp Ser Leu Leu Ser Glu
        100                 105                 110

Glu Val Ala Ser Ala Leu Ala Glu Leu Leu Pro Ala Trp Ser Gln Leu
    115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
            165                 170                 175

Gly Val Glu Ala His Glu Val Ser Met Leu Phe Leu Thr Asp Tyr Ile
        180                 185                 190

Lys Ser Ala Thr Gly Leu Ser Asn Ile Phe Ser Glu Lys Lys Asp Gly
    195                 200                 205
```

```
Gly Gln Tyr Met Arg Cys Lys Thr Gly Met Gln Ser Leu Cys His Ala
    210                 215                 220
Met Ser Lys Glu Leu Val Pro Gly Ser Val Arg Leu Asn Thr Pro Val
225                 230                 235                 240
Ala Glu Ile Glu Gln Ser Ala Ser Gly Cys Thr Val Arg Ser Ala Ser
            245                 250                 255
Gly Ala Val Phe Arg Ser Lys Lys Val Val Ser Leu Pro Thr Thr
        260                 265                 270
Leu Tyr Pro Thr Leu Thr Phe Ser Pro Pro Leu Pro Ala Glu Lys Gln
            275                 280                 285
Ala Leu Ala Glu Asn Ser Ile Leu Gly Tyr Tyr Ser Lys Ile Val Phe
        290                 295                 300
Val Trp Asp Lys Pro Trp Trp Arg Glu Gln Gly Phe Ser Gly Val Leu
305                 310                 315                 320
Gln Ser Ser Cys Gly Pro Ile Ser Phe Ala Arg Asp Thr Ser Ile Glu
            325                 330                 335
Ala Asp Arg Gln Trp Ser Ile Thr Cys Phe Met Val Gly Asp Pro Gly
            340                 345                 350
Arg Lys Trp Ser Gln Gln Ser Lys Gln Val Arg Gln Lys Ser Val Trp
        355                 360                 365
Asp Gln Leu Arg Ala Ala Tyr Glu Asn Ala Gly Ala Gln Val Pro Glu
    370                 375                 380
Pro Ala Asn Val Leu Glu Ile Glu Trp Ser Lys Gln Gln Tyr Phe Gln
385                 390                 395                 400
Gly Ala Pro Ser Ala Val Tyr Gly Leu Asn Asp Leu Val Thr Leu Gly
            405                 410                 415
Ser Ala Leu Arg Thr Pro Phe Lys Cys Val His Phe Val Gly Thr Glu
        420                 425                 430
Thr Ser Leu Val Trp Lys Gly Tyr Met Glu Gly Ala Ile Arg Ser Gly
        435                 440                 445
Gln Arg Gly Ala Ala Glu Val Val Ala Ser Leu Val Pro Ala Ala
    450                 455                 460

<210> SEQ ID NO 120
<211> LENGTH: 1392
<212> TYPE: DNA
<213> ORGANISM: Artificial Sequence
<220> FEATURE:
<223> OTHER INFORMATION: Synthetic Construct Clone 9D9
<220> FEATURE:
<221> NAME/KEY: CDS
<222> LOCATION: (1)...(1392)

<400> SEQUENCE: 120 aaa gac aat gtt gcg gac gtg gtg gtg gtg ggc gct ggc ttg agc ggt      48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt     96
Leu Glu Thr Ala Arg Lys Val Gln Ala Ala Gly Leu Ser Cys Leu Val
            20                  25                  30 ctt gag gcg atg gat cgt gta ggg gga aag act ctg agc gta caa tcg    144
Leu Glu Ala Met Asp Arg Val Gly Gly Lys Thr Leu Ser Val Gln Ser
        35                  40                  45 ggt ccc ggc agg acg act atc gac gac ctc ggc gct gcg tgg atc aat    192
Gly Pro Gly Arg Thr Thr Ile Asp Asp Leu Gly Ala Ala Trp Ile Asn
    50                  55                  60 gac agc aac caa agc gaa gta ttc aaa tta ttt gaa aga ttt cat ttg    240
Asp Ser Asn Gln Ser Glu Val Phe Lys Leu Phe Glu Arg Phe His Leu
```

-continued

```
       65                  70                  75                  80 gag ggc gag ctc cag agg acg acc gga aat tca atc cat caa gca caa      288
Glu Gly Glu Leu Gln Arg Thr Thr Gly Asn Ser Ile His Gln Ala Gln
                     85                  90                  95 gac ggt aca atc act aca gct cct tat ggt gac tcc ttg ctg agc gag      336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg      384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag      432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac      480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
                    165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
                180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
            195                 200                 205 ggg cag tat atg cga tgc aaa aca ggt atg cag tcg ctt tgc cat gcc      672
Gly Gln Tyr Met Arg Cys Lys Thr Gly Met Gln Ser Leu Cys His Ala
        210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                    245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
                260                 265                 270 ttg tat ccc acc ttg aca ttt tca ccg cct ctt ccc gcc gag aag caa      864
Leu Tyr Pro Thr Leu Thr Phe Ser Pro Pro Leu Pro Ala Glu Lys Gln
            275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
        290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                    325                 330                 335 gcc gat cgg caa tgg tcc att acc tgt ttc atg gtc gga gac ccg gga     1056
Ala Asp Arg Gln Trp Ser Ile Thr Cys Phe Met Val Gly Asp Pro Gly
                340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
            355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
        370                 375                 380 ccg gcc aac gtg ctc gaa atc gag tgg tcg aag cag cag tat ttc caa     1200
```

```
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt        1248
Gly Ala Pro Ser Ala Val Tyr Gly Leu Asn Asp Leu Ile Thr Leu Gly
            405                 410                 415 tcg gcg ctc aga acg ccg ttc aag tgt gtt cat ttc gtc gga acg gag        1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt        1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag        1392
Gln Arg Gly Ala Ala Glu Val Val Ala Ser Leu Val Pro Ala Ala  *
450                 455                 460

<210> SEQ ID NO 121
<211> LENGTH: 463
<212> TYPE: PRT
<213> ORGANISM: Artificial Sequence
<220> FEATURE:
<223> OTHER INFORMATION: Translation of Synthetic Construct Clone 9D9

<400> SEQUENCE: 121

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Met Asp Arg Val Gly Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
    130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Ser Leu Pro Thr Thr
            260                 265                 270
```

```
Leu Tyr Pro Thr Leu Thr Phe Ser Pro Pro Leu Pro Ala Glu Lys Gln
            275                 280                 285

Ala Leu Ala Glu Asn Ser Ile Leu Gly Tyr Tyr Ser Lys Ile Val Phe
        290                 295                 300

Val Trp Asp Lys Pro Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
                325                 330                 335

Ala Asp Arg Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Asn Ala Gly Ala Gln Val Pro Glu
    370                 375                 380

Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 122
<211> LENGTH: 1392
<212> TYPE: DNA
<213> ORGANISM: Artificial Sequence
<220> FEATURE:
<223> OTHER INFORMATION: Synthetic Construct Clone 9F2
<220> FEATURE:
<221> NAME/KEY: CDS
<222> LOCATION: (1)...(1392)

<400> SEQUENCE: 122 aaa gac aat gtt gcg gac gtg gta gtg gtg ggc gct ggc ttg agc ggt      48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt      96
Leu Glu Thr Ala Arg Lys Val Gln Ala Ala Gly Leu Ser Cys Leu Val
             20                  25                  30 ctt gag gcg ttg gat cgt gta ggg gga aag act ctg agc gta caa tcg     144
Leu Glu Ala Leu Asp Arg Val Gly Gly Lys Thr Leu Ser Val Gln Ser
         35                  40                  45 ggt ccc ggc agg acg act atc gac gac ctc ggc gct gcg tgg atc aat     192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg     240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa     288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag     336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg     384
Glu Val Ala Ser Ala Leu Ala Glu Leu Leu Pro Ala Trp Ser Gln Leu
```

```
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag    432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac    480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc    528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc    576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt    624
Lys Ser Ala Thr Gly Leu Ser Asn Ile Phe Ser Glu Lys Lys Asp Gly
        195                 200                 205 ggg cag tat atg cga tgc aaa aca ggt atg cag tcg ctt tgc cat gcc    672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc    720
Met Ser Lys Glu Leu Val Pro Gly Ser Val Arg Leu Asn Thr Pro Val
225                 230                 235                 240 gct gaa att gag cag tcg gcg tct ggc tgt aca gta cga tcg gcc tcg    768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc    816
Gly Ala Val Phe Arg Ser Lys Lys Val Val Val Ser Leu Pro Thr Thr
            260                 265                 270 ttg tat ccc acc ttg aca ttt tca ccg cct ctt ccc gcc gag aag caa    864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc    912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc    960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa    1008
Gln Ser Ser Gly Gly Pro Ile Ser Phe Ala Arg Asp Thr Ser Ile Glu
                325                 330                 335 gcc gat cag caa tgg tcc att acc tgt ttc atg gtc gga gac ccg gga    1056
Ala Asp Gln Gln Trp Ser Ile Thr Cys Phe Met Val Gly Asp Pro Gly
            340                 345                 350 cgg aag tgg tcc caa cag tcc aag cag gta cga caa aag tct gtc tgg    1104
Arg Lys Trp Ser Gln Gln Ser Lys Gln Val Arg Gln Lys Ser Val Trp
        355                 360                 365 gac caa ctc cgc gca gcc tac gag agc gct ggg gcc caa gtc cca gag    1152
Asp Gln Leu Arg Ala Ala Tyr Glu Ser Ala Gly Ala Gln Val Pro Glu
    370                 375                 380 ccg gcc aac gtg ctc gaa atc gag tgg tcg aag cag cag tat ttc cca    1200
Pro Ala Asn Val Leu Glu Ile Glu Trp Ser Lys Gln Gln Tyr Phe Pro
385                 390                 395                 400 gga gct ccg agc gcc gtc tat ggg ctg aac gat ctc atc aca ctg ggt    1248
Gly Ala Pro Ser Ala Val Tyr Gly Leu Asn Asp Leu Ile Thr Leu Gly
                405                 410                 415 tcg gcg ctc aga acg ccg ttc aag tgt gtt cat ttc gtc gga acg gag    1296
Ser Ala Leu Arg Thr Pro Phe Lys Cys Val His Phe Val Gly Thr Glu
            420                 425                 430
```

```
acg tct tta gtt tgg aaa ggg tat atg gaa ggg gcc ata cga tcg ggt    1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag    1392
Gln Arg Gly Ala Ala Glu Val Val Ala Ser Leu Val Pro Ala Ala *
    450                 455                 460
```

<210> SEQ ID NO 123
<211> LENGTH: 463
<212> TYPE: PRT
<213> ORGANISM: Artificial Sequence
<220> FEATURE:
<223> OTHER INFORMATION: Translation of Synthetic Construct Clone 9F2

<400> SEQUENCE: 123

```
Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Leu Asp Arg Val Gly Lys Thr Leu Ser Val Gln Ser
        35                  40                  45

Gly Pro Gly Arg Thr Thr Ile Asp Asp Leu Gly Ala Ala Trp Ile Asn
    50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
                85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
        115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
                165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
        195                 200                 205

Gly Gln Tyr Met Arg Cys Lys Thr Gly Met Gln Ser Leu Cys His Ala
    210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
                245                 250                 255

Gly Ala Val Phe Arg Ser Lys Lys Val Val Val Ser Leu Pro Thr Thr
            260                 265                 270

Leu Tyr Pro Thr Leu Thr Phe Ser Pro Pro Leu Pro Ala Glu Lys Gln
        275                 280                 285

Ala Leu Ala Glu Asn Ser Ile Leu Gly Tyr Tyr Ser Lys Ile Val Phe
    290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
```

```
                    325                 330                 335
Ala Asp Gln Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
        355                 360                 365

Asp Gln Leu Arg Ala Ala Tyr Glu Ser Ala Gly Ala Gln Val Pro Glu
    370                 375                 380

Pro Ala Asn Val Leu Glu Ile Glu Trp Ser Lys Gln Gln Tyr Phe Pro
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 124
<211> LENGTH: 1392
<212> TYPE: DNA
<213> ORGANISM: Artificial Sequence
<220> FEATURE:
<223> OTHER INFORMATION: Synthetic Construct Clone 9F3
<220> FEATURE:
<221> NAME/KEY: CDS
<222> LOCATION: (1)...(1392)

<400> SEQUENCE: 124 aaa gac aat gtt gcg gac gtg gta gtg gtg ggc gct ggc ttg agc ggt     48
Lys Asp Asn Val Ala Asp Val Val Val Val Gly Ala Gly Leu Ser Gly
  1               5                  10                  15 ttg gag acg gca cgc aaa gtc cag gcc gcc ggt ctg tcc tgc ctc gtt    96
Leu Glu Thr Ala Arg Lys Val Gln Ala Ala Gly Leu Ser Cys Leu Val
             20                  25                  30 ctt gag gcg ttg gat cgt gta ggg gga aag act ctg agc gta caa tcg   144
Leu Glu Ala Leu Asp Arg Val Gly Gly Lys Thr Leu Ser Val Gln Ser
         35                  40                  45 ggt ccc ggc agg acg act atc gac gac ctc ggc gct gcg tgg atc aat   192
Gly Pro Gly Arg Thr Thr Ile Asp Asp Leu Gly Ala Ala Trp Ile Asn
     50                  55                  60 gac agc aac caa agc gaa gta ttc aaa tta ttt gaa aga ttt cat ttg   240
Asp Ser Asn Gln Ser Glu Val Phe Lys Leu Phe Glu Arg Phe His Leu
 65                  70                  75                  80 gag ggc gag ctc cag agg acg acc gga aat tca atc cat caa gca caa   288
Glu Gly Glu Leu Gln Arg Thr Thr Gly Asn Ser Ile His Gln Ala Gln
                 85                  90                  95 gac ggt aca atc act aca gct cct tat ggt gac tcc ttg ctg agc gag   336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg   384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag   432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac   480
Gln Leu Asp Ser Val Ser Phe Ala His Tyr Cys Glu Lys Asp Leu Asn
145                 150                 155                 160
```

```
ttg cct gct gtt ctc ggc gtg gca aac cag atc aca cgc gct ctg ctc      528
Leu Pro Ala Val Leu Gly Val Ala Asn Gln Ile Thr Arg Ala Leu Leu
            165                 170                 175 ggt gtg gaa gcc cac gag gtc agc atg ctt ttt ctc acc gac tac atc      576
Gly Val Glu Ala His Glu Val Ser Met Leu Phe Leu Thr Asp Tyr Ile
        180                 185                 190 aag agt gcc acc ggt ctc agt aat att ttc tcg gag aag aaa gac ggt      624
Lys Ser Ala Thr Gly Leu Ser Asn Ile Phe Ser Glu Lys Lys Asp Gly
    195                 200                 205 ggg cag tat atg cga tgc aaa aca ggt atg cag tcg ctt tgc cat gcc      672
Gly Gln Tyr Met Arg Cys Lys Thr Gly Met Gln Ser Leu Cys His Ala
210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tct ggc tgt aca gta cga tcg gcc tcg      768
Ala Glu Ile Glu Gln Ser Ala Ser Gly Cys Thr Val Arg Ser Ala Ser
            245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
        260                 265                 270 ttg tat ccc acc ttg aca ttt tca ccg cct ctt ccc gcc gag aag caa      864
Leu Tyr Pro Thr Leu Thr Phe Ser Pro Pro Leu Pro Ala Glu Lys Gln
    275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
            325                 330                 335 gcc gat cag caa tgg tcc att acc tgt ttc atg gtc gga gac ccg gga     1056
Ala Asp Gln Gln Trp Ser Ile Thr Cys Phe Met Val Gly Asp Pro Gly
        340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
    355                 360                 365 gac caa ctc cgc gca gcc tac gag agc gct ggg gcc caa gtc cca gag     1152
Asp Gln Leu Arg Ala Ala Tyr Glu Ser Ala Gly Ala Gln Val Pro Glu
370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc atc aca ctg ggt     1248
Gly Ala Pro Ser Ala Val Tyr Gly Leu Asn Asp Leu Ile Thr Leu Gly
            405                 410                 415 tcg gcg ctc aga acg ccg ttc aag tgt gtt cat ttc gtc gga acg gag     1296
Ser Ala Leu Arg Thr Pro Phe Lys Cys Val His Phe Val Gly Thr Glu
        420                 425                 430 acg tct tta gtt tgg aaa ggg tat atg gaa ggg gcc ata cga tcg ggt     1344
Thr Ser Leu Val Trp Lys Gly Tyr Met Glu Gly Ala Ile Arg Ser Gly
    435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala  *
450                 455                 460

<210> SEQ ID NO 125
<211> LENGTH: 463
```

<212> TYPE: PRT
<213> ORGANISM: Artificial Sequence
<220> FEATURE:
<223> OTHER INFORMATION: Translation of Synthetic Construct Clone 9F3

<400> SEQUENCE: 125

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
            20                  25                  30

Leu Glu Ala Leu Asp Arg Val Gly Gly Lys Thr Leu Ser Val Gln Ser
            35                  40                  45

Gly Pro Gly Arg Thr Thr Ile Asp Asp Leu Gly Ala Ala Trp Ile Asn
50                  55                  60

Asp Ser Asn Gln Ser Glu Val Phe Lys Leu Phe Glu Arg Phe His Leu
65                  70                  75                  80

Glu Gly Glu Leu Gln Arg Thr Thr Gly Asn Ser Ile His Gln Ala Gln
            85                  90                  95

Asp Gly Thr Ile Thr Thr Ala Pro Tyr Gly Asp Ser Leu Leu Ser Glu
            100                 105                 110

Glu Val Ala Ser Ala Leu Ala Glu Leu Leu Pro Ala Trp Ser Gln Leu
            115                 120                 125

Ile Glu Glu His Ser Leu Glu Asp Pro Lys Ala Ser Pro Gln Ala Lys
130                 135                 140

Gln Leu Asp Ser Val Ser Phe Ala His Tyr Cys Glu Lys Asp Leu Asn
145                 150                 155                 160

Leu Pro Ala Val Leu Gly Val Ala Asn Gln Ile Thr Arg Ala Leu Leu
            165                 170                 175

Gly Val Glu Ala His Glu Val Ser Met Leu Phe Leu Thr Asp Tyr Ile
            180                 185                 190

Lys Ser Ala Thr Gly Leu Ser Asn Ile Phe Ser Glu Lys Lys Asp Gly
            195                 200                 205

Gly Gln Tyr Met Arg Cys Lys Thr Gly Met Gln Ser Leu Cys His Ala
210                 215                 220

Met Ser Lys Glu Leu Val Pro Gly Ser Val Arg Leu Asn Thr Pro Val
225                 230                 235                 240

Ala Glu Ile Glu Gln Ser Ala Ser Gly Cys Thr Val Arg Ser Ala Ser
            245                 250                 255

Gly Ala Val Phe Arg Ser Lys Lys Val Val Ser Leu Pro Thr Thr
            260                 265                 270

Leu Tyr Pro Thr Leu Thr Phe Ser Pro Pro Leu Pro Ala Glu Lys Gln
            275                 280                 285

Ala Leu Ala Glu Asn Ser Ile Leu Gly Tyr Tyr Ser Lys Ile Val Phe
290                 295                 300

Val Trp Asp Lys Pro Trp Trp Arg Glu Gln Gly Phe Ser Gly Val Leu
305                 310                 315                 320

Gln Ser Ser Gly Gly Pro Ile Ser Phe Ala Arg Asp Thr Ser Ile Glu
            325                 330                 335

Ala Asp Gln Gln Trp Ser Ile Thr Cys Phe Met Val Gly Asp Pro Gly
            340                 345                 350

Arg Lys Trp Ser Gln Gln Ser Lys Gln Val Arg Gln Lys Ser Val Trp
            355                 360                 365

Asp Gln Leu Arg Ala Ala Tyr Glu Ser Ala Gly Ala Gln Val Pro Glu
            370                 375                 380

```
Pro Ala Asn Val Leu Glu Ile Glu Trp Ser Lys Gln Gln Tyr Phe Gln
385                 390                 395                 400

Gly Ala Pro Ser Ala Val Tyr Gly Leu Asn Asp Leu Ile Thr Leu Gly
                405                 410                 415

Ser Ala Leu Arg Thr Pro Phe Lys Cys Val His Phe Val Gly Thr Glu
            420                 425                 430

Thr Ser Leu Val Trp Lys Gly Tyr Met Glu Gly Ala Ile Arg Ser Gly
        435                 440                 445

Gln Arg Gly Ala Ala Glu Val Val Ala Ser Leu Val Pro Ala Ala
    450                 455                 460

<210> SEQ ID NO 126
<211> LENGTH: 1392
<212> TYPE: DNA
<213> ORGANISM: Artificial Sequence
<220> FEATURE:
<223> OTHER INFORMATION: Synthetic Construct Clone 9G10
<220> FEATURE:
<221> NAME/KEY: CDS
<222> LOCATION: (1)...(1392)

<400> SEQUENCE: 126 aaa gac aat gtt gcg gac gtg gta gtg gtg ggc gct ggc ttg agc ggt    48
Lys Asp Asn Val Ala Asp Val Val Val Val Gly Ala Gly Leu Ser Gly
1               5                   10                  15 ttg gag acg gca cgc aaa gtc cag gcc gcc ggt ctg tcc tgc ctc gtt    96
Leu Glu Thr Ala Arg Lys Val Gln Ala Ala Gly Leu Ser Cys Leu Val
            20                  25                  30 ctt gag gcg ttg gat cgt gta ggg gga aag act ctg agc gta caa tcg   144
Leu Glu Ala Leu Asp Arg Val Gly Gly Lys Thr Leu Ser Val Gln Ser
        35                  40                  45 ggt ccc ggc agg acg act atc gac gac ctc ggc gct gcg tgg atc aat   192
Gly Pro Gly Arg Thr Thr Ile Asp Asp Leu Gly Ala Ala Trp Ile Asn
    50                  55                  60 gac agc aac caa agc gaa gta ttc aaa tta ttt gaa aga ttt cat ttg   240
Asp Ser Asn Gln Ser Glu Val Phe Lys Leu Phe Glu Arg Phe His Leu
65                  70                  75                  80 gag ggc gag ctc cag agg acg acc gga aat tca atc cat caa gca caa   288
Glu Gly Glu Leu Gln Arg Thr Thr Gly Asn Ser Ile His Gln Ala Gln
                85                  90                  95 gac ggt aca atc act aca gct cct tat ggt gac tcc ttg ctg agc gag   336
Asp Gly Thr Ile Thr Thr Ala Pro Tyr Gly Asp Ser Leu Leu Ser Glu
            100                 105                 110 gag gtt gca agt gca ctc gcg gaa ctc ctt ccc gca tgg tct cag ctg   384
Glu Val Ala Ser Ala Leu Ala Glu Leu Leu Pro Ala Trp Ser Gln Leu
        115                 120                 125 atc gaa gag cat agt ctt gaa gac ccc aag gcg agc cct cag gcg aag   432
Ile Glu Glu His Ser Leu Glu Asp Pro Lys Ala Ser Pro Gln Ala Lys
    130                 135                 140 cag ctc gac agt gtg agc ttc gca cac tac tgt gag aag gac cta aac   480
Gln Leu Asp Ser Val Ser Phe Ala His Tyr Cys Glu Lys Asp Leu Asn
145                 150                 155                 160 ttg cct gct gtt ctc ggc gtg gca aac cag atc aca cgc gct ctg ctc   528
Leu Pro Ala Val Leu Gly Val Ala Asn Gln Ile Thr Arg Ala Leu Leu
                165                 170                 175 ggt gtg gaa gcc cac gag gtc agc atg ctt ttt ctc acc gac tac atc   576
Gly Val Glu Ala His Glu Val Ser Met Leu Phe Leu Thr Asp Tyr Ile
            180                 185                 190 aag agt gcc acc ggt ctc agt aat att ttc tcg gag aag aaa gac ggt   624
Lys Ser Ala Thr Gly Leu Ser Asn Ile Phe Ser Glu Lys Lys Asp Gly
        195                 200                 205
```

```
ggg cag tat atg cga tgc aaa aca ggt atg cag tcg ctt tgc cat gcc      672
Gly Gln Tyr Met Arg Cys Lys Thr Gly Met Gln Ser Leu Cys His Ala
    210                 215                 220 atg tca aag gaa ctt gtt cca ggc tca gtg cgc ctc aac acc ccc gtc      720
Met Ser Lys Glu Leu Val Pro Gly Ser Val Arg Leu Asn Thr Pro Val
225                 230                 235                 240 gct gaa att gag cag tcg gcg tcc ggc tgt aca gta cga tcg gcc tcg      768
Ala Glu Ile Glu Gln Ser Ala Ser Gly Cys Thr Val Arg Ser Ala Ser
                245                 250                 255 ggc gcc gtg ttc cga agc aaa aag gtg gtg gtt tcg tta ccg aca acc      816
Gly Ala Val Phe Arg Ser Lys Lys Val Val Val Ser Leu Pro Thr Thr
            260                 265                 270 ttg tat ccc acc ttg aca ttt tca cca cct ctt ccc gcc gag aag caa      864
Leu Tyr Pro Thr Leu Thr Phe Ser Pro Pro Leu Pro Ala Glu Lys Gln
        275                 280                 285 gca ttg gcg gaa aat tct atc ctg ggc tac tat agc aag ata gtc ttc      912
Ala Leu Ala Glu Asn Ser Ile Leu Gly Tyr Tyr Ser Lys Ile Val Phe
    290                 295                 300 gta tgg gac aag ccg tgg tgg cgc gaa caa ggc ttc tcg ggc gtc ctc      960
Val Trp Asp Lys Pro Trp Trp Arg Glu Gln Gly Phe Ser Gly Val Leu
305                 310                 315                 320 caa tcg agc ggt ggc ccc atc tca ttt gcc aga gat acc agc atc gaa     1008
Gln Ser Ser Gly Gly Pro Ile Ser Phe Ala Arg Asp Thr Ser Ile Glu
                325                 330                 335 gcc gat cag caa tgg tcc att acc tgt ttc atg gtc gga gac ccg gga     1056
Ala Asp Gln Gln Trp Ser Ile Thr Cys Phe Met Val Gly Asp Pro Gly
            340                 345                 350 cgg aag tgg tcc caa cag tcc aag cag gta cga caa aag tct gtc tgg     1104
Arg Lys Trp Ser Gln Gln Ser Lys Gln Val Arg Gln Lys Ser Val Trp
        355                 360                 365 gac caa ctc cgc gca gcc tac gag aac gct ggg gcc caa gtc cca gag     1152
Asp Gln Leu Arg Ala Ala Tyr Glu Asn Ala Gly Ala Gln Val Pro Glu
    370                 375                 380 ccg gcc aac gtg ctc gaa atc gag tgg tcg aag cag cag tat ttc caa     1200
Pro Ala Asn Val Leu Glu Ile Glu Trp Ser Lys Gln Gln Tyr Phe Gln
385                 390                 395                 400 gga gct ccg agc gcc gtc tat ggg ctg aac gat ctc gtc aca ctg ggt     1248
Gly Ala Pro Ser Ala Val Tyr Gly Leu Asn Asp Leu Val Thr Leu Gly
                405                 410                 415 tcg gcg ctc aga acg ccg ttc aag tgt gtt cat ttc gtc gga gcg gag     1296
Ser Ala Leu Arg Thr Pro Phe Lys Cys Val His Phe Val Gly Ala Glu
            420                 425                 430 acg tct tta gtt tgg aaa ggg tat atg gaa ggg gcc ata cgg tcg ggc     1344
Thr Ser Leu Val Trp Lys Gly Tyr Met Glu Gly Ala Ile Arg Ser Gly
        435                 440                 445 caa cga ggt gct gca gaa gtt gtg gct agc ctg gtg cca gca gca tag     1392
Gln Arg Gly Ala Ala Glu Val Val Ala Ser Leu Val Pro Ala Ala  *
    450                 455                 460

<210> SEQ ID NO 127
<211> LENGTH: 463
<212> TYPE: PRT
<213> ORGANISM: Artificial Sequence
<220> FEATURE:
<223> OTHER INFORMATION: Translation of Synthetic Construct Clone 9G10

<400> SEQUENCE: 127

Lys Asp Asn Val Ala Asp Val Val Val Gly Ala Gly Leu Ser Gly
1               5                   10                  15

Leu Glu Thr Ala Arg Lys Val Gln Ala Ala Gly Leu Ser Cys Leu Val
```

-continued

```
            20                  25                  30
Leu Glu Ala Leu Asp Arg Val Gly Gly Lys Thr Leu Ser Val Gln Ser
        35                  40                  45
Gly Pro Gly Arg Thr Thr Ile Asp Asp Leu Gly Ala Ala Trp Ile Asn
 50                  55                  60
Asp Ser Asn Gln Ser Glu Val Phe Lys Leu Phe Glu Arg Phe His Leu
 65                  70                  75                  80
Glu Gly Glu Leu Gln Arg Thr Thr Gly Asn Ser Ile His Gln Ala Gln
                 85                  90                  95
Asp Gly Thr Ile Thr Thr Ala Pro Tyr Gly Asp Ser Leu Leu Ser Glu
            100                 105                 110
Glu Val Ala Ser Ala Leu Ala Glu Leu Leu Pro Ala Trp Ser Gln Leu
        115                 120                 125
Ile Glu Glu His Ser Leu Glu Asp Pro Lys Ala Ser Pro Gln Ala Lys
    130                 135                 140
Gln Leu Asp Ser Val Ser Phe Ala His Tyr Cys Glu Lys Asp Leu Asn
145                 150                 155                 160
Leu Pro Ala Val Leu Gly Val Ala Asn Gln Ile Thr Arg Ala Leu Leu
                165                 170                 175
Gly Val Glu Ala His Glu Val Ser Met Leu Phe Leu Thr Asp Tyr Ile
            180                 185                 190
Lys Ser Ala Thr Gly Leu Ser Asn Ile Phe Ser Glu Lys Lys Asp Gly
        195                 200                 205
Gly Gln Tyr Met Arg Cys Lys Thr Gly Met Gln Ser Leu Cys His Ala
    210                 215                 220
Met Ser Lys Glu Leu Val Pro Gly Ser Val Arg Leu Asn Thr Pro Val
225                 230                 235                 240
Ala Glu Ile Glu Gln Ser Ala Ser Gly Cys Thr Val Arg Ser Ala Ser
                245                 250                 255
Gly Ala Val Phe Arg Ser Lys Val Val Ser Leu Pro Thr Thr
            260                 265                 270
Leu Tyr Pro Thr Leu Thr Phe Ser Pro Pro Leu Pro Ala Glu Lys Gln
        275                 280                 285
Ala Leu Ala Glu Asn Ser Ile Leu Gly Tyr Tyr Ser Lys Ile Val Phe
    290                 295                 300
Val Trp Asp Lys Pro Trp Trp Arg Glu Gln Gly Phe Ser Gly Val Leu
305                 310                 315                 320
Gln Ser Ser Gly Gly Pro Ile Ser Phe Ala Arg Asp Thr Ser Ile Glu
                325                 330                 335
Ala Asp Gln Gln Trp Ser Ile Thr Cys Phe Met Val Gly Asp Pro Gly
            340                 345                 350
Arg Lys Trp Ser Gln Gln Ser Lys Gln Val Arg Gln Lys Ser Val Trp
        355                 360                 365
Asp Gln Leu Arg Ala Ala Tyr Glu Asn Ala Gly Ala Gln Val Pro Glu
    370                 375                 380
Pro Ala Asn Val Leu Glu Ile Glu Trp Ser Lys Gln Gln Tyr Phe Gln
385                 390                 395                 400
Gly Ala Pro Ser Ala Val Tyr Gly Leu Asn Asp Leu Val Thr Leu Gly
                405                 410                 415
Ser Ala Leu Arg Thr Pro Phe Lys Cys Val His Phe Val Gly Ala Glu
            420                 425                 430
Thr Ser Leu Val Trp Lys Gly Tyr Met Glu Gly Ala Ile Arg Ser Gly
        435                 440                 445
```

```
Gln Arg Gly Ala Ala Glu Val Val Ala Ser Leu Val Pro Ala Ala
    450                 455                 460
```